US010913742B2

(12) United States Patent
Chen et al.

(10) Patent No.: US 10,913,742 B2
(45) Date of Patent: Feb. 9, 2021

(54) OXADIAZOLONES AS TRANSIENT RECEPTOR POTENTIAL CHANNEL INHIBITORS

(71) Applicant: Genentech, Inc., South San Francisco, CA (US)

(72) Inventors: Huifen Chen, South San Francisco, CA (US); Daniel Shore, South San Francisco, CA (US); Elisia Villemure, South San Francisco, CA (US); Matthew Volgraf, South San Francisco, CA (US); Baihua Hu, Beijing (CN); Aijun Lu, Beijing (CN); Andrew Cridland, Harlow (GB); Stuart Ward, Harlow (GB); Francis Beaumier, Montreal (CA); Martin Dery, Montreal (CA); Robin Larouche-Gauthier, Montreal (CA)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 16/421,114

(22) Filed: May 23, 2019

(65) Prior Publication Data
US 2019/0284189 A1 Sep. 19, 2019

Related U.S. Application Data

(63) Continuation of application No. PCT/EP2017/080571, filed on Nov. 27, 2017.

(30) Foreign Application Priority Data

Nov. 14, 2017 (CN) .......................... 2017 1 1122317

(51) Int. Cl.
*C07D 487/04* (2006.01)
*C07D 473/30* (2006.01)
*C07D 471/04* (2006.01)
*C07D 513/04* (2006.01)
*A61K 31/519* (2006.01)
*A61P 11/06* (2006.01)
*C07D 498/04* (2006.01)

(52) U.S. Cl.
CPC .......... *C07D 473/30* (2013.01); *A61K 31/519* (2013.01); *A61P 11/06* (2018.01); *C07D 471/04* (2013.01); *C07D 487/04* (2013.01); *C07D 498/04* (2013.01); *C07D 513/04* (2013.01)

(58) Field of Classification Search
CPC .. C07D 487/04; C07D 473/30; C07D 471/04; C07D 513/04; A61K 31/519; A61P 11/06
USPC ............ 544/265; 548/132; 514/260.1, 263.2, 514/354
See application file for complete search history.

(56) References Cited

U.S. PATENT DOCUMENTS

| | | |
|---|---|---|
| 3,773,919 A | 11/1973 | Boswell et al. |
| 4,485,045 A | 11/1984 | Regen |
| 4,544,545 A | 10/1985 | Ryan et al. |
| 5,004,697 A | 4/1991 | Pardridge et al. |
| 5,112,596 A | 5/1992 | Malfroy-Camine |
| 5,268,164 A | 12/1993 | Kozarich et al. |
| 5,506,206 A | 4/1996 | Kozarich et al. |
| 5,686,416 A | 11/1997 | Kozarich et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0162695 A1 | 8/2003 | Schatzberg et al. |
| 2004/0131692 A1 | 7/2004 | Kreuter et al. |
| 2004/0204354 A1 | 10/2004 | Nelson et al. |
| 2005/0089473 A1 | 4/2005 | Black et al. |
| 2005/0124533 A1 | 6/2005 | Schatzberg et al. |

FOREIGN PATENT DOCUMENTS

| | | |
|---|---|---|
| EP | 0102324 A2 | 3/1984 |
| EP | 0133988 | 8/1984 |
| WO | 2008/119741 A2 | 10/2008 |
| WO | 2011/114184 A1 | 9/2011 |
| WO | 2017/060488 A1 | 4/2017 |
| WO | 2017/064068 A1 | 4/2017 |

OTHER PUBLICATIONS

Chen et al., Naunyn-Schnniedeberg's Arch Pharmacol (2015) 388:451-463.*
Dietrich A., Pharmaceuticals 2019, 12, 1-23.*
Freshney et al.,Culture of Animal Cells, A Manual of Basic Technique, Alan R. Liss, Inc., 1983, New York, p. 4.*
Dermeret al., Bio/Technology, 1994, 12:320.*
(Database PubChem Compound [Online] NCBI, Sep. 8, 2005, Database accession No. CID 3437423 abstract).
(Database Registry [Online] Chemical Abstracts Service, Columbus, Ohio, US; Jul. 4, 2012 Database accession No. 1381342-13-7 abstract).

(Continued)

*Primary Examiner* — Venkataraman Balasubramanian
(74) *Attorney, Agent, or Firm* — Robert C. Hall

(57) ABSTRACT

The invention relates to compounds of formula (I):

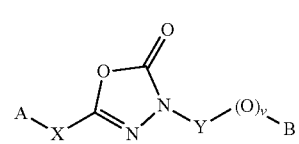

and pharmaceutically acceptable salts thereof. In addition, the present invention relates to methods of manufacturing and methods of using the compounds of formula (I) as well as pharmaceutical compositions containing such compounds. The compounds may be useful in treating diseases and conditions mediated by TRPA1, such as respiratory disorders or pain.

13 Claims, No Drawings

(56) References Cited

OTHER PUBLICATIONS (Database Registry [online] Chemical Abstracts Service, Columbus, Ohio, US; Jun. 7, 2006, Database accession No. 887037-04-9 abstract).
Ackley, David C., et al. Optimization in Drug Discovery: In Vitro Methods "Metabolic Stability Assessed by Liver Microsomes and Hepatocytes" Yan, Zhengyin, ed., Totowa, New Jersey:Humana Press,:151-162 (Jan. 1, 2004).
Agopyan, N., et al., "TRPV1 receptors mediate particulate matter-induced apoptosis" Am J Physiol Lung Cell Mol Physiol 286:L563-L572 (Oct. 30, 2003).
Agopyan, N., et al., "Vanilloid receptor activation by 2- and 10-µm particles induces responses leading to apoptosis in human airway epithelial cells" Toxicol Appl Pharm 192:21-35 (May 28, 2003).
Ansel's Pharmaceutical Dosage Forms and Drug Delivery Systems (Table of Contents only, in 6 pages), Allen et al., 8th edition, Philadelphia, PA:Lippincott Williams & Wilkins, (2004).
Asai, Hideaki, et al., "Heat and mechanical hyperalgesia in mice model of cancer pain" Pain 117:19-29 (May 3, 2005).
Barton, N.J., et al., "Attenuation of experimental arthritis in TRPV1R knockout mice" Exp Mol Pathol 81:166-170 (Jun. 16, 2006).
Bobo et al., "Convection-enhanced delivery of macromolecules in the brain" Proc. Natl. Acad. Sci. USA 91:2076-2080 ( 1994).
Bolcskei, Kata, et al., "Investigation of the role of TRPV1 receptors in acute and chronic nociceptive processes using gene-deficient mice" Pain 117:368-376 (Jun. 27, 2005).
Bundgaard A Textbook of Drug Design and Development; Chapter 5 "Design and Application of Prodrugs":113-191( 1991).
Bundgaard et al., "(C) Means to Enhance Penetration (1) Prodrugs as a means to improve the delivery of peptide drugs" Advanced Drug Delivery Reviews 8: 1-38 ( 1992).
Bundgaard, "Design of prodrugs: Bioreversible derivatives for various functional groups and chemical entities" Design of Prodrugs:1 ( 1985).
Bundgaard, "Formation of Prodrugs of Amines, Amides, Ureides and Imides" Methods in Enzymology 112:347( 1985).
Chan, C.L.H., et al., "Sensory fibres expressing capsaicin receptor TRPV1 in patients with rectal hypersensitivity and faecal urgency" Lancet 361:385-391 (Feb. 1, 2003).
Coffey, S. Rodd's Chemistry of Carbon Compounds Coffey, S., Second edition, Elsevier B.V.:Elsevier B.V., vol. I-IV ( 2008).
De Yebenes et al., "Continuous Intracerebroventricular Infusion of Dopamine and Dopamine Agonists Through a Totally Implanted Drug Delivery System in Animal Models of Parkinson's Disease" Movement Disorders 2(3):143-158 ( 1987).
Dinis, Paulo, et al., "Anandamide-Evoked Activation of Vanilloid Receptor 1 Contributes to the Development of Bladder Hyper-reflexia and Nociceptive Transmission to Spinal Dorsal Horn Neurons in Cystitis" J Neurol Sci 24(50):11253-11263 (Dec. 15, 2004).
Epstein et al., "Biological activity of liposome-encapsulated mutine interferon y is mediated by a cell membrane receptor" Proc Natl Acad Sci USA 82:3688-3692 (Jun. 1985).
Fleisher et al., "Improved oral drug delivery: solubility limitations overcome by the use of prodrugs" Advanced Drug Delivery Reviews 19:115-130 ( 1996).
Gennaro et al. Remington: The Science And Practice of Pharmacy (Press), Philadelphia:Lippincott, Williams & Wilkins, ( 2000).
Geppetti, P., et al., "Activation and sensitisation of the vanilloid receptor: role in gastrointestinal inflammation and function" Brit J Pharmacol 141: 1313-1320 (Mar. 29, 2004).
Ghilardi, J .R., et al., "Selective Blockade of the Capsaicin Receptor TRPV1 Attenuates Bone Cancer Pain" J Neurol Sci 25(12):3126-3131 (Mar. 23, 2005).
Gill et al., "Direct Brain Infusion of Glial Cell Line-Derived Neurotrophic Factor in Parkinson Disease" Nature Med. 9:589-595 (Mar. 31, 2003).
Goadsby, P. J., "Post-triptan Era for the Treatment of Acute Migraine" Curr Pain Head Reports 8:393-398 (Jan. 1, 2004).

Harbaugh, "Intracerebroventricular cholinergic drug administration in Alzheimer's disease: preliminary results of a double-blind study" J. Neural. Transm. 24 Suppl.:271-277 ( 1987).
HO Fiesers' Reagents for Organic Synthesis (Table of Contents, in 5 pages), Hoboken, New Jersey:John Wiley & Sons, Inc., vol. 23 (2007).
Honore, P., et al., "A-425619 [1-Isoquinolin-5-yl-3-(4-trifluoromethyl-benzyl)-urea], a Novel Transient Receptor Potential Type V1 Receptor Antagonist, Relieves Pathophysiological Pain Associated with Inflammation and Tissue Injury in Rats" J Pharmacol Exp Ther 314(1):410-421 (Apr. 14, 2005).
Hwang et al., "Hepatic uptake and degradation of unilamellar sphingomyelin/cholesterol liposomes: A kinetic study" Proc. Natl. Acad. Sci. USA 77(7):4030-4034 ( 1980).
"International Preliminary Report on Patentability—PCT/EP2017/080571":1-28 (dated Feb. 7, 2018).
"International Search Report—PCT/EP2017/080571":1-5 (Jan. 26, 2017).
Kakeya et al., "Studies on Prodrugs of Cephalosporins.I. ///superscript:1)/// Synthesis and Biological Properties of Glycyloxbenzoyloxymethyl and Glycylaminobenzoyloxymethyl Esters of 7β-[2-(2-Aminothiazol-4yl)-(Z)-2-methoxyiminoacetamido]-3-3-methyl-3-cephem-4-carboxylic Acid" Chem. Pharm. Bull. 32(2):692-698 ( 1984).
Kimball, E.S., et al., "Vanilloid receptor 1 antagonists attenuate disease severity in dextran sulphate sodium-induced colitis in mice" Neurogastroent Motil 16:811-818 (Jan. 5, 2004).
Kosugi, Masafumi, et al., "Activation of TRPA1 Channel Facilitates Excitatory Synaptic Transmission in Substantia Gelatinosa Neurons of the Adult Rat Spinal Cord" J Neurol Sci 27(16):4443-4451 (Apr. 18, 2007).
Kremeyer, Barbara, et al., "A Gain-of-Function Mutation in TRPA1 Causes Familial Episodic Pain Syndrome" Neuro 66:671-680 (Jun. 10, 2010).
Lalloo, Umesh G., et al., "Capsazepine inhibits cough induced by capsaicin and citric acid but not by hypertonic saline in guinea pigs" J Appl Physiol:1082-1087 (May 23, 1995).
Langer et al., "Biocompatibility of polymeric delivery systems for macromolecules" Journal of Biomedical Materials Research 15:267-277 ( 1981).
Menendez, L., et al., "Analgesic effects of capsazepine and resiniferatoxin on bone cancer pain in mice" Neurosci Lett 393:70-73 (Sep. 19, 2005).
Monge et al., "The Reaction of 2-Indolecarbohydrazones With Ethoxycarbonylchloride. New Syntheses of 2,3-Dihydro-2-oxo-1,3,4-oxadiazoles and 1,2,3,4-Tetrahydro-4-oxo-5H-pyridazino [4,5-b]indoles" Journal of Heterocyclic Chemistry 21(2):397-400 (Jan. 1, 1984).
Musser et al., "Synthesis of 2-/2,3-Dihydro-2-oxo-1,3,4-oxadiazol-5-yl) Benzo Heteroeyles. A Novel Series of Orally Active Antiallergic Agents" J. Med. Chem. 27:121-125 (Jan. 1, 1984).
Neuwelt, E. A. Implications of the Blood-Brain Barrier and Its Manipulation Neuwelt, E.A., ed.,Plenum Publishing Corporation—Springer, vol. vols. 1-2:1-434, (Jan. 1, 1989).
Nielsen et al., "Glycolamide Esters as Biolabile Prodrugs of Carboxylic Acid Agents: Synthesis, Stability, Bioconversion, and Physicochemical Properties" Journal of Pharmaceutical Sciences 77(4):285 ( 1988).
Notari, Robert, et al. Methods of Enzymology: Drug and Enzyme Targeting "Theory and Practice of Prodrug Kinetics" Widder, Kenneth J., eds, First edition, Waltham, MA:Academic Press, vol. 112:309-396 (Jun. 11, 1985).
Papanastassiou et al., "The Potential for Efficacy of The Modified (ICP 34.5) Herpes Simplex Virus HSV1716 Following Intratumoural Injection into Human Malignant Glioma: A Proof of Principle Study" Gene Therapy 9:398-406 (Apr. 2, 2002).
Pomonis, J.D., et al., "N-(4-Tertiarybutylphenyl)-4-(3-cholorphyridin-2-yl)tetrahydropyrazine-1(2H)-carbox-amide (BCTC), a Novel, Orally Effective Vanilloid Receptor 1 Antagonist with Analgesic Properties: 11. In Vivo Characterization in Rat Models of Inflammatory and Neuropathic Pain" J Pharmacol Exp Ther 306(1):387-393 (Apr. 31, 2003).

(56) References Cited

OTHER PUBLICATIONS

Remington's Pharmaceutical Sciences (Table of Contents, total in 6 pages), Osol et al., 15th edition, Easton, PA:Mack Publishing Company, ( 1975).

Robinson et al., "Discovery of the Hemifumarate and (α-L-Alanyloxy)methyl Ether as Prodrugs of an Antirheumatic Oxindole: Prodrugs for the Enolic OH Group" J. Med. Chem. 39:10-18 ( 1996).

Rowe. R. C. et al. Handbook of Pharmaceutical Exeipients, [GB] "Chemical Industry Press" (in Chinese with English Abstract),:137-139, 530-532,667-669.

Sanchez, Maria, et al., "Expression of the transient receptor potential vanilloid 1 (TRPV1) in LNCaP and PC-3 prostate cancer cells and in human prostate tissue" Eur J Pharmacol 515:20-27 (Apr. 8, 2005).

Sehenkel et al., "Optimization of a Novel Quinazolinone-Based Series of Transient Receptor Potential A1 (TRA1) Antagonists Demonstrating Potent in Vivo Activity" J Med Chem 59(6):2794-2809 (Mar. 24, 2016).

Sculptoreanu, A., et al., "Protein kinase C contributes to abnormal capsaicin responses in DRG neurons from cats with feline interstitial cystitis" Neurosci Lett 381:42-46 (Jan. 28, 2005).

Shyam Sunder Patel et al., "I 2 mediated synthesis of 5-substituted-3-methyl/benzyl-1,3,4-oxadiazol-2(3H)-ones via sequential condensation/oxidative cyclization and rearrangement" Organic & Biomolecular Chemistry 14(24):5683-5689 (Jan. 1, 2016).

Sidman et al., "Controlled Release of Macromolecules and Pharmaceuticals from Synthetic Polypeptides Based on Glutamic Acid" Biopolymers 22:547-556 ( 1983).

Sugimoto et al., "The use of a Mitsunobu reagent for the formation of heterocycles: a simple method for the preparation of 3-alkyl-e-aryl-1,3,4-oxadiazol-2(3H)-ones from carboxylic acids" Chemical Communications 50(55):7314-7317 (Jan. 1, 2014).

Szabo, A., et al., "Role of Transient Receptor Potential Vanilloid 1 Receptors in Adjuvant-Induced Chronic Arthritis: In Vivo Study Using Gene-Deficient Mice" J Pharmacol Exp Ther 314(1):111-119 (Apr. 5, 2005).

Walker, Katherine, et al., "The VR1 Antagonist Capsazepine Reverses Mechanical Hyperalgesia in Models of Inflammatory and Neuropathic Pain" J Pharmacol Exp Ther 304(1):56-62 (Sep. 9, 2002).

Wei, Hong, et al., "Spinal transient receptor potential ankyrin 1 channel contributes to central pain hypersensitivity in various pathophysiological conditions in the rat" Pain 152:582-591 (Nov. 29, 2010).

Wei, Hong, et al., "Spinal TRPA1 ion channels contribute to cutaneous neurogenic inflammation in the rat" Neurosci Lett 479:253-256 (May 23, 2010).

Yiangou, Y., et al., "Vanilloid receptor 1 immunoreactivity in inflamed human bowel" Lancet 357:1338-1339 (Apr. 28, 2001).

\* cited by examiner

OXADIAZOLONES AS TRANSIENT RECEPTOR POTENTIAL CHANNEL INHIBITORS

CROSS-REFERENCE TO RELATED APPLICATION

This application is a continuation of International Patent Application No. PCT/EP2017/080571 filed on Nov. 27, 2017, which claims priority to Chinese Patent Application No. 201711122317.2, filed on 14 Nov. 2017, and International Patent Application No. PCT/CN2016/107423, filed on 28 Nov. 2016, the entire disclosures of which are hereby incorporated by reference in their entirety.

FIELD OF THE INVENTION

The present invention relates to oxadiazolone compounds, their manufacture, pharmaceutical compositions containing them and their use as Transient Receptor Potential (TRP) cation channel antagonists.

BACKGROUND OF THE INVENTION

TRP channels are a class of ion channels found on the plasma membrane of a variety of human (and other animal) cell types. There are at least 28 known human TRP channels which are broken into a number of families or groups based upon sequence homology and function. Transient receptor potential cation channel, subfamily A, member 1 (TRPA1) is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a chemosensor.

Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress (e.g., 4-hydroxynonenal and related compounds) activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation. Moreover, recently findings have correlated activation of TRPA1 channels with increased pain perception (Kosugi et al., J. Neurosci 27, (2007) 4443-4451; Kremayer et al., Neuron 66 (2010) 671-680; Wei et al., Pain 152 (2011) 582-591; Wei et al., Neurosci Lett 479 (2010) 253-256)), providing additional rationale for the utility of small molecule TRPA1 inhibitors in the treatment of pain disorders.

BRIEF DESCRIPTION OF THE INVENTION

In some embodiments, a compound or a pharmaceutically acceptable salt thereof of the following formula (I) is provided:

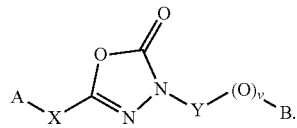

A is selected from substituted and unsubstituted 6-6 fused bicyclic heteroaryl and 6-5 fused bicyclic heteroaryl. X is selected from a bond, $C_{1-4}$ alkylene, —O—, —S—; —$SO_2$—, and —N($R^1$)—, wherein $R^1$ is selected from H and $C_{1-6}$ alkyl. Y is selected from substituted and unsubstituted $C_{2-4}$ alkylene $C_{2-4}$ alkenylene, and $C_{3-6}$cycloalkylene wherein one or more carbons of $C_{1-4}$ alkylene or $C_{2-4}$ alkenylene may be replaced with —O— and —C(O)—. B is selected from substituted and unsubstituted 5-membered aryl, 6-membered aryl, 5-membered heteroaryl, 6-membered heteroaryl, 6-6 fused bicyclic aryl, 6-6 fused bicyclic heteroaryl, 6-5 fused bicyclic aryl, 6-5 fused bicyclic heteroaryl, 6-5 fused bicyclic aryl-heteroaryl, 6-5 fused bicyclic aryl-cycloalkylene, and 6-6 fused bicyclic aryl-heteroaryl. v is 0 or 1.

In other embodiments, the following compounds or pharmaceutically acceptable salts thereof are provided:

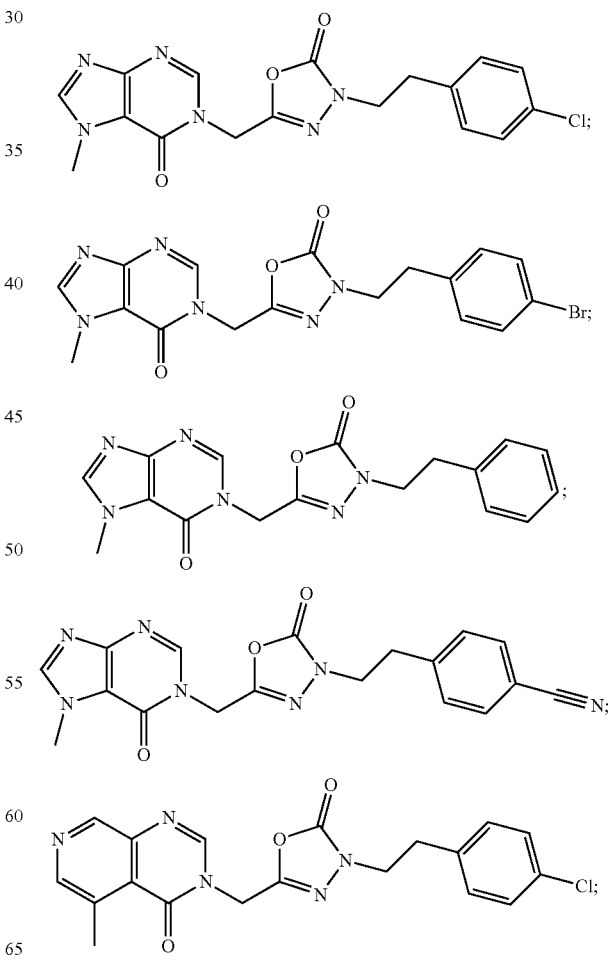

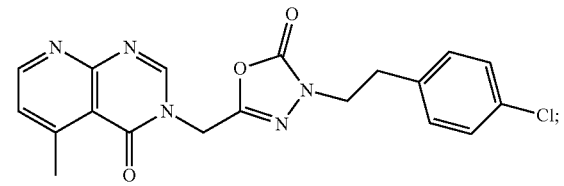
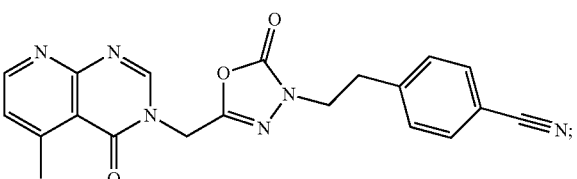
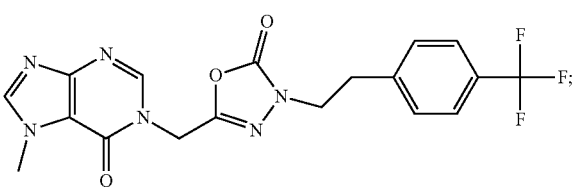
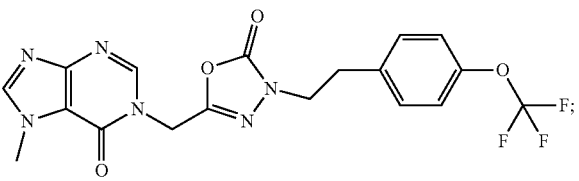
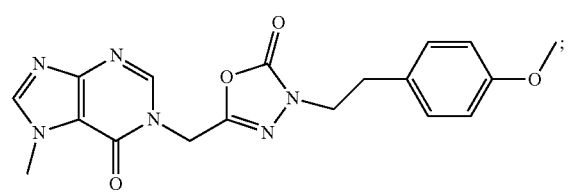
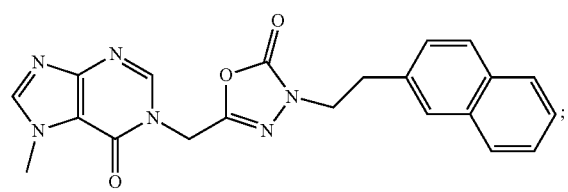
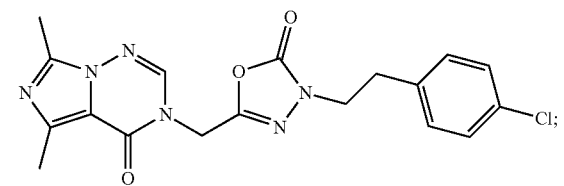
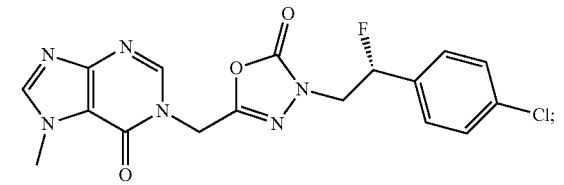
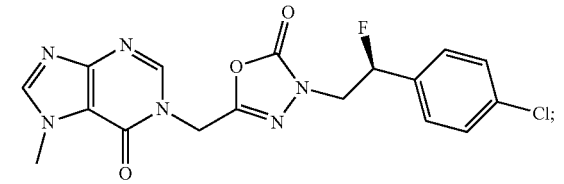
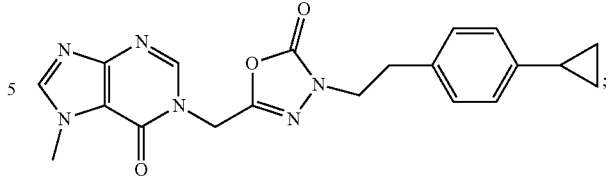
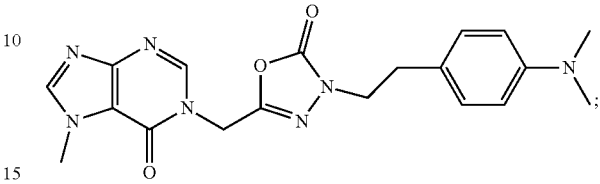
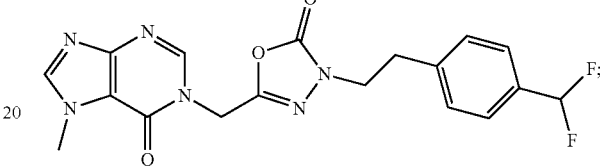
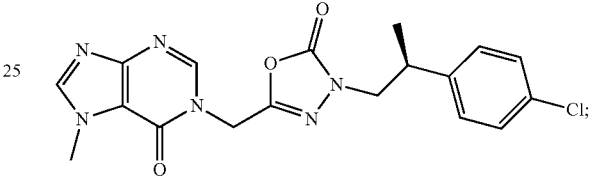
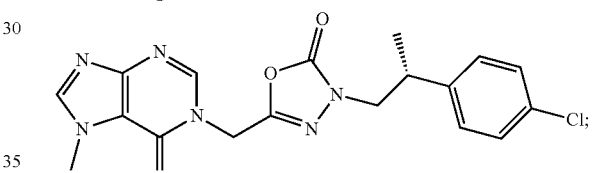
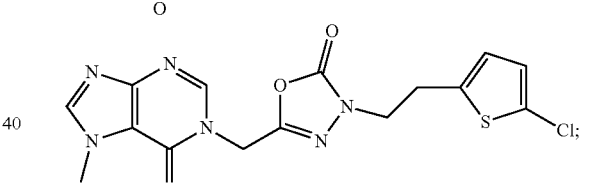
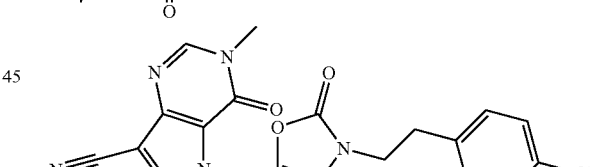
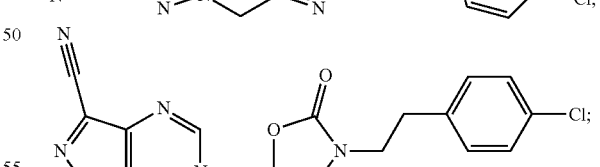
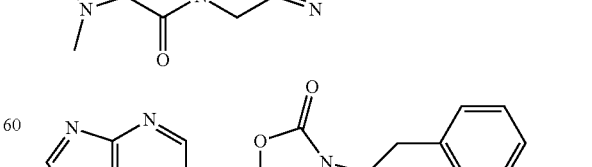

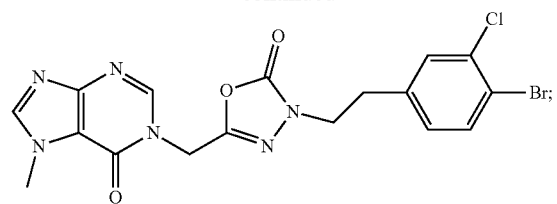
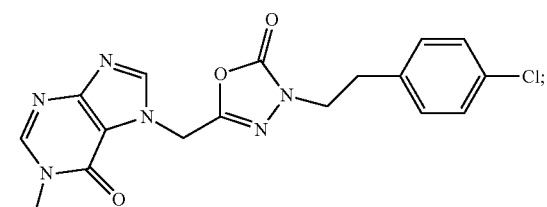
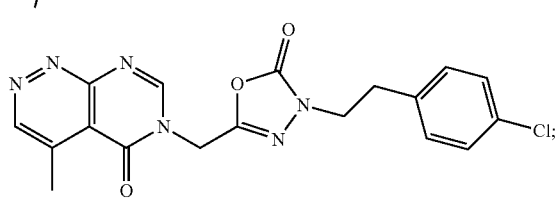
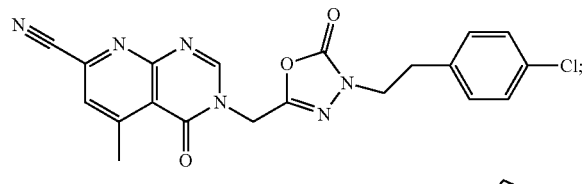
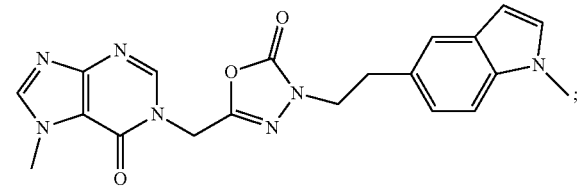
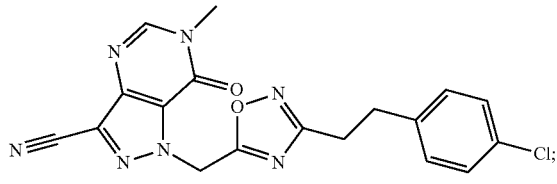
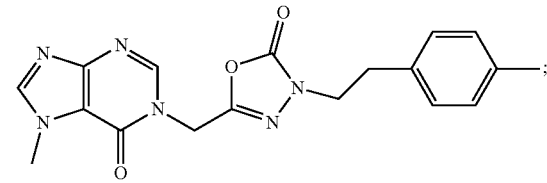
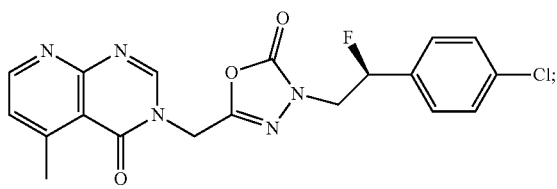
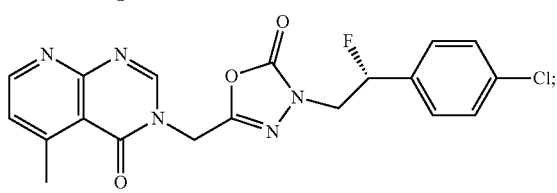
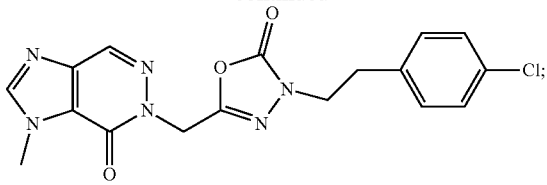
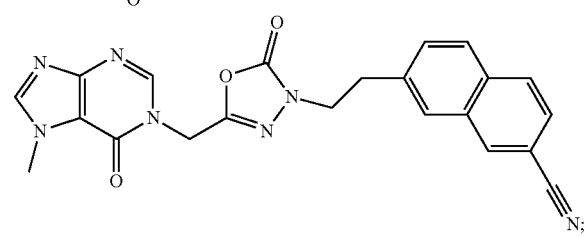
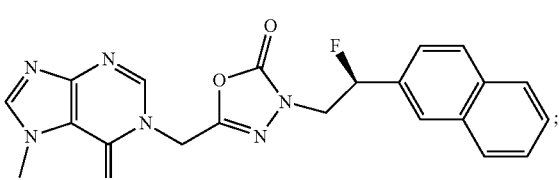
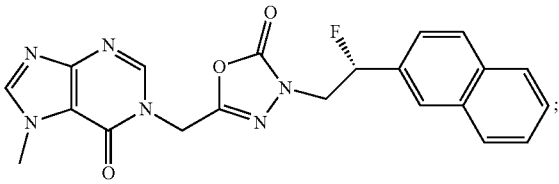
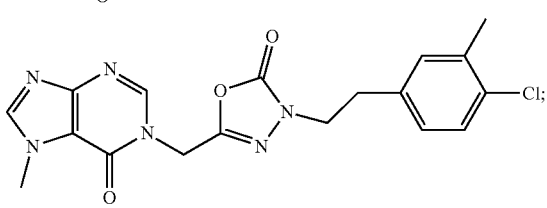
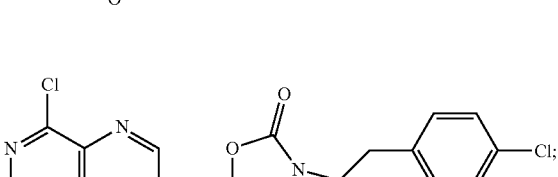
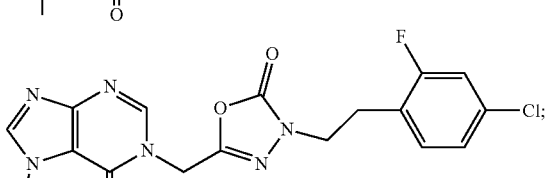
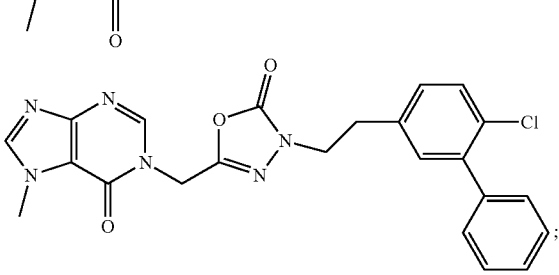

-continued
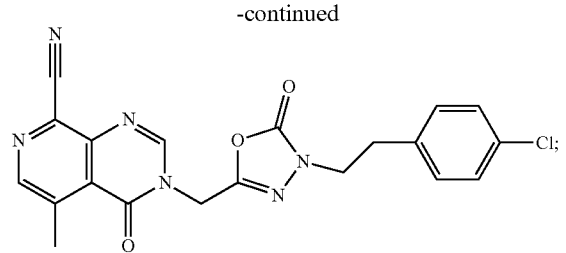
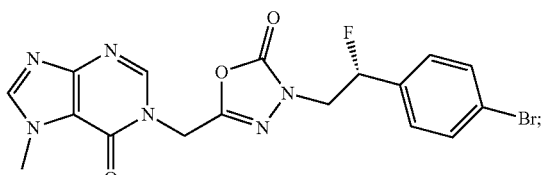
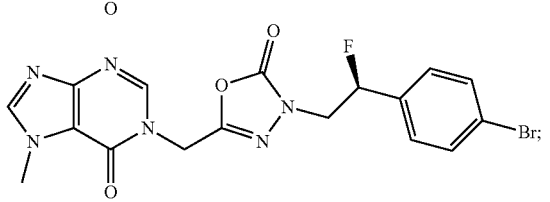
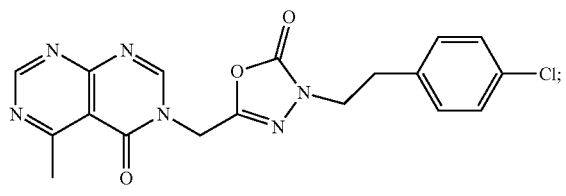
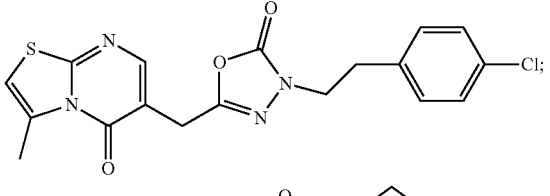
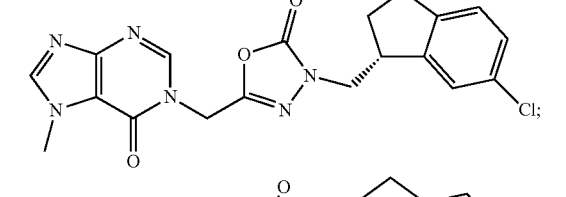
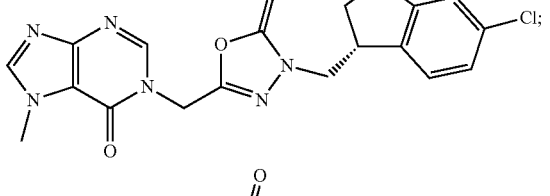
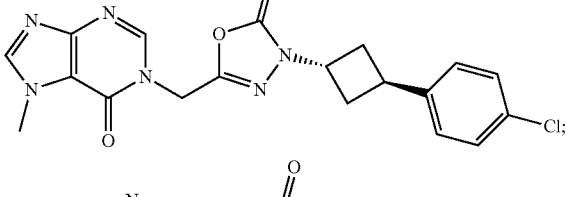
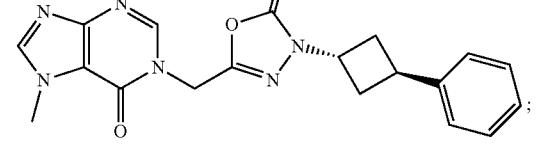
-continued
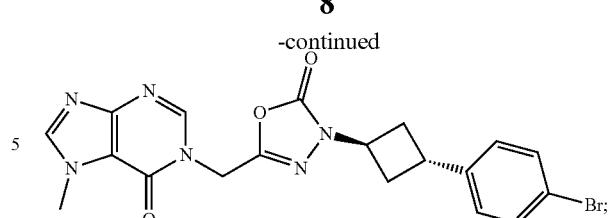
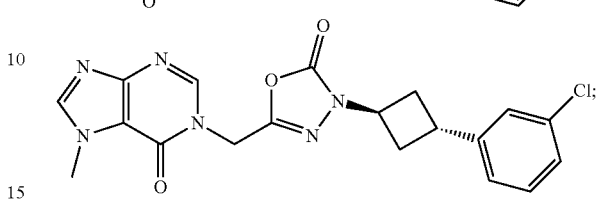
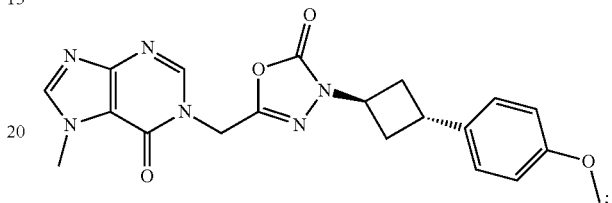
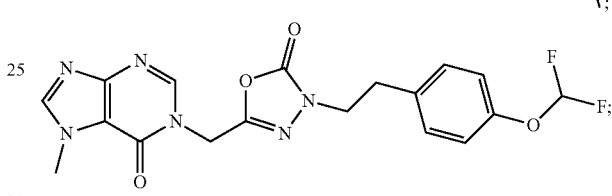
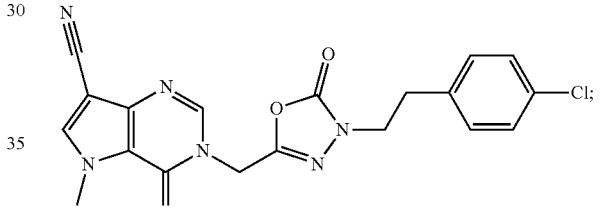
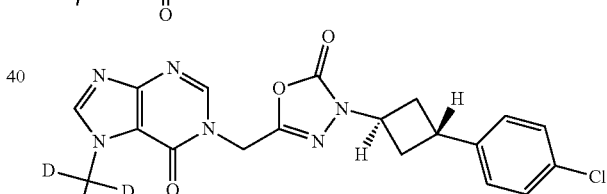
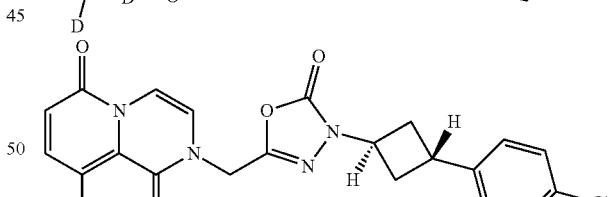
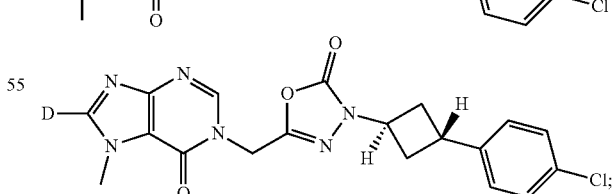
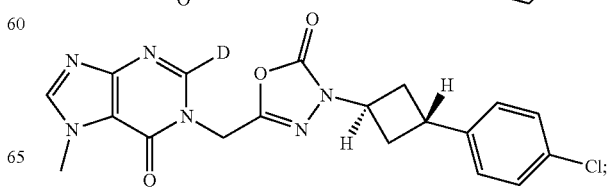

-continued
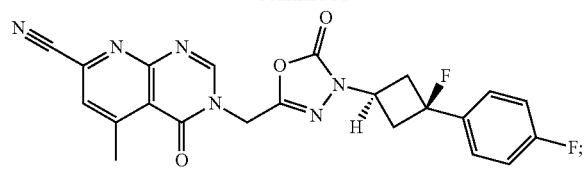
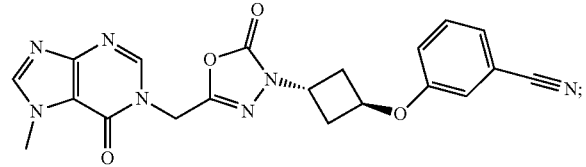
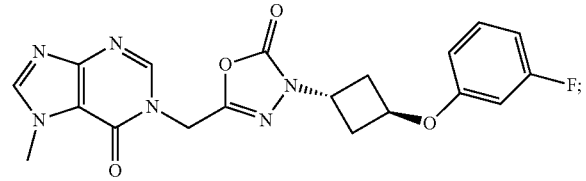
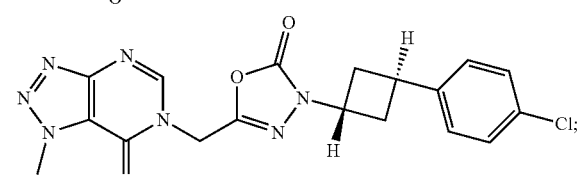
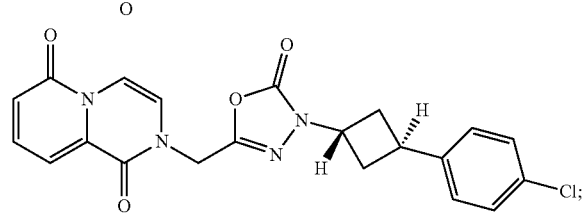
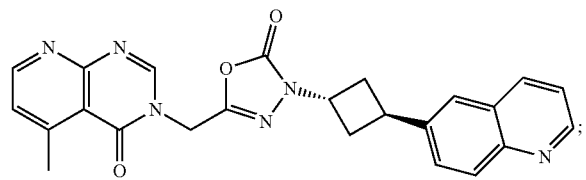
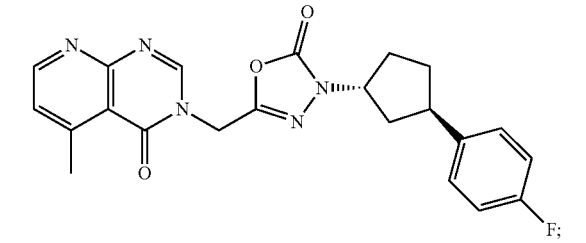
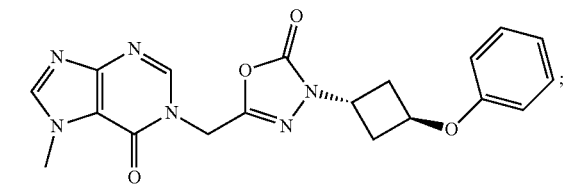
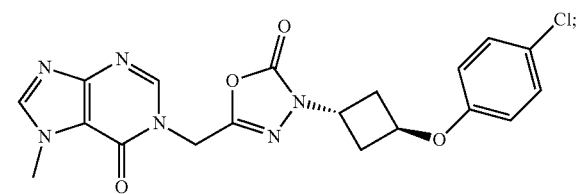
-continued
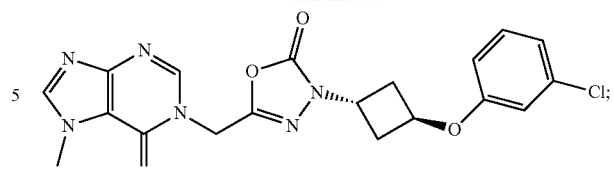
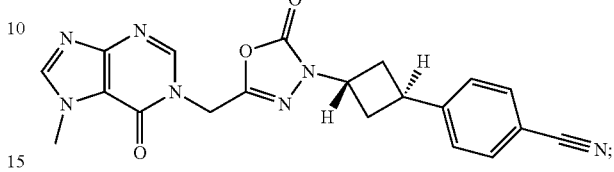
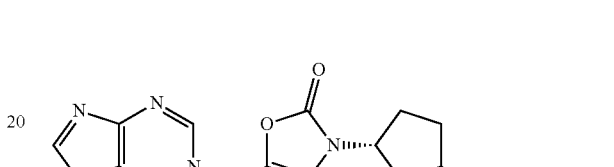
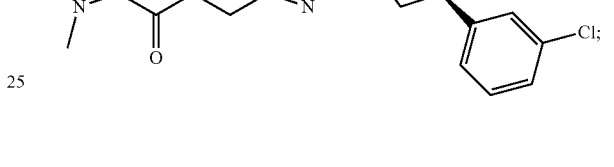
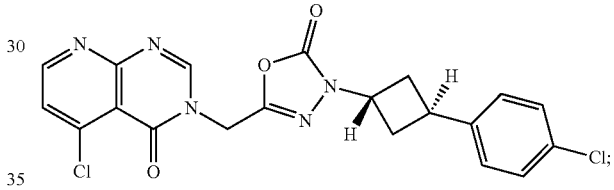
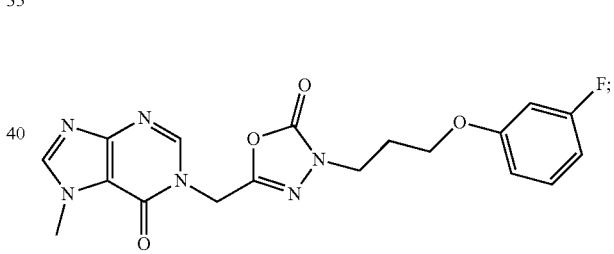
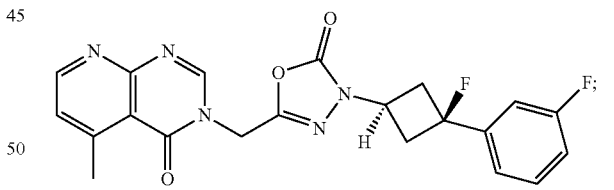
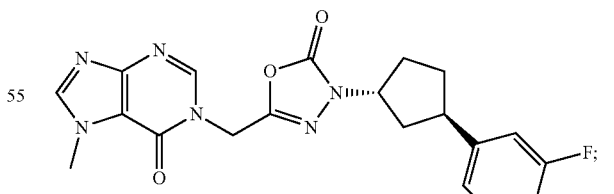
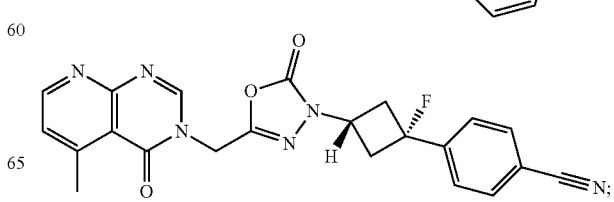

11
-continued
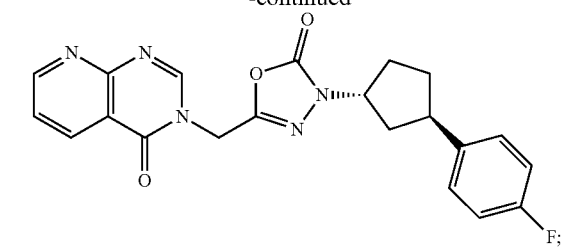
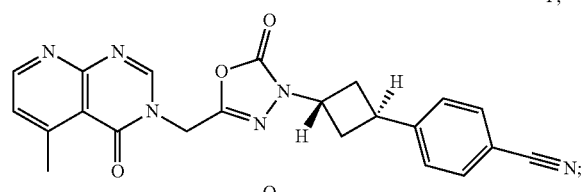
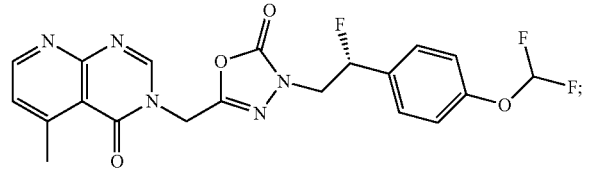
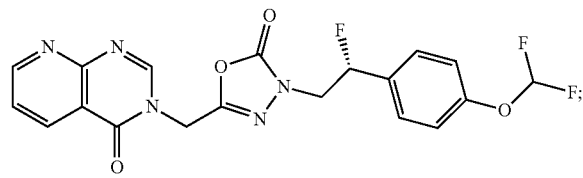
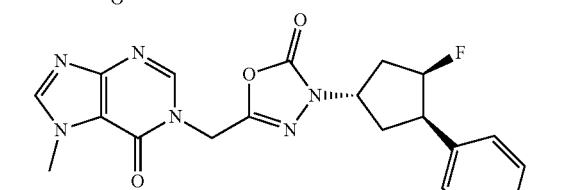
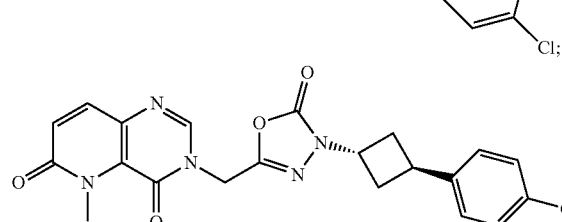
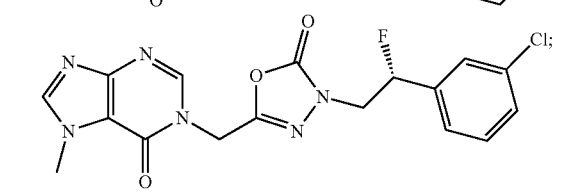
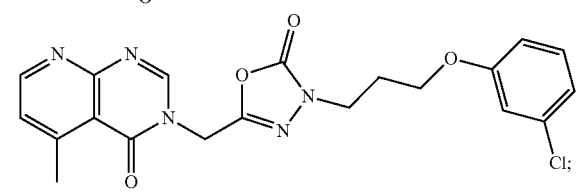
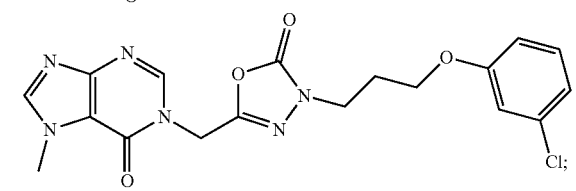
12
-continued
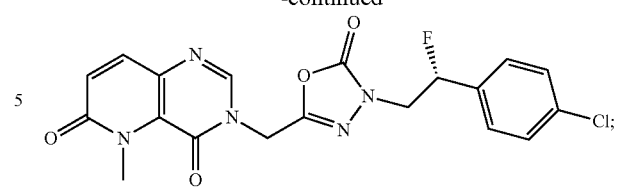
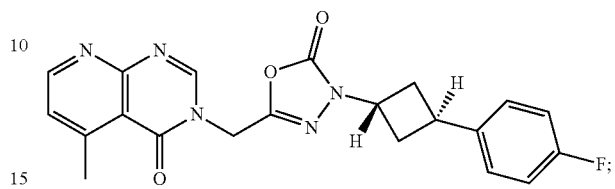
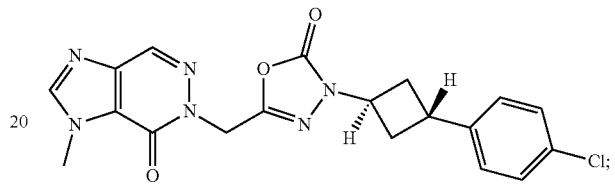
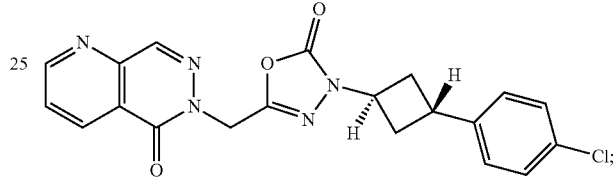
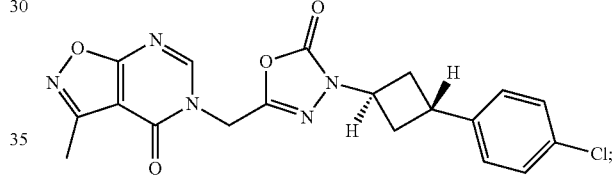
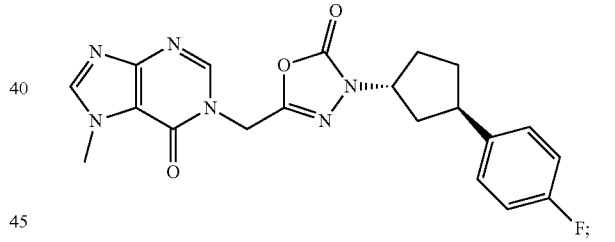
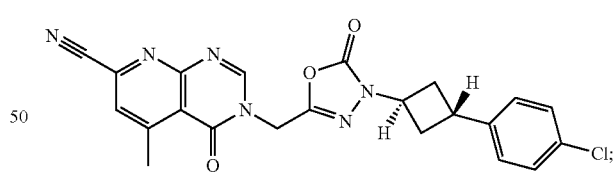
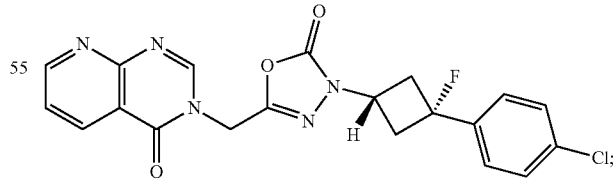
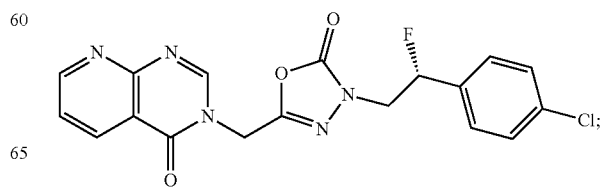

-continued
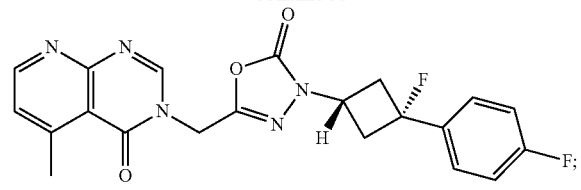
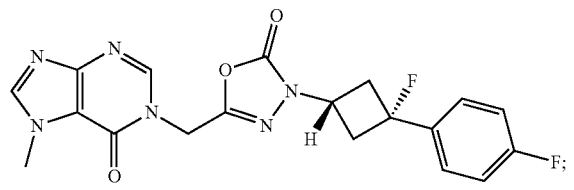
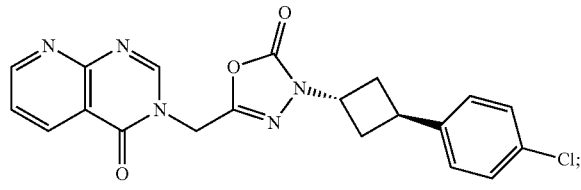
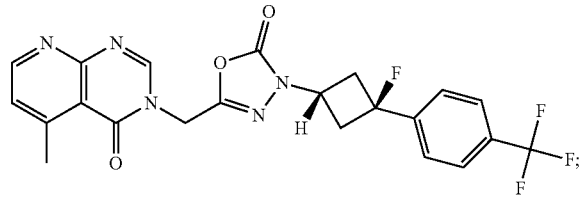
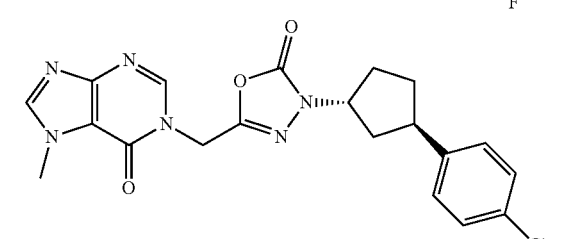
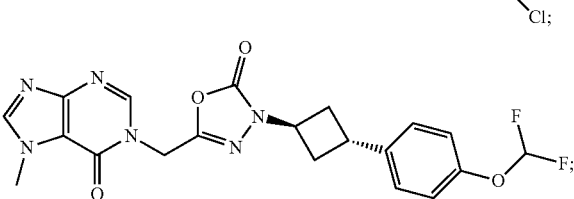
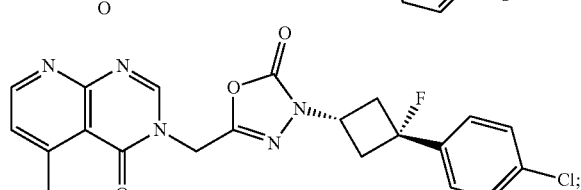
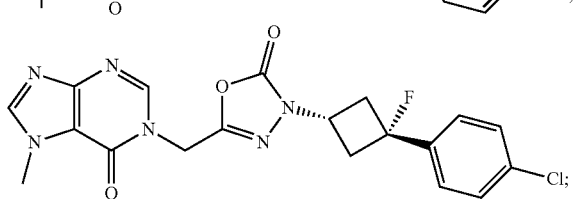
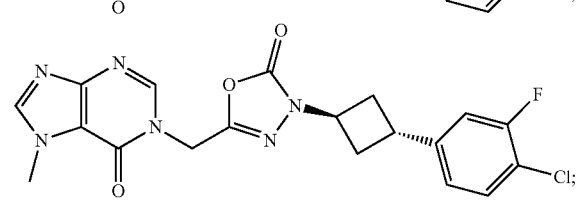
-continued
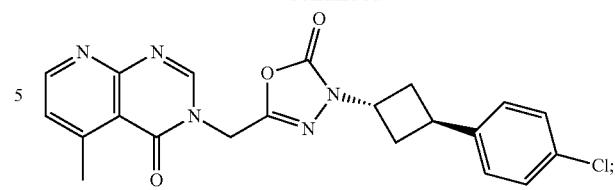
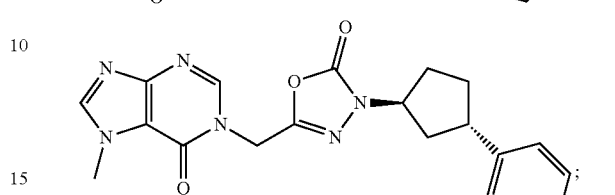
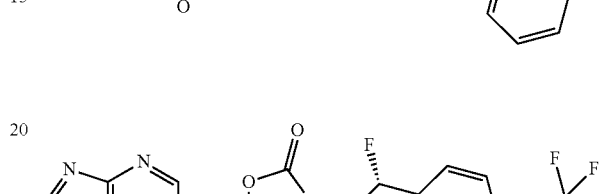
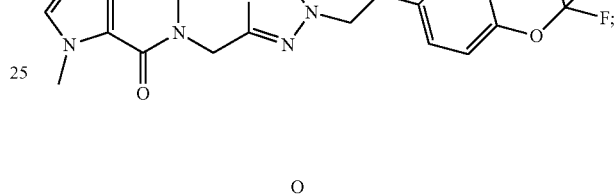
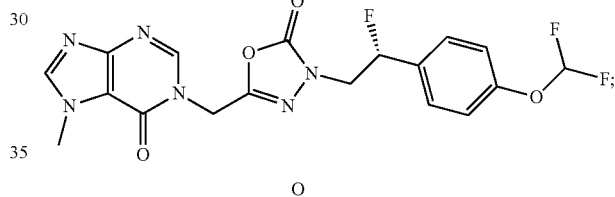
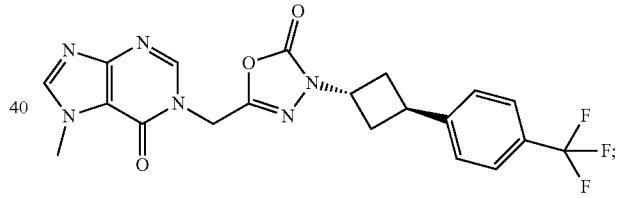
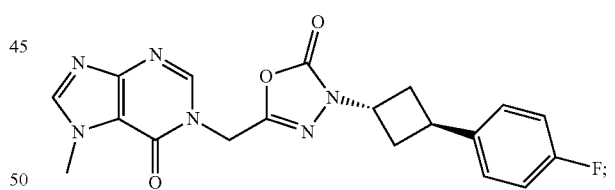
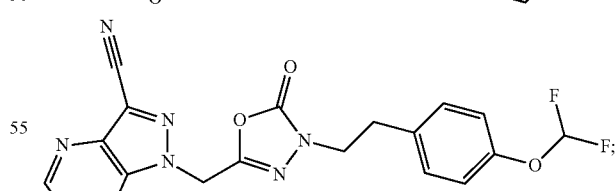
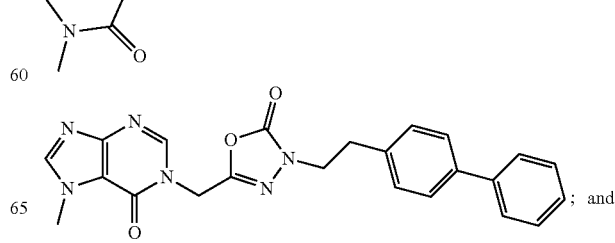
; and -continued

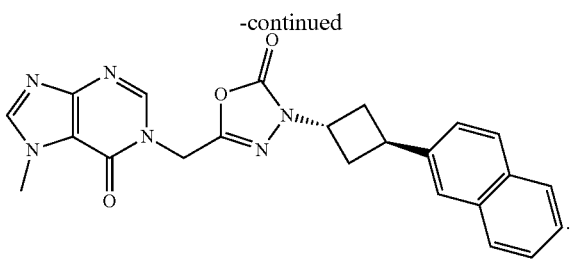

Some other embodiments provide pharmaceutical compositions comprising a compound described above, or a pharmaceutically acceptable salt thereof, and a pharmaceutically acceptable carrier, diluent or excipient.

Some other embodiments provide a compound as described above, or a pharmaceutically acceptable salt thereof, for use in medical therapy.

Some other embodiments provide a compound as described above, or a pharmaceutically acceptable salt thereof, for the treatment or prophylaxis of a respiratory disorder.

Some other embodiments provide a compound as described above, or a pharmaceutically acceptable salt thereof, for the preparation of a medicament for the treatment or prophylaxis of a respiratory disorder.

Some other embodiments provide a method for treating a respiratory disorder in a mammal comprising, administering a therapeutically effective amount of a compound as described above, or a pharmaceutically acceptable salt thereof, to the mammal.

Some other embodiments provide a compound as described above, or a pharmaceutically acceptable salt thereof, for modulating TRPA1 activity.

Some other embodiments provide a compound as described above, or a pharmaceutically acceptable salt thereof, for the treatment or prophylaxis of a disease or condition mediated by TRPA1 activity.

Some other embodiments provide a use of a compound as described above, or a pharmaceutically acceptable salt thereof, for the preparation of a medicament for the treatment or prophylaxis of a disease or condition that is mediated by TRPA1 activity.

Some other embodiments provide a method for modulating TRPA1 activity, comprising contacting TRPA1 with a compound as described above, or a pharmaceutically acceptable salt thereof.

Some other embodiments provide a method for treating a disease or condition mediated by TRPA1 activity in a mammal, comprising administering a therapeutically effective amount of a compound as described above, or a pharmaceutically acceptable salt thereof, to the mammal.

DETAILED DESCRIPTION OF THE INVENTION

Definitions

Unless otherwise indicated, the following specific terms and phrases used in the description and claims are defined as follows:

The terms "moiety" and "substituent" refer to an atom or group of chemically bonded atoms that is attached to another atom or molecule by one or more chemical bonds thereby forming part of a molecule.

The term "substituted" refers to the replacement of at least one of hydrogen atom of a compound or moiety with another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.). Examples of substituents include, but are not limited to, —$C_{1-4}$ alkyl (e.g., —$CH_3$), —$C_{1-4}$ alkoxy, oxo (=O), —OH, -halo$C_{1-4}$ alkyl, —O-halo$C_{1-4}$ alkyl, —CN, halogen (e.g., Cl and F), —C(O)$CH_3$, deuterium, -deuterio-$C_{1-4}$ alkyl (e.g., —$CD_3$), and —$C_{2-6}$ cycloalkyl (e.g., cyclopropyl).

The term "alkyl" refers to an aliphatic straight-chain or branched-chain saturated hydrocarbon moiety having 1 to 20 carbon atoms. In particular embodiments the alkyl has 1 to 10 carbon atoms. In particular embodiments the alkyl has 1 to 6 carbon atoms.

The term "alkylene" as used herein refers to a linear or branched saturated divalent hydrocarbon radical of one to twelve carbon atoms, and in another embodiment one to six carbon atoms, wherein the alkylene radical may be optionally substituted independently with one or more substituents described herein. Examples include, but are not limited to, methylene, ethylene, propylene, 2-methylpropylene, pentylene, and the like.

The term "alkenylene" refers to linear or branched-chain divalent hydrocarbon radical of two to eight carbon atoms ($C_{2-8}$) with at least one site of unsaturation, i.e., a carbon-carbon double bond, wherein the alkenylene radical may be optionally substituted. Examples include, but are not limited to, ethylenylene or vinylene (—CH=CH—), allyl (—$CH_2$CH=CH—), and the like.

The term "fused bicyclic" refers to a compound having two fused rings. Each ring of the fused bicyclic may be independently selected from mono-cycloalkylene, mono-heterocycloalkylene, mono-aryl and mono-heteroaryl. Examples of fused bicyclics include, but are not limited to 6-6 fused bicyclic aryl (where "6" refers to a six-membered ring), 6-6 fused bicyclic heteroaryl, 6-5 fused bicyclic aryl (where "5" refers to a six-membered ring), 6-5 fused bicyclic heteroaryl, 6-5 fused bicyclic aryl-heteroaryl, 6-5 fused bicyclic aryl-cycloalkylene, and 6-6 fused bicyclic aryl-heteroaryl. In some aspects, one or both of the rings in a fused bicyclic ring system is substituted with at least =O.

The term "alkoxy" refers to a group of the formula —O—R', wherein R' is an alkyl group. Examples of alkoxy moieties include methoxy, ethoxy, isopropoxy, and tert-butoxy.

The term "Aryl" refers to a cyclic aromatic hydrocarbon moiety having a mono-, bi- or tricyclic aromatic ring of 5 to 16 carbon ring atoms. Bicyclic aryl ring systems include fused bicyclics having two fused five-membered aryl rings (denoted as 5-5), having a five-membered aryl ring and a fused six-membered aryl ring (denoted as 5-6), and having two fused six-membered aryl rings (denoted as 6-6). The aryl group can be optionally substituted as defined herein. Examples of aryl moieties include, but are not limited to, phenyl, naphthyl, phenanthryl, fluorenyl, indenyl, pentalenyl, azulenyl, and the like. The term "aryl" also includes partially hydrogenated derivatives of the cyclic aromatic hydrocarbon moiety provided that at least one ring of the cyclic aromatic hydrocarbon moiety is aromatic, each being optionally substituted.

The term "heteroaryl" refers to an aromatic heterocyclic mono- or bicyclic ring system of 5 to 12 ring atoms, comprising 1, 2, 3 or 4 heteroatoms selected from N, O and S, the remaining ring atoms being carbon. Bicyclic heteroaryl ring systems include fused bicyclics having two fused five-membered heteroaryl rings (denoted as 5-5), having a five-membered heteroaryl ring and a fused six-membered heteroaryl ring (denoted as 5-6), and having two fused six-membered heteroaryl rings (denoted as 6-6). The aryl group can be optionally substituted as defined herein. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, purinyl, pyridopyrimidinyl, pyrrolopyrimidinyl, imidazotriazinyl, pyrazolopyrimidinyl, pyrimidopyridazinyl, pyrimidopyrimidinyl, thiazolopyrimidinyl, pyrazolopyridinyl, imidazopyridazinyl, pyridopyrazinyl, triazolopyrimidinyl, isoxazolopyrimidinyl, and quinoxalinyl.

The terms "halo", "halogen" and "halide", which may be used interchangeably, refer to a substituent including fluoro, chloro, bromo, or iodo.

The term "haloalkyl" refers an alkyl group wherein one or more of the hydrogen atoms of the alkyl group has been replaced by the same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

The term "deuterioalkyl" refers to an alkyl group as defined above substituted with one or more deuterium, e.g. deuteriomethyl, dideuteriomethyl, trideuteriomethyl, 2-deuterioethyl, 2,2-dideuterioethyl, 2,2,2-trideuterioethyl or 1,1,2,2,2-pentadeuterioethyl.

The terms "cycloalkyl" and "cycloalkylene" refer to a saturated or partially unsaturated carbocyclic moiety having mono- or bicyclic (including bridged bicyclic) rings and 3 to 10 carbon atoms in the ring. The cycloalkyl moiety can optionally be substituted with one or more substituents. In particular embodiments cycloalkyl contains from 3 to 8 carbon atoms (i.e., $(C_3-C_8)$cycloalkyl). In other particular embodiments cycloalkyl contains from 3 to 6 carbon atoms (i.e., $(C_3-C_6)$cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl). The cycloalkyl moiety can be attached in a "spirocycloakyl" fashion such as "spirocyclopropyl":

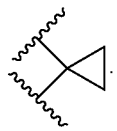 [SMILES: *C1(*)CC1]

The terms "heterocycle" and "heterocycloalkylene" refer to a 4, 5, 6 and 7-membered monocyclic or 7, 8, 9 and 10-membered bicyclic (including bridged bicyclic) heterocyclic moiety that is saturated or partially unsaturated, and has one or more (e.g., 1, 2, 3 or 4 heteroatoms selected from oxygen, nitrogen and sulfur in the ring with the remaining ring atoms being carbon. In particular embodiments heterocycloalkylene refers to a 4 to 7-membered heterocycloalkylene. When used in reference to a ring atom of a heterocycle, a nitrogen or sulfur may also be in an oxidized form, and a nitrogen may be substituted with one or more ($C_1$-$C_6$)alkyl or groups. The heterocycle can be attached to its pendant group at any heteroatom or carbon atom that results in a stable structure and any of the ring atoms can be optionally substituted. Examples of such saturated or partially unsaturated heterocycles include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term the term heterocycle also includes groups in which a heterocycle is fused to one or more aryl, heteroaryl, or cycloalkyl rings, such as indolinyl, 3H-indolyl, chromanyl, 2-azabicyclo[2.2.1]heptanyl, octahydroindolyl, or tetrahydroquinolinyl.

Unless otherwise indicated, the term "hydrogen" and "hydro" refer to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. As used herein, "pharmaceutically acceptable" refers to a carrier, diluent or excipient that is compatible with the other ingredients of the formulation and not deleterious to the recipient thereof. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. Another embodiment provides non-pharmaceutically acceptable salts of a compound of formula (I), which can be useful as an intermediate for isolating or purifying a compound of formula (I). The compounds of the present invention can also be present in the form of pharmaceutically acceptable esters (i.e., the methyl and ethyl esters of the acids of formula (I) to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula (I).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". In certain embodiments the compound is enriched by at least about 90% by weight with a single diastereomer or enantiomer. In other embodiments the compound is enriched by at least about 95%, 98%, or 99% by weight with a single diastereomer or enantiomer.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned. Many organic compounds exist in optically active forms, i.e., they have the ability to rotate the plane of plane polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in compounds (1), (m) and (n) for illustrative purposes, while stereochemistry is definitively established, such as from x-ray crystallographic data.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, a therapeutically effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Compounds

One embodiment of the present invention provides for compounds of formula (I):

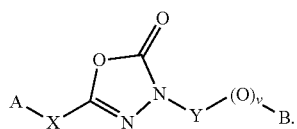

v is 0 or 1.

A is selected from substituted and unsubstituted 6-6 fused bicyclic heteroaryl and 6-5 fused bicyclic heteroaryl.

In some aspects, A is a fused heteroaryl moiety selected from:

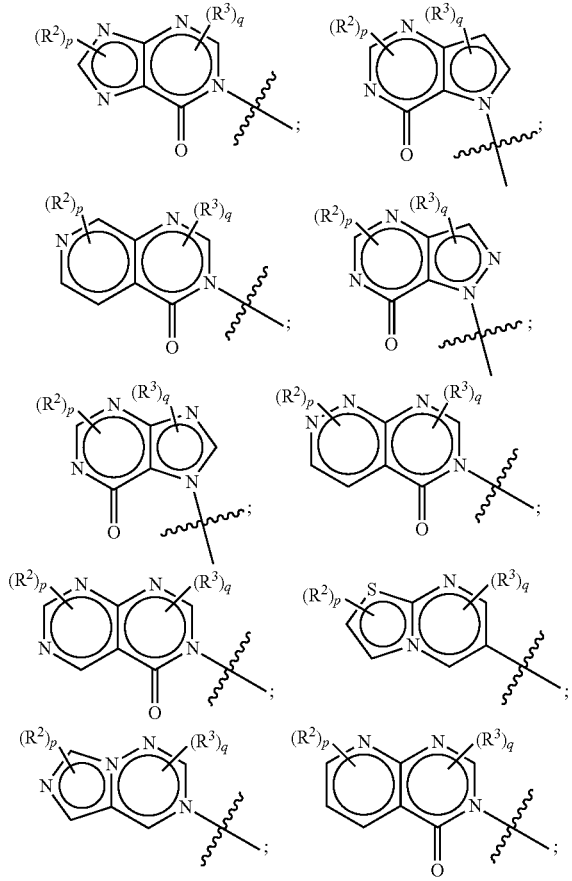

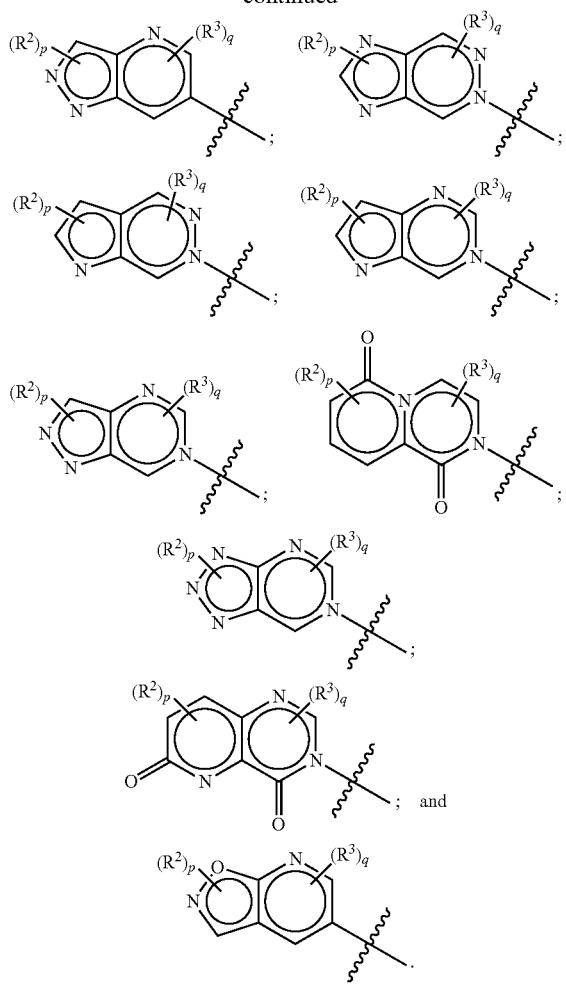

Each $R^2$ is independently selected from —$C_{1-4}$ alkyl, -halo$C_{1-4}$ alkyl, —CN, halo, —C(O)CH$_3$, deuterium, and -deuterio-$C_{1-4}$ alkyl. p is 0, 1 or 2. In some aspects, each $R^2$ is independently selected from —CH$_3$, —CD$_3$, —C(O)CH$_3$, —CN, —Cl, and F. $R^3$ is selected from —$C_{1-4}$ alkyl, -halo$C_{1-4}$ alkyl, —CN, halo, deuterium, and -deuterio-$C_{1-4}$ alkyl. q is 0 or 1. In some aspects, $R^3$ is selected from deuterium and —CN.

In some aspects, A is selected from:

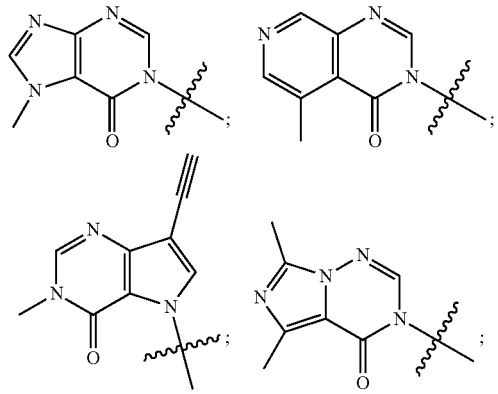

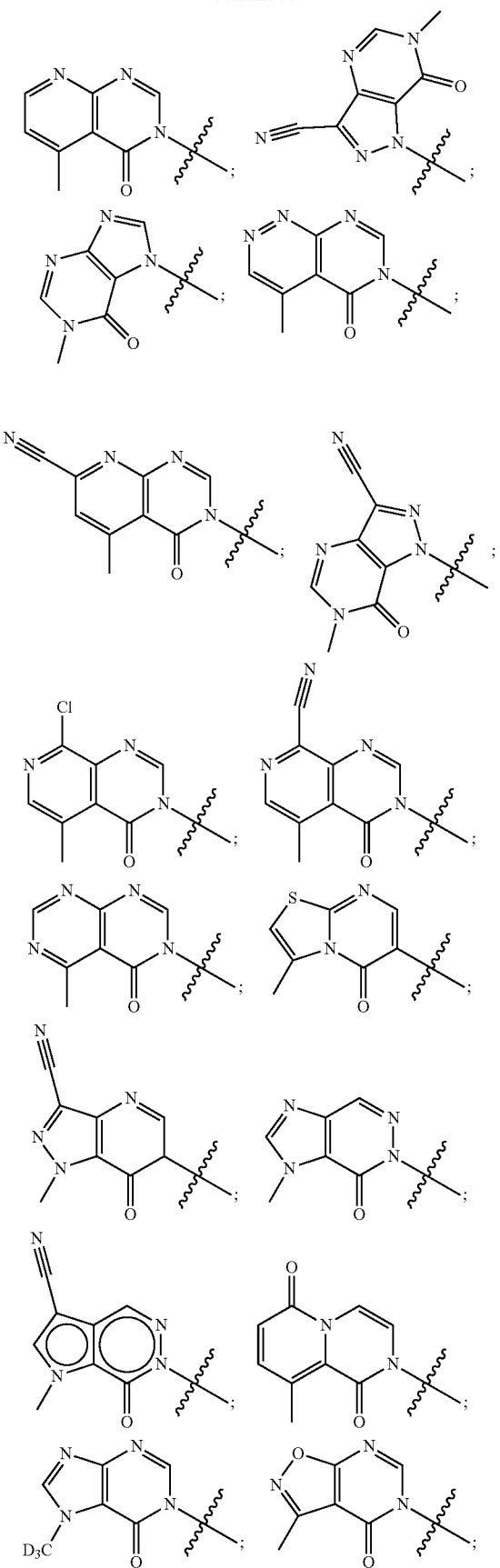

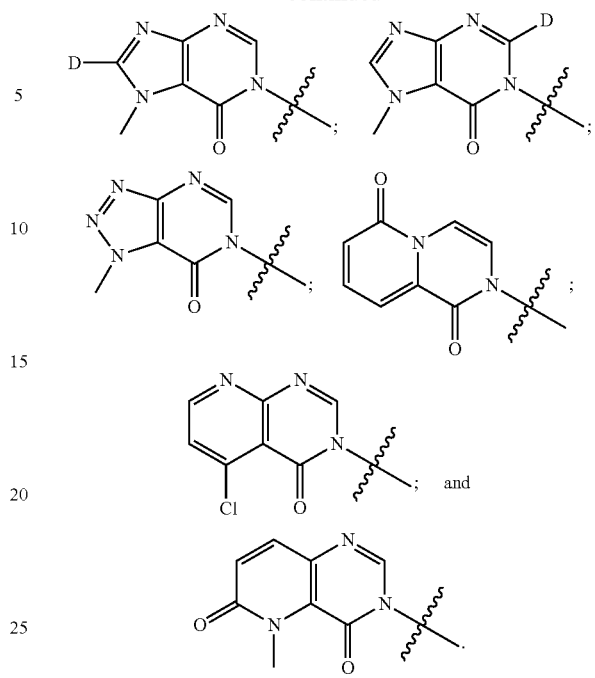

X is selected from a bond, $C_{1-4}$ alkylene, —O—, —S—, —SO$_2$—, and —N(R$^1$)—, wherein R$^1$ is selected from H and $C_{1-6}$ alkyl. In some aspects, X is —CH$_2$—.

Y is selected from substituted and unsubstituted $C_{1-4}$ alkylene, $C_{2-4}$ alkenylene, and $C_{3-6}$ cycloalkylene wherein one or more carbons of $C_{1-4}$ alkylene or $C_{2-4}$ alkenylene may be replaced with —O— or —C(O)—. In some aspects, Y is selected from substituted and unsubstituted $C_{2-3}$ alkylene, $C_2$ alkenylene, and $C_{4-8}$ cycloalkylene. In some aspects, Y is substituted with one or more substituents independently selected from —$C_{1-4}$ alkyl, -halo$C_{1-4}$ alkyl, —CN, —OH, halogen, -cyclopropyl, deuterium, and -deuterio-$C_{1-4}$ alkyl. In some aspects, Y is substituted with at least one of halo, —$C_{1-4}$ alkyl, —OH, and —$C_{3-4}$ cycloalkyl. In some other aspects, Y is substituted with F, —CH$_3$, —OH or -cyclopropyl.

In some aspects, Y is selected from:

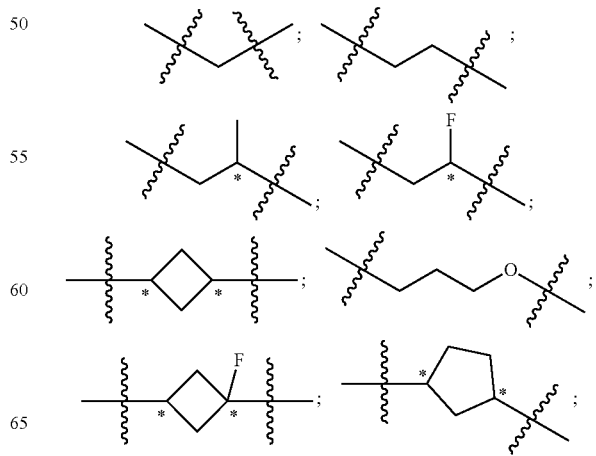

-continued

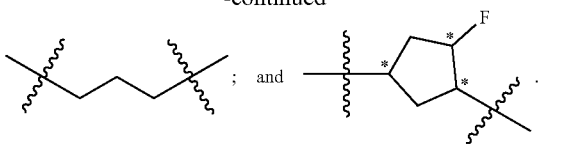
; and wherein * denotes a chiral center (i) in an R configuration or in an S configuration or (ii) a mixture of R and S configurations for a plurality of compounds of formula (I).

B is selected from substituted and unsubstituted 5-membered aryl, 6-membered aryl, 5-membered heteroaryl, 6-membered heteroaryl, 6-6 fused bicyclic aryl, 6-6 fused bicyclic heteroaryl, 6-5 fused bicyclic aryl, 6-5 fused bicyclic heteroaryl, 6-5 fused bicyclic aryl-heteroaryl, 6-5 fused bicyclic aryl-cycloalkylene, and 6-6 fused bicyclic aryl-heteroaryl.

In some other aspects, B is selected from:

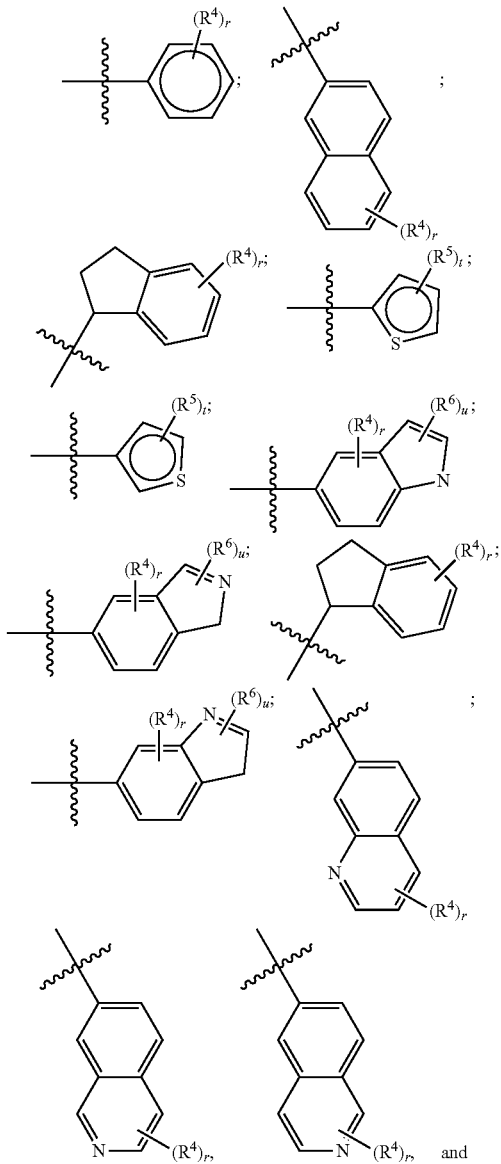

-continued

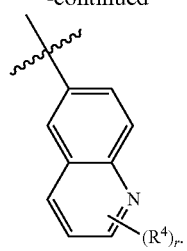

In such aspects, r is selected from 0, 1 and 2 and $R^4$ is independently selected from $C_{1-4}$ alkyl, halo$C_{1-4}$ alkyl, —O-halo$C_{1-4}$ alkyl, —$C_{1-4}$ alkoxy, halogen, —CN, —N(CH$_3$)$_2$, and -phenyl,

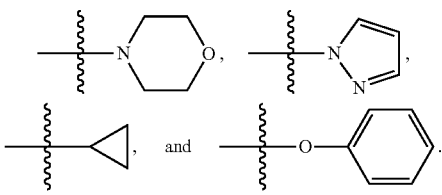

In some aspects, —O-halo$C_{1-4}$ alkyl is selected from —OCHF$_2$ and —OCF$_3$. In some aspects, halo$C_{1-4}$ alkyl is selected from —CHF$_2$ and —CF$_3$. In some aspects, $C_{1-4}$-alkoxy is —OCH$_3$. t is selected from 0 and 1, and $R^5$ is halogen. u is selected from 0 and 1. $R^6$ is selected from $C_{1-4}$ alkyl and

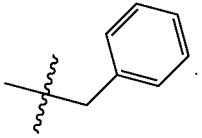 [SMILES: *Cc1ccccc1]

In some aspects, B is selected from:

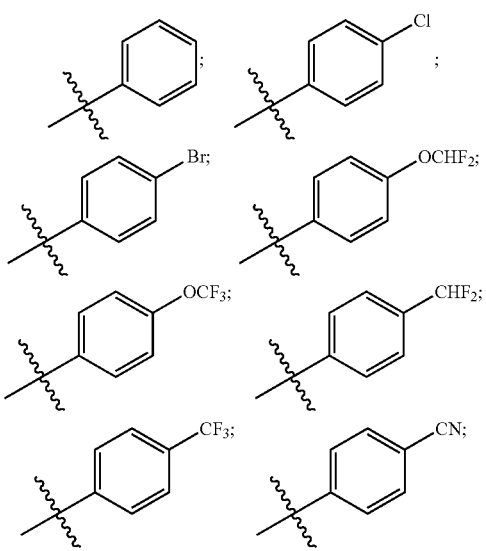

-continued
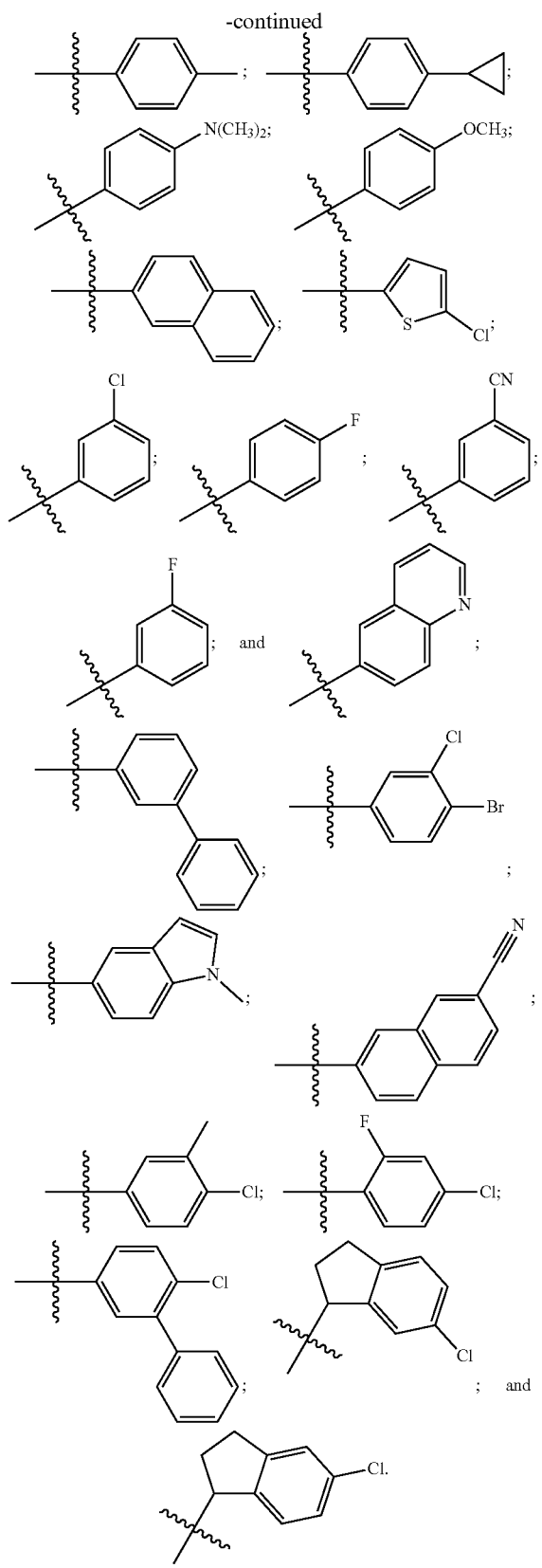
In some aspects, the compound of formula (I), or a pharmaceutically acceptable salt thereof, is selected from the following:
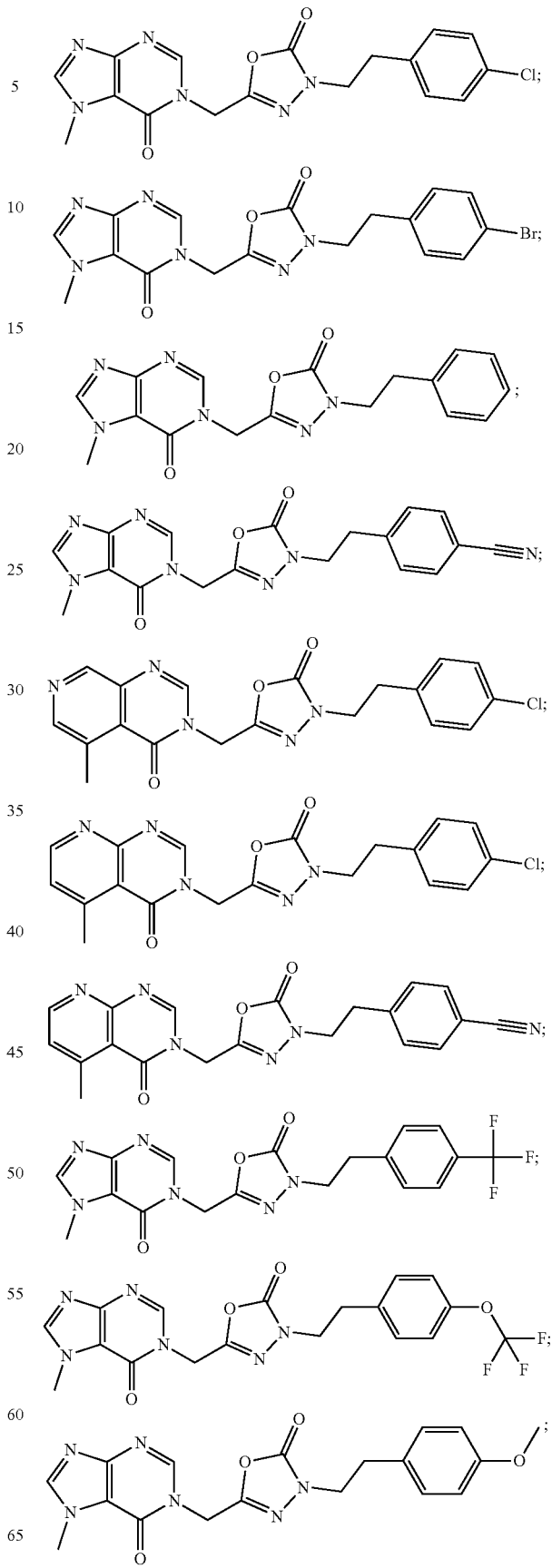

29
-continued
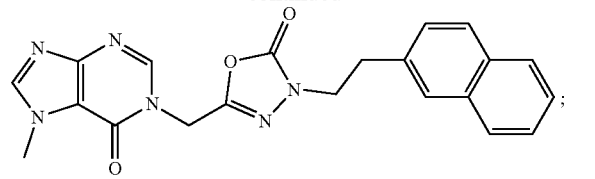
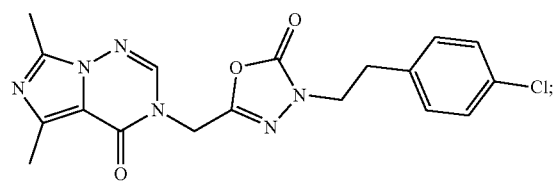
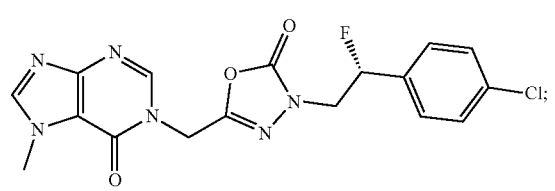
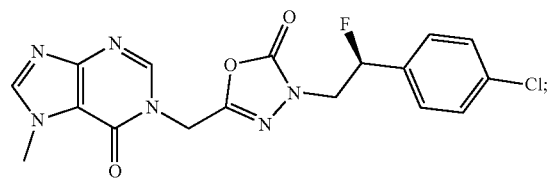
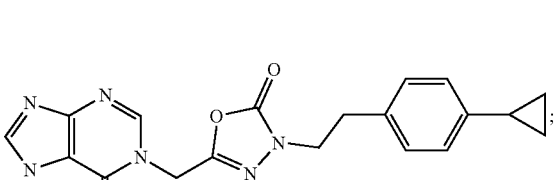
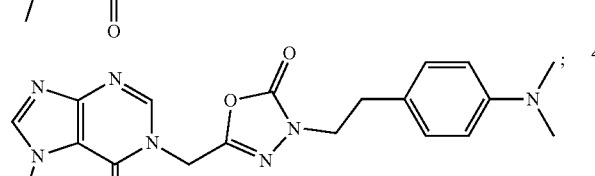
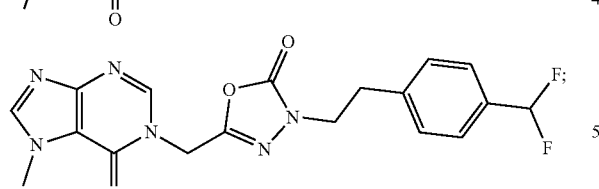
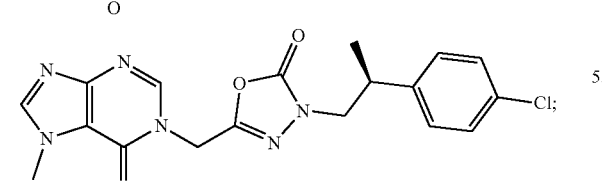
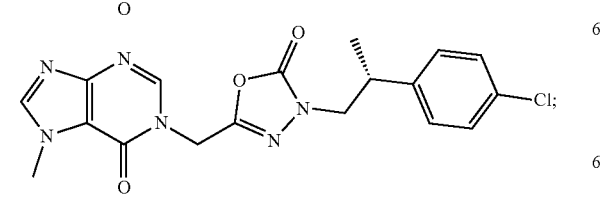
30
-continued
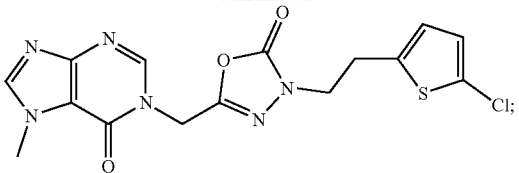
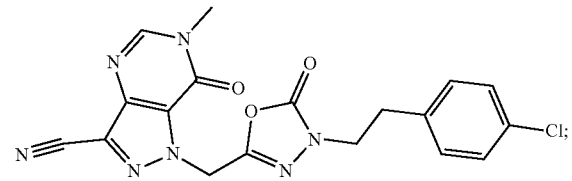
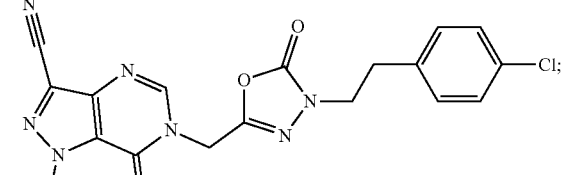
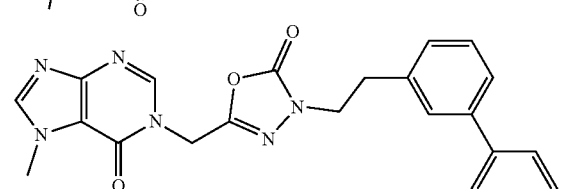
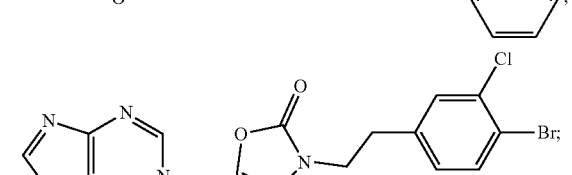
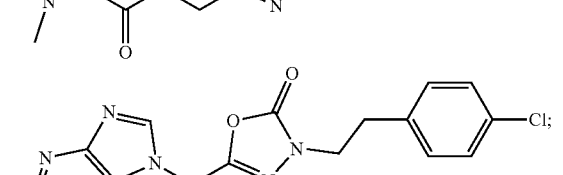
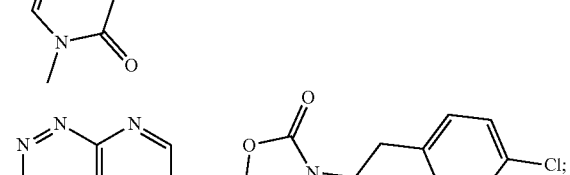
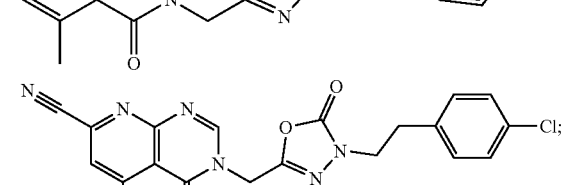
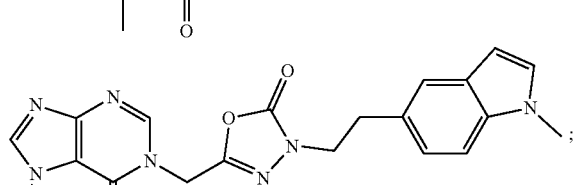

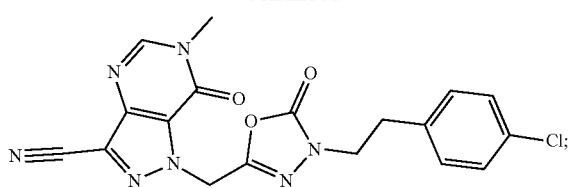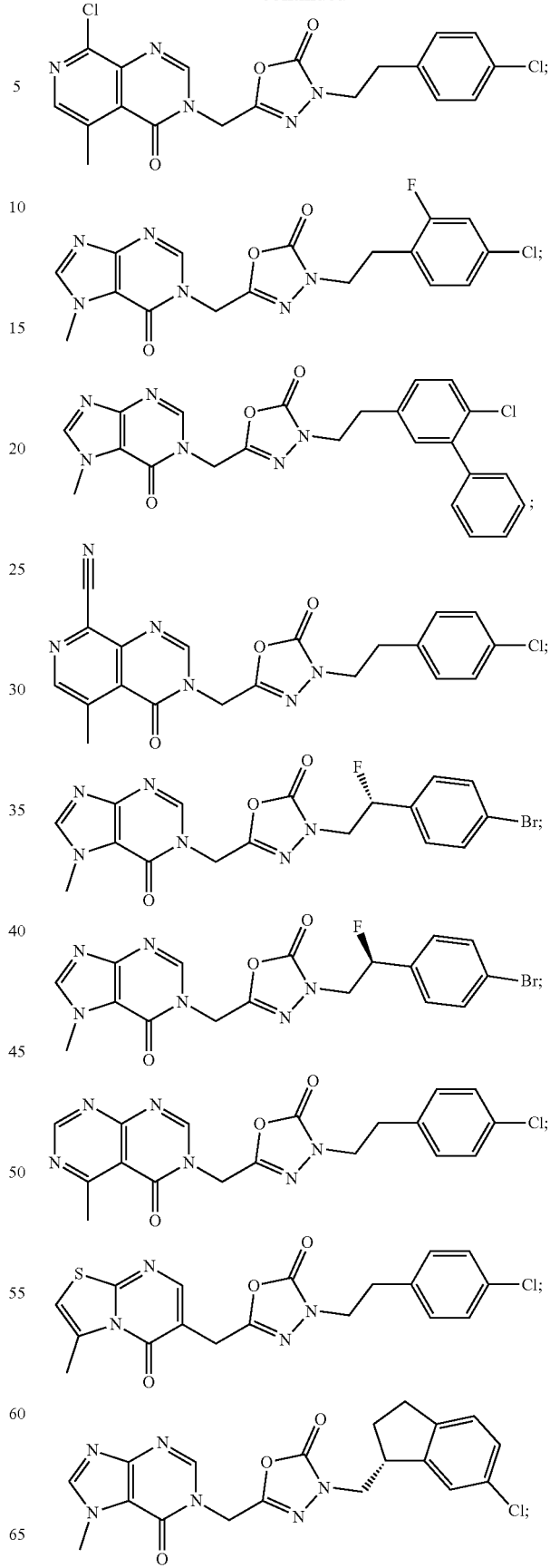

33
-continued
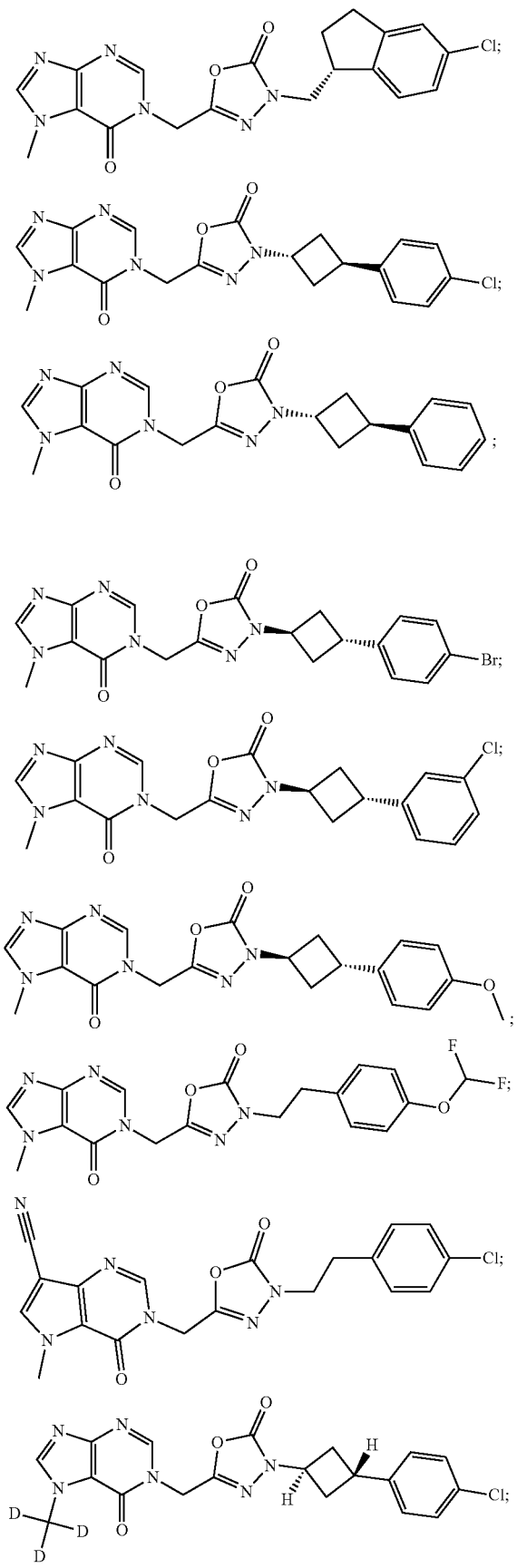
34
-continued
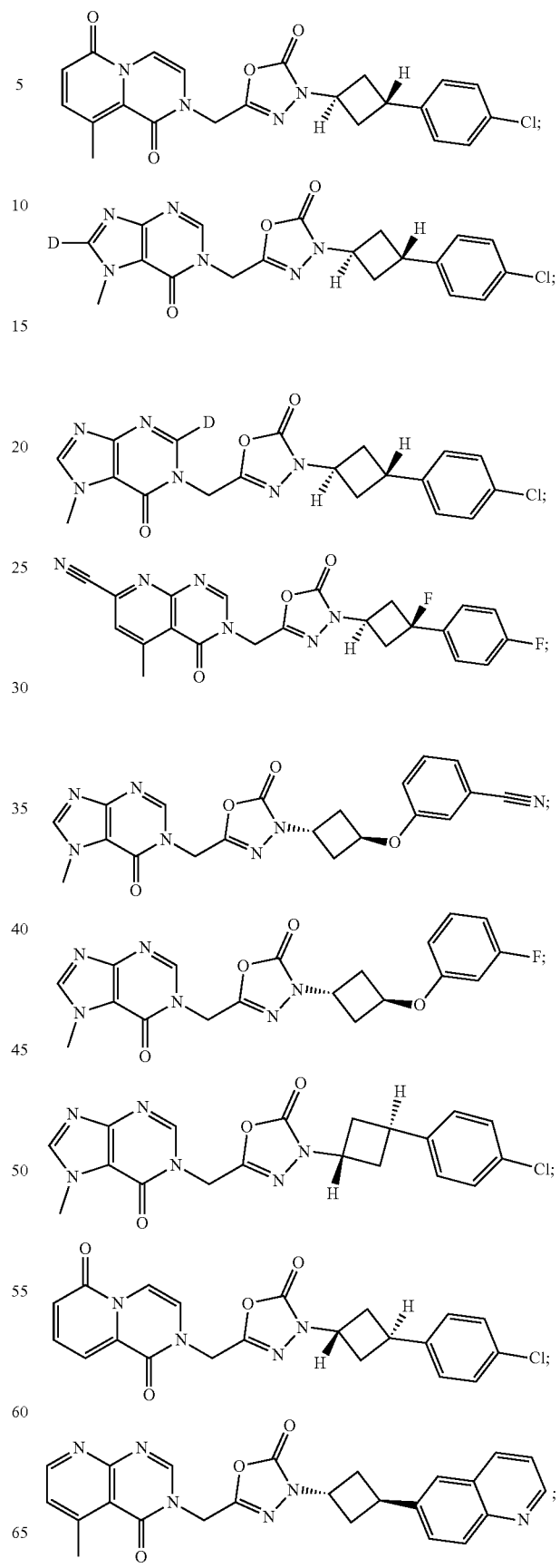

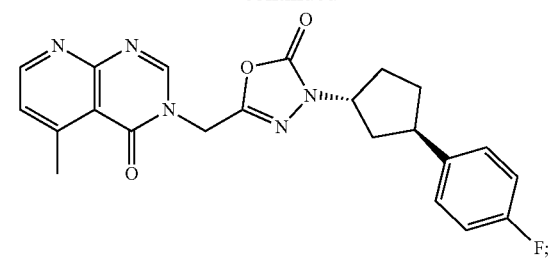
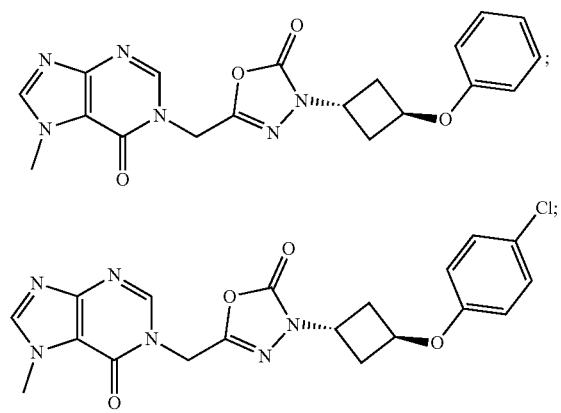
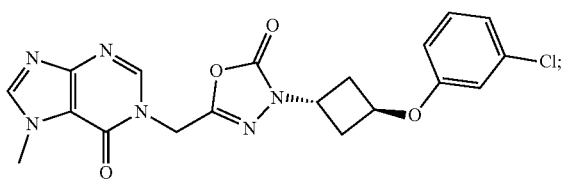
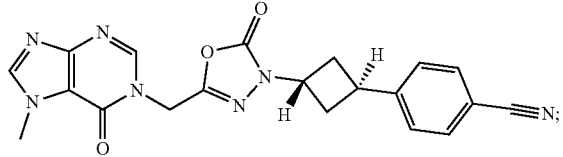
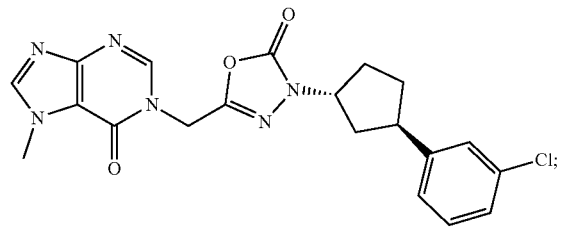
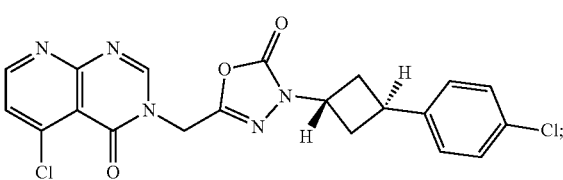
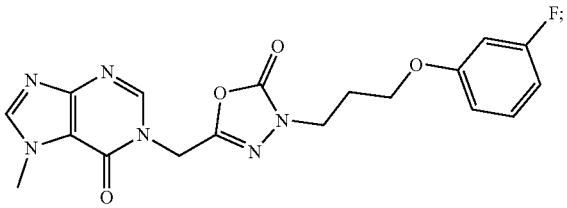
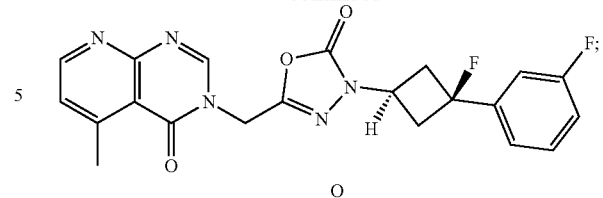
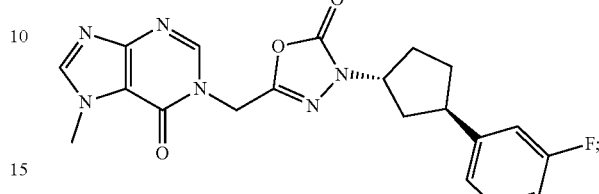
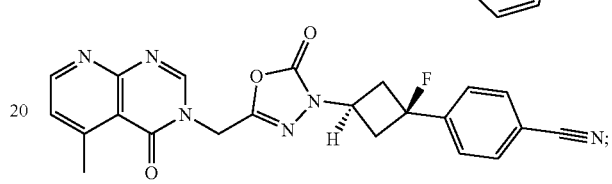
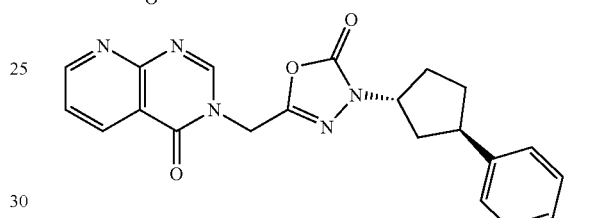
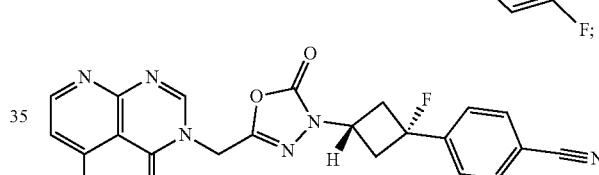
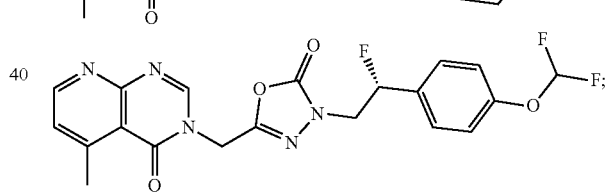
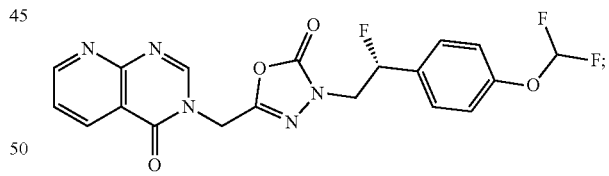
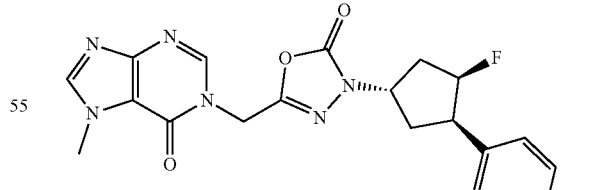
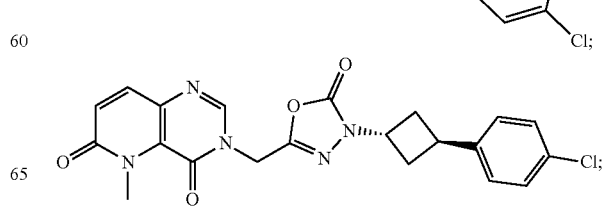

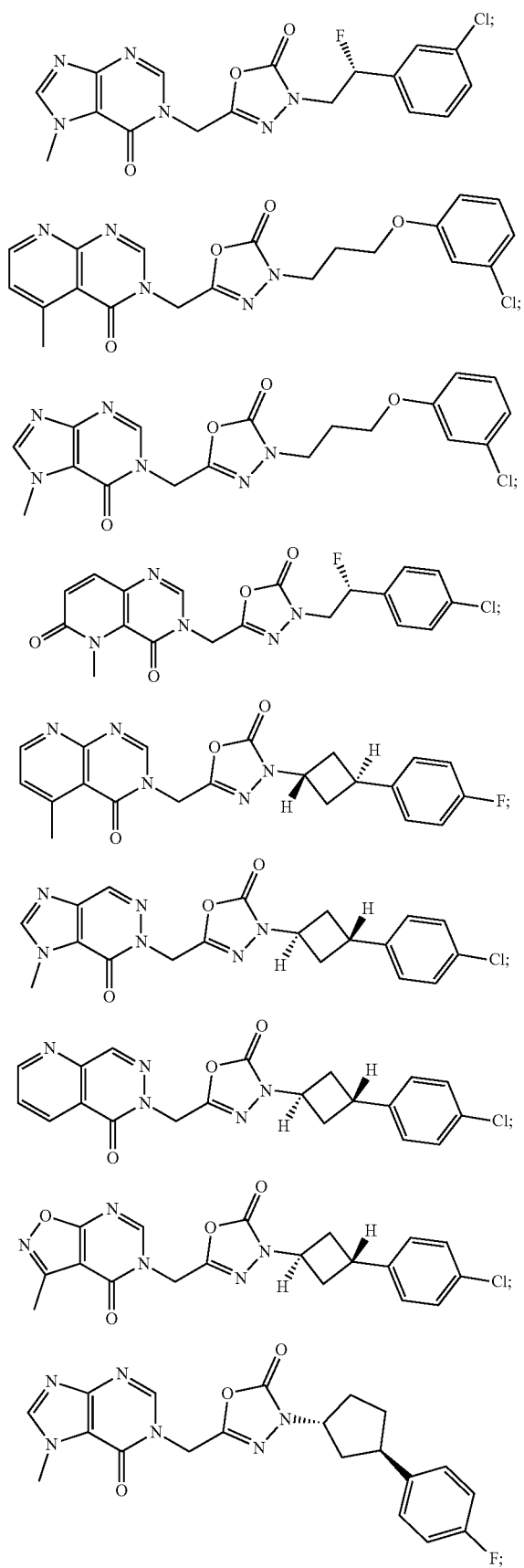
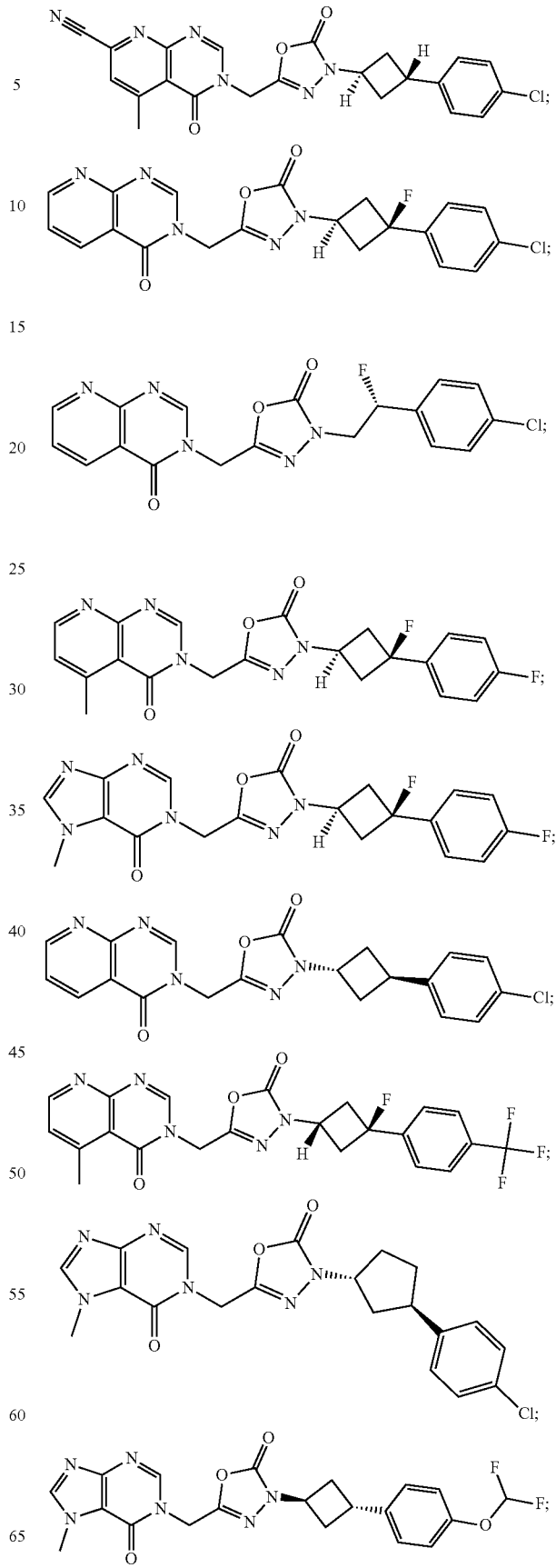

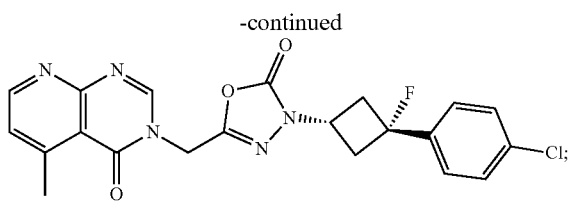

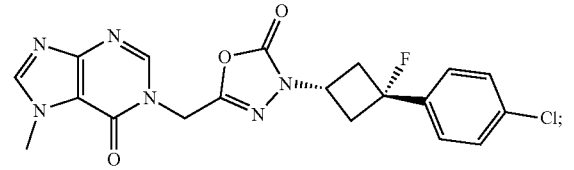

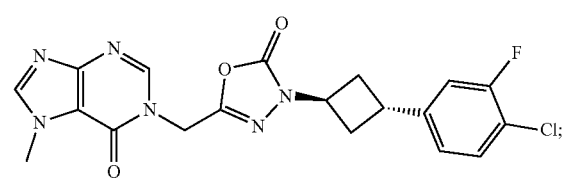

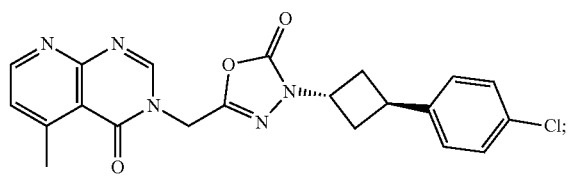

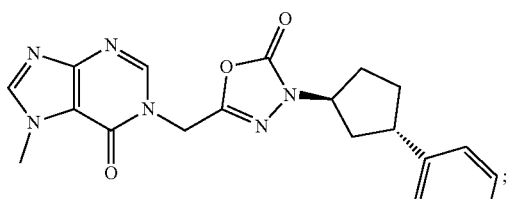

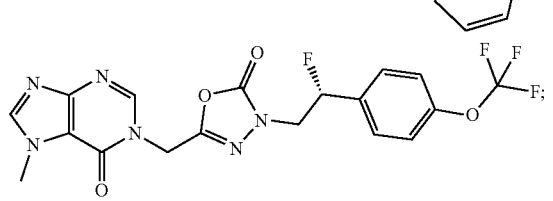

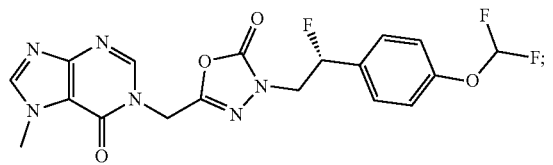

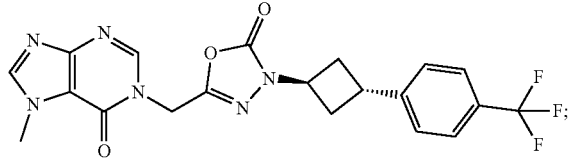

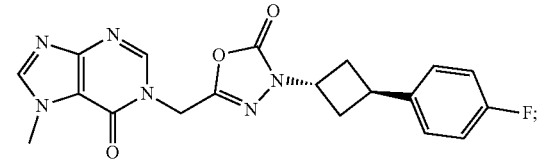

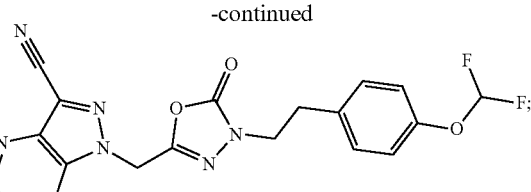

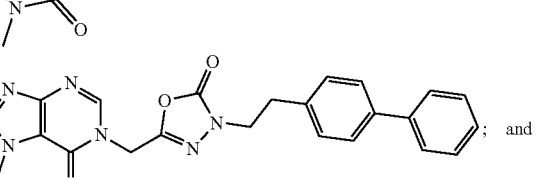

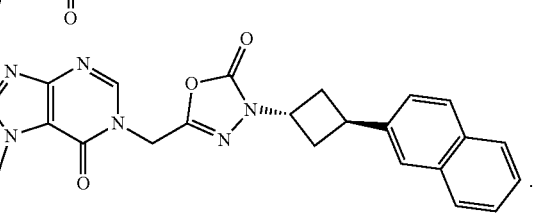

In another embodiment of the invention, the compounds of formula (I) are isotopically-labeled by having one or more atoms therein replaced by an atom having a different atomic mass or mass number. Such isotopically-labeled (i.e., radio-labeled) compounds of formula (I) are considered to be within the scope of this invention. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action on the ion channels, or binding affinity to pharmacologically important site of action on the ion channels, particularly TRPA1. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

In another embodiment, the invention provides for a pharmaceutical composition, comprising a therapeutically effective amount of a compound according to formula (I) and a pharmaceutically acceptable carrier, diluent and/or excipient.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention may include phosphates, phosphate esters, alkyl phosphates, alkyl phosphate esters, acyl ethers, or other prodrug moieties as discussed below. In some embodiments, the prodrug moiety is:

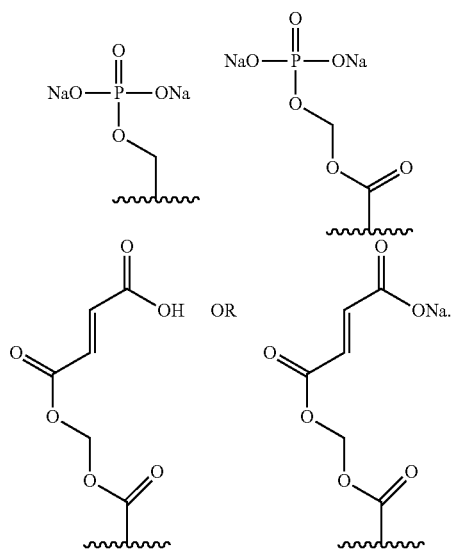

Additional types of prodrugs are also encompassed. For example, where an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methylalanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxyl groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$alkanoyloxy)ethyl, $(C_{1-6})$ alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabeled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Pharmaceutical Compositions and Administration

In addition to one or more of the compounds provided above (including stereoisomers, geometric isomers, tautomers, solvates, metabolites, isotopes, pharmaceutically acceptable salts, or prodrugs thereof), the invention also provides for compositions and medicaments comprising a compound of formula (I) or and embodiment thereof and at least one pharmaceutically acceptable carrier. The compositions of the invention can be used to selectively inhibit TRPA1 in patients (e.g., humans).

The term "composition" as used herein, is intended to encompass a product comprising the specified ingredients in the specified amounts, as well as any product which results, directly or indirectly, from combination of the specified ingredients in the specified amounts.

In one embodiment, the invention provides for pharmaceutical compositions or medicaments comprising a compound of formula (I) or an embodiment thereof, and its stereoisomers, geometric isomers, tautomers, solvates, metabolites, isotopes, pharmaceutically acceptable salts, or prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of formula (I) or its embodiments and compositions comprising compounds of formula (I) or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TRPA1 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of formula (I) or an embodiment thereof are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., a compound of formula (I) or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21st Edition, Lippincott Williams & Wilkins, Philadelphia, Pa. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed.

Sustained-release preparations of a compound of the invention (e.g., compound of formula (I) or an embodiment thereof) can be prepared. Suitable examples of sustained-release preparations include semipermeable matrices of solid hydrophobic polymers containing a compound of formula (I) or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula (I) or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) (or an embodiment thereof) is formulated in an acetate buffer, at pH 5. In another embodiment, the compounds of formula (I) or an embodiment thereof are sterile. The compound may be stored, for example, as a solid or amorphous composition, as a lyophilized formulation or as an aqueous solution.

Formulations of a compound of the invention (e.g., compound of formula (I) or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of formula (I) or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 1 mg, 5 mg, 10 mg, 25 mg, 30 mg, 50 mg, 80 mg, 100 mg, 150 mg, 250 mg, 300 mg and 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

For topical formulations, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula (I) (or an embodiment thereof) to traverse the blood-brain barrier. Certain neurodegenerative diseases are associated with an increase in permeability of the blood-brain barrier, such that a compound of formula (I) (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula (I) (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula (I) (or an embodiment thereof) across the blood-brain barrier include, but are not limited to, encapsulating the a compound of formula (I) (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula (I) (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula (I) (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula (I) (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

Representative compounds of the invention have been shown to modulate TRPA1activity. Accordingly, the compounds of the invention are useful for treating diseases and conditions mediated by TRPA1 activity. Such diseases and conditions include but are not limited to: pain (acute, chronic, inflammatory, or neuropathic pain); itch or various inflammatory disorders; inner ear disorders; fever or other disorders of thermoregulation; tracheobronchial or diaphragmatic dysfunction; gastrointestinal or urinary tract disorders; chronic obstructive pulmonary disease; incontinence; and disorders associated with reduced blood flow to the CNS or CNS hypoxia.

In a specific embodiment, compounds of the invention can be administered to treat pain, including but not limited to neuropathic and inflammatory pain, among others. Certain types of pain may be considered a disease or disorder, while other types may be considered symptoms of various diseases or disorders, and pain may include various etiologies. Exemplary types of pain treatable with a TRPA1-modulating agent according to the invention include pain associated with, arising from, or caused by: osteoarthritis, rotator cuff disorders, arthritis (e.g., rheumatoid arthritis or inflammatory arthritis; see, Barton et al. Exp. Mol. Pathol. 2006, 81(2), 166-170), fibromyalgia, migraine and headache (e.g. cluster headache, sinus headache, or tension headache; see, Goadsby Curr. Pain Headache Reports 2004, 8, 393), sinusitis, oral mucositis, toothache, dental trauma, dental extractions, dental infections, burn (Bolcskei et al., Pain 2005, 117(3), 368-376), sunburn, dermatitis, psoriasis, eczema, insect sting or bite, musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, Gl tract disorders, cystitis, interstitial cystitis, cholecystitis, urinary tract infection, urethral colic, renal colic, pharyngitis, cold sores, stomatitis, external otitis, otitis media (Chan et al., Lancet, 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., J Pharmacal Exp Ther., 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barre syndrome, Raynaud's syndrome, coronary artery spasm (Printzmetal's or variant angina), visceral hyperalgesia (Pomonis, J. D. et al. J. Pharmacal. Exp. Ther. 2003, 306, 387; Walker, K. M. et al., J. Pharmacal. Exp. Ther. 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., Neurosci. Lett. 2005, 393 (1), 70-73; Asai, H. et al., Pain 2005, 117, 19-29), or bone destruction pain (see, Ghilardi, J. R. et al., J. Neurosci. 2005, 25, 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another specific embodiment, compounds of the invention can be administered to treat itch, which may arise from various sources, such as dermatological or inflammatory disorders.

In another specific embodiment, compounds of the invention can be administered to treat inflammatory disorders, including disorders selected from the group consisting of: renal or hepatobiliary disorders, immunological disorders, medication reactions and unknown/idiopathic conditions. Inflammatory disorders treatable with an inventive agent include, for example, inflammatory bowel disease (IBO), Crohn's disease, and ulcerative colitis (Geppetti, P. et al., Br. J. Pharmacal. 2004, 141, 1313-20; Yiangou, Y. et al., Lancet 2001, 357, 1338-39; Kimball, E. S. et al., Neurogastroenterol. Motif., 2004, 16, 811), osteoarthritis (Szabo, A. et al., J. Pharmacal. Exp. Ther. 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another specific embodiment, compounds of the invention can be administered to treat inner ear disorders. Such disorders include, for example, hyperacusis, tinnitus, vestibular hypersensitivity, and episodic vertigo.

For example, compounds of the invention can be administered to treat tracheobronchial and diaphragmatic dysfunctions including, for example, asthma and allergy-related immune responses (Agopyan, N. et al., Am. J. Physiol. Lung Cell Mol. Physiol. 2004, 286, L563-72; Agopyan, N. et al., Toxicol. Appl. Pharmacal. 2003, 192, 21-35), cough (e.g., acute or chronic cough, or cough caused by irritation from gastroesophageal reflux disease; see, Lalloo, U. G. et al., J. Appl. Physiol. 1995, 79(4), 1082-7), bronchospasm, chronic obstructive pulmonary disease, chronic bronchitis, emphysema, and hiccups (hiccoughs, singultus).

In another specific embodiment, compounds of the invention can be administered to treat gastrointestinal and urinary tract disorders such as, bladder overactivity, inflammatory hyperalgesia, visceral hyperreflexia of the urinary bladder, hemorrhagic cystitis (Dinis, P. et al., J Neurosci., 2004, 24, 11253-11263), interstitial cystitis (Sculptoreanu, A. et al., Neurosci Lett., 2005, 381, 42-46), inflammatory prostate disease, prostatitis (Sanchez, M. et al., Eur J Pharmacal., 2005, 515, 20-27), nausea, vomiting, intestinal cramping, intestinal bloating, bladder spasms, urinary urgency, defecation urgency and urge incontinence.

In another specific embodiment, compounds of the invention can be administered to treat disorders associated with reduced blood flow to the CNS or CNS hypoxia. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, compounds of the invention can be administered to treat other diseases, disorders, or conditions mediated through TRPA1 activity, such as anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In one specific embodiment, compounds of the invention are administered to treat pain (including but not limited to acute, chronic, neuropathic and inflammatory pain), arthritis, itch, cough, asthma, or inflammatory bowel disease.

In another embodiment, the invention provides for a method for treating neuropathic pain or inflammatory pain, comprising the step of administering a therapeutically effective amount of a compound as described herein to a subject in need thereof.

In another embodiment, the invention provides for a compound as described herein or a pharmaceutically acceptable salt thereof for modulating TRPA1 activity.

In another embodiment, the invention provides for a compound as described herein or a pharmaceutically acceptable salt thereof for use in medical therapy.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound as described herein to a subject in need thereof.

In another embodiment, the invention provides for a compound as described herein or a pharmaceutically acceptable salt thereof for the treatment or prophylaxis of a respiratory disorder.

In another embodiment, the invention provides for the use of a compound as described herein or a pharmaceutically acceptable salt thereof for the preparation of a medicament for the treatment or prophylaxis of a respiratory disorder.

In another embodiment, the invention provides for a method for treating a respiratory disorder in a mammal (e.g., a human) comprising administering a compound as described herein or a pharmaceutically acceptable salt thereof to the mammal.

In another embodiment, the invention provides for a method for modulating TRPA1 activity, comprising contacting TRPA1 with a compound as described herein or a pharmaceutically acceptable salt thereof.

In another embodiment, the invention provides for a compound as described herein or a pharmaceutically acceptable salt thereof for the treatment or prophylaxis of a disease or condition mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, wherein the disease or condition is pain (including but not limited to acute, chronic, neuropathic and inflammatory pain), arthritis, itch, cough, asthma, inflammatory bowel disease, or an inner ear disorder.

In another embodiment, the invention provides for the use of a compound as described herein or a pharmaceutically acceptable salt thereof for the preparation of a medicament for the treatment or prophylaxis of a disease or condition that is mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within aspects of this embodiment, the disease or condition is pain (including but not limited to acute, chronic, neuropathic and inflammatory pain), arthritis, itch, cough, asthma, inflammatory bowel disease, or an inner ear disorder.

In another embodiment, the invention provides for a method for treating a disease or condition mediated by TRPA1 activity in a mammal (e.g., a human), comprising administering a compound as described herein or a pharmaceutically acceptable salt thereof to the mammal. Within certain aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain (including but not limited to acute, chronic, neuropathic and inflammatory pain), arthritis, itch, cough, asthma, inflammatory bowel disease, or an inner ear disorder. In some embodiments, the disease or condition is asthma.

Combination Therapy

The compounds of the invention may be usefully combined with one or more other compounds of the invention or one or more other therapeutic agent or as any combination thereof, in the treatment of ion channel-mediated diseases and conditions. For example, a compound of the invention may be administered simultaneously, sequentially or separately in combination with other therapeutic agents, including, but not limited to the following.

Opiate analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine.

Non-opiate analgesics, e.g., acetomeniphen, and salicylates (e.g., aspirin).

Nonsteroidal antiinflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac.

Anticonvulsants, e.g., carbamazepine, oxcarbazepine, lamotrigine, valproate, topiramate, gabapentin and pregabalin.

Antidepressants such as tricyclic antidepressants, e.g., amitriptyline, clomipramine, despramine, imipramine and nortriptyline.

COX-2 selective inhibitors, e.g., celecoxib, rofecoxib, parecoxib, valdecoxib, deracoxib, etoricoxib, and lumiracoxib.

Alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline.

Barbiturate sedatives, e.g., amobarbital, aprobarbital, butabarbital, butabital, mephobarbital, metharbital, methohexital, pentobarbital, phenobartital, secobarbital, talbutal, theamylal and thiopental.

Tachykinin (NK) antagonist, particularly an NK-3, NK-2 or NK-1 antagonist, e.g., (aR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis (trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S).

Coal-tar analgesics, e.g., paracetamol.

Serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine.

Noradrenaline (norepinephrine) reuptake inhibitors, e.g., maprotiline, lofepramine, mirtazepine, oxaprotiline, fezolamine, tomoxetine, mianserin, buproprion, buproprion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics.

Dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine.

Acetylcholinesterase inhibitors, e.g., donepezil.

5-HT3 antagonists, e.g., ondansetron.

Metabotropic glutamate receptor (mGluR) antagonists.

Local anaesthetics, e.g., mexiletine and lidocaine.

Corticosteroids, e.g., dexamethasone.

Antiarrhythimics, e.g., mexiletine and phenytoin.

Muscarinic antagonists, e.g., tolterodine, propiverine, tropsium chloride, darifenacin, solifenacin, temiverine and ipratropium.

Cannabinoids.

Vanilloid receptor agonists (e.g., resinferatoxin) or antagonists (e.g., capsazepine).

Sedatives, e.g., glutethimide, meprobamate, methaqualone, and dichloralphenazone.

Anxiolytics, e.g., benzodiazepines.

Antidepressants, e.g., mirtazapine.

Topical agents, e.g., lidocaine, capsacin and resiniferotoxin.

Muscle relaxants, e.g., benzodiazepines, baclofen, carisoprodol, chlorzoxazone, cyclobenzaprine, methocarbamol and orphrenadine.

Anti-histamines or H1 antagonists.

NMDA receptor antagonists.

5-HT receptor agonists/antagonists.

PDEV inhibitors.

Tramadol®.

Cholinergic (nicotinc) analgesics.

Alpha-2-delta ligands.

Prostaglandin E2 subtype antagonists.

Leukotriene B4 antagonists.

5-lipoxygenase inhibitors.

5-HT3 antagonists.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

EXAMPLES

General Preparation of Compounds of Formula (I)

The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, 1991, Volumes 1-15; Rodd's Chemistry of Carbon Compounds, Elsevier Science Publishers, 1989, Volumes 1-5 and Supplementals; and Organic Reactions, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Although certain exemplary embodiments are depicted and described herein, the compounds of the present invention can be prepared using appropriate starting materials according to the methods described generally herein and/or by methods available to one of ordinary skill in the art.

Intermediates and final compounds may be purified by either flash chromatography, and/or by reverse-phase preparative HPLC (high performance liquid chromatography), and/or by supercritical fluid chromatography. Unless otherwise noted, flash chromatography may be carried out using prepacked silica gel cartridges from either ISCO or SiliCycle on an ISCO CombiFlash® chromatography instrument (from Teledyne Isco, Inc.). Reverse-phase preparative HPLC may be performed using a (1) Polaris C-18 5 µM column (50×21 mm), or (2) XBridge Prep C-18 OBD 5 µM column (19×150 mm). Supercritical fluid chromatography may be carried out using packed columns by Chiral Technologies, Chiralpak AD, Chiralpak AS, Chiralpak IA, Chiralpak IB, Chiralpak IC, Chiralcel OD, or Chiralcel OJ with column dimensions such as (1) 4.6 cm×5 cm, 3 µM, (2) 4.6 cm×5 cm, 5 µM, or (3) 15 cm×21.2 mm, 5 µM.

Mass spectrometry (MS) may be performed using a (1) Sciex 15 mass spectrometer in ES+ mode, or (2) Shimadzu LCMS 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) may be performed using a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

All reactions involving air-sensitive reagents were performed under an inert atmosphere. Reagents were used as received from commercial suppliers unless otherwise noted.

Various compounds of the present disclosure are described by chemical structure and chemical name. The chemical structure predominates in the case of any inconsistency between the chemical structure and the chemical name.

Example 1: Preparation of Example Compounds

Example Compound 1: Preparation of 3-[2-(4-chlorophenyl)ethyl]-5-[(7-methyl-6-oxo-purin-1-yl)methyl]-1,3,4-oxadiazol-2-one The overall Example Compound 1 reaction scheme is as follows:

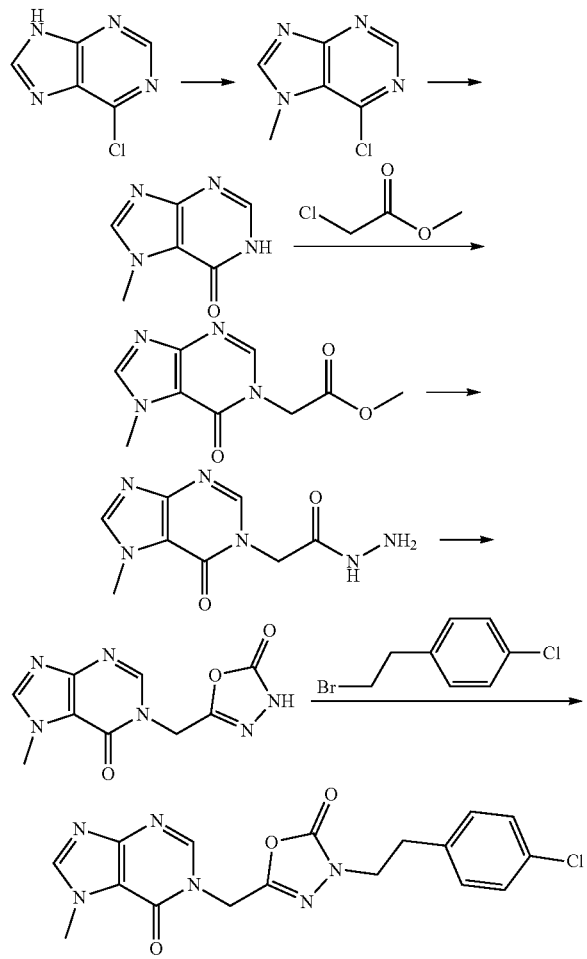

Step 1: Preparation of 6-chloro-7-methyl-7H-purine

To a 1 L 3-necked round-bottom flask purged and maintained with an inert atmosphere of nitrogen was placed 6-chloro-9H-purine (15.4 g, 0.1 mol, 1 equiv) and tetrahydrofuran (155 mL) at 0° C. followed by the addition of MeMgCl (36.6 mL, 1.0M THF solution, 1.1 equiv) dropwise with stirring. The mixture was stirred at 0° C. for 30 min. To this was added iodomethane (42.6 g, 3 equiv) dropwise with stirring. The resulting solution was stirred at 50° C. in an oil bath for 5 h, quenched by the addition of 50 mL of aqueous NH$_4$Cl and extracted with dichloromethane (3×50 mL). The combined organic layers were washed with brine (2×50 mL) and concentrated under vacuum. The crude product was re-crystallized from CH$_2$Cl$_2$/petroleum ether in the ratio of 1:10 to afford desired product as a greenish solid (7 g, 42%).

Step 2: Preparation of 7-methyl-1H-purin-6(7H)-one

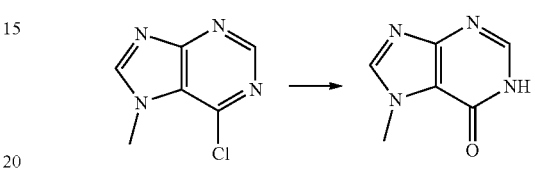

To a 1 L 3-necked round-bottom flask was placed 6-chloro-7-methyl-7H-purine (100 g, 590 mmol, 1 eq) and formic acid (1 L). The resulting solution was stirred at 70° C. for 3 h. The resulting mixture was concentrated under vacuum, and the residue was diluted with 500 mL of water. The resulting solution was extracted with 3×250 mL of ether/ethyl acetate (20:1) and the aqueous layers were concentrated under vacuum with toluene to remove water and formic acid. The residue was dissolved in water. The pH value of the solution was adjusted to 9 with NH$_3$.H$_2$O (25%) and the aqueous layer was concentrated under vacuum. The solids were collected by filtration, washed with water twice and dried to afford desired product (55 g, 62%) as yellow solid.

Step 3: Preparation of methyl 2-(7-methyl-6-oxo-6,7-dihydro-1H-purin-1-yl)acetate

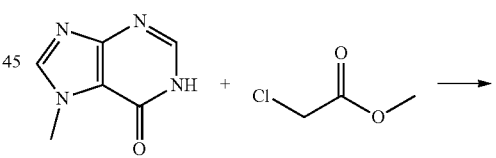

A mixture of 7-methyl-6,7-dihydro-1H-purin-6-one (2 g, 13.32 mmol), methyl 2-chloroacetate (1.44 g, 13.27 mmol), N,N-dimethylformamide (50 mL), Cs$_2$CO$_3$ (6.5 g, 19.95 mmol), and TBAI (49 mg, 0.13 mmol) was stirred for 1 h at 60° C. The resulting mixture was concentrated under vacuum. The residue was purified by a silica gel column eluting with dichloromethane/methanol (10/1) to afford the title compound (1.3 g, 44%) as a light yellow solid. LCMS [M+H$^+$] 223.

Step 4: Preparation of 2-(7-methyl-6-oxo-6,7-dihydro-1H-purin-1-yl)acetohydrazide

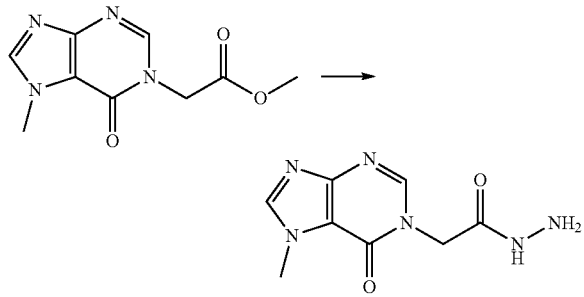

A mixture of methyl 2-(7-methyl-6-oxo-6,7-dihydro-1H-purin-1-yl)acetate (666 mg, 3.00 mmol), methanol (10 mL), and hydrazine hydrate (1.55 g, 80%) was stirred overnight at 80° C. The resulting mixture was concentrated under vacuum to afford the title compound (550 mg, 83%) as a light yellow solid. LCMS [M+H$^+$] 223.

Step 5: Preparation of 7-methyl-1-[(5-oxo-4,5-dihydro-1,3,4-oxadiazol-2-yl)methyl]-6,7-dihydro-1H-purin-6-one

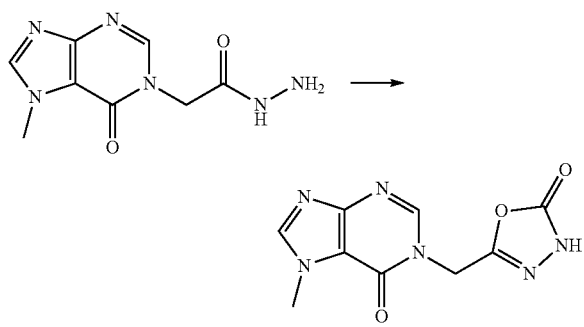

A mixture of 2-(7-methyl-6-oxo-6,7-dihydro-1H-purin-1-yl)acetohydrazide (222 mg, 1.00 mmol), N,N-dimethylformamide (5 mL), and CDI (178 mg, 1.10 mmol) was stirred for 3 h at room temperature. This resulted in a light brown solution of the title compound in DMF which was used for the next step without any further purification. LCMS [M+H$^+$] 249.

Step 6: Preparation of 3-[2-(4-chlorophenyl)ethyl]-5-[(7-methyl-6-oxo-purin-1-yl)methyl]-1,3,4-oxadiazol-2-one

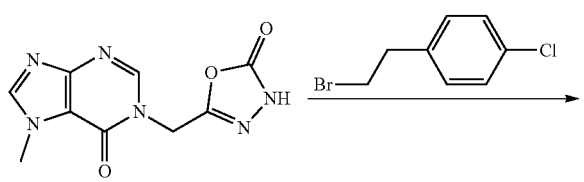

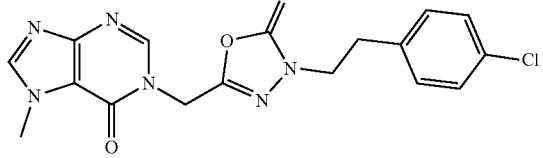

The solution of 7-methyl-1-[(5-oxo-4,5-dihydro-1,3,4-oxadiazol-2-yl)methyl]-6,7-dihydro-1H-purin-6-one (~0.2M, 4.5 mL, prepared from step 3) was added dropwise into a mixture of 1-(2-bromoethyl)-4-chlorobenzene (216 mg, 0.98 mmol), Cs$_2$CO$_3$ (396 mg, 1.22 mmol), TBAI (31 mg, 0.08 mmol), and N,N-dimethylformamide (5 mL) at room temperature. The mixture was stirred for 1 h at 60° C. The solids were filtered out. The resulting solution was purified on a C18 silica gel column eluting with CH$_3$CN/H$_2$O (10 mmol/L NH$_4$HCO$_3$, 5% to 95%, over 30 min). This resulted in the title compound (37.3 mg, 11%) as a white solid. LCMS [M+H$^+$] 387. $^1$H NMR (400 MHz, DMSO) δ 8.34 (s, 1H), 8.23 (s, 1H), 7.29 (d, J=8.4 Hz, 2H), 7.20 (d, J=8.4 Hz, 2H), 5.22 (s, 2H), 3.98 (s, 3H), 3.85 (t, J=6.8 Hz, 2H), 2.91 (t, J=6.8 Hz, 2H).

Example Compound 2: Preparation of 3-(4-(difluoromethoxy)phenethyl)-5-((7-methyl-6-oxo-6H-purin-1(7H)-yl)methyl)-1,3,4-oxadiazol-2(3H)-one The overall Example Compound 2 reaction scheme is as follows:

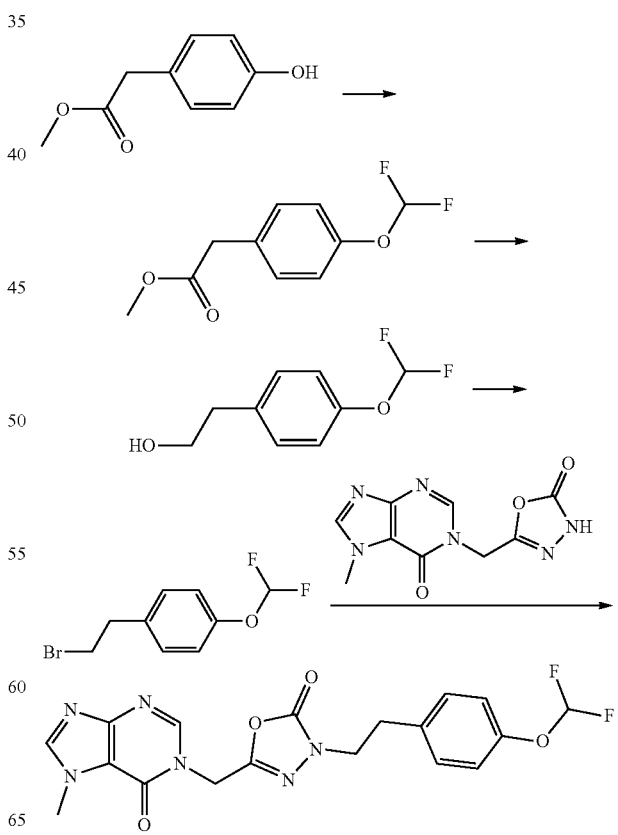

Step 1: Preparation of methyl 2-[4-(difluoromethoxy)phenyl] acetate

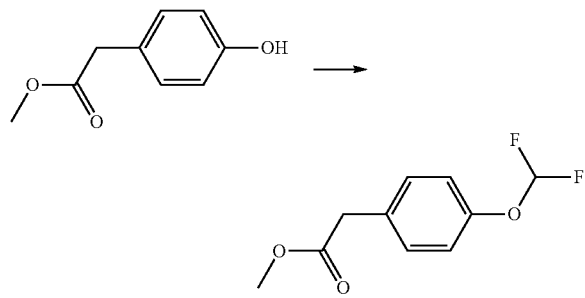

A mixture of methyl 2-(4-hydroxyphenyl)acetate (2 g, 12.04 mmol), sodium 2-chloro-2,2-difluoroacetate (2.19 g, 14.36 mmol), Cs$_2$CO$_3$ (4.71 g, 14.46 mmol), and N,N-dimethylformamide (50 mL) was stirred for 3 h at 80° C. in an oil bath. The resulting solution was diluted with ethyl acetate, washed with brine, dried over anhydrous sodium sulfate, and concentrated under vacuum. The residue was purified by a silica gel column eluting with petroleum ether/ethyl acetate (10:1) to afford the title compound (2 g, 77%) as brown oil.

Step 2: Preparation of 2-[4-(difluoromethoxy)phenyl]ethan-1-ol

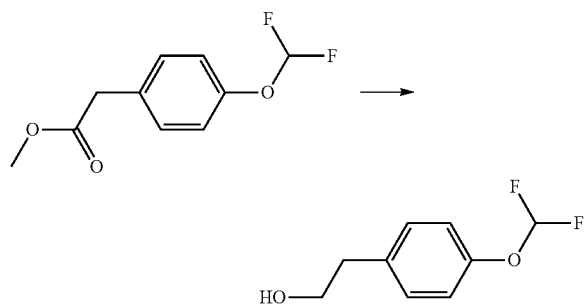

LiAlH$_4$ (704 mg, 18.55 mmol) was added dropwise into a mixture of methyl 2-[4-(difluoromethoxy)phenyl] acetate (2 g, 9.25 mmol) and tetrahydrofuran (50 mL) at 0° C. in an ice/salt bath under nitrogen. The resulting solution was stirred for 2 h at 0° C. The reaction was then quenched by the addition of 1 g of Na$_2$SO$_4$.10H$_2$O. The solids were filtered out. The resulting mixture was concentrated under vacuum to afford the title compound (1.2 g, 69%) as colorless oil.

Step 3: Preparation of 1-(2-bromoethyl)-4-(difluoromethoxy)benzene

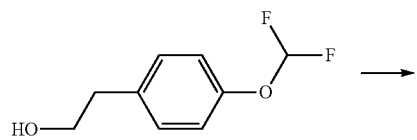

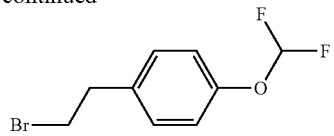

A mixture of 2-[4-(difluoromethoxy)phenyl]ethan-1-ol (1 g, 5.31 mmol), dichloromethane (50 mL), PPh$_3$ (2.79 g, 10.64 mmol), and CBr$_4$ (2.67 g, 8.05 mmol) was stirred for 2 hours at room temperature. The resulting mixture was concentrated under vacuum. The residue was purified on a silica gel column eluting with ethyl acetate/petroleum ether (1:10) to afford the title compound (1.06 g, 79%) as a white solid.

Step 4: Preparation of 3-(4-(difluoromethoxy)phenethyl)-5-((7-methyl-6-oxo-6H-purin-1(7H)-yl)methyl)-1,3,4-oxadiazol-2(3H)-one

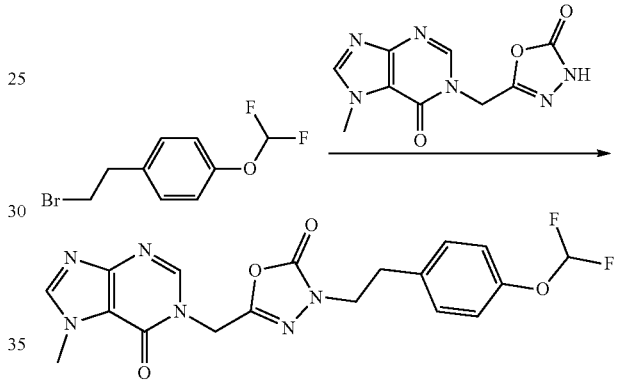

The solution of 7-methyl-1-[(5-oxo-4,5-dihydro-1,3,4-oxadiazol-2-yl)methyl]-6,7-dihydro-1H-purin-6-one (~0.2M, 1.6 mL, prepared according to Example Compound 1 step 3) was added dropwise into a mixture of 1-(2-bromoethyl)-4-(difluoromethoxy)benzene (89 mg, 0.35 mmol), Cs$_2$CO$_3$ (315 mg, 0.96 mmol), TBAI (16 mg, 0.04 mmol), and N,N-dimethylformamide (5 mL) at room temperature. The resulting solution was stirred for 12 h at 50° C. The reaction mixture was purified on C18 silica gel column eluting with CH$_3$CN/H$_2$O (10 mmol/L NH$_4$HCO$_3$, 5% to 95%, 30 min). This resulted in the title compound (27.1 mg, 20.3%) as a white solid. LCMS [M+H$^+$]=419. $^1$H NMR (300 MHz, DMSO-d6) δ 8.35 (s, 1H), 8.24 (s, 1H), 7.44-6.90 (m, 5H), 5.23 (s, 2H), 3.99 (s, 3H), 3.85 (t, J=6.9 Hz, 2H), 2.92 (t, J=6.9 Hz, 2H).

Example Compound 3: Preparation of 3-(4-bromophenethyl)-5-((7-methyl-6-oxo-6H-purin-1(7H)-yl)methyl)-1,3,4-oxadiazol-2(3H)-one The Example Compound 3 reaction scheme is as follows:

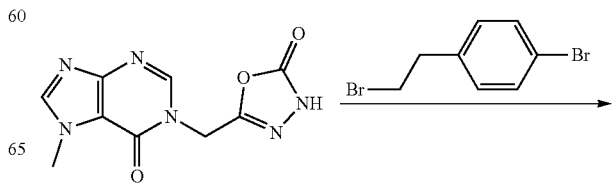

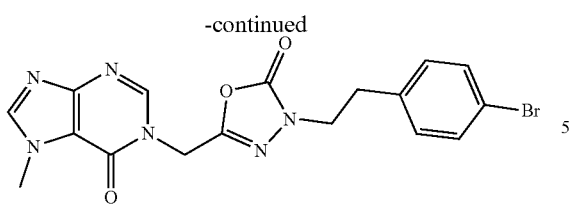

The solution of 7-methyl-1-[(5-oxo-4,5-dihydro-1,3,4-oxadiazol-2-yl)methyl]-6,7-dihydro-1H-purin-6-one (~0.2M, 1.5 mL, prepared according to Example Compound 1 step 3) was added dropwise into a mixture of TBAI (12 mg, 0.03 mmol), Cs$_2$CO$_3$ (222 mg, 0.68 mmol), N,N-dimethylformamide (10 mL), and 1-bromo-4-(2-bromoethyl)benzene (88 mg, 0.33 mmol) at room temperature. The mixture was stirred for 1.5 h at 60° C. The reaction mixture was purified on a C18 silica gel column eluting with CH$_3$CN/H$_2$O (10 mmol/L NH$_4$HCO$_3$) increasing from 5% to 95% over 30 min. This resulted in the title compound (21.3 mg, 15%) as a gray solid. LCMS [M+H$^+$] 431. $^1$H NMR (400 MHz, DMSO-d$_6$) δ 8.35 (s, 1H), 8.25 (s, 1H), 7.46-7.38 (m, 2H), 7.22-7.10 (m, 2H), 5.22 (s, 2H), 3.99 (s, 3H), 3.86 (t, J=6.8 Hz, 2H), 2.89 (t, J=6.8 Hz, 2H).

Example Compound 4: Preparation of 5-((7-methyl-6-oxo-6H-purin-1(7H)-yl)methyl)-3-phenethyl-1,3,4-oxadiazol-2(3H)-one The Example Compound 4 reaction scheme is as follows:

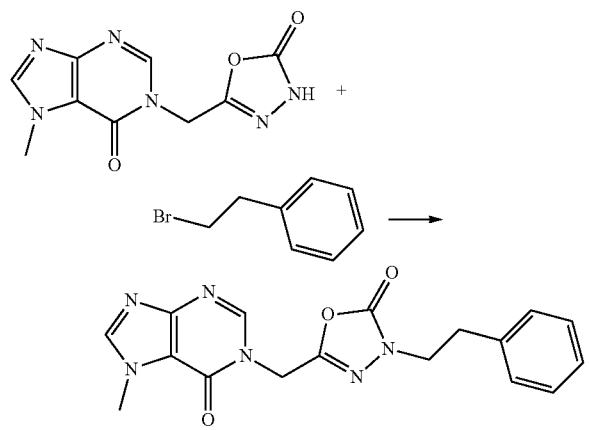

The solution of 7-methyl-1-[(5-oxo-4,5-dihydro-1,3,4-oxadiazol-2-yl)methyl]-6,7-dihydro-1H-purin-6-one (~0.2M, 2 mL, prepared according to Example Compound 1 step 3) was added dropwise into a mixture of (2-bromoethyl)benzene (77 mg, 0.42 mmol), TBAI (1.5 mg, 0.004 mmol), Cs$_2$CO$_3$ (269 mg, 0.83 mmol), and N,N-dimethylformamide (5 mL) at room temperature. The resulting solution was stirred for 3 h at 60° C. The reaction mixture was purified on a C18 silica gel column eluting with CH$_3$CN/H$_2$O (10 mmol/L NH$_4$HCO$_3$) increasing from 5% to 95% over 30 min. This resulted in the title compound (35.8 mg, 24%) as an off-white solid. LCMS [M+H$^+$] 353. $^1$H NMR (400 MHz, DMSO-d6) δ 8.35 (s, 1H), 8.25 (s, 1H), 7.29-7.13 (m, 5H), 5.23 (s, 2H), 3.99 (s, 3H), 3.86 (t, J=7.0 Hz, 2H), 2.91 (t, J=7.0 Hz, 2H).

Example Compound 5: Preparation of 4-(2-(5-((7-methyl-6-oxo-6H-purin-1(7H)-yl)methyl)-2-oxo-1,3,4-oxadiazol-3(2H)-yl)ethyl)benzonitrile The Example Compound 5 reaction scheme is as follows:

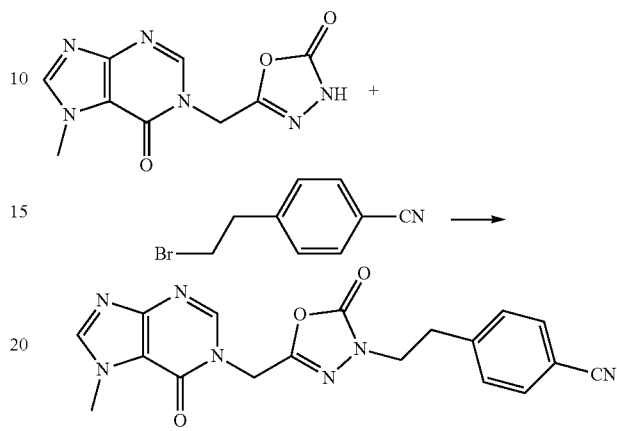

The solution of 7-methyl-1-[(5-oxo-4,5-dihydro-1,3,4-oxadiazol-2-yl)methyl]-6,7-dihydro-1H-purin-6-one (~0.2M, 5 mL, prepared according to Example Compound 1 step 3) was added dropwise into a mixture of 4-(2-bromoethyl)benzonitrile (222 mg, 1.06 mmol), TBAI (36.9 mg, 0.100 mmol), Cs$_2$CO$_3$ (658 mg, 2.02 mmol), and N,N-dimethylformamide (10 mL, 129.22 mmol) at room temperature. The resulting solution was stirred for 3 h at 60° C. The reaction mixture was purified on a C18 silica gel column eluting with CH$_3$CN/H$_2$O (10 mmol/L NH$_4$HCO$_3$) increasing from 5% to 95% over 30 min. This resulted in the title compound (41.1 mg, 9%) as a light yellow solid. LCMS [M+H$^+$] 378. $^1$H NMR (400 MHz, DMSO-d$_6$) δ 8.34 (s, 1H), 8.25 (s, 1H), 7.75-7.67 (m, 2H), 7.46-7.36 (m, 2H), 5.21 (s, 2H), 4.03 (s, 3H), 3.93 (t, J=6.8 Hz, 2H), 3.02 (t, J=6.8 Hz, 2H).

Example Compound 6: Preparation of 3-(4-chlorophenethyl)-5-((5-methyl-4-oxopyrido[3,4-d]pyrimidin-3(4H)-yl)methyl)-1,3,4-oxadiazol-2(3H)-one The overall Example Compound 6 reaction scheme is as follows:

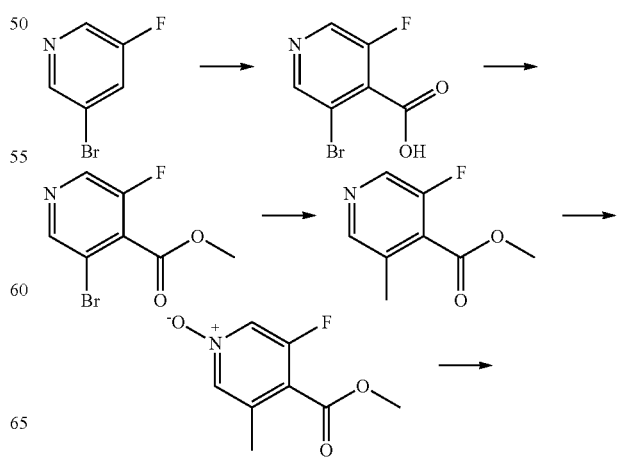

-continued

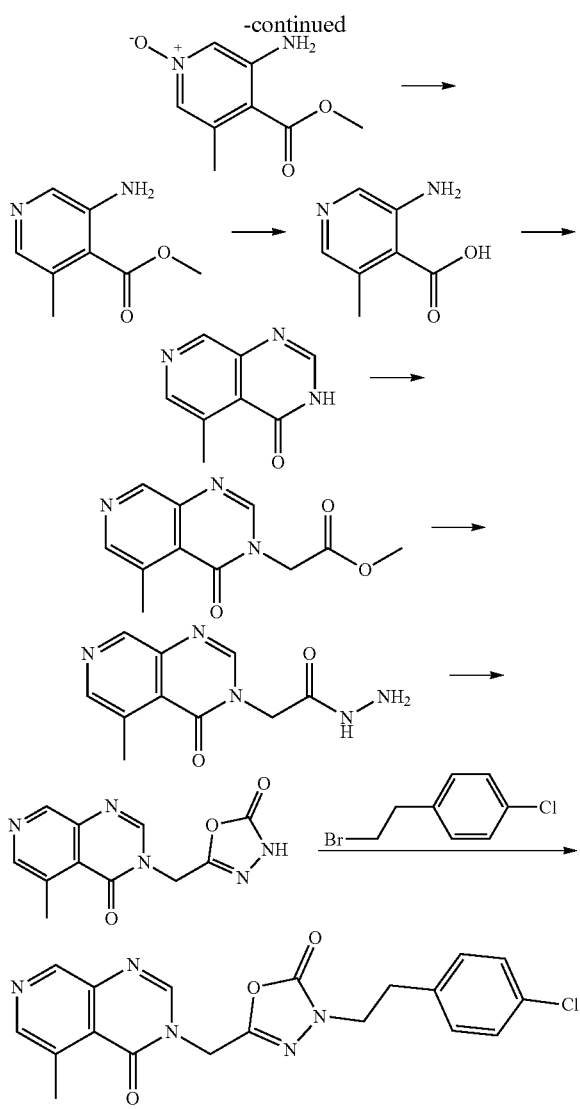

Step 1: Preparation of 3-bromo-5-fluoroisonicotinic acid

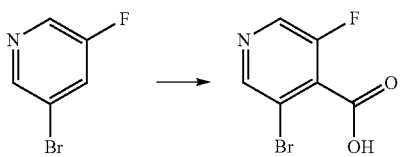 [SMILES: Fc1cncc(Br)c1 ; O=C(O)c1c(F)cncc1Br]

n-BuLi (250 mL, 0.62 mol, 2.5 equiv) was added dropwise into a solution of bis(propan-2-yl)amine (76 g, 0.75 mmol, 3 equiv) and tetrahydrofuran (1 L) at 0° C. under nitrogen. The mixture was stirred for 30 min at 0° C. To this was added 3-bromo-5-fluoropyridine (44 g, 0.25 mol, 1 equiv) dropwise with stirring at −70° C. The resulting solution was stirred for 1 h at −70° C. The reaction mixture was then poured into a mixture of dry ice in 500 mL of THF. The resulting mixture was stirred for 30 min and then concentrated under vacuum. The residue was dissolved in water. The pH value of the solution was adjusted to 3 with hydrogen chloride (1 mol/L). The mixture was extracted with ethyl acetate, dried over anhydrous sodium sulfate and concentrated under vacuum to give the product (40 g, 72%) as yellow solid.

Step 2: Preparation of methyl 3-bromo-5-fluoroisonicotinate

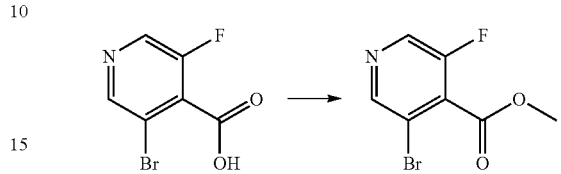

TMSCHN$_2$ (180 mL, 360 mmol, 2 equiv) was added into a solution of 3-bromo-5-fluoroisonicotinic acid (40 g, 182 mmol, 1 equiv), THF (240 mL), and MeOH (80 mL) dropwise with stirring at 0° C. under nitrogen. The resulting solution was stirred for 3 h at room temperature. The resulting mixture was concentrated under vacuum. The residue was purified by a silica gel column eluting with ethyl acetate/petroleum ether (1/9) to afford the title compound (35 g, 83%) as yellow oil.

Step 3: Preparation of methyl 3-fluoro-5-methylisonicotinate

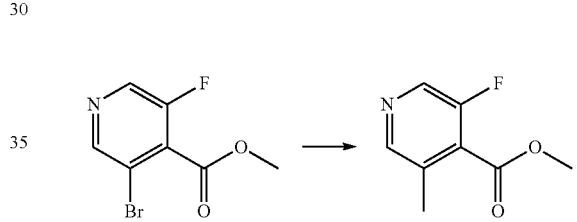

Zn(CH$_3$)$_2$ (225 mL, 0.22 mol, 1.5 equiv) was added into a mixture of 3-bromo-5-fluoroisonicotinate (35 g, 0.15 mol, 1 equiv), dioxane (1 L), and Pd(dppf)Cl$_2$ (11 g, 15 mmol, 0.1 equiv) at room temperature under nitrogen. The resulting solution was stirred for 3 h at 50° C. The reaction was then quenched by the addition of methanol. The solids were filtered out. The resulting mixture was concentrated under vacuum. The residue was dissolved in ethyl acetate, washed with brine, dried over anhydrous sodium sulfate and concentrated under vacuum. The residue was purified by silica column chromatography to give the product (17 g, 69%).

Step 4: Preparation of 3-fluoro-4-(methoxycarbonyl)-5-methylpyridine 1-oxide

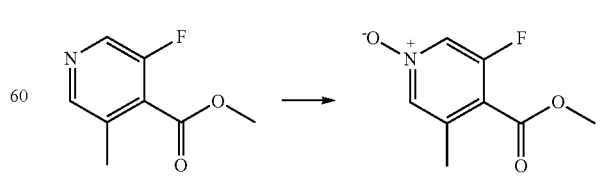

m-CPBA (96 g, 0.56 mol, 1.5 equiv) was added into a solution of methyl 5-fluoro-3-methylpyridine-4-carboxylate (63 g, 0.37 mol, 1 equiv) in dichloromethane (1.7 L) at 0° C.

under nitrogen. The resulting mixture was stirred for 15 h at room temperature. The reaction was quenched by the addition of saturated solution of sodium bicarbonate, extracted with ethyl acetate, washed with saturated solution of Na₂S₂O₃ and brine, dried over anhydrous sodium sulfate, and concentrated under vacuum. The residue was purified by a silica gel column eluting with ethyl acetate/heptane (9/1) to afford the title compound (62 g, 89%) as a yellow solid.

Step 5: Preparation of 3-amino-4-(methoxycarbonyl)-5-methylpyridine 1-oxide

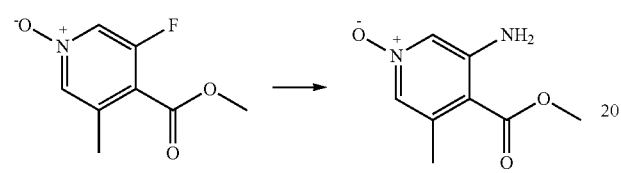

To a mixture of 3-fluoro-4-(methoxycarbonyl)-5-methylpyridine 1-oxide (62 g, 0.34 mol, 1 equiv) in DMSO (600 mL) was bubbled NH₃ (g) and the mixture was stirred for 12 h at 80° C. After completion, the mixture was diluted with water (1500 mL) and extracted with EA (800 mL×3). The combined organic layer was washed with brine twice. The resulting mixture was concentrated under vacuum to afford the title compound (62 g, crude) as a yellow solid, which was used in the next step without further purification.

Step 6: Preparation of methyl 3-amino-5-methylisonicotinate

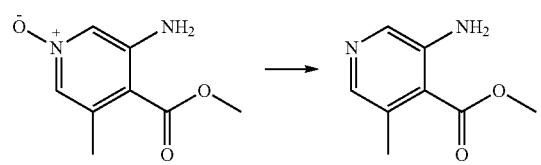

A mixture of 3-amino-4-(methoxycarbonyl)-5-methylpyridine 1-oxide (62 g, 0.34 mol, 1 equiv), methanol (400 mL), and Raney Nickel (10 g) was stirred for 30 min at room temperature under hydrogen atmosphere. The solids were filtered out. The resulting solution was concentrated under vacuum to afford the title compound (40 g, 71% for 2 steps) as a yellow solid.

Step 7: Preparation of 3-amino-5-methylisonicotinic acid

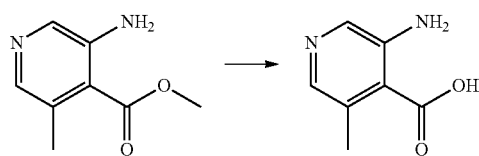

A mixture of methyl 3-amino-5-methylpyridine-4-carboxylate (40 g, 0.24 mol, 1 equiv), methanol (450 mL), water (90 mL), and sodium hydroxide (38 g, 0.96 mol, 4 equiv) was stirred for 12 h at room temperature. The pH value of the solution was adjusted to 3 with hydrogen chloride (1 mol/L). The resulting mixture was concentrated under vacuum. The residue was dissolved in ethanol. The solids were filtered out. The resulting filtrate was concentrated under vacuum to afford the title compound (35 g, 95%) as a yellow solid.

Step 8: Preparation of 5-methylpyrido[3,4-d]pyrimidin-4(3H)-one

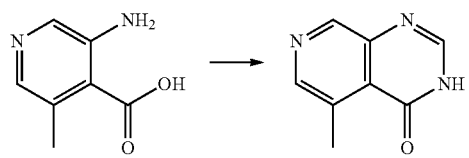

A mixture of 3-amino-5-methylpyridine-4-carboxylic acid (35 g, 0.23 mol, 1 equiv), ethanol (450 mL), and acetic acid, methanimidamide (35 g, 0.34 mol, 1.5 equiv) was stirred for 3 h at 80° C. The resulting mixture was concentrated under vacuum. The residue was purified by a silica gel column eluting with dichloromethane/methanol (5/1) to afford the title compound (22 g, 59%) as a yellow solid.

Step 9: Preparation of methyl 2-[5-methyl-4-oxo-3H,4H-pyrido[3,4-d]pyrimidin-3-yl] acetate

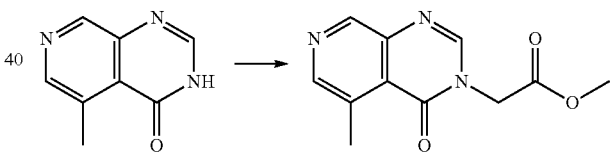

A mixture of 5-methyl-3H,4H-pyrido[3,4-d]pyrimidin-4-one (300 mg, 1.86 mmol), methyl 2-chloroacetate (240 mg, 2.21 mmol), potassium carbonate (520 mg, 3.76 mmol), TBAI (70 mg, 0.19 mmol), and N,N-dimethylformamide (10 mL) was stirred for 3 h at room temperature. The reaction mixture was purified on a C18 silica gel column eluting with CH₃CN/H₂O (10 mmol/L NH₄HCO₃) increasing from 5% to 95% over 30 min. This resulted in the title compound (250 mg, 58%) as a yellow solid. LCMS [M+H⁺] 234.

Step 10: Preparation of 2-[5-methyl-4-oxo-3H,4H-pyrido[3,4-d]pyrimidin-3-yl]acetohydrazide

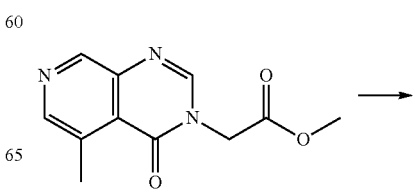

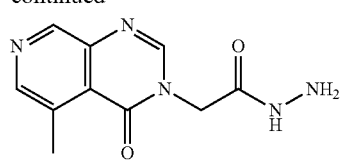

A mixture of methyl 2-[5-methyl-4-oxo-3H,4H-pyrido[3,4-d] pyrimidin-3-yl] acetate (250 mg, 1.07 mmol), hydrazine hydrate (2 mL, 80%), and methanol (5 mL) was stirred for 1 h at room temperature. The resulting mixture was concentrated under vacuum. This resulted in the title compound (200 mg, 80%) as a white solid. LCMS [M+H$^+$] 234.

Step 11: Preparation of 5-([5-methyl-4-oxo-3H,4H-pyrido[3,4-d]pyrimidin-3-yl]methyl)-2,3-dihydro-1,3,4-oxadiazol-2-one

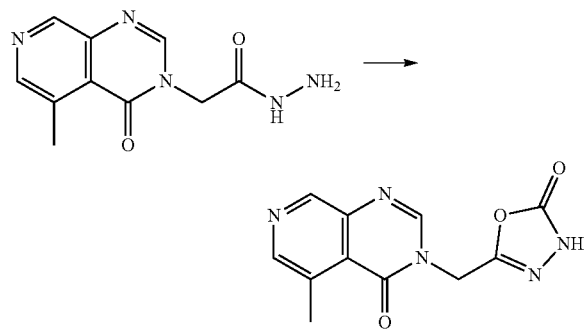

A mixture of 2-[5-methyl-4-oxo-3H,4H-pyrido[3,4-d]pyrimidin-3-yl]acetohydrazide (200 mg, 0.86 mmol), CDI (208 mg, 1.28 mmol), and N,N-dimethylformamide (10 mL) was stirred for 3 h at room temperature. This resulted in a light brown solution of the title compound in DMF which was used for the next step without any further purification. LCMS [M+H$^+$] 260.

Step 12: Preparation of 3-(4-chlorophenethyl)-5-((5-methyl-4-oxopyrido[3,4-d]pyrimidin-3(4H)-yl)methyl)-1,3,4-oxadiazol-2(3H)-one

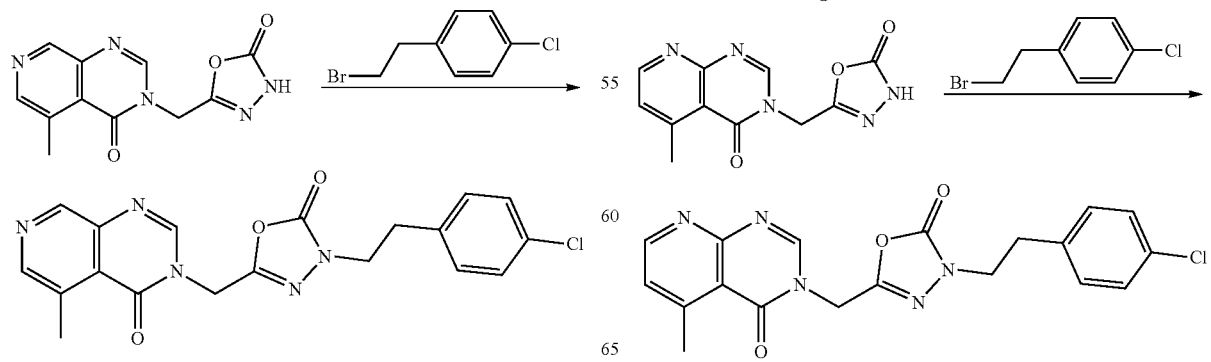

The solution of 5-([5-methyl-4-oxo-3H,4H-pyrido[3,4-d]pyrimidin-3-yl]methyl)-2,3-dihydro-1,3,4-oxadiazol-2-one (~0.09M, 10 mL, prepared from step 3) was added dropwise into a mixture of 1-(2-bromoethyl)-4-chlorobenzene (158 mg, 0.72 mmol), potassium carbonate (167 mg, 1.21 mmol), TBAI (22 mg, 0.06 mmol), and N,N-dimethylformamide (10 mL) at room temperature. The mixture was stirred for 5 h at room temperature. The reaction mixture was purified on a C18 silica gel column eluting with CH$_3$CN/H$_2$O (10 mmol/L NH$_4$HCO$_3$) increasing from 5% to 95% over 30 min. This resulted in the title compound (50 mg, 22%) as a white solid. LCMS [M+H$^+$] 398. $^1$H-NMR (400 MHz, DMSO-d6) δ 8.93 (s, 1H), 8.54 (d, J=4.3 Hz, 2H), 7.32-7.15 (m, 4H), 5.19 (s, 2H), 3.87 (t, J=6.8 Hz, 2H), 2.92 (t, J=6.7 Hz, 2H), 2.75 (s, 3H).

Example Compound 7: Preparation of 3-[2-(4-chlorophenyl)ethyl]-5-[(5-methyl-4-oxo-pyrido[2,3-d]pyrimidin-3-yl)methyl]-1,3,4-oxadiazol-2-one The overall Example Compound 7 reaction scheme is as follows:

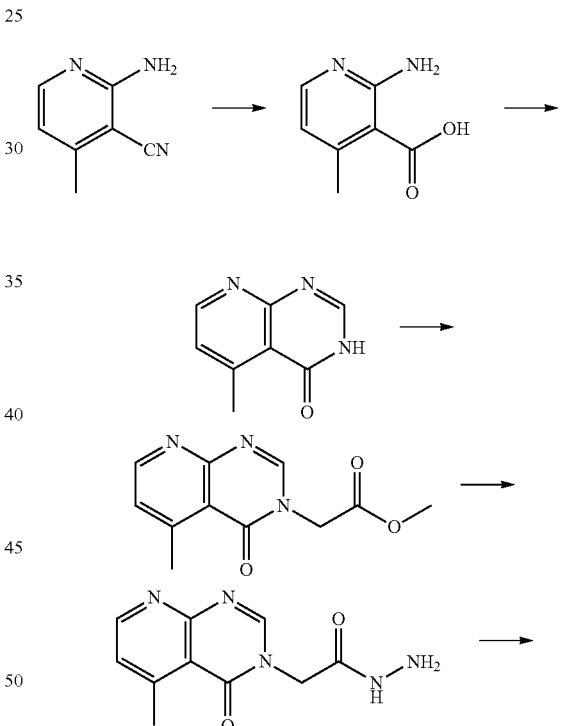

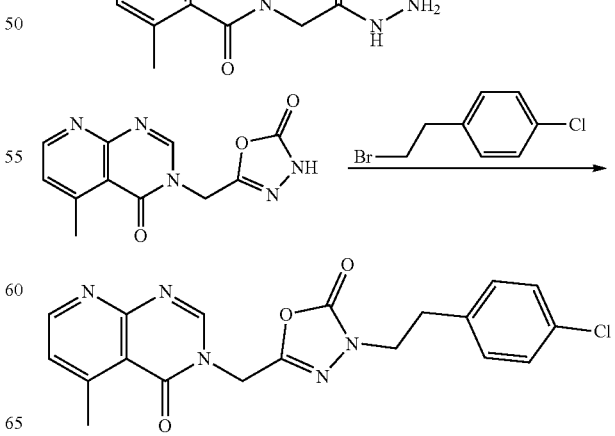

Step 1: Preparation of 2-amino-4-methylnicotinic acid

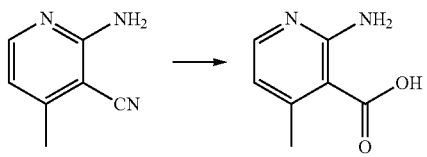

To a 2-L round-bottom flask was placed 2-amino-4-methylpyridine-3-carbonitrile (50 g, 375.51 mmol, 1.00 equiv.) and aqueous potassium hydroxide solution (20%, 700 mL). The resulting solution was stirred at 110° C. in an oil bath overnight and cooled to room temperature. The pH value of the mixture was adjusted to 3 with aqueous HCl solution (2 N). The mixture was concentrated under vacuum. The residue was washed with 2×400 mL of ethanol. The solid was filtered out. The filtrate was concentrated under vacuum to afford 40 g (crude) of 2-amino-4-methylpyridine-3-carboxylic acid as a yellow solid which was directly used in the next step.

Step 2: Preparation of 5-methylpyrido[2,3-d]pyrimidin-4(3H)-one

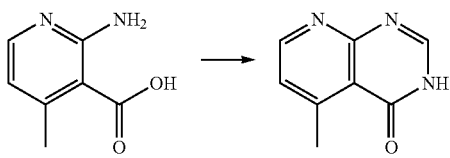

To a 1-L round-bottom flask was placed a solution of 2-amino-4-methylpyridine-3-carboxylic acid (40 g, 262.90 mmol, 1.00 equiv.) in ethanol (500 mL) and formamidine acetate (82.11 g, 788.69 mmol, 3.00 equiv.). The resulting solution was stirred at 100° C. in an oil bath overnight and cooled to room temperature. The solids were collected by filtration, washed with 3×100 mL of MeOH, and dried under vacuum to afford 21 g (50%) of 5-methyl-3H, 4H-pyrido[2,3-d] pyrimidin-4-one as a white solid.

Step 3: Preparation of methyl 2-[5-methyl-4-oxo-3H,4H-pyrido[2,3-d]pyrimidin-3-yl] acetate

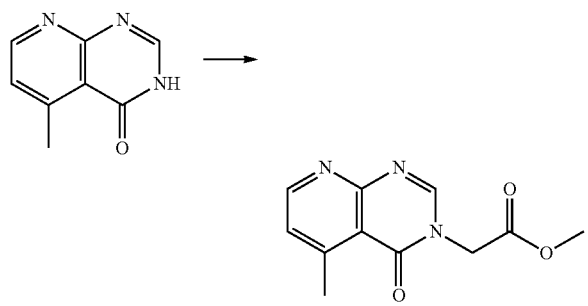

A mixture of 5-methylpyrido[2,3-d]pyrimidin-4(3H)-one (300 mg, 1.86 mmol), methyl 2-chloroacetate (240 mg, 2.21 mmol), potassium carbonate (520 mg, 3.76 mmol), TBAI (70 mg, 0.19 mmol), and N,N-dimethylformamide (10 mL) was stirred for 3 h at room temperature. The solids were filtered out. The resulting mixture was concentrated under vacuum. The reaction mixture was purified on a C18 silica gel column eluting with $CH_3CN/H_2O$ (10 mmol/L $NH_4HCO_3$) increasing from 5% to 95% over 30 min. This resulted in the title compound (220 mg, 51%) as a white solid. LCMS [M+H$^+$] 234.

Step 4: Preparation of 2-[5-methyl-4-oxo-3H,4H-pyrido[2,3-d]pyrimidin-3-yl] acetohydrazide

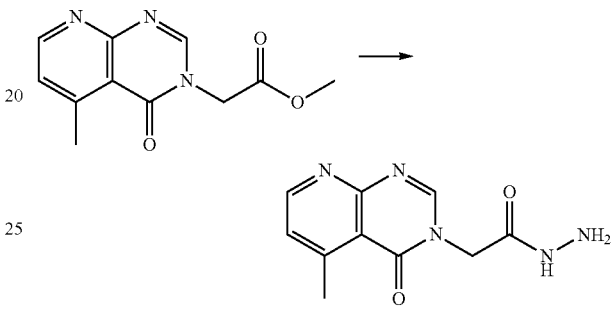

A mixture of methyl 2-[5-methyl-4-oxo-3H,4H-pyrido[2,3-d]pyrimidin-3-yl]acetate (220 mg, 0.94 mmol), methanol (5 mL), and hydrazine hydrate (2 mL, 80%) was stirred for 3 h at room temperature. The resulting mixture was concentrated under vacuum. This resulted in the title compound (200 mg, 91%) as a white solid. LCMS [M+H$^+$] 234.

Step 5: Preparation of 5-([5-methyl-4-oxo-3H,4H-pyrido[2,3-d]pyrimidin-3-yl]methyl)-2,3-dihydro-1,3,4-oxadiazol-2-one

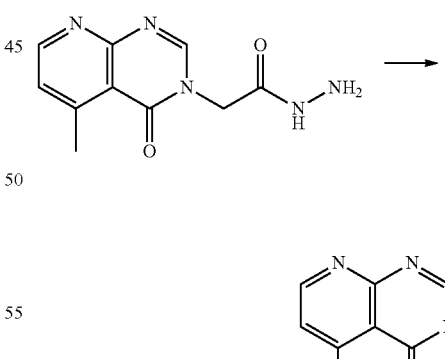

A mixture of 2-[5-methyl-4-oxo-3H,4H-pyrido[2,3-d]pyrimidin-3-yl]acetohydrazide (200 mg, 0.86 mmol), CDI (208 mg, 1.28 mmol), and N,N-dimethylformamide (10 mL) was stirred for 5 h at room temperature. This resulted in a light brown solution of the title compound in DMF which was used for the next step without any further purification. LCMS [M+H$^+$] 260.

Step 6: Preparation of 3-[2-(4-chlorophenyl)ethyl]-5-[(5-methyl-4-oxo-pyrido[2,3-d] pyrimidin-3-yl)methyl]-1,3,4-oxadiazol-2-one

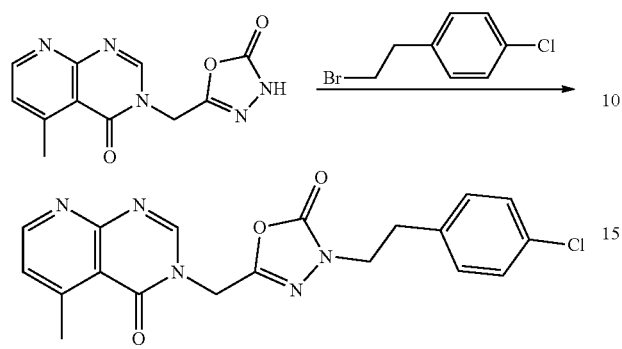

The solution of 5-([5-methyl-4-oxo-3H,4H-pyrido[2,3-d]pyrimidin-3-yl]methyl)-2,3-dihydro-1,3,4-oxadiazol-2-one (~0.09M, 10 mL, prepared from step 3) was added dropwise into a mixture of 1-(2-bromoethyl)-4-chlorobenzene (158 mg, 0.72 mmol), potassium carbonate (167 mg, 1.21 mmol), TBAI (22 mg, 0.06 mmol), and N,N-dimethylformamide (5 mL) at room temperature. The mixture was stirred for 5 h at room temperature. The reaction mixture was purified on a C18 silica gel column eluting with CH$_3$CN/H$_2$O (10 mmol/L NH$_4$HCO$_3$) increasing from 5% to 95% over 30 min. This resulted in the title compound (46.4 mg, 20%) as a white solid. LCMS [M+H$^+$] 398. $^1$H-NMR (400 MHz, DMSO-d6) δ 8.79 (d, J=4.8 Hz, 1H), 8.62 (s, 1H), 7.42 (d, J=4.8 Hz, 1H), 7.32-7.15 (m, 4H), 5.19 (s, 2H), 3.87 (t, J=6.8 Hz, 2H), 2.92 (t, J=6.8 Hz, 2H), 2.82 (s, 3H).

Example Compound 8: Preparation of 4-[2-[5-[(5-methyl-4-oxo-pyrido[2,3-d]pyrimidin-3-yl)methyl]-2-oxo-1,3,4-oxadiazol-3-yl] ethyl]benzonitrile The Example Compound 8 reaction scheme is as follows:

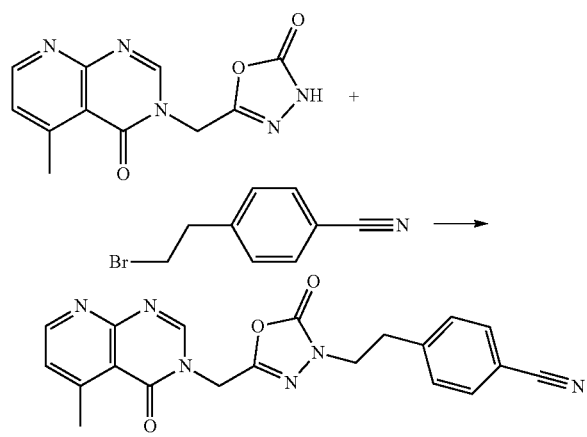

The solution of 5-([5-methyl-4-oxo-3H,4H-pyrido[2,3-d]pyrimidin-3-yl]methyl)-2,3-dihydro-1,3,4-oxadiazol-2-one (~0.09M, 9 mL, prepared according to Example 7, step 3) was added dropwise into a mixture of 4-(2-bromoethyl)benzonitrile (204 mg, 0.97 mmol), potassium carbonate (336 mg, 2.43 mmol), TBAI (30 mg, 0.08 mmol), and N,N-dimethylformamide (5 mL) at room temperature. The mixture was stirred for 5 h at room temperature. The reaction mixture was purified on a C18 silica gel column eluting with CH$_3$CN/H$_2$O (10 mmol/L NH$_4$HCO$_3$) increasing from 5% to 95% over 30 min. This resulted in the title compound (41.7 mg, 13%) as a white solid. LCMS [M+H$^+$] 389. $^1$H NMR δ 8.84 (d, J=4.8 Hz, 1H), 8.28 (s, 1H), 7.64-7.55 (m, 2H), 7.34-7.29 (m, 3H), 5.05 (s, 2H), 3.96 (t, J=7.2 Hz, 2H), 3.11 (t, J=7.3 Hz, 2H), 2.95-2.90 (m, 3H).

Example Compound 9: Preparation of 5-((7-methyl-6-oxo-6H-purin-1 (7H)-yl)methyl)-3-(4-(trifluoromethyl)phenethyl)-1,3,4-oxadiazol-2(3H)-one

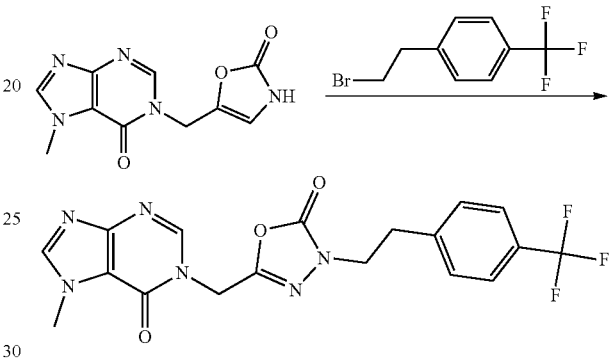

The solution of 7-methyl-1-[(5-oxo-4,5-dihydro-1,3,4-oxadiazol-2-yl)methyl]-6,7-dihydro-1H-purin-6-one (~0.2M, 2 mL, prepared according to Example Compound 1 step 3) was added dropwise into a mixture of 1-(2-bromoethyl)-4-(trifluoromethyl)benzene (102 mg, 0.40 mmol), potassium carbonate (167 mg, 1.21 mmol), TBAI (15 mg, 0.04 mmol), and DMF (3 mL) at room temperature. The reaction was stirred for 3 h at room temperature. The reaction mixture was purified on a C18 silica gel column eluting with CH$_3$CN/H$_2$O (10 mmol/L NH$_4$HCO$_3$) increasing from 5% to 95% over 30 min. This resulted in the title compound (25.3 mg, 15%) as a white solid. LCMS [M+H$^+$] 421. $^1$H NMR (400 MHz, DMSO) δ 8.35 (s, 1H), 8.25 (s, 1H), 7.60 (d, J=8.0 Hz, 2H), 7.42 (d, J=8.0 Hz, 2H), 5.23 (s, 2H), 3.99 (s, 3H), 3.92 (t, J=6.8 Hz, 2H), 3.02 (t, J=6.8 Hz, 2H).

Example Compound 10: Preparation of 5-((7-methyl-6-oxo-6H-purin-1 (7H)-yl)methyl)-3-(4-(trifluoromethoxy)phenethyl)-1,3,4-oxadiazol-2(3H)-one The overall Example Compound 10 reaction scheme is as follows:

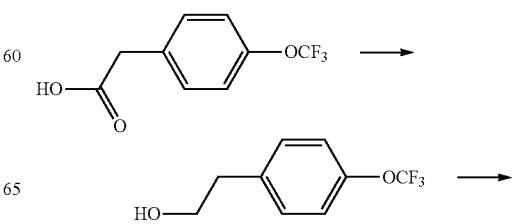

-continued

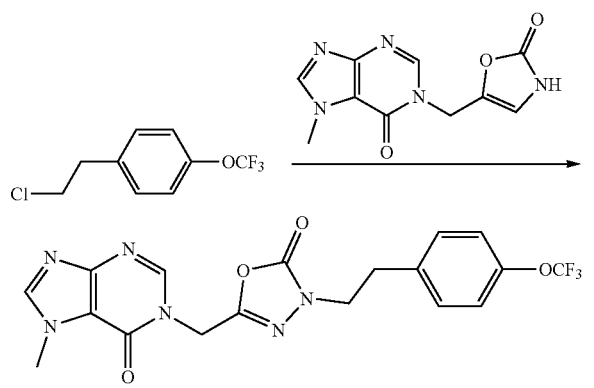

Step 1: Preparation of 2-[4-(trifluoromethoxy)phenyl] ethan-1-ol

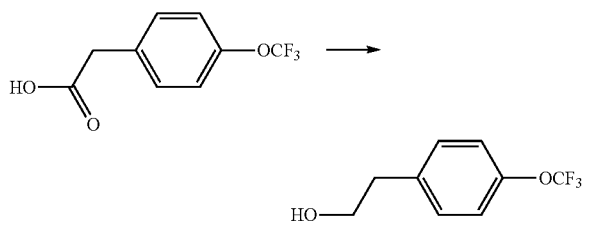

BH$_3$.THF (13.6 mL, 1M in THF) was added dropwise into a mixture of 2-[4-(trifluoromethoxy)phenyl] acetic acid (1 g, 4.54 mmol) in tetrahydrofuran (10 mL) at 0° C. under nitrogen. The resulting solution was stirred for 2 h at 0° C. The reaction was then quenched by the addition of water, extracted with ethyl acetate, washed with brine, dried over anhydrous sodium sulfate, and concentrated under vacuum. This resulted in the title compound (1 g, crude) as a white solid.

Step 2: Preparation of 1-(2-chloroethyl)-4-(trifluoromethoxy)benzene

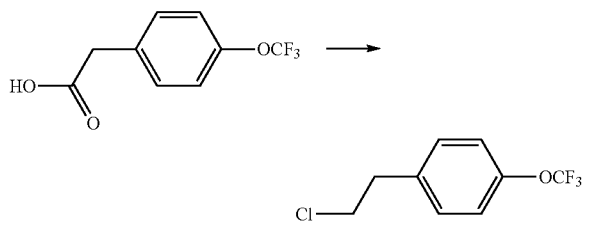

MsCl (199 mg, 1.74 mmol) was added dropwise into a mixture of 2-[4-(trifluoromethoxy)phenyl]ethan-1-ol (300 mg, 1.46 mmol), dichloromethane (10 mL), and TEA (439 mg, 4.34 mmol) at 0° C. in 5 min under nitrogen. The resulting solution was stirred for 12 h at room temperature and concentrated under vacuum. This resulted in the title compound (410 mg, crude) as a white solid

Step 3: Preparation of 5-((7-methyl-6-oxo-6H-purin-1(7H)-yl)methyl)-3-(4-(trifluoromethoxy)phenethyl)-1,3,4-oxadiazol-2(3H)-one

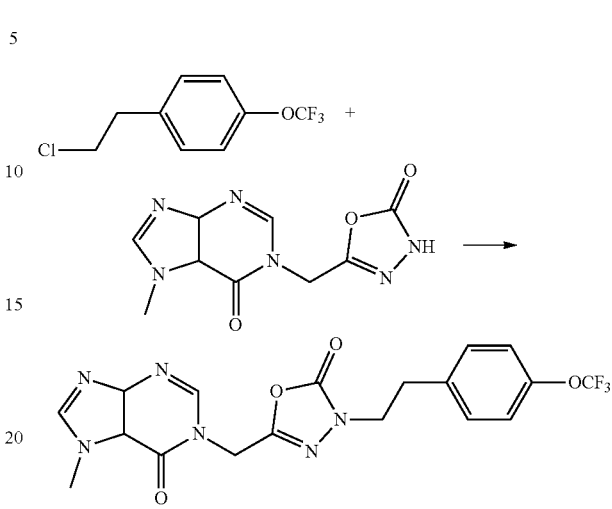

The solution of 7-methyl-1-[(5-oxo-4,5-dihydro-1,3,4-oxadiazol-2-yl)methyl]-6,7-dihydro-1H-purin-6-one (~0.2M, 2 mL, prepared according to Example Compound 1 step 3) was added dropwise into a mixture of 1-(2-chloroethyl)-4-(trifluoromethoxy)benzene (90.2 mg, 0.40 mmol), potassium carbonate (167 mg, 1.21 mmol), TBAI (15 mg, 0.04 mmol), and DMF (3 mL) at room temperature. The reaction was stirred for 3 h at room temperature. The reaction mixture was purified on a C18 silica gel column eluting with CH$_3$CN/H$_2$O (10 mmol/L NH$_4$HCO$_3$) increasing from 5% to 95% over 30 min. This resulted in the title compound (55.4 mg, 32%) as a white solid. LCMS [M+H$^+$] 437. $^1$H NMR (400 MHz, DMSO) δ 8.35 (s, 1H), 8.24 (s, 1H), 7.32 (d, J=8.7 Hz, 2H), 7.23 (d, J=8.0 Hz, 2H), 5.23 (s, 2H), 3.98 (s, 3H), 3.88 (t, J=6.9 Hz, 2H), 2.95 (t, J=6.9 Hz, 2H).

Example Compound 11: Preparation of 3-(4-methoxyphenethyl)-5-((7-methyl-6-oxo-6H-purin-1(7H)-yl)methyl)-1,3,4-oxadiazol-2(3H)-one The overall Example Compound 11 reaction scheme is as follows:

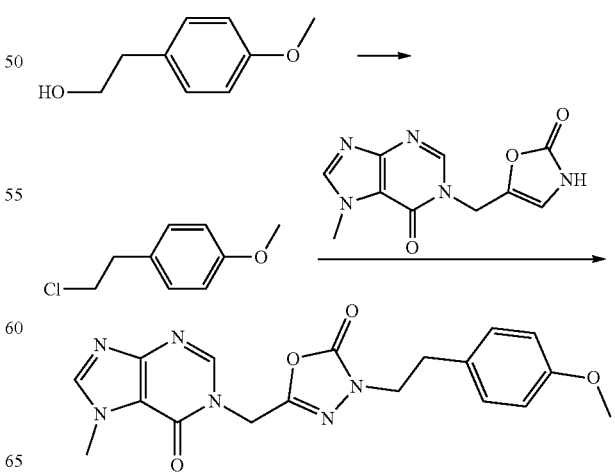

Step 1: Preparation of 1-(2-chloroethyl)-4-methoxybenzene

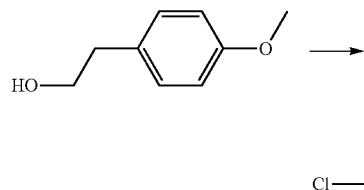

MsCl (270 mg, 2.36 mmol) was added dropwise into a mixture of 2-(4-methoxyphenyl)ethan-1-ol (300 mg, 1.97 mmol), dichloromethane (10 mL), and TEA (596.9 mg, 5.90 mmol) at 0° C. in 5 min under nitrogen. The resulting solution was stirred for 12 h at room temperature. The resulting mixture was concentrated under vacuum. This resulted in the title compound (430 mg, crude) as a white solid, which was used for the next step without any further purification.

Step 2: Preparation of 3-(4-methoxyphenethyl)-5-((7-methyl-6-oxo-6H-purin-1(7H)-yl)methyl)-1,3,4-oxadiazol-2(3H)-one

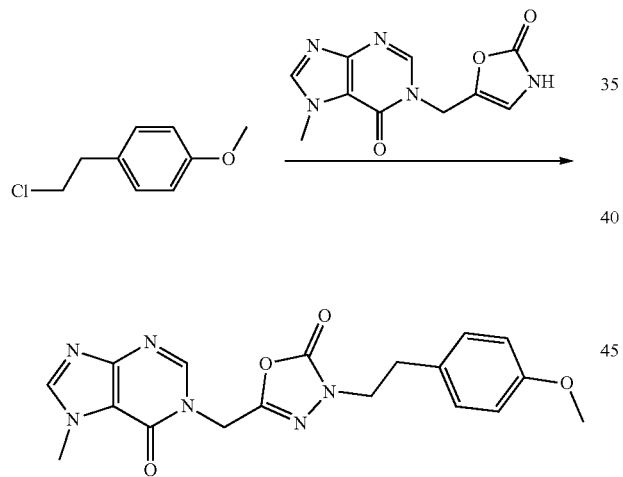

The solution of 7-methyl-1-[(5-oxo-4,5-dihydro-1,3,4-oxadiazol-2-yl)methyl]-6,7-dihydro-1H-purin-6-one (~0.2M, 2 mL, prepared according to Example Compound 1 step 3) was added dropwise into a mixture of 1-(2-chloroethyl)-4-methoxybenzene (68.5 mg, 0.40 mmol), potassium carbonate (167 mg, 1.21 mmol), TBAI (15 mg, 0.04 mmol), and DMF (3 mL) at room temperature. The reaction was stirred for 12 h at 50° C. The reaction mixture was purified on a C18 silica gel column eluting with $CH_3CN/H_2O$ (10 mmol/L $NH_4HCO_3$) increasing from 5% to 95% over 30 min. This resulted in the title compound (61.9 mg, 40%) as a white solid. LCMS [M+1] 383. $^1$H NMR (400 MHz, DMSO) δ 8.36 (s, 1H), 8.24 (s, 1H), 7.15-7.01 (m, 2H), 6.86-6.73 (m, 2H), 5.23 (s, 2H), 3.99 (s, 3H), 3.81 (t, J=7.0 Hz, 2H), 3.69 (s, 3H), 2.84 (t, J=6.9 Hz, 2H).

Example Compound 12: Preparation of 5-((7-methyl-6-oxo-6H-purin-1(7H)-yl)methyl)-3-(2-(naphthalen-2-yl)ethyl)-1,3,4-oxadiazol-2(3H)-one The overall Example Compound 12 reaction scheme is as follows:

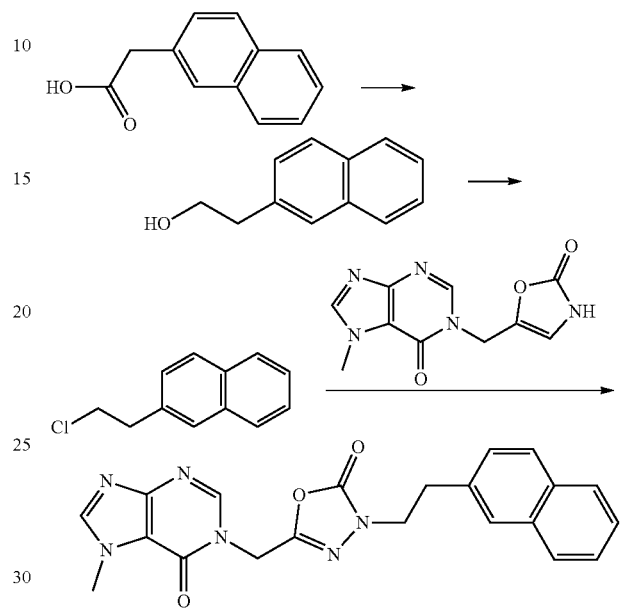

Step 1: Preparation of 2-(naphthalen-2-yl)ethan-1-ol

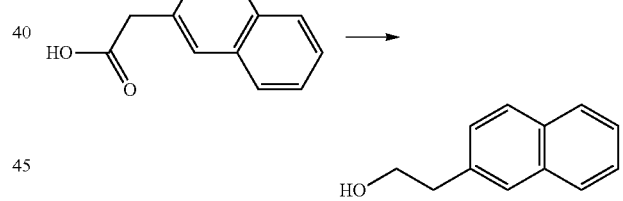

$BH_3$.THF (16.1 mL, 1M in THF) was added dropwise into a mixture of 2-(naphthalen-2-yl)acetic acid (300 mg, 1.61 mmol), tetrahydrofuran (10 mL), at 0° C. in 10 min under nitrogen. The resulting solution was stirred for 1 h at 0° C. in a water/ice bath. The reaction was then quenched by water, extracted with ethyl acetate, washed with brine, dried over anhydrous sodium sulfate, and concentrated under vacuum. This resulted in the title compound (1 g, crude) as an off-white solid, which was used for the next step without any further purification.

Step 2: Preparation of 2-(2-chloroethyl)naphthalene

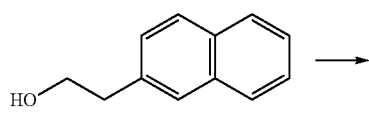

-continued

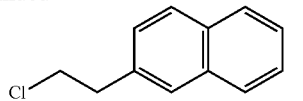

MsCl (238 mg, 2.08 mmol) was added dropwise into a mixture of 2-(naphthalen-2-yl)ethan-1-ol (300 mg, 1.74 mmol), dichloromethane (10 mL), and TEA (527 mg, 5.21 mmol) at 0° C. in 5 min under nitrogen. The resulting solution was stirred for 12 h at room temperature. The resulting mixture was concentrated under vacuum. This resulted in the title compound (400 mg, crude) as a white solid, which was used for the next step without any further purification.

Step 3: Preparation of 5-((7-methyl-6-oxo-6H-purin-1(7H)-yl)methyl)-3-(2-(naphthalen-2-yl)ethyl)-1,3,4-oxadiazol-2(3H)-one

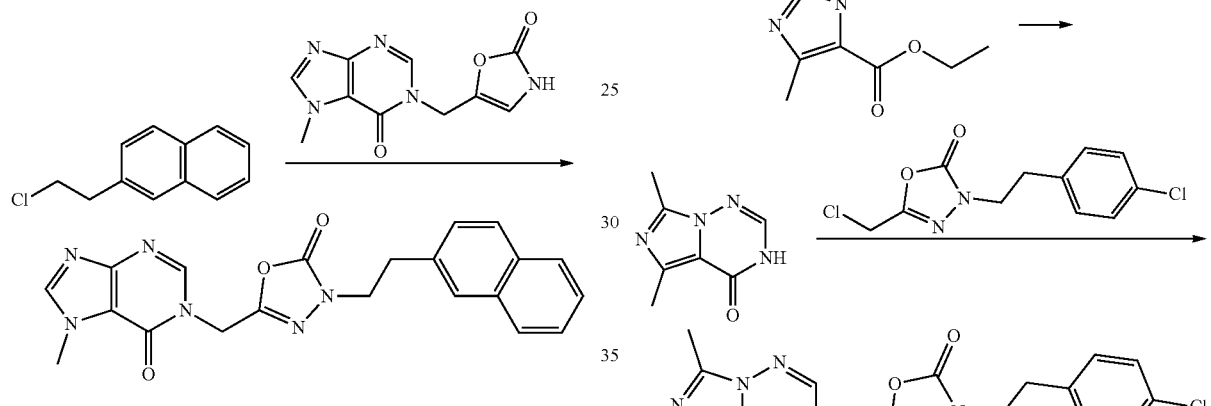

The solution of 7-methyl-1-[(5-oxo-4,5-dihydro-1,3,4-oxadiazol-2-yl)methyl]-6,7-dihydro-1H-purin-6-one (~0.2M, 2 mL, prepared according to Example Compound 1 step 3) was added dropwise into a mixture of 1-(2-chloroethyl)naphthalene (76.5 mg, 0.40 mmol), potassium carbonate (167 mg, 1.21 mmol), TBAI (15 mg, 0.04 mmol), and DMF (3 mL) at room temperature. The reaction was stirred for 12 h at 60° C. The reaction mixture was purified on a C18 silica gel column eluting with CH$_3$CN/H$_2$O (10 mmol/L NH$_4$HCO$_3$) increasing from 5% to 95% over 30 min. This resulted in the title compound (18.3 mg, 11%) as a white solid. LCMS [M+H$^+$] 403. $^1$H NMR (400 MHz, DMSO) δ 8.37 (s, 1H), 8.26 (s, 1H), 7.86 (dd, J=6.0, 3.4 Hz, 1H), 7.80 (dd, J=7.0, 4.4 Hz, 2H), 7.64 (s, 1H), 7.50-7.42 (m, 2H), 7.37 (dd, J=8.4, 1.6 Hz, 1H), 5.24 (s, 2H), 4.00 (s, 3H), 3.96 (t, J=6.9 Hz, 2H), 3.09 (t, J=6.8 Hz, 2H).

Example Compound 13: Preparation of 3-(4-chlorophenethyl)-5-((5,7-dimethyl-4-oxoimidazo[1,5-f][1,2,4]triazin-3(4H)-yl)methyl)-1,3,4-oxadiazol-2(3H)-one The overall Example Compound 13 reaction scheme is as follows:

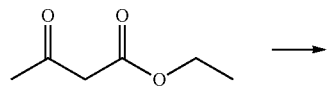

-continued

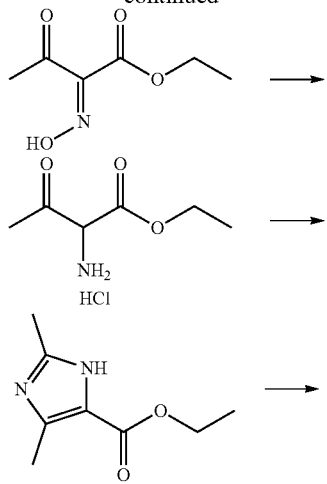

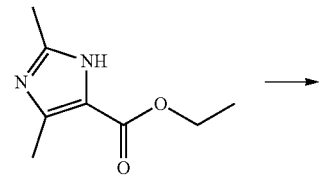

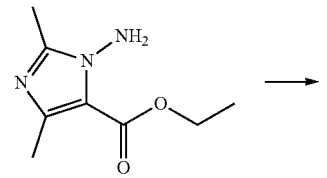

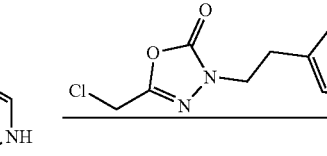

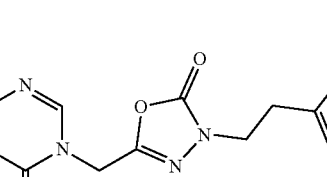

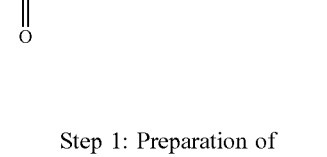

Step 1: Preparation of ethyl-2-(hydroxyimino)-3-oxobutanoate

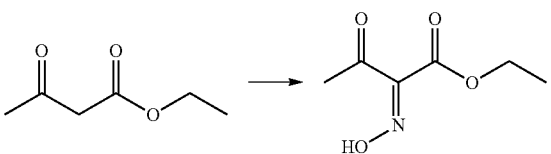

A solution of NaNO$_2$ (3.6 g, 52.18 mmol) in water (6 mL) was added dropwise into a mixture of ethyl 3-oxobutanoate (5.2 g, 39.96 mmol) and AcOH (6 mL) with stirring at 0° C. The resulting solution was stirred for 12 h at room temperature. The pH value of the solution was adjusted to 7 to 8 with sodium bicarbonate (saturated solution). The resulting solution was extracted with ethyl acetate, washed with brine, dried over anhydrous sodium sulfate and concentrated under vacuum. This resulted in the title compound (5.2 g, 82%) as colorless oil which was used for the next step without any further purification. LCMS [M+H$^+$] 160.

Step 2: Preparation of ethyl 2-amino-3-oxobutanoate hydrochloride

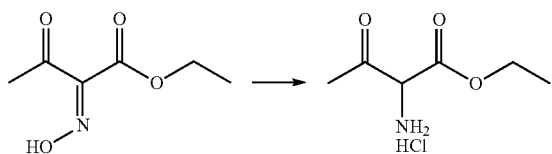

A mixture of ethyl-2-(hydroxyimino)-3-oxobutanoate (5.2 g, 32.68 mmol), ethanol (50 mL), concentrate hydrogen chloride (5 mL), and Pd/C (1 g, 10%) was stirred for 48 h at room temperature under hydrogen atmosphere. The solids were filtered out. The resulting mixture was concentrated under vacuum. This resulted in the title compound (5 g, 84%) as an off-white solid which was used for the next step without any further purification. LCMS [M+H$^+$] 146.

Step 3: Preparation of ethyl 2,4-dimethyl-1H-imidazole-5-carboxylate

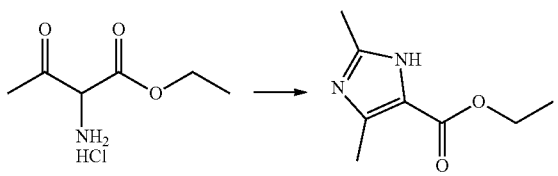

A solution of ethyl 2-amino-3-oxobutanoate hydrochloride (4.6 g, 25.33 mmol) in ethanol (10 mL) was added dropwise into a mixture of ethyl ethanecarboximidate hydrochloride (8.1 g, 65.54 mmol), ethanol (100 mL), and TEA (8.4 g, 83.01 mmol) with stirring at room temperature. The resulting solution was stirred for 12 h at room temperature. The resulting solution was diluted with ethyl acetate, washed with brine, dried over anhydrous sodium sulfate and concentrated under vacuum. The residue was purified on a silica gel column eluting with dichloromethane/methanol (10/1) to afford the title compound (1.3 g, 31%) as a light yellow solid. LCMS [M+H$^+$] 169.

Step 4: Preparation of ethyl 1-amino-2,4-dimethyl-1H-imidazole-5-carboxylate

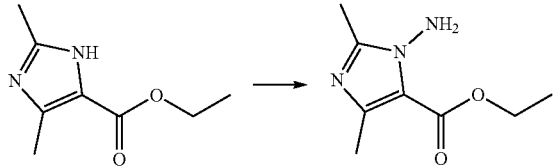

LiHMDS (8.5 mL, 1M in THF) was added dropwise into a mixture of ethyl 2,4-dimethyl-1H-imidazole-5-carboxylate (1.3 g, 7.73 mmol) and N,N-dimethylformamide (200 mL) with stirring at −10° C. in a dry ice bath under nitrogen. The resulting solution was stirred for 30 min at −10° C. To this was added amino diphenylphosphinate (2.2 g, 9.43 mmol) in portions at 0° C. The resulting solution was allowed to react, with stirring, for an additional 12 h at room temperature. The resulting solution was diluted with of water, extracted with ethyl acetate, washed with brine, dried over anhydrous sodium sulfate and concentrated under vacuum. The residue was purified by a silica gel column eluting with dichloromethane/methanol (10/1) to afford the title compound (1.0 g, 71%) as a light yellow solid. LCMS [M+H$^+$] 184.

Step 5: Preparation of 5,7-dimethyl-3H,4H-imidazo[4,3-f][1,2,4]triazin-4-one

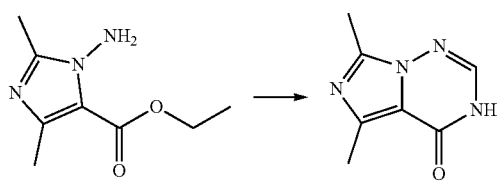

A mixture of ethyl 1-amino-2,4-dimethyl-1H-imidazole-5-carboxylate (1.0 g, 5.46 mmol), formamide (10 mL), and MeONa (3.0 mL, 5.4M in MeOH) was stirred for 1 h at 100° C. in an oil bath. The resulting solution was diluted with water. The pH value of the solution was adjusted to 5 with hydrogen chloride (1N). The solids were collected by filtration and dried under vacuum to afford 130 mg of white solid. The filtrate was purified on a C18 silica gel column eluting with CH$_3$CN/H$_2$O (10 mmol/L of NH$_4$HCO$_3$) increasing from 5% to 95% within 30 min. The fractions were collected and concentrated to afford 370 mg of white solid. This resulted in the title compound (total of 500 mg, 56%) as a white solid. LCMS [M+H$^+$] 165.

Step 6: Preparation of 3-(4-chlorophenethyl)-5-((5, 7-dimethyl-4-oxoimidazo[1,5-f][1,2,4]triazin-3 (4H)-yl)methyl)-1,3,4-oxadiazol-2(3H)-one

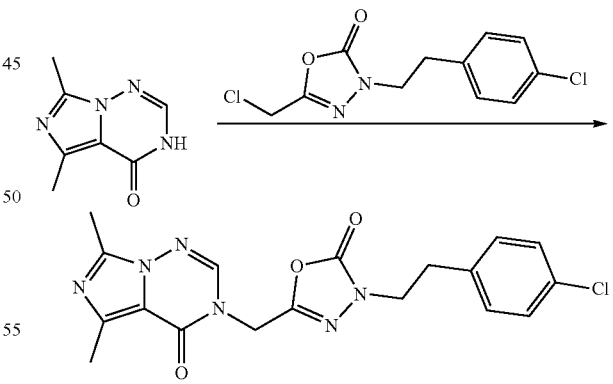

A mixture of 5,7-dimethyl-3H,4H-imidazo[4,3-f][1,2,4] triazin-4-one (60 mg, 0.37 mmol), 5-(chloromethyl)-3-[2-(4-chlorophenyl)ethyl]-2,3-dihydro-1,3,4-oxadiazol-2-one (120 mg, 0.44 mmol), potassium carbonate (153 mg, 1.11 mmol), TBAI (15 mg, 0.04 mmol), and N,N-dimethylformamide (5 mL) was stirred for 1 h at room temperature. The solids were filtered out. The resulting solution was purified on a C18 silica gel column eluting with CH$_3$CN/H$_2$O (10 mmol/L NH$_4$HCO$_3$) increasing from 5% to 95% over 30 min. This resulted in the title compound (40.8 mg, 28%) as a white solid. LCMS [M+H+] 401. ¹H NMR (400 MHz, DMSO-d6) δ 8.11 (s, 1H), 7.36-7.13 (m, 4H), 5.04 (s, 2H), 3.87 (t, J=6.8 Hz, 2H), 2.92 (t, J=6.8 Hz, 2H), 2.48 (s, 2H), 2.47 (s, 2H).

Example Compounds 14 and 15: Preparation of (S)-3-(2-(4-chlorophenyl)-2-fluoroethyl)-5-((7-methyl-6-oxo-6H-purin-1 (7H)-yl)methyl)-1,3,4-oxadiazol-2(3H)-one and (R)-3-(2-(4-chlorophenyl)-2-fluoroethyl)-5-((7-methyl-6-oxo-6H-purin-1 (7H)-yl)methyl)-1,3,4-oxadiazol-2(3H)-one The overall Example Compounds 14 and 15 reaction scheme is as follows:

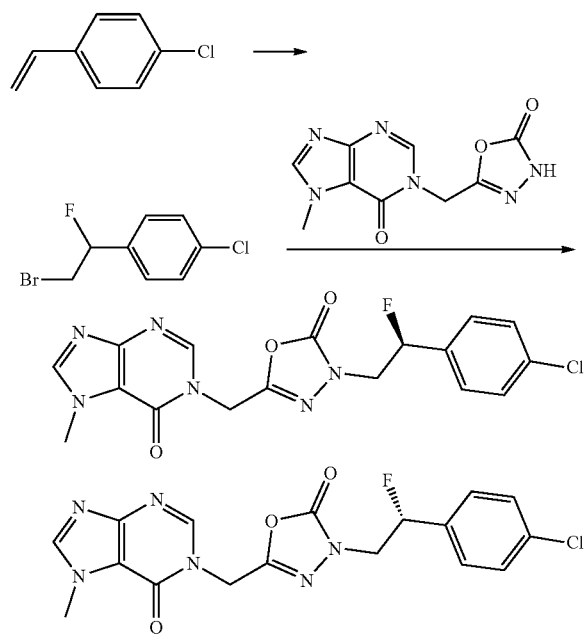

Step 1: Preparation of 1-(2-bromo-1-fluoroethyl)-4-chlorobenzene

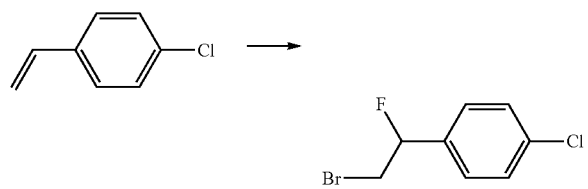

Et₃N.3HF (4.89 g, 30.33 mmol) was added dropwise into a mixture of 1-chloro-4-ethenylbenzene (3.00 g, 21.65 mmol), NBS (5.78 g, 32.47 mmol), and dichloromethane (30 mL) with stirring at 0° C. under nitrogen. The resulting solution was stirred for 1 overnight at room temperature. The resulting solution was diluted with ethyl acetate, washed with brine, dried over anhydrous sodium sulfate, and concentrated under vacuum. The residue was purified by a silica gel column eluting with petroleum ether to afford the title compound (2.0 g, 39%) as yellow oil.

Step 2: Preparation of (S)-3-(2-(4-chlorophenyl)-2-fluoroethyl)-5-((7-methyl-6-oxo-6H-purin-1(7H)-yl)methyl)-1,3,4-oxadiazol-2(3H)-one and (R)-3-(2-(4-chlorophenyl)-2-fluoroethyl)-5-((7-methyl-6-oxo-6H-purin-1 (7H)-yl)methyl)-1,3,4-oxadiazol-2(3H)-one

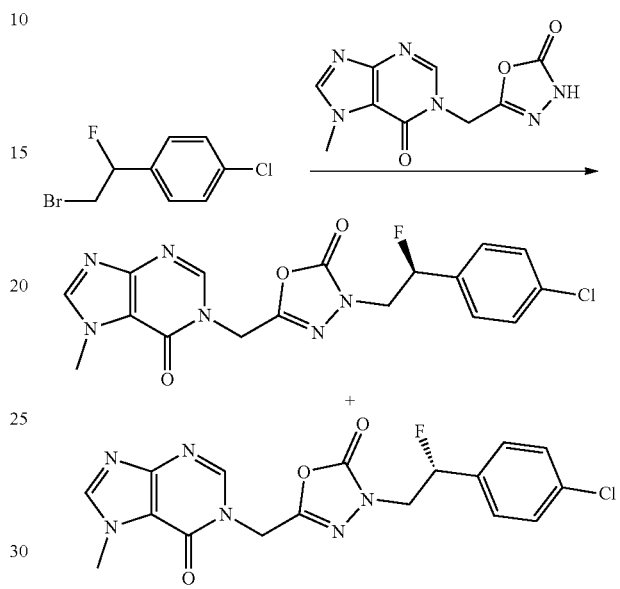

The solution of 7-methyl-1-[(5-oxo-4,5-dihydro-1,3,4-oxadiazol-2-yl)methyl]-6,7-dihydro-1H-purin-6-one (~0.2M, 6 mL, prepared according to Example Compound 1 step 3) was added dropwise into a mixture of 1-(2-bromo-1-fluoroethyl)-4-chlorobenzene (1.15 mg, 4.84 mmol), TBAI (45 mg, 0.12 mmol), potassium carbonate (1.0 g, 7.25 mmol), and N,N-dimethylformamide (4 mL) at room temperature. The mixture was stirred for 12 h at 60° C. The solids were filtered out. The resulting solution was purified on a C18 silica gel column eluting with CH₃CN/H₂O (10 mmol/L NH₄HCO₃) increasing from 5% to 95% over 30 min. This resulted in 15 mg of a racemic mixture. The product was then purified by Chiral-Prep-HPLC with the following conditions (Prep-HPLC-009): Column, Chiralpak IA, 2*25 cm, 5 um; mobile phase, Hex and ethanol (hold 50.0% ethanol—in 28 min); Detector, UV 220/254 nm.

This resulted in 3.9 mg of (S)-3-(2-(4-chlorophenyl)-2-fluoroethyl)-5-((7-methyl-6-oxo-6H-purin-1 (7H)-yl)methyl)-1,3,4-oxadiazol-2(3H)-one as a white solid. LCMS [M+H+] 405. $t_R$=4.63 min (Repaired IA, 0.46×10 cm, 5 μm, (Hex:DCM=5:1)(0.1% DEA):EtOH=50:50, 1.0 ml/min). ¹H NMR (400 MHz, CD₃CN) δ 8.09 (s, 1H), 7.91 (s, 1H), 7.45-7.39 (m, 4H), 8.86-5.72 (m, 1H), 5.11 (s, 2H), 4.20-4.10 (m, 1H), 4.05-3.93 (m, 4H).

This also resulted in 3.4 mg of (R)-3-(2-(4-chlorophenyl)-2-fluoroethyl)-5-((7-methyl-6-oxo-6H-purin-1 (7H)-yl)methyl)-1,3,4-oxadiazol-2(3H)-one as a white solid. LCMS [M+H+]405. $t_R$=6.69 min (Repaired IA, 0.46×10 cm, 5 μm, (Hex:DCM=5:1)(0.1% DEA):EtOH=50:50, 1.0 ml/min). ¹H NMR (400 MHz, CD₃CN) δ 8.09 (s, 1H), 7.91 (s, 1H), 7.45-7.39 (m, 4H), 8.86-5.72 (m, 1H), 5.11 (s, 2H), 4.20-4.10 (m, 1H), 4.05-3.93 (m, 4H).

Example Compound 16: Preparation of 3-(4-cyclopropylphenethyl)-5-((7-methyl-6-oxo-6H-purin-1(7H)-yl)methyl)-1,3,4-oxadiazol-2(3H)-one The overall Example Compound 16 reaction scheme is as follows:

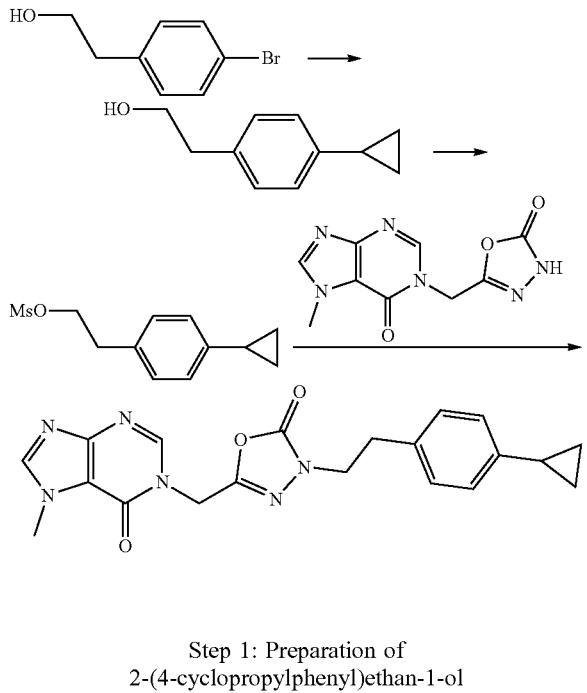

Step 1: Preparation of 2-(4-cyclopropylphenyl)ethan-1-ol

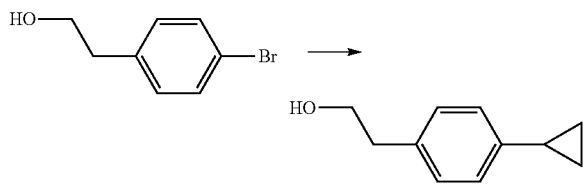

A mixture of 2-(4-bromophenyl)ethan-1-ol (1.00 g, 4.97 mmol), cyclopropylboronic acid (510 mg, 5.94 mmol), Pd(OAc)$_2$ (110 mg, 0.49 mmol), SPhos (610 mg, 1.49 mmol), K$_3$PO$_4$ (3.17 g, 14.93 mmol), dioxane (10 mL), and water (2 mL) was stirred for 16 h at 100° C. under nitrogen. The solids were filtered out. The resulting mixture was concentrated under vacuum. The residue was purified by a silica gel column eluting with ethyl acetate/petroleum ether (10:1) to afford the title compound (800 mg, 99%) as light yellow oil.

Step 2: Preparation of 2-(4-cyclopropylphenyl)ethyl methanesulfonate

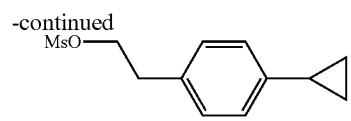

MsCl (254.20 mg, 2.22 mmol) was added dropwise into a mixture of 2-(4-cyclopropylphenyl)ethan-1-ol (300 mg, 1.85 mmol), TEA (561.38 mg, 5.55 mmol), and dichloromethane (4 mL) with stirring at 0° C. under nitrogen. The resulting solution was stirred for 10 min at 0° C. The reaction was then quenched by water, extracted with dichloromethane, washed with brine, dried over anhydrous sodium sulfate and concentrated under vacuum. This resulted in the title compound (200 mg, 45%) as yellow oil.

Step 3: Preparation of 3-(4-cyclopropylphenethyl)-5-((7-methyl-6-oxo-6H-purin-1(7H)-yl)methyl)-1,3,4-oxadiazol-2(3H)-one

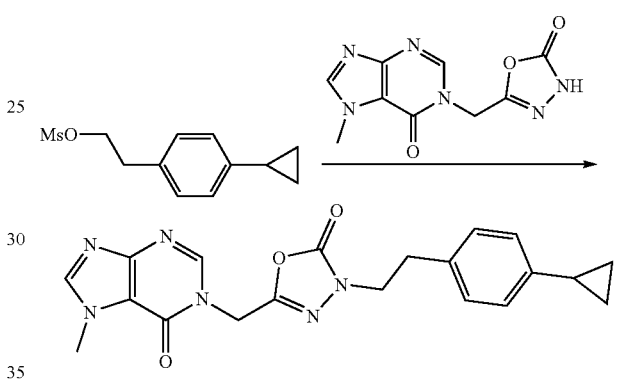

The solution of 7-methyl-1-[(5-oxo-4,5-dihydro-1,3,4-oxadiazol-2-yl)methyl]-6,7-dihydro-1H-purin-6-one (~0.2M, 2 mL, prepared according to Example Compound 1 step 3) was added dropwise into a mixture of 2-(4-cyclopropylphenyl)ethyl methanesulfonate (116 mg, 0.48 mmol), TBAI (15 mg, 0.04 mmol), potassium carbonate (167 mg, 1.21 mmol), and N,N-dimethylformamide (3 mL) at room temperature. The mixture was stirred for 2 h at 50° C. The solids were filtered out. The resulting solution was purified on a C18 silica gel column eluting with CH$_3$CN/H$_2$O (10 mmol/L NH$_4$HCO$_3$) increasing from 5% to 95% over 30 min. This resulted in the title compound (24.3 mg, 15%) as a white solid. LCMS [M+H$^+$] 393. $^1$H NMR (400 MHz, DMSO-d6) δ 8.35 (s, 1H), 8.24 (s, 1H), 7.04-6.91 (m, 4H), 5.23 (s, 2H), 3.99 (s, 3H), 3.81 (t, J=7.0 Hz, 2H), 2.85 (t, J=7.0 Hz, 2H), 1.86-1.82 (m, 1H), 0.93-0.86 (m, 2H), 0.61-0.59 (m, 2H).

Example Compound 17: Preparation of 3-(4-(dimethylamino)phenethyl)-5-((7-methyl-6-oxo-6H-purin-1(7H)-yl)methyl)-1,3,4-oxadiazol-2(3H)-one The overall Example Compound 17 reaction scheme is as follows:

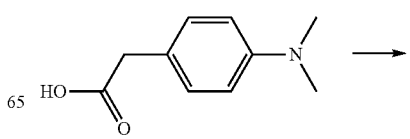

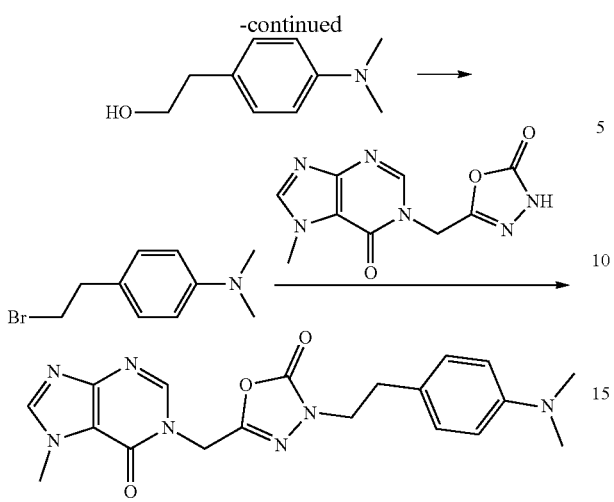

Step 1: Preparation of
2-[4-(dimethylamino)phenyl]ethan-1-ol

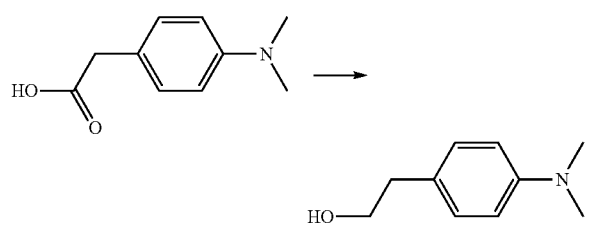

BH₃.THF (5 mL, 1M in THF) was added dropwise into a mixture of 2-[4-(dimethylamino)phenyl]acetic acid (300 mg, 1.67 mmol) and tetrahydrofuran (10 mL) at 0° C. under nitrogen. The resulting solution was stirred for 1 h at room temperature. The reaction was then quenched by water, extracted with ethyl acetate, washed with brine, dried over anhydrous sodium sulfate, and concentrated under vacuum. The residue was purified by a silica gel column eluting with ethyl acetate/petroleum ether (1:4) to afford the title compound (190 mg, 69%) as a white solid. LCMS [M+H⁺] 166.

Step 2: Preparation of
4-(2-bromoethyl)-N,N-dimethylaniline

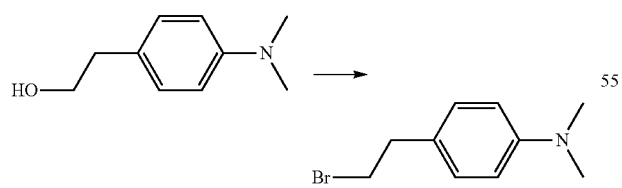

PPh₃ (79 mg, 0.30 mmol) in 0.5 mL of THF was added dropwise into a mixture of 2-[4-(dimethylamino)phenyl]ethan-1-ol (50 mg, 0.30 mmol), CBr₄ (149 mg, 0.45 mmol), and dichloromethane (3 mL) at 0° C. under nitrogen. The resulting solution was stirred for 2 h at room temperature. The resulting mixture was concentrated under vacuum. The residue was purified by a silica gel column eluting with ethyl acetate/petroleum ether (1:6) to afford the title compound (33 mg, 48%) as a white solid. LCMS [M+H⁺] 228.

Step 3: Preparation of 3-(4-(dimethylamino)phen-ethyl)-5-((7-methyl-6-oxo-6H-purin-1(7H)-yl)methyl)-1,3,4-oxadiazol-2(3H)-one

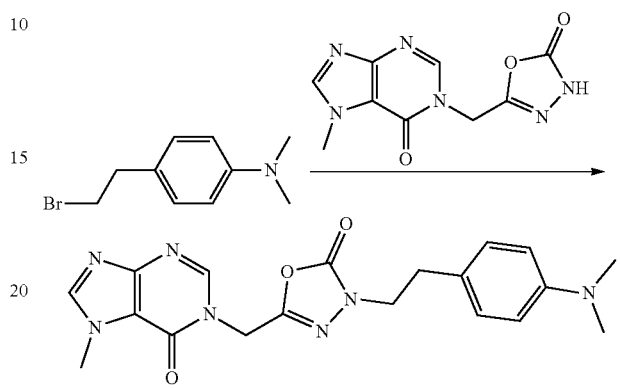

The solution of 7-methyl-1-[(5-oxo-4,5-dihydro-1,3,4-oxadiazol-2-yl)methyl]-6,7-dihydro-1H-purin-6-one (~0.2M, 0.75 mL, prepared according to Example Compound 1 step 3) was added dropwise into a mixture of 4-(2-bromoethyl)-N,N-dimethylaniline (33 mg, 0.15 mmol), potassium carbonate (40 mg, 0.29 mmol), TBAI (5 mg, 0.014 mmol), and N,N-dimethylformamide (4 mL) at room temperature. The mixture was stirred for 12 h at room temperature. The solids were filtered out. The resulting solution was purified on a C18 silica gel column eluting with CH₃CN/H₂O (10 mmol/L NH₄HCO₃) increasing from 5% to 95% over 30 min. This resulted in the title compound (7.1 mg, 12%) LCMS [M+H⁺] 396. ¹H NMR (400 MHz, DMSO-d6) δ 8.36 (s, 1H), 8.24 (s, 1H), 6.96 (d, J=8.2 Hz, 2H), 6.61-6.53 (m, 2H), 5.24 (s, 2H), 3.99 (s, 3H), 3.77 (t, J=7.0 Hz, 2H), 2.82 (s, 8H).

Example Compound 18: Preparation of 3-(4-(difluoromethyl)phenethyl)-5-((7-methyl-6-oxo-6H-purin-1(7H)-yl)methyl)-1,3,4-oxadiazol-2(3H)-one The overall Example Compound 18 reaction scheme is as follows:

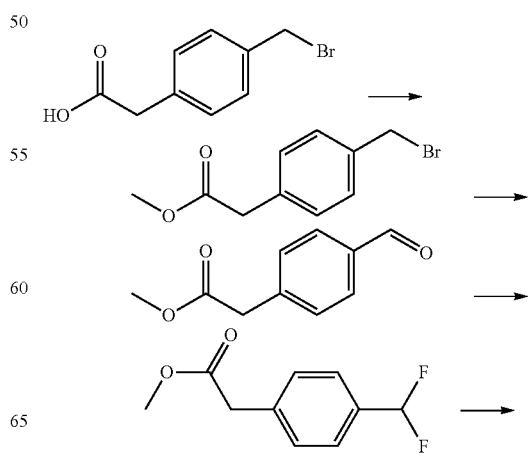

-continued

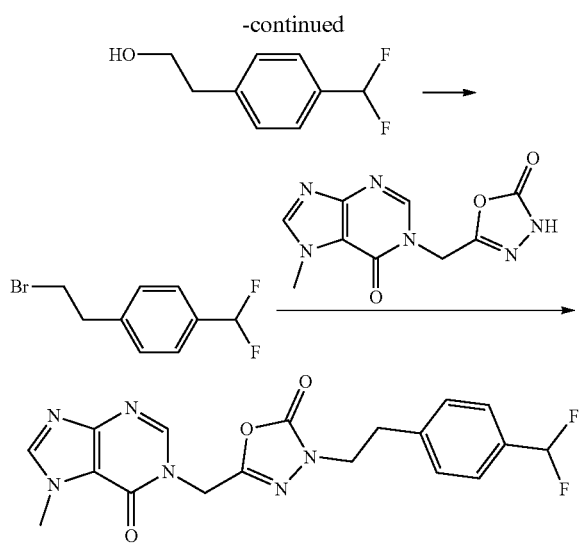

Step 1: Preparation of methyl 2-[4-(bromomethyl)phenyl]acetate

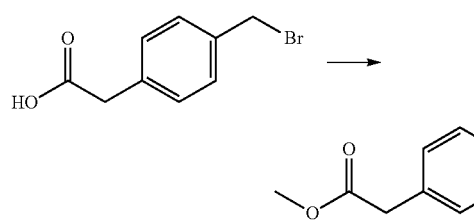

A mixture of 2-[4-(bromomethyl)phenyl]acetic acid (3 g, 13.10 mmol), methanol (100 mL), thionyl chloride (2.3 g, 19.33 mmol) was stirred for 3 h at 60° C. The resulting mixture was concentrated under vacuum. This resulted in the title compound (2.5 g, 79%) as colorless oil.

Step 2: Preparation of methyl 2-(4-formylphenyl)acetate

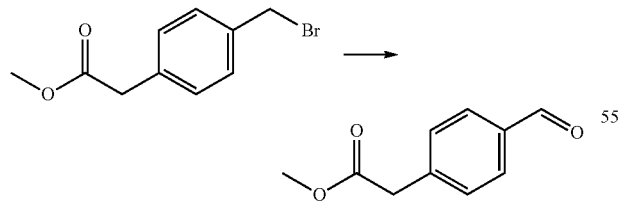

A mixture of methyl 2-[4-(bromomethyl)phenyl]acetate (2.5 g, 10.28 mmol), acetonitrile (50 mL), and NMO (3.6 g, 30.73 mmol) was stirred for 3 h at room temperature. The resulting mixture was concentrated under vacuum. The residue was purified by a silica gel column eluting with ethyl acetate/petroleum ether (1/3). This resulted in the title compound (1.2 g, 65%) as colorless oil.

Step 3: Preparation of methyl 2-[4-(difluoromethyl)phenyl]acetate

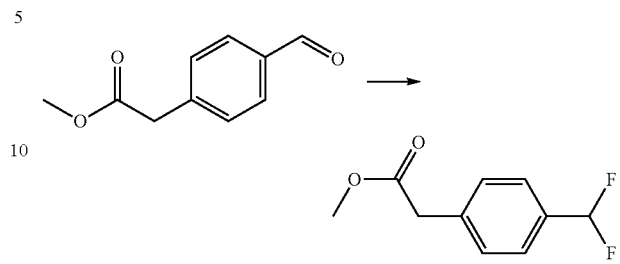

DAST (2.2 g, 13.65 mmol) was added dropwise into a mixture of methyl 2-(4-formylphenyl)acetate (1.2 g, 6.74 mmol) and dichloromethane (30 mL) at 0° C. under nitrogen. The resulting solution was stirred for 2 h at 0° C. The reaction was then quenched by water, extracted with ethyl acetate, washed with brine, dried over anhydrous sodium sulfate, and concentrated under vacuum. The residue was purified by a silica gel column eluting with ethyl acetate/petroleum ether (1/10). This resulted in the title compound (1 g, 74%) as colorless oil.

Step 4: Preparation of 2-[4-(difluoromethyl)phenyl]ethan-1-ol

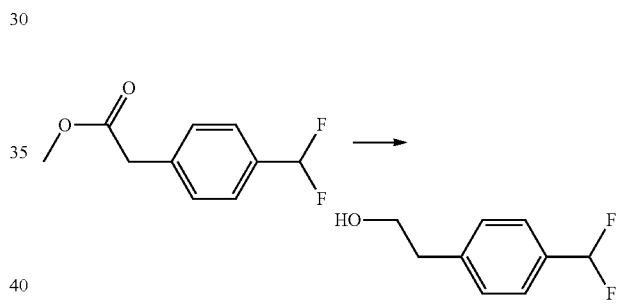

LiAlH$_4$ (380 mg, 10.01 mmol) was added in portions into a mixture of methyl 2-[4-(difluoromethyl)phenyl] acetate (1 g, 5.00 mmol) and tetrahydrofuran (20 mL) at 0° C. under nitrogen. The resulting solution was stirred for 1 h at 0° C. The reaction was then quenched by Na$_2$SO$_4$.10H$_2$O. The solids were filtered out. The resulting mixture was concentrated under vacuum. The residue was purified by a silica gel column eluting with ethyl acetate/petroleum ether (1/3). This resulted in title compound (800 mg, 93%) as colorless oil.

Step 5: Preparation of 1-(2-bromoethyl)-4-(difluoromethyl)benzene

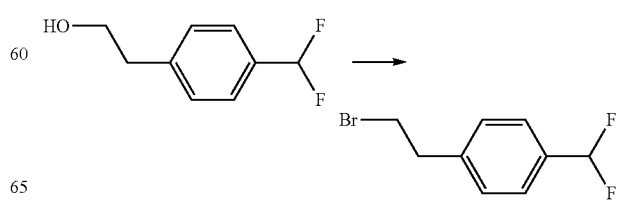

PPh₃ (1.8 g, 6.86 mmol) was added in portions into a mixture of 2-[4-(difluoromethyl)phenyl]ethan-1-ol (600 mg, 3.49 mmol), CBr₄ (3.2 g, 9.65 mmol), and dichloromethane (100 mL) at 0° C. under nitrogen. The reaction was stirred for 2 h at room temperature. The resulting mixture was concentrated under vacuum. The residue was purified by a silica gel column eluting with ethyl acetate/petroleum ether (1/10) to afford the title compound (500 mg, 61%) as colorless oil.

Step 6: Preparation of 3-(4-(difluoromethyl)phenethyl)-5-((7-methyl-6-oxo-6H-purin-1(7H)-yl)methyl)-1,3,4-oxadiazol-2(3H)-one

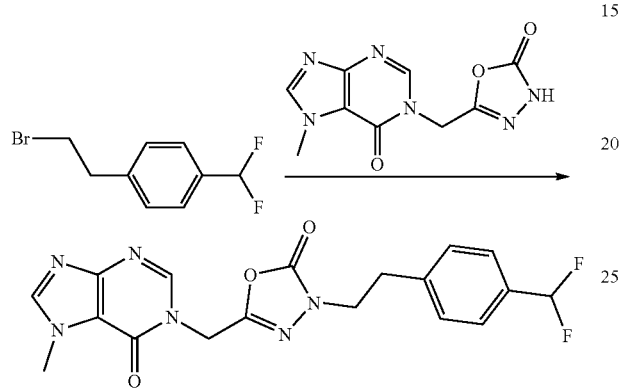

The solution of 7-methyl-1-[(5-oxo-4,5-dihydro-1,3,4-oxadiazol-2-yl)methyl]-6,7-dihydro-1H-purin-6-one (~0.2M, 4 mL, prepared according to Example Compound 1 step 3) was added dropwise into a mixture of 1-(2-bromoethyl)-4-(difluoromethyl)benzene (212 mg, 0.90 mmol), potassium carbonate (236 mg, 1.71 mmol), TBAI (31 mg, 0.08 mmol), and DMF (3 mL) at room temperature. The reaction was stirred for 4 h at room temperature. The reaction mixture was purified on a C18 silica gel column eluting with CH₃CN/H₂O (10 mmol/L NH₄HCO₃) increasing from 5% to 95% over 30 min. This resulted in the title compound (21.9 mg, 7%) as a white solid. LCMS [M+H⁺] 403. ¹H NMR (400 MHz, DMSO) δ 8.36 (s, 1H), 8.25 (s, 1H), 7.44 (d, J=7.8 Hz, 2H), 7.32 (d, J=7.9 Hz, 2H), 7.13-6.99 (m, 1H), 5.23 (s, 2H), 3.99 (s, 3H), 3.89 (t, J=6.9 Hz, 2H), 2.98 (t, J=6.9 Hz, 2H).

Example Compounds 19 and 20: Preparation of (S)-3-(2-(4-chlorophenyl)propyl)-5-((7-methyl-6-oxo-6H-purin-1(7H)-yl)methyl)-1,3,4-oxadiazol-2(3H)-one and (R)-3-(2-(4-chlorophenyl)propyl)-5-((7-methyl-6-oxo-6H-purin-1(7H)-yl)methyl)-1,3,4-oxadiazol-2(3H)-one The overall Example Compounds 19 and 20 reaction scheme is as follows:

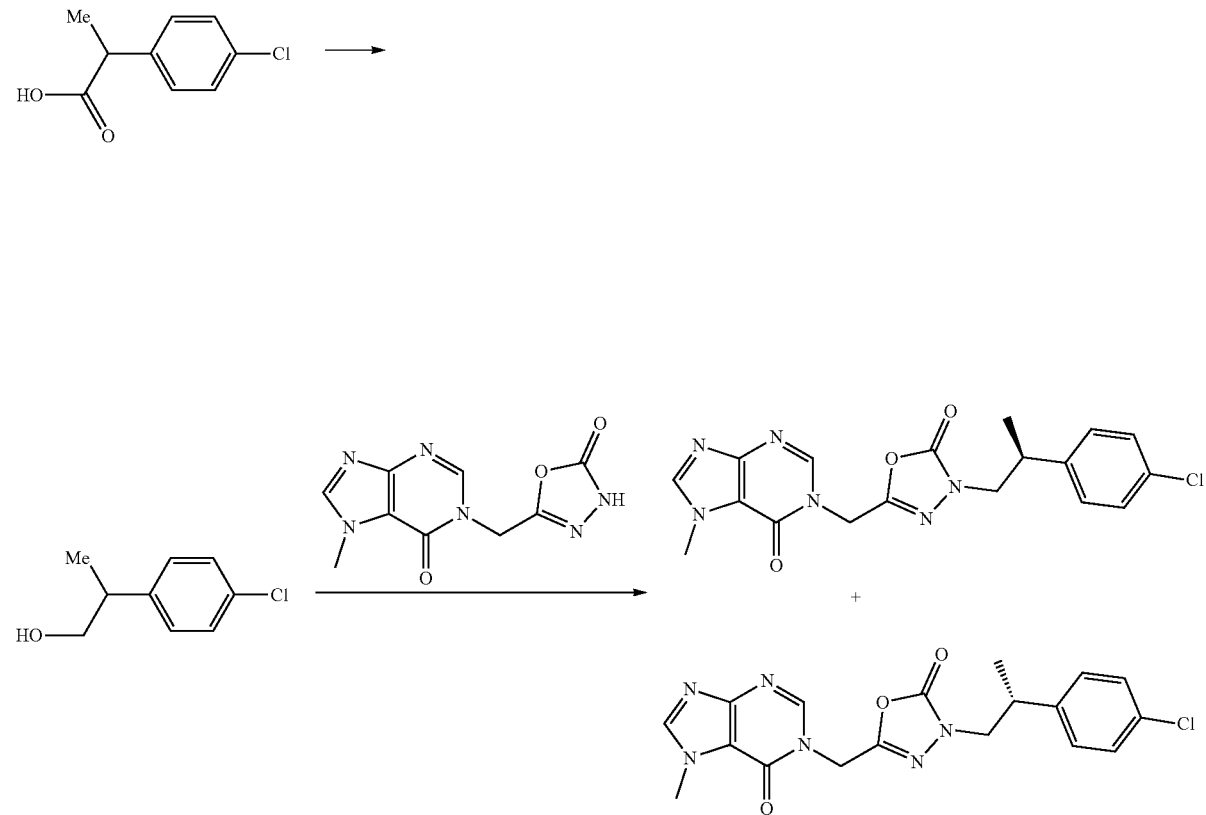

Step 1: Preparation of 2-(4-chlorophenyl)propan-1-ol

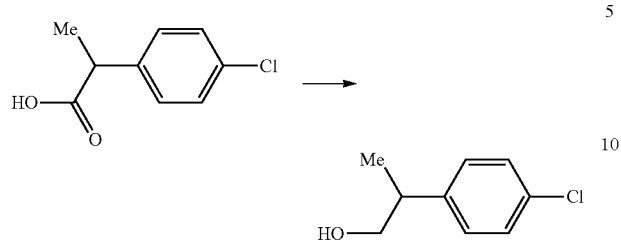

BH₃.THF (16.3 mL, 170.32 mmol) was added dropwise into a mixture of 2-(4-chlorophenyl)propanoic acid (1 g, 5.42 mmol) and tetrahydrofuran (50 mL) at 0° C. under nitrogen. The resulting solution was stirred for 2 h at 0° C. The reaction was then quenched by water, extracted with ethyl acetate, washed with brine, dried over anhydrous sodium sulfate, and concentrated under vacuum. This resulted in the title compound (800 mg, 87%) as colorless oil.

Step 2: Preparation of (S)-3-(2-(4-chlorophenyl)propyl)-5-((7-methyl-6-oxo-6H-purin-1(7H)-yl)methyl)-1,3,4-oxadiazol-2(3H)-one and (R)-3-(2-(4-chlorophenyl)propyl)-5-((7-methyl-6-oxo-6H-purin-1(7H)-yl)methyl)-1,3,4-oxadiazol-2(3H)-one

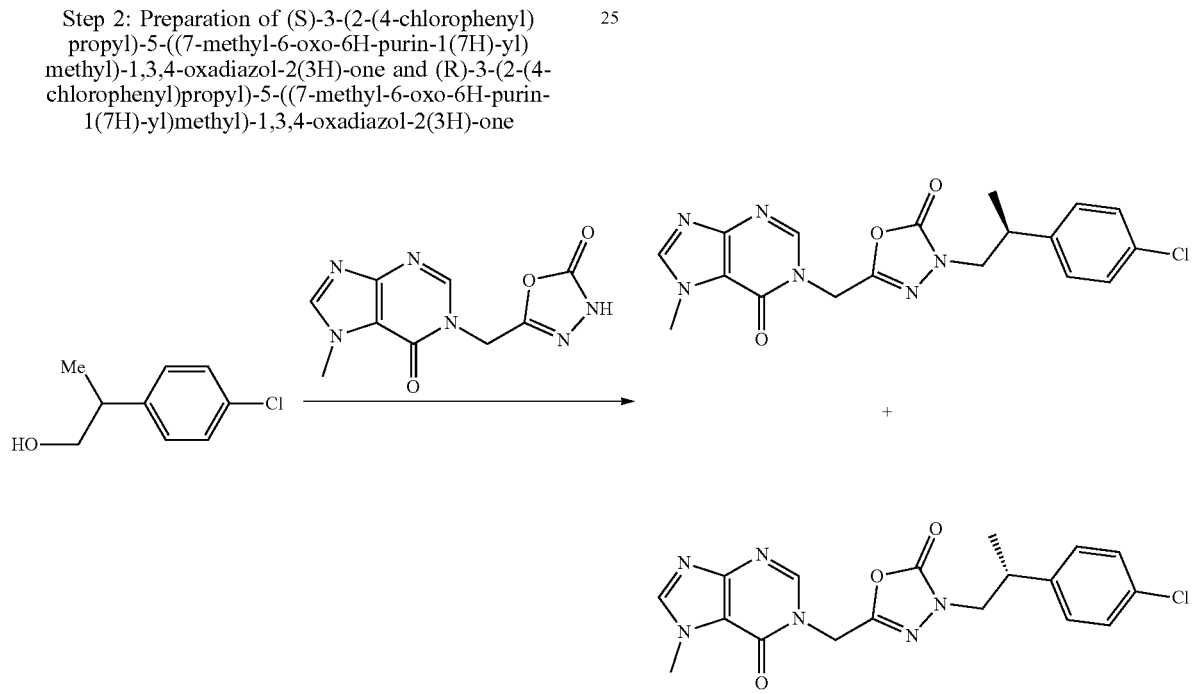

DIAD (238 mg, 1.18 mmol) was added dropwise into a mixture of 2-(4-chlorophenyl)propan-1-ol (200 mg, 1.17 mmol), 7-methyl-1-[(5-oxo-4,5-dihydro-1,3,4-oxadiazol-2-yl)methyl]-6,7-dihydro-1H-purin-6-one (146 mg, 0.59 mmol), N,N-dimethylformamide (10 mL), and PPh₃ (308 mg, 1.17 mmol) at 0° C. under nitrogen. The resulting solution was stirred for 1 h at room temperature. The resulting mixture was concentrated under vacuum. The reaction mixture was purified on a C18 silica gel column eluting with CH₃CN/H₂O (10 mmol/L NH₄HCO₃) increasing from 5% to 95% over 30 min.

This resulted in (S)-3-(2-(4-chlorophenyl)propyl)-5-((7-methyl-6-oxo-6H-purin-1(7H)-yl)methyl)-1,3,4-oxadiazol-2(3H)-one (31.5 mg, 13%) as a white solid. LCMS [M+H]⁺ 401. $t_R$=1.76 min (CHIRALPAK IA-3, 0.46×5 cm, 3 μm, 100% MeOH (0.1% DEA), 1.0 ml/min). ¹H NMR (300 MHz, DMSO-d6) δ 8.31 (s, 1H), 8.22 (s, 1H), 7.32-7.17 (m, 4H), 5.17 (s, 2H), 3.96 (s, 3H), 3.75 (d, J=7.6 Hz, 2H), 3.13 (q, J=7.4 Hz, 1H), 1.18 (d, J=7.0 Hz, 3H).

This further resulted in (R)-3-(2-(4-chlorophenyl)propyl)-5-((7-methyl-6-oxo-6H-purin-1(7H)-yl)methyl)-1,3,4-oxadiazol-2(3H)-one (34.4 mg, 15%) as a white solid. LCMS [M+H]⁺ 401. $t_R$=2.64 min (CHIRALPAK IA-3, 0.46×5 cm, 3 μm, 100% MeOH (0.1% DEA), 1.0 ml/min). ¹H NMR (300 MHz, DMSO-d6) δ 8.30 (s, 1H), 8.22 (s, 1H), 7.31-7.16 (m, 4H), 5.17 (s, 2H), 3.96 (s, 3H), 3.75 (d, J=7.5 Hz, 2H), 3.12 (q, J=7.2 Hz, 1H), 1.18 (d, J=7.0 Hz, 3H).

Example Compound 21: Preparation of 3-(2-(5-chlorothiophen-2-yl)ethyl)-5-((7-methyl-6-oxo-6H-purin-1(7H)-yl)methyl)-1,3,4-oxadiazol-2(3H)-one The overall Example Compound 21 reaction scheme is as follows:

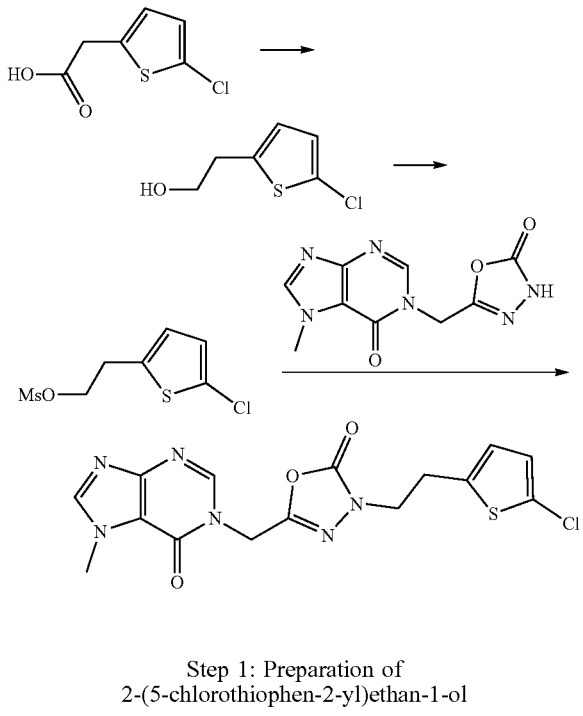

Step 1: Preparation of 2-(5-chlorothiophen-2-yl)ethan-1-ol

BH$_3$·THF (5.1 mL, 5.1 mmol) was added dropwise into a mixture of 2-(5-chlorothiophen-2-yl)acetic acid (300 mg, 1.7 mmol) in tetrahydrofuran (10 mL) at 0° C. under nitrogen. The resulting solution was stirred for 3 h at 0° C. in an ice/salt bath. The reaction was then quenched by water, extracted with ethyl acetate, washed with brine, dried over anhydrous sodium sulfate, and concentrated under vacuum. This resulted in the title compound (200 mg, 72%) as yellow oil which was used for the next step without any further purification. LCMS [M+H$^+$] 163.

Step 2: Preparation of 2-chloro-5-(2-chloroethyl)thiophene

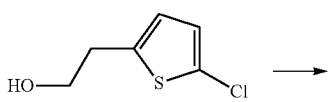

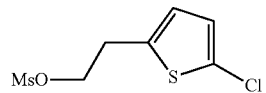

Methanesulfonyl chloride (211 mg, 1.85 mmol) was added dropwise into a mixture of 2-(5-chlorothiophen-2-yl)ethan-1-ol (200 mg, 1.23 mmol), triethylamine (249 mg, 2.46 mmol), and dichloromethane (5 mL) at 0° C. under nitrogen. The resulting solution was stirred for 30 min at 0° C. in an ice/salt bath. The resulting mixture was concentrated under vacuum. This resulted in the title compound (150 mg, 67%) as a white solid which was used for the next step without any further purification. LCMS [M+H$^+$] 241.

Step 3: Preparation of 3-(2-(5-chlorothiophen-2-yl)ethyl)-5-((7-methyl-6-oxo-6H-purin-1(7H)-yl)methyl)-1,3,4-oxadiazol-2(3H)-one

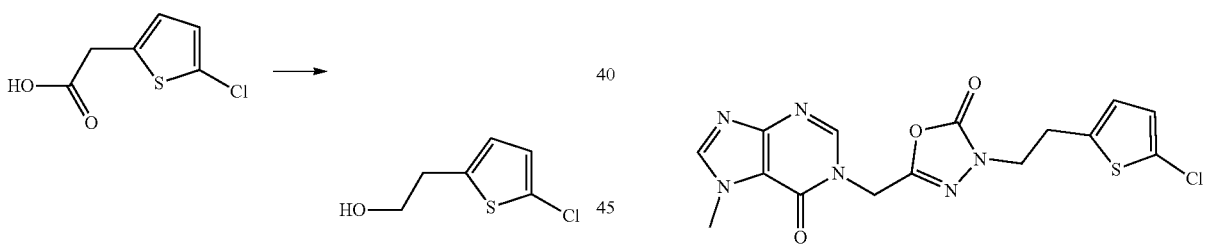

The solution of 7-methyl-1-[(5-oxo-4,5-dihydro-1,3,4-oxadiazol-2-yl)methyl]-6,7-dihydro-1H-purin-6-one (~0.2M, 2 mL, prepared according to Example Compound 1 step 3) was added dropwise into a mixture of 2-(5-chlorothiophen-2-yl)ethyl methanesulfonate (100.00 mg, 0.42 mmol), TBAI (15 mg, 0.04 mmol), potassium carbonate (167 mg, 1.21 mmol), and DMF (3 mL) at room temperature. The reaction was stirred for 1 h at 60° C. in an oil bath. The reaction mixture was purified on a C18 silica gel column eluting with CH$_3$CN/H$_2$O (10 mmol/L NH$_4$HCO$_3$) increasing from 5% to 95% over 30 min. This resulted in the title compound (36.5 mg, 22%) as a white solid. LCMS [M+H] 393. $^1$H NMR (400 MHz, CDCl$_3$) δ 8.07 (s, 1H), 7.87 (s, 1H), 6.74 (d, J=3.7 Hz, 1H), 6.62 (dt, J=3.7, 0.9 Hz, 1H), 5.13 (s, 2H), 4.12 (s, 3H), 3.94 (t, J=7.1 Hz, 2H), 3.16 (t, J=7.1 Hz, 2H).

95

Example Compound 22: Preparation of 1-([4-[2-(4-chlorophenyl)ethyl]-5-oxo-4,5-dihydro-1,3,4-oxadiazol-2-yl]methyl)-6-methyl-7-oxo-1H,6H,7H-pyrazolo[4,3-d]pyrimidine-3-carbonitrile The overall Example Compound 22 reaction scheme is as follows:

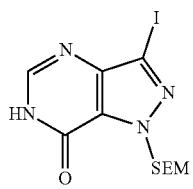

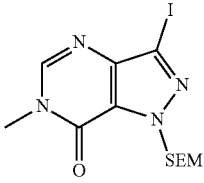

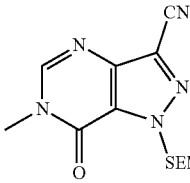

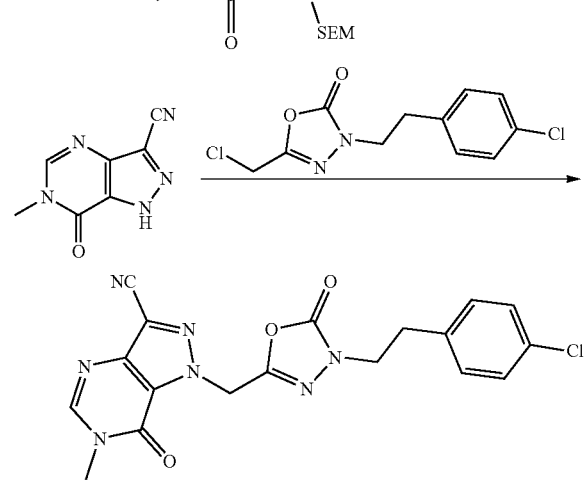

96

Step 1: Preparation of 3-iodo-1-[[2-(trimethylsilyl)ethoxy]methyl]-1H,6H,7H-pyrazolo[4,3-d]pyrimidin-7-one

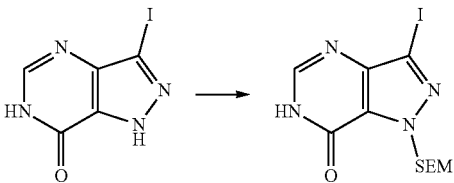 [SMILES: O=c1[nH]cnc2c(I)n[nH]c12 ; C[Si](C)(C)CCOCn1nc(I)c2nc[nH]c(=O)c21]

Sodium hydride (687 mg, 28.62 mmol) was added batchwise to a solution of 3-iodo-1H,6H,7H-pyrazolo[4,3-d]pyrimidin-7-one (1.5 g, 5.72 mmol) in N,N-dimethylformamide (50 mL) at 0° C. SEM-Cl (950 mg, 6.22 mmol) was added dropwise into the above solution after 20 min. The result solution was stirred for 12 h at room temperature and used for the next step without any further purification. LCMS [M+H$^+$] 393.

Step 2: Preparation of 3-iodo-6-methyl-1-[[2-(trimethylsilyl)ethoxy]methyl]-1H,6H,7H-pyrazolo[4,3-d]pyrimidin-7-one

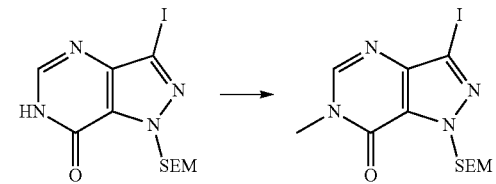 [SMILES: C[Si](C)(C)CCOCn1nc(I)c2nc[nH]c(=O)c21 ; Cn1cnc2c(I)nn(COCC[Si](C)(C)C)c2c1=O]

Sodium hydride (60 mg 2.50 mmol) was added into a solution of 3-iodo-1-[[2-(trimethylsilyl)ethoxy]methyl]-1H,6H,7H-pyrazolo[4,3-d]pyrimidin-7-one (~0.11M in DMF, 50 mL, prepared from step 1) at 0° C. After 20 min CH$_3$I (430 mg, 3.02 mmol) was added dropwise and the resulting mixture was stirred for 3 h at room temperature. The reaction solution was purified on a C18 silica gel column eluting with CH$_3$CN/H$_2$O (10 mmol/L NH$_4$HCO$_3$, 5% to 95%, over 30 min). This resulted in the title compound (250 mg, 24%) as a white solid. LCMS [M+H$^+$] 407.

Step 3: Preparation of 6-methyl-7-oxo-1-[[2-(trimethylsilyl)ethoxy]methyl]-1H,6H,7H-pyrazolo[4,3-d]pyrimidine-3-carbonitrile

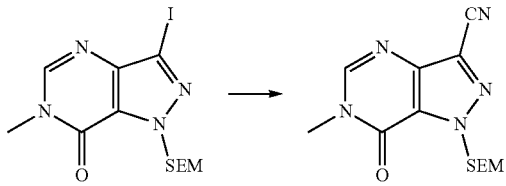 [SMILES: Cn1cnc2c(I)nn(COCC[Si](C)(C)C)c2c1=O ; Cn1cnc2c(C#N)nn(COCC[Si](C)(C)C)c2c1=O]

A mixture of 3-iodo-6-methyl-1-[[2-(trimethylsilyl)ethoxy]methyl]-1H,6H,7H-pyrazolo[4,3-d]pyrimidin-7-one (260 mg, 0.64 mmol), Zn(CN)$_2$ (148 mg, 1.26 mmol), Pd$_2$(dba)$_3$.CHCl$_3$ (66 mg, 0.06 mmol), dppf (71 mg, 0.13 mmol), and N,N-dimethylformamide (5 mL) was irradiated with microwave radiation for 1 h at 100° C. under nitrogen. The solids were filtered out. The filtrate was purified on a C18 silica gel column eluting with CH₃CN/H₂O (10 mmol/L NH₄HCO₃, 5% to 95%, over 30 min). This resulted in the title compound (150 mg, 77%) as a white solid. LCMS [M+H⁺] 306.

Step 4: Preparation of 6-methyl-7-oxo-1H,6H,7H-pyrazolo[4,3-d]pyrimidine-3-carbonitrile

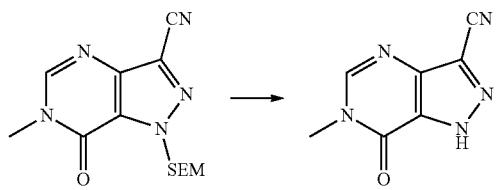 [SMILES: Cn1cnc2c(C#N)nn(COCC[Si](C)(C)C)c2c1=O ; Cn1cnc2c(C#N)n[nH]c2c1=O]

A mixture of 6-methyl-7-oxo-1-[[2-(trimethylsilyl)ethoxy]methyl]-1H,6H,7H-pyrazolo[4,3-d]pyrimidine-3-carbonitrile (120 mg, 0.39 mmol) and trifluoroacetic acid (3 mL) was stirred for 18 h at 60° C. The resulting mixture was concentrated under vacuum. This resulted in the title compound (60 mg, 87%) as a white solid. LCMS [M+H⁺] 176.

Step 5: Preparation of 1-([4-[2-(4-chlorophenyl)ethyl]-5-oxo-4,5-dihydro-1,3,4-oxadiazol-2-yl]methyl)-6-methyl-7-oxo-1H,6H,7H-pyrazolo[4,3-d]pyrimidine-3-carbonitrile

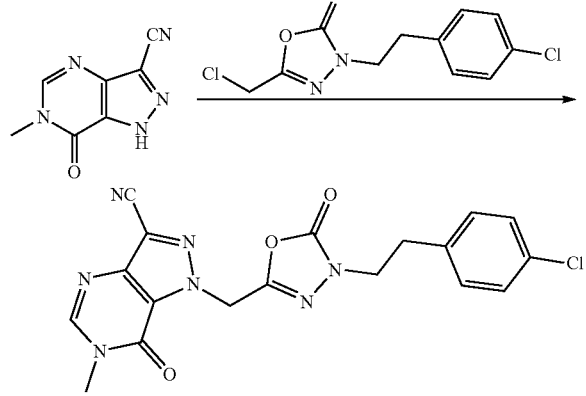

A mixture of 5-(chloromethyl)-3-[2-(4-chlorophenyl)ethyl]-2,3-dihydro-1,3,4-oxadiazol-2-one (93 mg, 0.34 mmol), 6-methyl-7-oxo-1H,6H,7H-pyrazolo[4,3-d]pyrimidine-3-carbonitrile (60 mg, 0.34 mmol), potassium carbonate (95 mg, 0.68 mmol), TBAI (6 mg, 0.02 mmol), and N,N-dimethylformamide (5 mL) was stirred for 3 h at room temperature. The reaction mixture was purified on a C18 silica gel column eluting with CH₃CN/H₂O (10 mmol/L NH₄HCO₃, 5% to 95%, over 30 min). This resulted in the title compound (36.6 mg, 26%) as a white solid. LCMS [M+H⁺] 412. ¹H NMR (300 MHz, DMSO-d₆) δ 8.47 (s, 1H), 7.30-7.17 (m, 4H), 5.91 (s, 2H), 3.90-3.85 (m, 2H), 3.55 (s, 3H), 2.94-2.90 (m, 3H).

Example Compound 23: Preparation of 6-([4-[2-(4-chlorophenyl)ethyl]-5-oxo-4,5-dihydro-1,3,4-oxadiazol-2-yl]methyl)-1-methyl-7-oxo-1H,3aH,6H,7H,7aH-pyrazolo[4,3-d]pyrimidine-3-carbonitrile The overall Example Compound 23 reaction scheme is as follows:

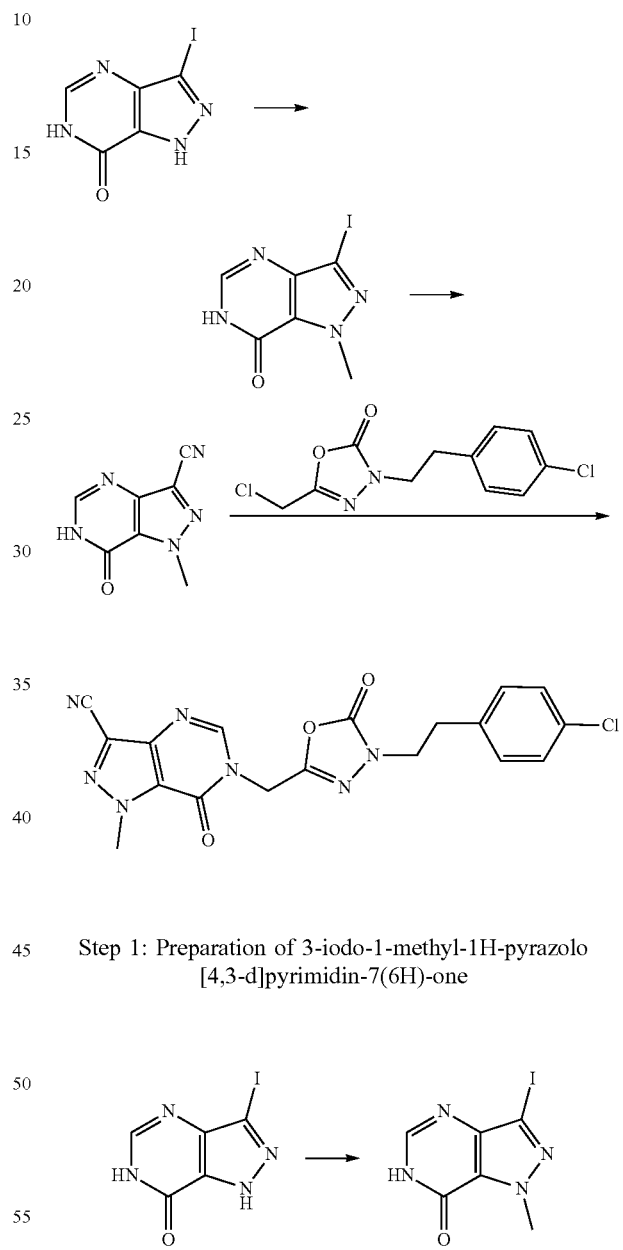

Step 1: Preparation of 3-iodo-1-methyl-1H-pyrazolo[4,3-d]pyrimidin-7(6H)-one

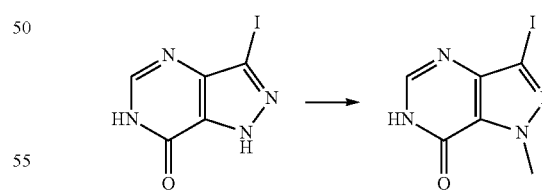

A mixture of 3-iodo-1H,6H,7H-pyrazolo[4,3-d]pyrimidin-7-one (2.2 g, 8.39 mmol), N,N-dimethylformamide (50 mL), potassium carbonate (2.3 g, 16.64 mmol), and CH₃I (1.2 g, 8.45 mmol) was stirred for 3 h at room temperature. The solids were filtered out. The filtrate was purified on a C18 silica gel column eluting with CH₃CN/H₂O (10 mmol/L NH₄HCO₃, 5% to 95%, over 30 min). This resulted in the title compound (1 g, 43%) as a white solid. LCMS [M+H⁺] 277.

Step 2: Preparation of 1-methyl-7-oxo-6,7-dihydro-1H-pyrazolo[4,3-d]pyrimidine-3-carbonitrile

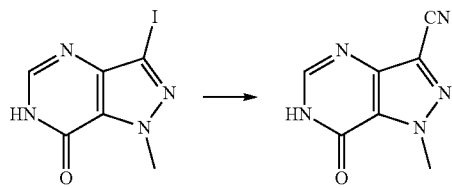

A mixture of 3-iodo-1-methyl-1H-pyrazolo[4,3-d]pyrimidin-7(6H)-one (300 mg, 1.08 mmol), Zn(CN)$_2$ (250 mg, 2.13 mmol), Pd$_2$(dba)$_3$CHCl$_3$ (112 mg, 0.11 mmol), dppf (120 mg, 0.22 mmol), and N,N-dimethylformamide (5 mL) was irradiated with microwave radiation for 1 h at 100° C. under nitrogen. The solids were filtered out. The filtrate was purified on a C18 silica gel column eluting with CH$_3$CN/H$_2$O (10 mmol/L NH$_4$HCO$_3$, 5% to 95%, over 30 min). This resulted in the title compound (40 mg, 21%) as a white solid. LCMS [M+H$^+$] 176.

Step 3: Preparation of 6-([4-[2-(4-chlorophenyl)ethyl]-5-oxo-4,5-dihydro-1,3,4-oxadiazol-2-yl]methyl)-1-methyl-7-oxo-1H,3aH,6H,7H,7aH-pyrazolo[4,3-d]pyrimidine-3-carbonitrile

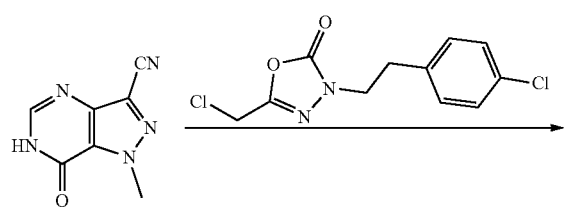

A mixture of 5-(chloromethyl)-3-[2-(4-chlorophenyl)ethyl]-2,3-dihydro-1,3,4-oxadiazol-2-one (62 mg, 0.23 mmol), 1-methyl-7-oxo-6,7-dihydro-1H-pyrazolo[4,3-d]pyrimidine-3-carbonitrile (40 mg, 0.23 mmol), potassium carbonate (63 mg, 0.46 mmol), TBAI (4 mg, 0.01 mmol), and N,N-dimethylformamide (5 mL) was stirred for 2 h at room temperature. The reaction mixture was purified on a C18 silica gel column eluting with CH$_3$CN/H$_2$O (10 mmol/L NH$_4$HCO$_3$, 5% to 95% over 30 min). This resulted in the title compound (34 mg, 36%) as a white solid. LCMS [M+H$^+$] 412. $^1$H NMR (300 MHz, DMSO-d$_6$) δ 8.46 (s, 1H), 7.30-7.19 (m, 4H), 5.25 (s, 2H), 4.30 (s, 3H), 3.88-3.85 (m, 2H), 2.93-2.90 (m, 2H).

Example Compound 24: Preparation of 7-methyl-1-([5-oxo-4-[2-(3-phenylphenyl)ethyl]-4,5-dihydro-1,3,4-oxadiazol-2-yl]methyl)-6,7-dihydro-1H-purin-6-one The overall Example Compound 24 reaction scheme is as follows:

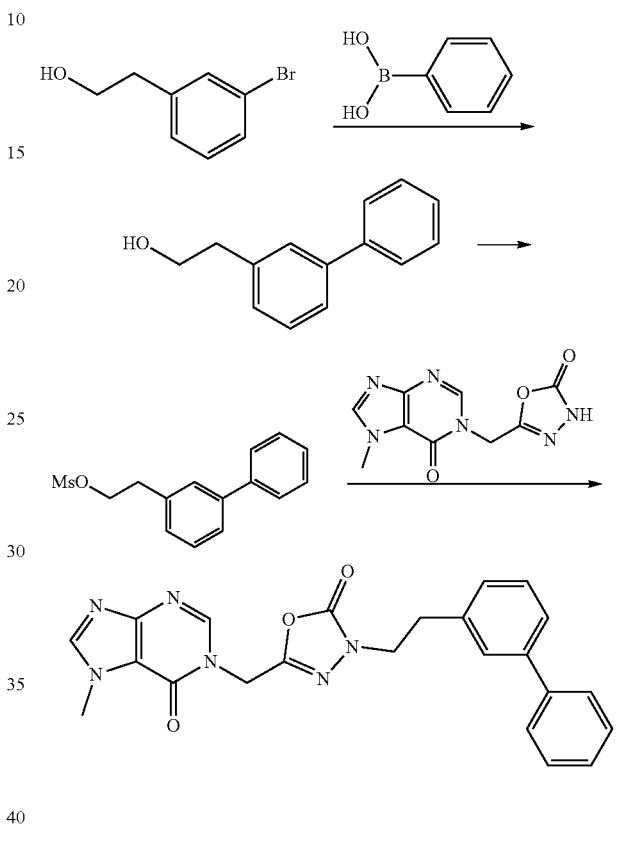

Step 1: Preparation of 2-(3-phenylphenyl)ethan-1-ol

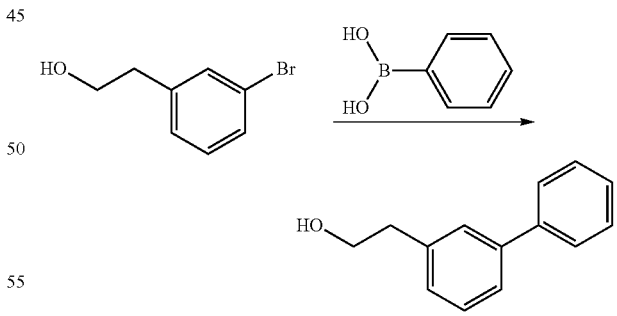

A mixture of 2-(4-bromophenyl)ethan-1-ol (1 g, 4.97 mmol), phenylboronic acid (915 mg, 7.50 mmol), Pd(dppf)Cl$_2$ (366 mg, 0.50 mmol), potassium carbonate (1.38 g, 9.98 mmol), and dioxane (20 mL) was stirred for 12 h at 100° C. under nitrogen. The solids were filtered out. The resulting solution was concentrated under vacuum. The residue was purified on a silica gel column eluting with ethyl acetate/petroleum ether (1/3) to afford the title compound (500 mg, 51%) as a white solid.

Step 2: Preparation of 2-(3-phenylphenyl)ethyl methanesulfonate

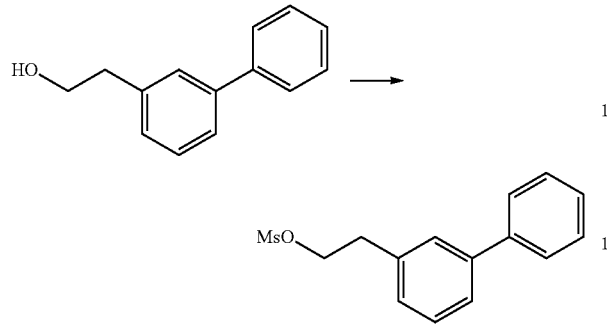

MsCl (170 mg, 1.48 mmol) was added dropwise into a mixture of 2-(3-phenylphenyl)ethan-1-ol (200 mg, 1.01 mmol), dichloromethane (3 mL), and triethylamine (204 mg, 2.02 mmol). The resulting solution was stirred for 30 min at 0° C. The reaction mixture was concentrated under vacuum. This resulted in the title compound (280 mg, crude) as a white solid.

Step 3: Preparation of 7-methyl-1-([5-oxo-4-[2-(3-phenylphenyl)ethyl]-4,5-dihydro-1,3,4-oxadiazol-2-yl]methyl)-6,7-dihydro-1H-purin-6-one

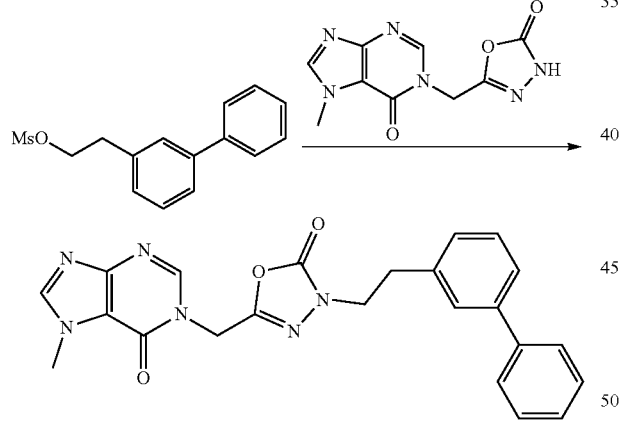

A mixture of 7-methyl-1-[(5-oxo-4,5-dihydro-1,3,4-oxadiazol-2-yl)methyl]-6,7-dihydro-1H-purin-6-one (50 mg, 0.20 mmol), 2-(3-phenylphenyl)ethyl methanesulfonate (84 mg, 0.30 mmol), potassium carbonate (56 mg, 0.41 mmol), TBAI (8 mg, 0.02 mmol), and N,N-dimethylformamide (1.5 mL) was stirred for 3 h at 50° C. The reaction mixture was purified on a C18 silica gel column eluting with $CH_3CN$/$H_2O$ (10 mmol/L $NH_4HCO_3$, 5% to 95% over 30 min). This resulted in the title compound (31.2 mg, 36%) as a white solid. LCMS [M+H$^+$] 429. $^1$H NMR (400 MHz, DMSO-$d_6$) δ 8.35 (s, 1H), 8.24 (s, 1H), 7.67-7.59 (m, 2H), 7.54-7.29 (m, 6H), 7.20-7.13 (m, 1H), 5.23 (s, 2H), 3.95-3.92 (m, 5H), 3.01-2.98 (t, J=7.1 Hz, 2H).

Example Compound 25: Preparation of 1-([4-[2-(4-bromo-3-chlorophenyl)ethyl]-5-oxo-4,5-dihydro-1,3,4-oxadiazol-2-yl]methyl)-7-methyl-6,7-dihydro-1H-purin-6-one The overall Example Compound 25 reaction scheme is as follows:

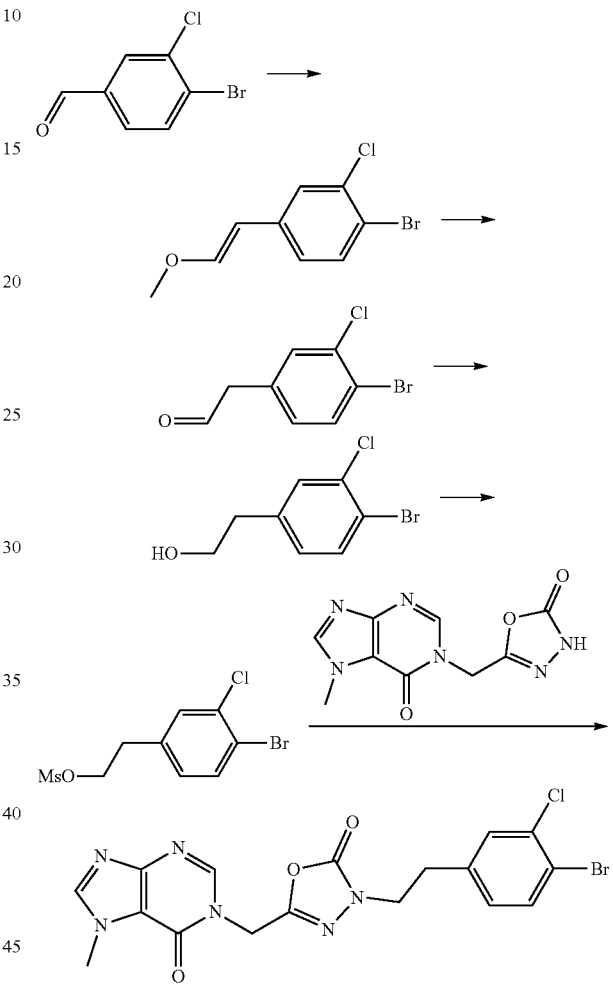

Step 1: Preparation of 1-bromo-2-chloro-4-[(E)-2-methoxyethenyl]benzene

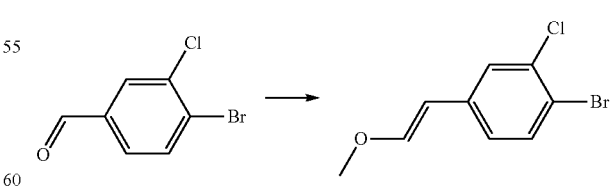

A mixture of t-BuOK (68 mL, 605.99 mmol), (methoxymethyl)triphenylphosphanium chloride (23.5 g, 68.55 mmol), and THF (200 mL) was stirred for 1 h in at 0° C. 4-Bromo-3-chlorobenzaldehyde (10 g, 45.57 mmol) was added dropwise into the above solution at 0° C. The resulting solution was stirred for 12 h at room temperature. The reaction was then quenched by water, extracted with petroleum ether, dried over anhydrous sodium sulfate, and concentrated under vacuum. The residue was purified on a silica gel column eluting with ethyl acetate/petroleum ether (1/100) to afford the title compound (9 g, 80%) as light yellow oil.

Step 2: Preparation of 2-(4-bromo-3-chlorophenyl)acetaldehyde

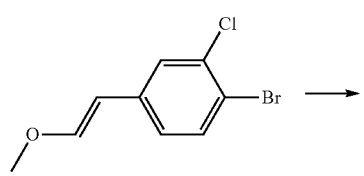

A mixture of 1-bromo-2-chloro-4-[(E)-2-methoxyethenyl]benzene (1 g, 4.04 mmol), tetrahydrofuran (20 mL) and hydrogen chloride (10%, 4 mL) was stirred for 2 h at room temperature. The resulting solution was diluted with ethyl acetate, washed with brine, dried over anhydrous sodium sulfate, and concentrated under vacuum. This resulted in the title compound (0.8 g, 85%) as light yellow oil.

Step 3: Preparation of 2-(4-bromo-3-chlorophenyl)ethan-1-ol

A mixture of 2-(4-bromo-3-chlorophenyl)acetaldehyde (800 mg, 3.43 mmol), methanol (10 mL), and NaBH$_4$ (124 mg, 3.28 mmol) was stirred for 10 min at 0° C. The reaction was then quenched by water, extracted with ethyl acetate, washed with brine, dried over anhydrous sodium sulfate, and concentrated under vacuum. The residue was purified by a silica gel column eluting with ethyl acetate/petroleum ether (1:10) to afford the title compound (0.5 g, 62%) as colorless oil.

Step 4: Preparation of 2-(4-bromo-3-chlorophenyl)ethyl methanesulfonate

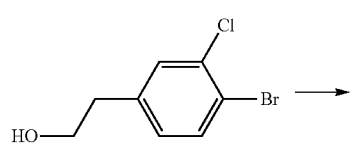

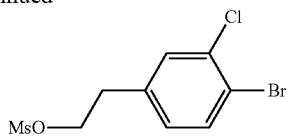

MsCl (37 mg, 0.32 mmol) was added into a mixture of 2-(4-bromo-3-chlorophenyl)ethan-1-ol (50 mg, 0.21 mmol), dichloromethane (4 mL), and TEA (44 mg, 0.43 mmol). The resulting solution was stirred for 30 min at 0° C. The resulting mixture was concentrated under vacuum. This resulted in the title compound (50 mg, 75%) as a white solid.

Step 5: Preparation of 1-([4-[2-(4-bromo-3-chlorophenyl)ethyl]-5-oxo-4,5-dihydro-1,3,4-oxadiazol-2-yl]methyl)-7-methyl-6,7-dihydro-1H-purin-6-one

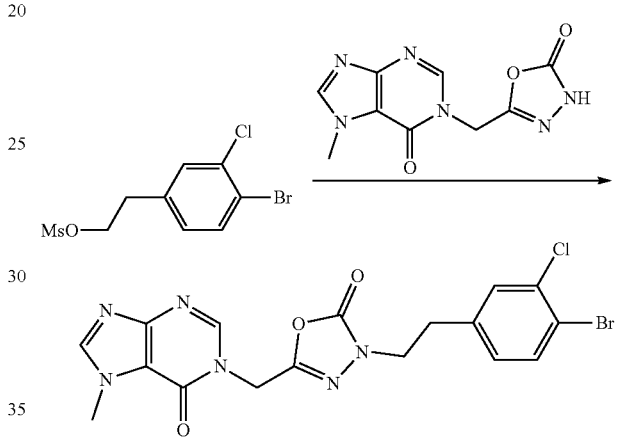

A mixture of 2-(4-bromo-3-chlorophenyl)ethyl methanesulfonate (50 mg, 0.16 mmol), 7-methyl-1-[(5-oxo-4,5-dihydro-1,3,4-oxadiazol-2-yl)methyl]-6,7-dihydro-1H-purin-6-one (40 mg, 0.16 mmol), potassium carbonate (45 mg, 0.33 mmol), TBAI (3 mg, 0.01 mmol), and N,N-dimethylformamide (3 mL) was stirred for 3 h at 50° C. The reaction mixture was purified on a C18 silica gel column eluting with CH$_3$CN/H$_2$O (10 mmol/L NH$_4$HCO$_3$, from 5% to 95% over 30 min). This resulted in the title compound (15.9 mg, 21%) as a white solid. LCMS [M+H$^+$] 466. $^1$H NMR (300 MHz, DMSO-d6) δ 8.35 (s, 1H), 8.24 (s, 1H), 7.61 (d, J=8.2 Hz, 1H), 7.49 (d, J=2.1 Hz, 1H), 7.09-7.02 (m, 1H), 5.22 (s, 2H), 3.99 (s, 3H), 3.90-3.87 (t, J=6.7 Hz, 2H), 2.93-2.89 (t, J=6.7 Hz, 2H), 1.25 (s, 1H).

Example Compound 26: Preparation of 7-([4-[2-(4-chlorophenyl)ethyl]-5-oxo-4,5-dihydro-1,3,4-oxadiazol-2-yl]methyl)-1-methyl-6,7-dihydro-1H-purin-6-one The overall Example Compound 26 reaction scheme is as follows:

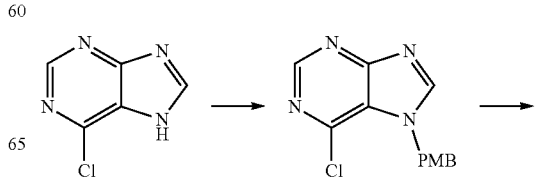

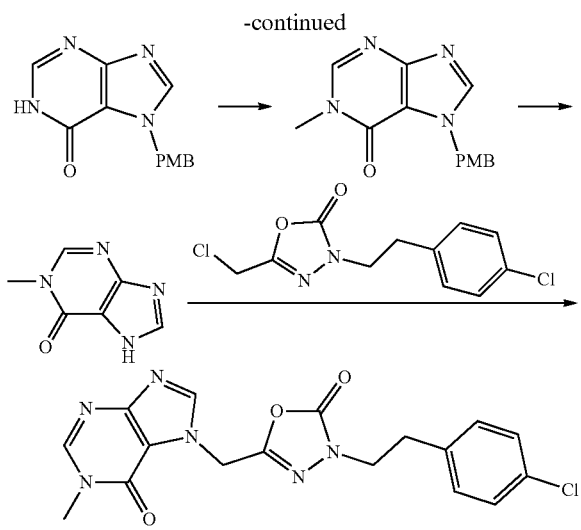

Step 1: Preparation of 6-chloro-7-[(4-methoxyphenyl)methyl]-7H-purine

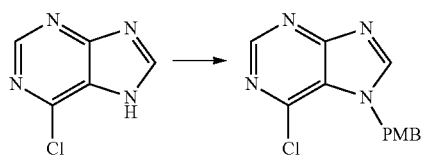

Sodium hydride (858 mg, 35.75 mmol) was added batchwise to a solution of 6-chloro-7H-purine (3 g, 19.41 mmol) in N,N-dimethylformamide (30 mL). After 20 min PMBCl (6.1 g, 38.81 mmol) was added dropwise into the above mixture. The resulting solution was stirred for 4 h at room temperature, diluted with ethyl acetate, washed with brine, dried over anhydrous sodium sulfate, and concentrated under vacuum. The residue was purified on a silica gel column eluting with ethyl acetate/petroleum ether (1:1) to afford the title compound (2.3 g, 43%) as light yellow oil. LCMS [M+H$^+$] 275.

Step 2: Preparation of 7-[(4-methoxyphenyl)methyl]-6,7-dihydro-1H-purin-6-one

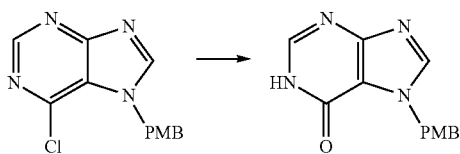

A mixture of 6-chloro-7-[(4-methoxyphenyl)methyl]-7H-purine (2.3 g, 8.37 mmol), 1,4-dioxane (3 mL), sodium hydroxide (1 g, 25.00 mmol) and water (25 mL) was stirred for 1.5 h at 90° C. The pH value of the solution was adjusted to 7 with HCl (2 M). The solids were collected by filtration to afford the title compound (1.95 g, 91%) as a white solid. LCMS [M+H$^+$] 257.

Step 3: Preparation of 7-[(4-methoxyphenyl)methyl]-1-methyl-6,7-dihydro-1H-purin-6-one

A mixture of 7-[(4-methoxyphenyl)methyl]-6,7-dihydro-1H-purin-6-one (1 g, 3.90 mmol), potassium carbonate (1.1 g, 7.80 mmol), N,N-dimethylformamide (12 mL) and CH$_3$I (666 mg, 4.69 mmol) was stirred for 1.5 h at room temperature. The solids were filtered out. The reaction mixture was purified on a C18 silica gel column eluting with CH$_3$CN/H$_2$O (10 mmol/L NH$_4$HCO$_3$, 5% to 95% over 30 min). This resulted in the title compound (700 mg, 66%) as a white solid. LCMS [M+H$^+$] 271.

Step 4: Preparation of 1-methyl-6,7-dihydro-1H-purin-6-one

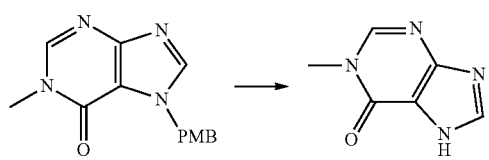

A mixture of 7-[(4-methoxyphenyl)methyl]-1-methyl-6,7-dihydro-1H-purin-6-one (700 mg, 2.590 mmol) and trifluoroacetic acid (10 mL) was stirred for 15 h at 70° C. The resulting mixture was concentrated under vacuum. This resulted in the title compound (700 mg, crude) as a white solid. LCMS [M+H$^+$] 151.

Step 5: Preparation of 7-([4-[2-(4-chlorophenyl)ethyl]-5-oxo-4,5-dihydro-1,3,4-oxadiazol-2-yl]methyl)-1-methyl-6,7-dihydro-1H-purin-6-one

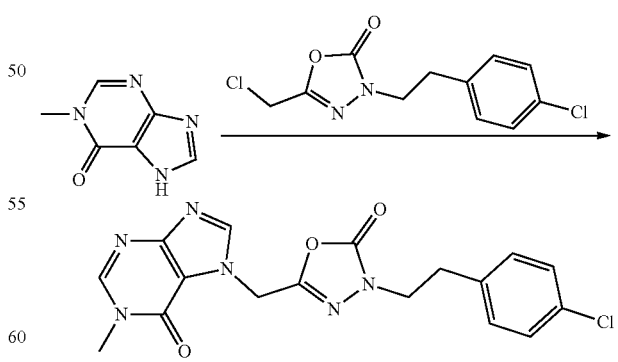

A mixture of 5-(chloromethyl)-3-[2-(4-chlorophenyl)ethyl]-2,3-dihydro-1,3,4-oxadiazol-2-one (64 mg, 0.23 mmol), 1-methyl-6,7-dihydro-1H-purin-6-one (35 mg, 0.23 mmol), potassium carbonate (97 mg, 0.70 mmol), TBAI (4 mg, 0.01 mmol), and N,N-dimethylformamide (3 mL) was stirred for 12 h at room temperature. The reaction mixture was purified on a C18 silica gel column eluting with CH₃CN/H₂O (10 mmol/L NH₄HCO₃) increasing from 5% to 95% over 30 min. This resulted in the title compound (34.3 mg, 38%) as a white solid. LCMS [M+H⁺] 387. ¹H NMR (300 MHz, DMSO-d₆) δ 8.36-8.33 (d, J=11.8 Hz, 2H), 7.31-7.23 (m, 2H), 7.22-7.13 (m, 2H), 5.65 (s, 2H), 3.86-3.82 (t, J=6.7 Hz, 2H), 3.34 (s, 3H), 2.89-2.86 (t, J=6.7 Hz, 2H).

Example Compound 27: Preparation of 3-(4-chlorophenethyl)-5-((4-methyl-5-oxopyridazino[3,4-d]pyrimidin-6(5H)-yl)methyl)-1,3,4-oxadiazol-2(3H)-one The overall Example Compound 27 reaction scheme is as follows:

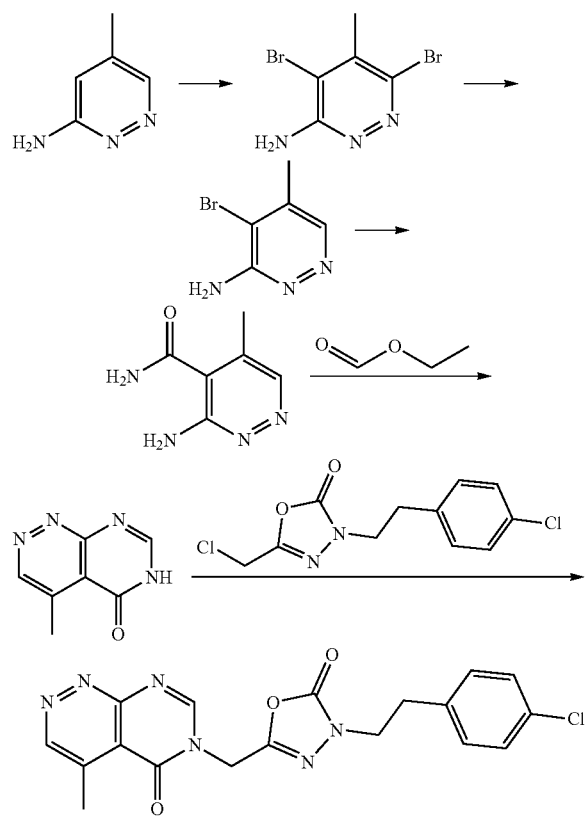

Step 1: Preparation of 4,6-dibromo-5-methylpyridazin-3-amine

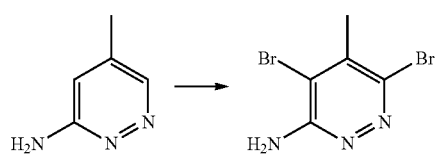

A solution of Br2 (9.6 g, 60.07 mmol) in methanol (30 mL) was added dropwise into the mixture of 5-methylpyridazin-3-amine (3 g, 27.49 mmol), methanol (100 mL), and sodium bicarbonate (11.5 g, 136.89 mmol) at 0° C. The resulting solution was stirred for 2 h at room temperature, diluted with water, extracted with ethyl acetate, dried over sodium sulfate, and concentrated under vacuum. The residue was purified by a silica gel column eluting with ethyl acetate/petroleum ether (1/4) to afford the title compound (4.0 g, 55%) as a brown solid. LCMS [M+H⁺] 266.

Step 2: Preparation of 4-bromo-5-methylpyridazin-3-amine

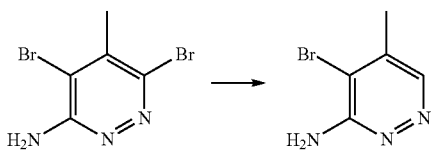

EtMgBr (2 mL, 15.15 mmol, 3M in THF) was added dropwise into a solution of 4,6-dibromo-5-methylpyridazin-3-amine (400 mg, 1.49 mmol) in tetrahydrofuran (8 mL) at 0-10° C. under nitrogen. The resulting solution was stirred for 35 min at 63° C. The reaction was quenched with water and concentrated under vacuum. The residue was purified on a C18 silica gel column eluting with CH₃CN/H₂O (10 mmol/L NH₄HCO₃, 5% to 95%, over 30 min). This resulted in the title compound (36 mg, 13%) as a white solid. LCMS [M+H⁺] 188.

Step 3: Preparation of 3-amino-5-methylpyridazine-4-carboxamide

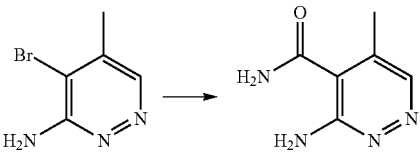

A mixture of 4-bromo-5-methylpyridazin-3-amine (80 mg, 425.47 mmol), NH₃/MeOH (7M) (4 mL), Pd(dppf)Cl₂ (31 mg, 0.04 mmol), TEA (128 mg, 1.26 mmol), and carbon monoxide was stirred overnight at 100° C. under 10 atm pressure. The reaction solution was purified on a C18 silica gel column eluting with CH₃CN/H₂O (10 mmol/L NH₄HCO₃, 5% to 95%, over 30 min). This resulted in the title compound (85 mg, crude) as a light yellow solid. LCMS [M+H⁺]153.

Step 4: Preparation of 4-methylpyrimido[4,5-c]pyridazin-5(6H)-one

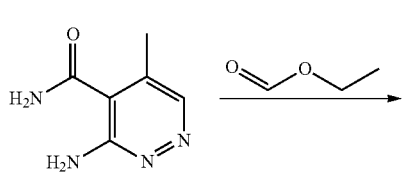

-continued

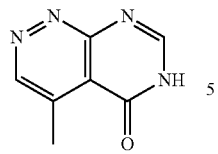

A mixture of 3-amino-5-methylpyridazine-4-carboxamide (150 mg, 0.98 mmol), ethanol (3 mL), EtONa (21%) (3.2 g, 0.04 mmol), ethyl formate (360 mg, 4.86 mmol) was stirred for 1 h at 80° C. under nitrogen. The resulting mixture was concentrated under vacuum. The pH value of the solution was adjusted to 8 with hydrogen chloride/H$_2$O (5%). The resulting mixture was concentrated under vacuum and diluted with ethanol. The solids were filtered out and the filtrate was concentrated under vacuum to afford the title compound (120 mg, 75%) as a brown solid. LCMS [M+H$^+$] 163.

Step 5: Preparation of 3-(4-chlorophenethyl)-5-((4-methyl-5-oxopyrimido[4,5-c]pyridazin-6(5H)-yl)methyl)-1,3,4-oxadiazol-2(3H)-one

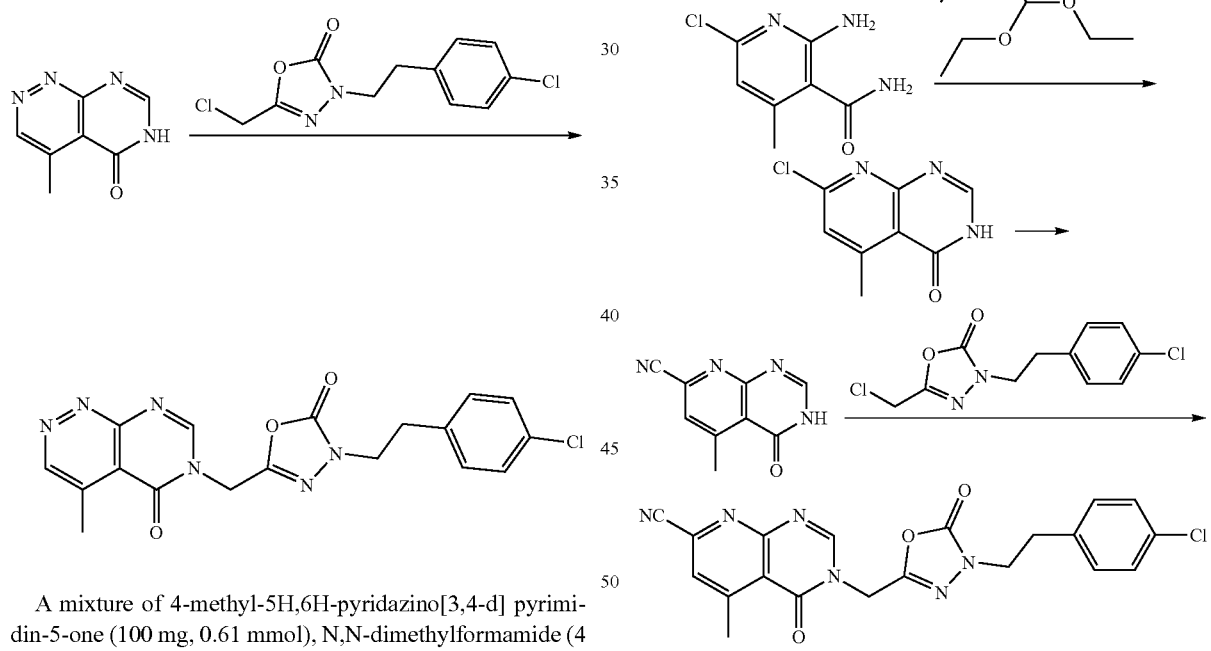

A mixture of 4-methyl-5H,6H-pyridazino[3,4-d] pyrimidin-5-one (100 mg, 0.61 mmol), N,N-dimethylformamide (4 mL), TBAI (12 mg, 0.03 mmol), potassium carbonate (138 mg, 0.99 mmol), and 5-(chloromethyl)-3-[2-(4-chlorophenyl)ethyl]-2,3-dihydro-1,3,4-oxadiazol-2-one (180 mg, 0.65 mmol) was stirred for 1 h at room temperature. The reaction solution was purified on a C18 silica gel column eluting with CH$_3$CN/H$_2$O (10 mmol/L NH$_4$HCO$_3$, 5% to 95%, over 30 min). The resulting solution was extracted with dichloromethane, dried over anhydrous sodium sulfate, and concentrated under vacuum. This resulted in the title compound (6 mg, 2%) as a light yellow solid. LCMS [M+H$^+$] 399. $^1$H NMR (400 MHz, DMSO-d$_6$) δ 9.37 (s, 1H), 8.71 (s, 1H), 7.26 (d, J=8.4 Hz, 2H), 7.21 (d, J=8.4 Hz, 2H), 5.19 (s, 2H), 3.86 (t, J=6.8 Hz, 2H), 2.92 (t, J=6.8 Hz, 2H), 2.79 (s, 3H).

Example Compound 28: Preparation of 3-((4-(4-chlorophenethyl)-5-oxo-4,5-dihydro-1,3,4-oxadiazol-2-yl)methyl)-5-methyl-4-oxo-3,4-dihydropyrido[2,3-d]pyrimidine-7-carbonitrile The overall Example Compound 28 reaction scheme is as follows:

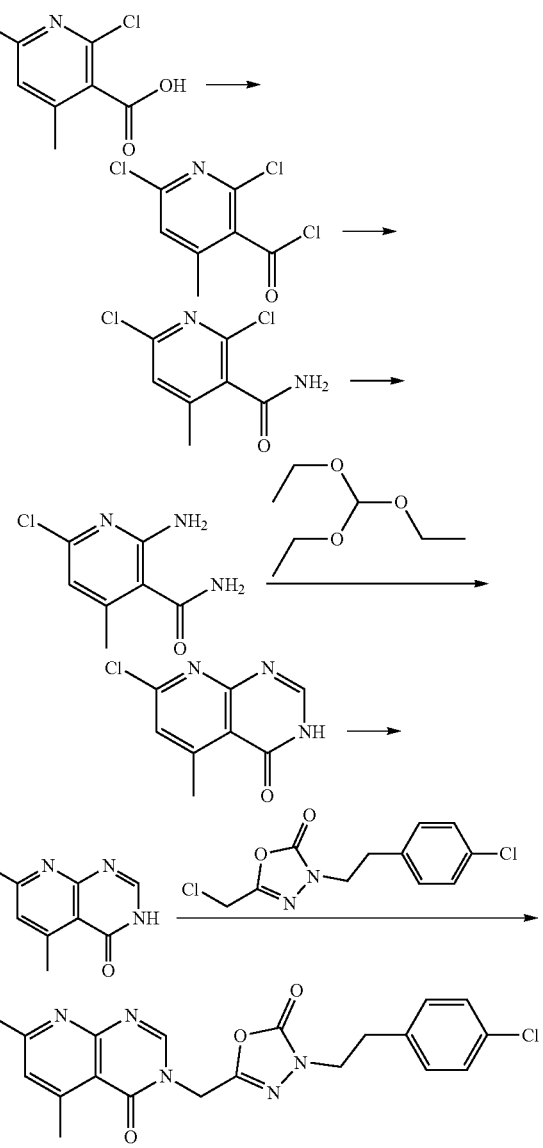

Step 1: Preparation of 2,6-dichloro-4-methylnicotinoyl chloride

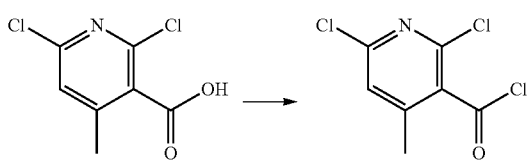

Oxalyl chloride (5.5 g, 43.33 mmol) was added dropwise into a solution of 2,6-dichloro-4-methylpyridine-3-carboxylic acid (3 g, 14.56 mmol), N,N-dimethylformamide (50 mg, 0.68 mmol), and dichloromethane (100 mL) at 0° C. The result solution was stirred overnight at room temperature and concentrated under vacuum. This resulted in the title compound (3.1 g, crude) as light yellow liquid.

Step 2: Preparation of
2,6-dichloro-4-methylnicotinamide

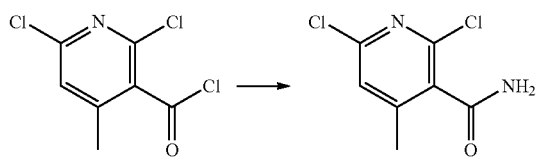

A solution of 2,6-dichloro-4-methylpyridine-3-carbonyl chloride (3.1 g, 13.81 mmol) in dichloromethane (15 mL) was added dropwise into a stirred solution NH$_3$/THF (0.5M) (42 mL) at 25° C. After being stirred for 1 h at room temperature the resulting mixture was concentrated under vacuum. The residue was purified by a silica gel column eluting with ethyl acetate/petroleum ether (1/1) to afford the title compound (1.5 g, 53%) as a white solid. LCMS [M+H$^+$] 205.

Step 3: Preparation of
2-amino-6-chloro-4-methylnicotinamide

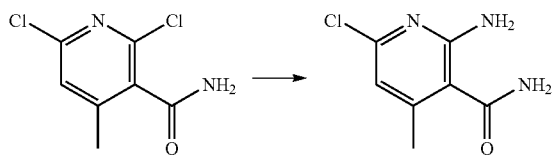

A mixture of 2,6-dichloro-4-methylpyridine-3-carboxamide (50 mg, 0.24 mmol), dioxane (2 mL, 23.60 mmol), and ammonia (30%, 0.5 mL) was stirred overnight at 130° C. The resulting mixture was concentrated under vacuum. The crude product was purified on a C18 silica gel column eluting with CH$_3$CN/H$_2$O (10 mmol/L NH$_4$HCO$_3$, 5% to 95%, over 30 min). This resulted in the title compound (25 mg, 55%) as a white solid. LCMS [M+H$^+$] 186.

Step 4: Preparation of 7-chloro-5-methylpyrido[2,3-d]pyrimidin-4(3H)-

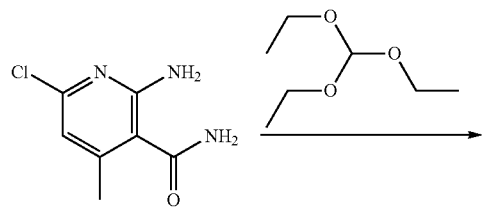

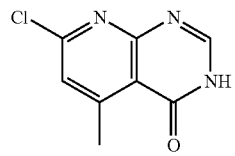

A mixture of 2-amino-6-chloro-4-methylpyridine-3-carboxamide (320 mg, 1.72 mmol) and (diethoxymethoxy)ethane (5 mL) was stirred overnight at 140° C. The solids were collected by filtration. This resulted in the title compound (180 mg, 53%) as a gray solid. LCMS [M+H$^+$]211.

Step 5: Preparation of 5-methyl-4-oxo-3,4-dihydropyrido[2,3-d]pyrimidine-7-carbonitrile

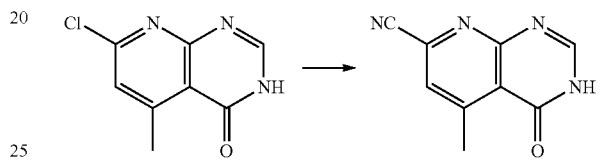

A mixture of 7-chloro-5-methyl-3H,4H-pyrido[2,3-d]pyrimidin-4-one (170 mg, 0.86 mmol), N,N-dimethylformamide (5 mL), Zn(CN)$_2$ (151 mg, 1.28 mmol), Pd$_2$(dba)$_3$·CHCl$_3$ (90 mg, 0.08 mmol), and dppf (96 mg, 0.17 mmol) was stirred for 3 h at 100° C. under nitrogen. The solids were filtered out. The crude product was purified on a C18 silica gel column eluting with CH$_3$CN/H$_2$O (10 mmol/L NH$_4$HCO$_3$, 5% to 95%, over 30 min). This resulted in the title compound (100 mg, 62%) as a white solid. LCMS [M+H$^+$] 187.

Step 6: Preparation of 3-((4-(4-chlorophenethyl)-5-oxo-4,5-dihydro-1,3,4-oxadiazol-2-yl)methyl)-5-methyl-4-oxo-3,4-dihydropyrido[2,3-d]pyrimidine-7-carbonitrile

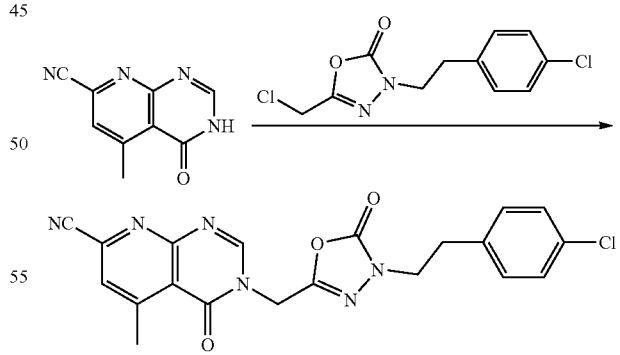

A mixture of 5-methyl-4-oxo-3H,4H-pyrido[2,3-d]pyrimidine-7-carbonitrile (20 mg, 0.10 mmol), N,N-dimethylformamide (1 mL), potassium carbonate (30 mg, 0.21 mmol), TBAI (2 mg, 0.01 mmol), and 5-(chloromethyl)-3-[2-(4-chlorophenyl)ethyl]-2,3-dihydro-1,3,4-oxadiazol-2-one (29 mg, 0.11 mmol) was stirred for 1 h at room temperature. The crude product was purified on a C18 silica gel column eluting with CH$_3$CN/H$_2$O (10 mmol/L NH$_4$HCO$_3$, 5% to 95%, over 30 min). This resulted in the title compound (16.7 mg, 37%) as a white solid. LCMS [M+H$^+$] 423. $^1$H NMR (400 MHz, DMSO-d$_6$) δ 8.71 (s, 1H), 8.06 (s, 1H), 7.28 (d, J=8.4 Hz, 2H), 7.20 (d, J=8.4 Hz, 2H), 5.19 (s, 2H), 3.86 (t, J=6.4 Hz, 2H), 2.91 (t, J=6.8 Hz, 2H), 2.85 (s, 3H).

Example Compound 29: Preparation of 3-[2-(1-methylindol-5-yl)ethyl]-5-[(7-methyl-6-oxo-purin-1-yl)methyl]-1,3,4-oxadiazol-2-one The overall Example Compound 29 reaction scheme is as follows:

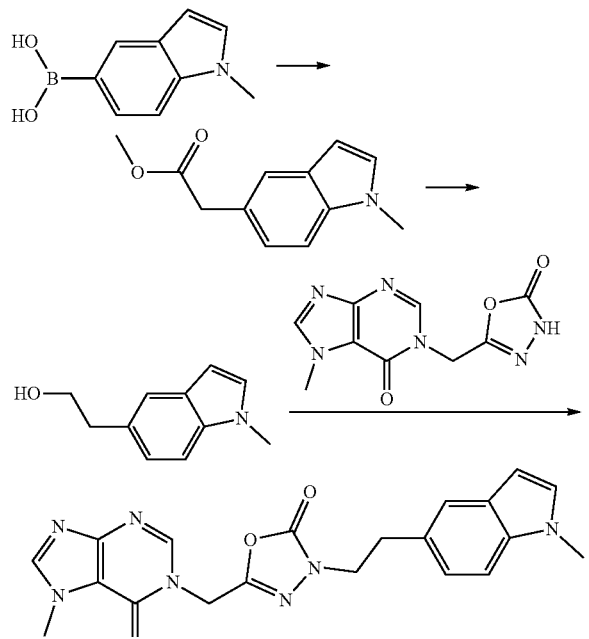

Step 1: Preparation of methyl 2-(1-methyl-1H-indol-5-yl)acetate

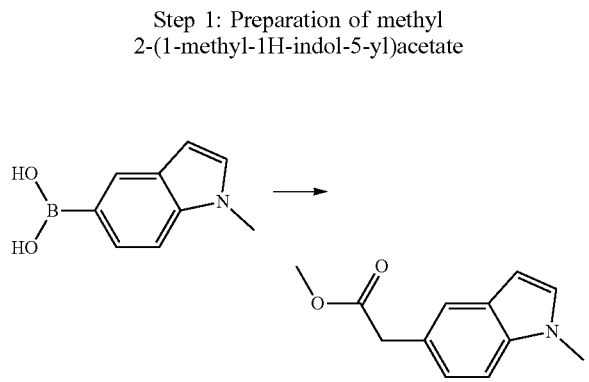

A mixture of (1-methyl-1H-indol-5-yl)boronic acid (500 mg, 2.86 mmol), methyl 2-bromoacetate (434 mg, 2.84 mmol), Pd(OAc)$_2$ (63 mg, 0.28 mmol), P(o-Tol)$_3$ (86 mg, 0.28 mmol), sodium carbonate (604 mg, 5.70 mmol), tetrahydrofuran (20 mL), and water (2 mL) was stirred overnight at 60° C. under nitrogen. The reaction was diluted with water, extracted with dichloromethane, dried over anhydrous sodium sulfate, and concentrated under vacuum. The residue was purified by a silica gel column eluting with petroleum ether/ethyl acetate (1/10) to afford the title compound (200 mg, 34%) as a light yellow solid. LCMS [M+H$^+$] 204.

Step 2: Preparation of 2-(1-methyl-1H-indol-5-yl)ethanol

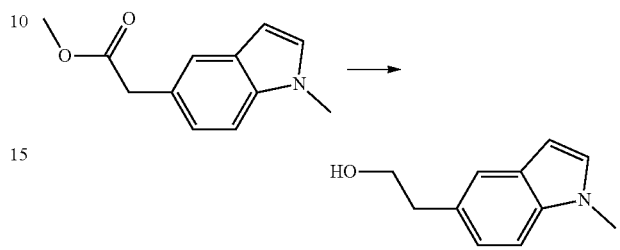

A mixture of methyl 2-(1-methyl-1H-indol-5-yl)acetate (203 mg, 1.00 mmol), tetrahydrofuran (15 mL), and LiAlH$_4$ (114 mg, 3.00 mmol) was stirred overnight at room temperature. The reaction was then quenched with water, extracted with ethyl acetate, dried over anhydrous sodium sulfate, and concentrated under vacuum. The residue was purified by a silica gel column eluting with petroleum ether/ethyl acetate (1/1) to afford the title compound (150 mg, 86%) as a light yellow solid. LCMS [M+H$^+$] 176.

Step 3: Preparation of 3-[2-(1-methylindol-5-yl)ethyl]-5-[(7-methyl-6-oxo-purin-1-yl)methyl]-1,3,4-oxadiazol-2-one

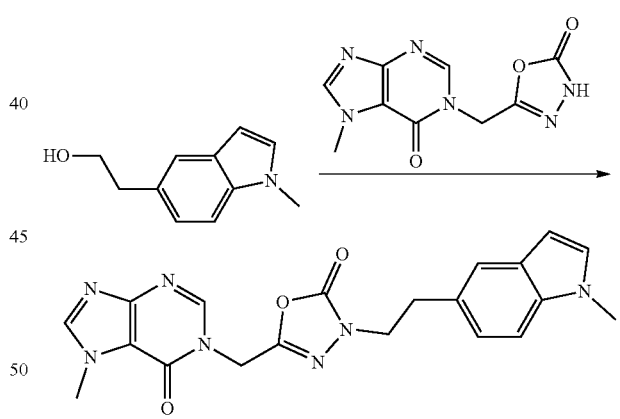

DIAD (230 mg, 1.13 mmol) was added dropwise into a mixture of 2-(1-methyl-1H-indol-5-yl)ethan-1-ol (80 mg, 0.46 mmol), 7-methyl-1-[(5-oxo-4,5-dihydro-1,3,4-oxadiazol-2-yl)methyl]-6,7-dihydro-1H-purin-6-one (113 mg, 0.46 mmol), PPh$_3$ (239 mg, 0.91 mmol) and N,N-dimethylformamide (10 mL). The resulting solution was stirred for 1 h at room temperature. The reaction mixture was purified on a C18 silica gel column eluting with CH$_3$CN/H$_2$O (10 mmol/L NH$_4$HCO$_3$, 5% to 95%, over 30 min). This resulted in the title compound 56.7 mg (31%) as a white solid. LCMS [M+H$^+$] 406. $^1$H NMR (300 MHz, DMSO-d$_6$) δ 8.37 (s, 1H), 8.26 (s, 1H), 7.35-7.23 (m, 3H), 6.96 (dd, J=8.4, 1.6 Hz, 1H), 6.29 (dd, J=3.1, 0.9 Hz, 1H), 5.25 (s, 2H), 4.00 (s, 3H), 3.87 (t, J=7.0 Hz, 2H), 3.35 (s, 3H), 2.98 (t, J=7.0 Hz, 2H).

Example Compound 30: Preparation of 1-[[3-[2-(4-chlorophenyl)ethyl]-1,2,4-oxadiazol-5-yl] methyl]-6-methyl-7-oxo-pyrazolo[4,3-d]pyrimidine-3-carbonitrile The overall Example Compound 30 reaction scheme is as follows:

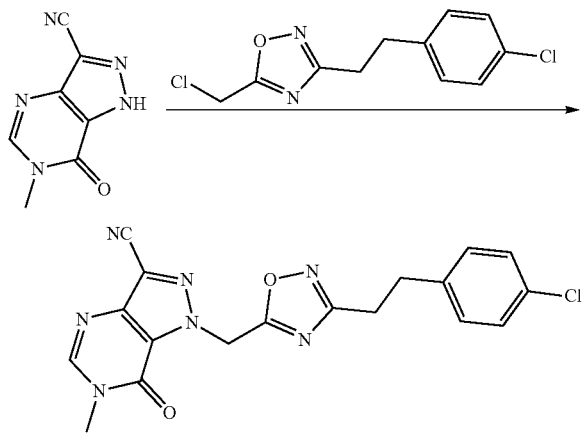

Step 1: Preparation of 1-[[3-[2-(4-chlorophenyl)ethyl]-1,2,4-oxadiazol-5-yl]methyl]-6-methyl-7-oxo-pyrazolo[4,3-d]pyrimidine-3-carbonitrile

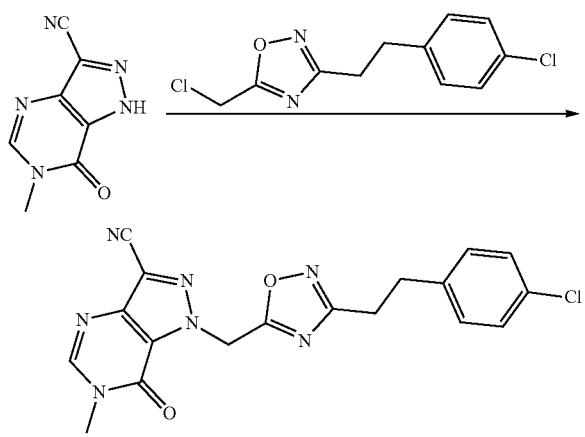

A mixture of 6-methyl-7-oxo-1H,6H,7H-pyrazolo[4,3-d]pyrimidine-3-carbonitrile (20 mg, 0.11 mmol), 5-(chloromethyl)-3-[2-(4-chlorophenyl)ethyl]-1,2,4-oxadiazole (29.26 mg, 0.11 mmol), TBAI (4.22 mg, 0.01 mmol), K$_2$CO$_3$ (47.32 mg, 0.34 mmol), and N,N-dimethylformamide (2 mL) was stirred for 2 h at room temperature. The reaction mixture was purified on a C18 silica gel column eluting with CH$_3$CN/H$_2$O (10 mmol/L NH$_4$HCO$_3$, 5% to 95%, 30 min). This resulted in the title compound (30.4 mg, 67%) as a white solid. LCMS [M+H$^+$] 396. $^1$H NMR (400 MHz, DMSO-d$_6$) δ 8.48 (s, 1H), 7.37-7.16 (m, 4H), 6.29 (s, 2H), 3.53 (s, 3H), 3.04-2.88 (m, 4H).

Example Compound 31: Preparation of 5-[(7-methyl-6-oxo-purin-1-yl)methyl]-3-[2-(p-tolyl)ethyl]-1,3,4-oxadiazol-2-one The overall Example Compound 31 reaction scheme is as follows:

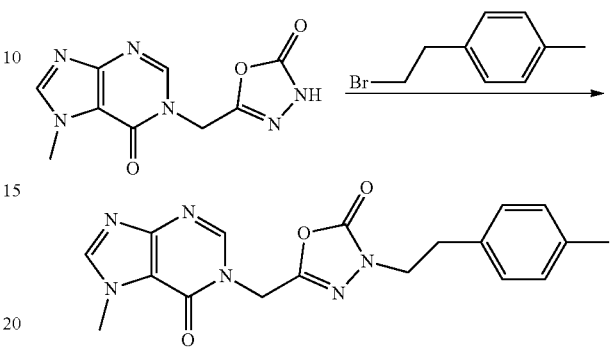

A mixture of 7-methyl-1-[(5-oxo-4,5-dihydro-1,3,4-oxadiazol-2-yl)methyl]-6,7-dihydro-1H-purin-6-one (50 mg, 0.20 mmol), TBAI (7.4 mg, 0.02 mmol), K$_2$CO$_3$ (83.47 mg, 0.60 mmol), N,N-dimethylformamide (2 mL), and 1-(2-bromoethyl)-4-methylbenzene (40 mg, 0.20 mmol) was stirred for 0.5 h at room temperature. The reaction mixture was purified on a C18 silica gel column eluting with CH$_3$CN/H$_2$O (10 mmol/L NH$_4$HCO$_3$, 5% to 95% over 30 min). This resulted in the title compound (39.5 mg, 54%) as a white solid. LCMS [M+H$^+$] 367. $^1$H NMR (400 MHz, DMSO-d$_6$) δ 8.36 (s, 1H), 8.25 (s, 1H), 7.05 (s, 4H), 5.24 (s, 2H), 4.00 (s, 3H), 3.83 (t, J=6.9 Hz, 2H), 2.87 (t, J=6.9 Hz, 2H), 2.24 (s, 3H).

Example Compound 32: Preparation of 1-[(4-[2-[4-(difluoromethoxy)phenyl]ethyl]-5-oxo-4,5-dihydro-1,3,4-oxadiazol-2-yl)methyl]-6-methyl-7-oxo-1H,6H,7H-pyrazol[4,3-d]pyrimidine-3-carbonitrile The overall Example Compound 32 reaction scheme is as follows:

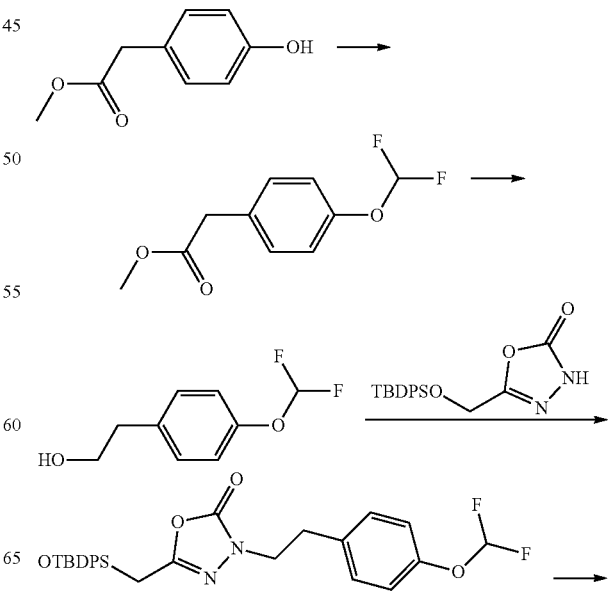

-continued

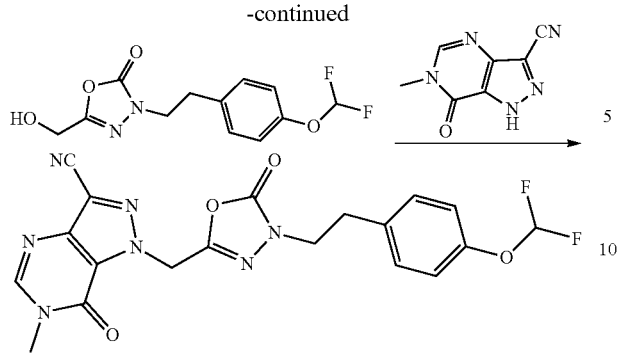

Step 1: Preparation of methyl 2-[4-(difluoromethoxy)phenyl]acetate

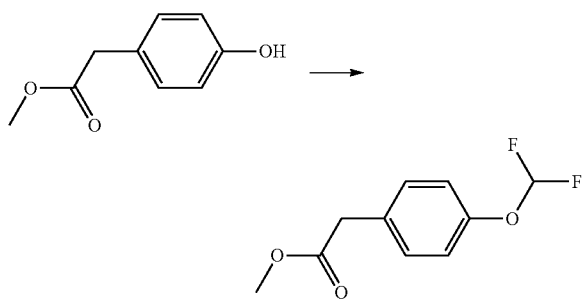

A mixture of methyl 2-(4-hydroxyphenyl)acetate (2 g, 12.04 mmol), sodium 2-chloro-2,2-difluoroacetate (2.19 g, 14.36 mmol), Cs$_2$CO$_3$ (4.71 g, 14.46 mmol), and N,N-dimethylformamide (50 mL) was stirred for 3 h at 80° C. in an oil bath. The resulting solution was diluted with ethyl acetate, washed with brine, dried over anhydrous sodium sulfate, and concentrated under vacuum. The residue was purified by a silica gel column eluting with petroleum ether/ethyl acetate (7/1) to afford the title compound (0.8 g, 31%) as yellow oil.

Step 2: Preparation of 2-[4-(difluoromethoxy)phenyl]ethan-1-ol

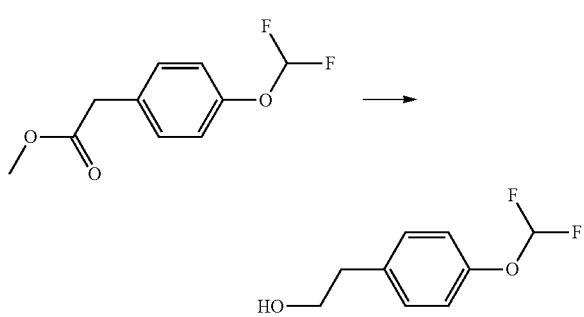

LiAlH$_4$ (263.9 mg, 6.95 mmol) was added batchwise to a solution of methyl 2-[4-(difluoromethoxy)phenyl] acetate (750 mg, 3.47 mmol) in tetrahydrofuran (50 mL) at 0° C. under nitrogen. The resulting solution was stirred for 2 h at room temperature. The reaction was quenched with water, extracted with ethyl acetate, washed with brine, dried over anhydrous sodium sulfate, and concentrated under vacuum. The residue was purified on a silica gel column eluting with ethyl acetate/petroleum ether (1/1.5) to afford the title compound (690 mg, crude) as colorless oil.

Step 3: Preparation of 5-[[(tert-butyldiphenylsilyl)oxy]methyl]-3-[2-[4-(difluoromethoxy)phenyl]ethyl]-2,3-dihydro-1,3,4-oxadiazol-2-one

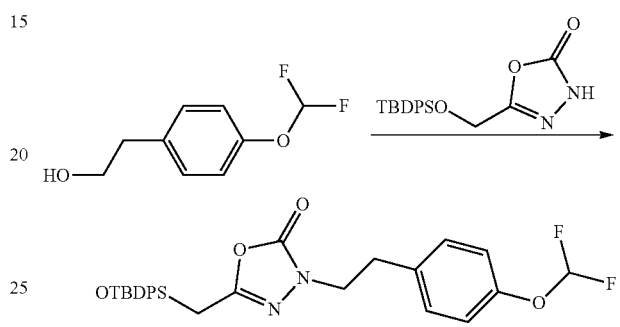

DIAD (228.2 mg, 1.13 mmol) was added dropwise into a stirred mixture of 2-[4-(difluoromethoxy)phenyl] ethan-1-ol (106.2 mg, 0.56 mmol),5-[(tert-butyldiphenylsilyl)oxy]methyl-2,3-dihydro-1,3,4-oxadiazol-2-one (200 mg, 0.56 mmol), PPh$_3$ (296.5 mg, 1.13 mmol), and N,N-dimethylformamide (7 mL). The resulting solution was stirred for 0.5 h at room temperature. The mixture was purified on a C18 silica gel column eluting with CH$_3$CN/H$_2$O (10 mmol/L NH$_4$HCO$_3$, 5% to 95%, over 30 min). This resulted in the title compound (171.6 mg, 58%) as brown oil.

Step 4: Preparation of 3-[2-[4-(difluoromethoxy)phenyl]ethyl]-5-(hydroxymethyl)-2,3-dihydro-1,3,4-oxadiazol-2-one

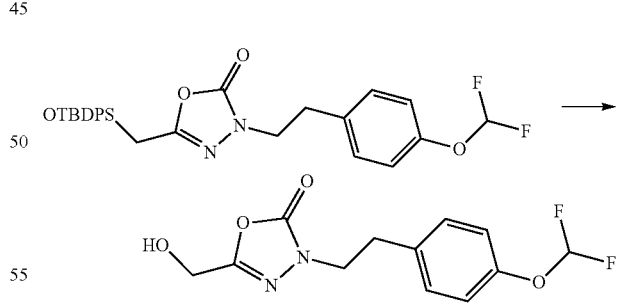

A mixture of 5-[[(tert-butyldiphenylsilyl)oxy]methyl]-3-[2-[4-(difluoromethoxy)phenyl]ethyl]-2,3-dihydro-1,3,4-oxadiazol-2-one (90 mg, 0.17 mmol) and trifluoroacetic acid (5 mL) was stirred overnight at room temperature. The resulting mixture was concentrated under vacuum. The residue was purified on a C18 silica gel column eluting with CH$_3$CN/H$_2$O (10 mmol/L NH$_4$HCO$_3$, 5% to 95%, over 30 min). This resulted in the title compound (22 mg, 45%) as brown oil. LCMS [M+H$^+$] 287.

Step 5: Preparation of 1-[(4-[2-[4-(difluoromethoxy)phenyl]ethyl]-5-oxo-4,5-dihydro-1,3,4-oxadiazol-2-yl)methyl]-6-methyl-7-oxo-1H,6H,7H-pyrazolo[4,3-d]pyrimidine-3-carbonitrile

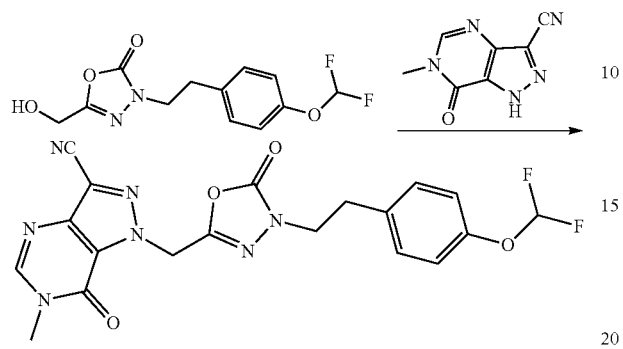

DIAD (31.08 mg, 0.15 mmol) was added dropwise into a mixture of 3-[2-[4-(difluoromethoxy)phenyl] ethyl]-5-(hydroxymethyl)-2,3-dihydro-1,3,4-oxadiazol-2-one (22 mg, 0.08 mmol), 6-methyl-7-oxo-1H,6H,7H-pyrazolo[4,3-d]pyrimidine-3-carbonitrile (13.61 mg, 0.078 mmol), PPh$_3$ (40.31 mg, 0.15 mmol) and N,N-dimethylformamide (2 mL). The resulting solution was stirred for 0.5 h at room temperature. The resulting mixture was purified on a C18 silica gel column eluting with CH$_3$CN/H$_2$O (10 mmol/L NH$_4$HCO$_3$, 5% to 95%, over 30 min). This resulted in the title compound 6.1 mg (18%) as a white solid. LCMS [M+H$^+$] 444. $^1$H NMR (400 MHz, CDCl$_3$) δ 8.05 (s, 1H), 7.28-7.06 (m, 4H), 6.70-6.33 (t, J=72.0 Hz, 1H), 5.82 (s, 2H), 3.95 (t, J=8.0 Hz, 2H), 3.67 (s, 3H), 3.04 (t, J=8.0 Hz, 2H).

Example Compounds 33 and 34: Preparation of 5-[(5-methyl-4-oxo-pyrido[2,3-d]pyrimidin-3-yl)methyl]-3-[rac-(2R)-2-(4-chlorophenyl)-2-fluoro-ethyl]-1,3,4-oxadiazol-2-one and 5-[(5-methyl-4-oxo-pyrido[2,3-d]pyrimidin-3-yl)methyl]-3-[rac-(2S)-2-(4-chlorophenyl)-2-fluoro-ethyl]-1,3,4-oxadiazol-2-one The overall Example Compounds 33 and 34 reaction scheme is as follows:

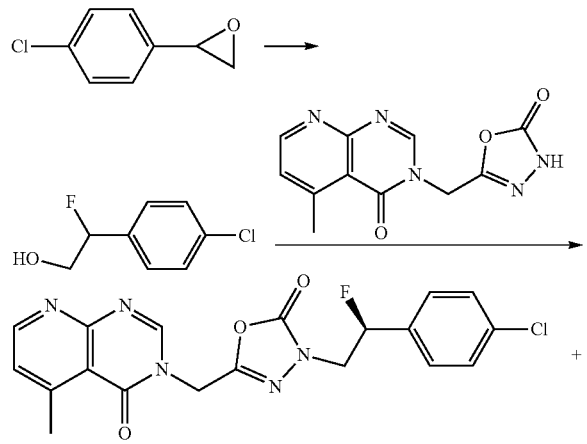

Step 1: Preparation of methyl 2-(4-chlorophenyl)-2-fluoroethanol

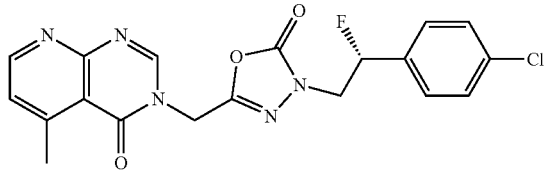

BF$_3$·Et$_2$O (549 mg, 3.87 mmol) was added to a stirred solution of 2-(4-chlorophenyl)oxirane (1 g, 6.47 mmol), dichloromethane (40 mL), and triethylamine.3HF (3.12 g, 19.35 mmol) at 0° C. under nitrogen. The resulting solution was stirred overnight at room temperature. The reaction was then quenched by water/ice. The pH value of the reaction solution was adjusted to 9. The resulting mixture was extracted with dichloromethane, washed with hydrogen chloride/H$_2$O, dried over anhydrous sodium sulfate, and concentrated under vacuum. The residue was purified by a silica gel column eluting with ethyl acetate/petroleum ether (1/1) to afford the title compound (500 mg, 44%) as greenish oil. GCMS [M] 174.

Step 2: Preparation of 5-[(5-methyl-4-oxo-pyrido[2,3-d]pyrimidin-3-yl)methyl]-3-[rac-(2R)-2-(4-chlorophenyl)-2-fluoro-ethyl]-1,3,4-oxadiazol-2-one and 5-[(5-methyl-4-oxo-pyrido[2,3-d] pyrimidin-3-yl) methyl]-3-[rac-(2S)-2-(4-chlorophenyl)-2-fluoro-ethyl]-1,3,4-oxadiazol-2-one

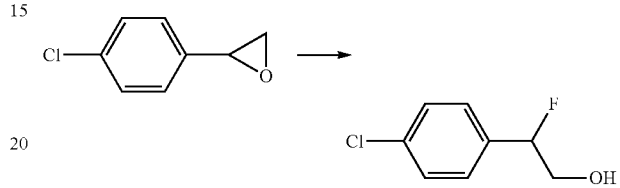

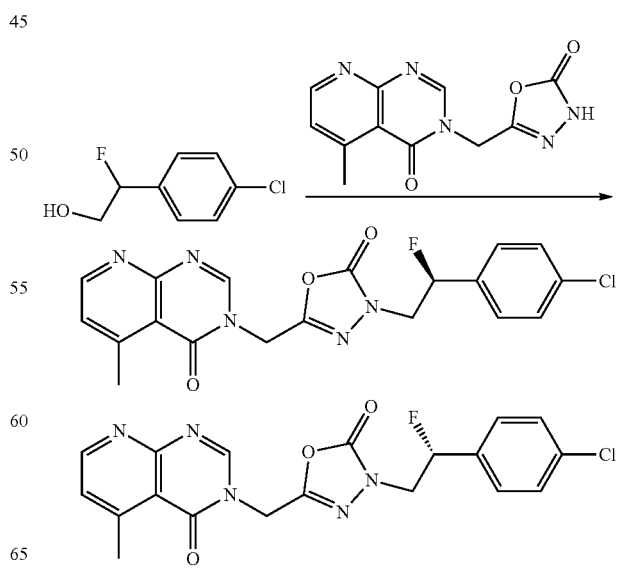

A mixture of 2-(4-chlorophenyl)-2-fluoroethan-1-ol (80 mg, 0.46 mmol),5-({5-methyl-4-oxo-3H,4H-pyrido[2,3-d]pyrimidin-3-yl}methyl)-2,3-dihydro-1,3,4-oxadiazol-2-one (100 mg, 0.39 mmol), N,N-dimethylformamide (5 mL), PPh₃ (200 mg, 0.76 mmol), and DIAD (388 mg, 1.92 mmol) was stirred for 1 h at room temperature. The resulting mixture was concentrated under vacuum. The filtrate was purified on a C18 silica gel column eluting with CH₃CN/H₂O (10 mmol/L NH₄HCO₃) increasing from 5% to 95% over 30 min. This resulted in 60 mg of a racemic mixture. The racemic was separated by Chiral-Prep-HPLC with the following conditions (Prep-HPLC-009): Column, Chiralpak IA, 2*25 cm, 5 um; mobile phase, Hex and ethanol (hold 50.0% ethanol—in 28 min); Detector, UV 220/254 nm. This resulted in 25.4 mg of 5-[(5-methyl-4-oxo-pyrido[2,3-d]pyrimidin-3-yl)methyl]-3-[rac-(2R)-2-(4-chlorophenyl)-2-fluoro-ethyl]-1,3,4-oxadiazol-2-one as a white solid. LCMS [M+H⁺] 416. $t_R$=4.63 min (Repaired IA, 0.46×10 cm, 5 μm, (Hex:DCM=5:1)(0.1% DEA):EtOH=50:50, 1.0 ml/min). ¹H NMR (300 MHz, DMSO-$d_6$) δ 8.79 (d, J=4.8 Hz, 1H), 8.61 (s, 1H), 7.45 (s, 5H), 5.92-5.76 (dd, J=7.8, 3.3 Hz, 1H), 5.21 (s, 2H), 4.27-3.96 (m, 2H), 2.81 (d, J=0.8 Hz, 3H). This also resulted in 26.6 mg of 5-[(5-methyl-4-oxo-pyrido[2,3-d]pyrimidin-3-yl)methyl]-3-[rac-(2S)-2-(4-chlorophenyl)-2-fluoro-ethyl]-1,3,4-oxadiazol-2-one as a white solid. LCMS [M+H⁺] 416. $t_R$=6.69 min (Repaired IA, 0.46×10 cm, 5 μm, (Hex:DCM=5:1)(0.1% DEA):EtOH=50:50, 1.0 ml/min). ¹H NMR (300 MHz, DMSO-$d_6$) δ 8.79 (d, J=4.8 Hz, 1H), 8.61 (s, 1H), 7.45 (s, 5H), 5.92-5.76 (dd, J=7.8, 3.3 Hz, 1H), 5.21 (s, 2H), 4.27-3.96 (m, 2H), 2.81 (d, J=0.8 Hz, 3H).

Example Compound 35: Preparation of 3-[2-(4-chlorophenyl)ethyl]-5-[(3-methyl-4-oxo-imidazo[4,5-d]pyridazin-5-yl)methyl]-1,3,4-oxadiazol-2-one The overall Example Compound 35 reaction scheme is as follows:

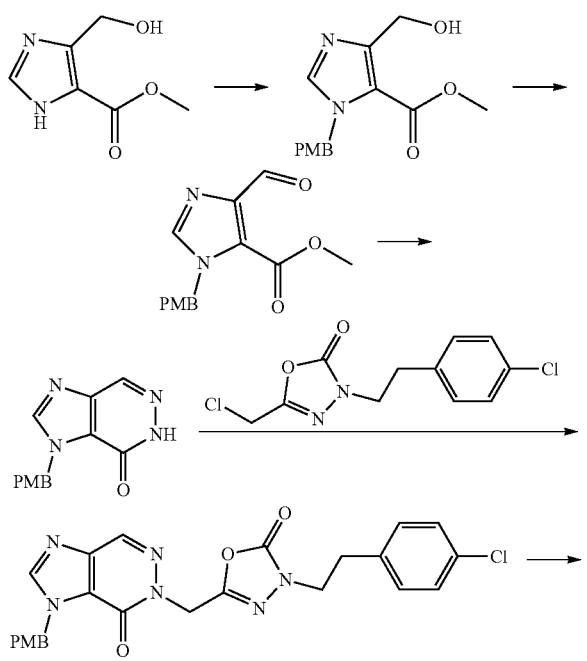

-continued

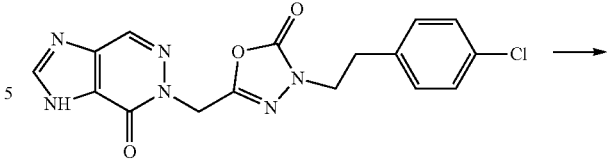

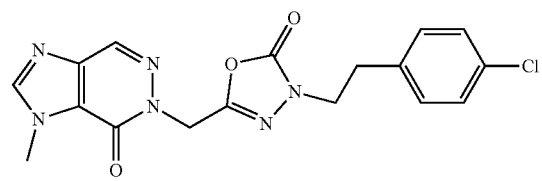

Step 1: Preparation of methyl 4-(hydroxymethyl)-1-(4-methoxybenzyl)-1H-imidazole-5-carboxylate

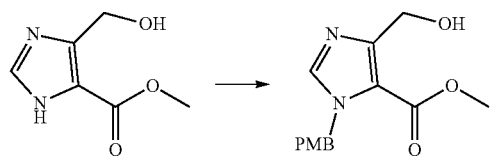

A mixture of methyl 4-(hydroxymethyl)-1H-imidazole-5-carboxylate (500 mg, 3.20 mmol), N,N-dimethylformamide (10 mL), potassium carbonate (885 mg, 6.40 mmol), PMBCl (550 mg, 3.51 mmol) was stirred overnight at room temperature. The solids were filtered out. The resulting mixture was concentrated under vacuum. The residue was purified by a silica gel column eluting with dichloromethane/methanol (10/1) to afford the title compound (600 mg, 68%) as a greenish solid. LCMS [M+H⁺] 277.

Step 2: Preparation of methyl 4-formyl-1-(4-methoxybenzyl)-1H-imidazole-5-carboxylate

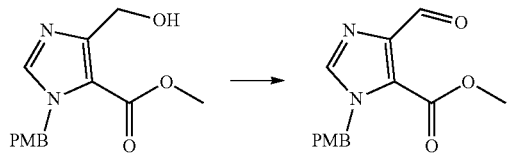

A mixture of methyl 4-(hydroxymethyl)-1-[(4-methoxyphenyl)methyl]-1H-imidazole-5-carboxylate (580 mg, 2.10 mmol), dichloromethane (20 mL), and Dess-Martin (888 mg, 2.09 mmol) was stirred for 1 h at room temperature. The solids were filtered out. The resulting mixture was concentrated under vacuum to afford the title compound (460 mg, 80%) as greenish oil. LCMS [M+H⁺] 275.

Step 3: Preparation of 1-[(4-methoxyphenyl) methyl]-1H,6H,7H-imidazo[4,5-d] pyridazin-7-one

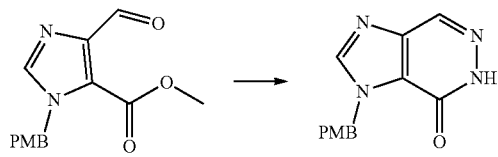

A mixture of methyl 4-formyl-1-[(4-methoxyphenyl) methyl]-1H-imidazole-5-carboxylate (460 mg, 1.68 mmol), ethanol (20 mL), and $NH_2NH_2 \cdot H_2O$ (1.045 g, 20.88 mmol) was stirred for 1 h at 80° C. The resulting mixture was concentrated under vacuum. The residue was purified by a silica gel column eluting with dichloromethane/methanol (20/1) to give the title compound (400 mg, 93%) as a white solid. LCMS [M+H$^+$] 257.

Step 4: Preparation of 3-(4-chlorophenethyl)-5-((3-(4-methoxybenzyl)-4-oxo-3H-imidazo[4,5-d] pyridazin-5(4H)-yl)methyl)-1,3,4-oxadiazol-2(3H)-one

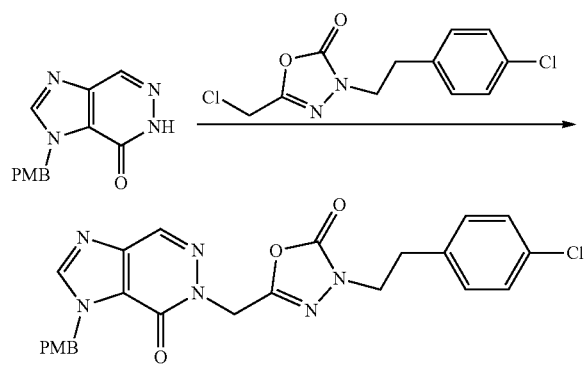

A mixture of 1-[(4-methoxyphenyl)methyl]-1H,6H,7H-imidazo[4,5-d]pyridazin-7-one (300 mg, 1.171 mmol), 5-(chloromethyl)-3-[2-(4-chlorophenyl)ethyl]-2,3-dihydro-1,3,4-oxadiazol-2-one (320 mg, 1.17 mmol), N,N-dimethylformamide (8 mL), potassium carbonate (323 mg, 2.34 mmol), and TBAI (43 mg, 0.12 mmol) was stirred overnight at room temperature. The solids were filtered out. The resulting mixture was concentrated under vacuum. The residue was purified by a silica gel column eluting with dichloromethane/ethyl acetate (1/2) to give the title compound (530 mg, 92%) as a brown solid. LCMS [M+H$^+$] 493.

Step 5: Preparation of 3-[2-(4-chlorophenyl)ethyl]-5-([7-oxo-1H,6H,7H-imidazo[4,5-d]pyridazin-6-yl] methyl)-2,3-dihydro-1,3,4-oxadiazol-2-one

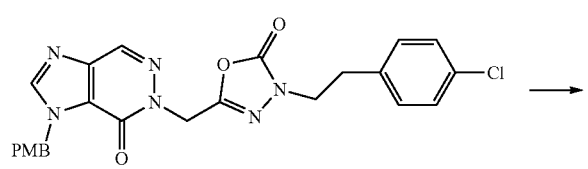

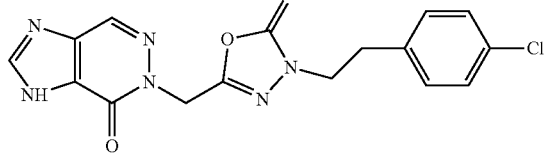

A mixture of 3-[2-(4-chlorophenyl)ethyl]-5-([1-[(4-methoxyphenyl)methyl]-7-oxo-1H,6H,7H-imidazo[4,5-d] pyridazin-6-yl]methyl)-2,3-dihydro-1,3,4-oxadiazol-2-one (520 mg, 1.06 mmol) and trifluoroacetic acid (20 mL) was stirred for 2 h at 70° C. The resulting mixture was concentrated under vacuum to afford the title compound (400 mg, crude) as a brown solid. LCMS [M+H$^+$] 373.

Step 6: Preparation of 3-[2-(4-chlorophenyl)ethyl]-5-[(3-methyl-4-oxo-imidazo[4,5-d]pyridazin-5-yl) methyl]-1,3,4-oxadiazol-2-one

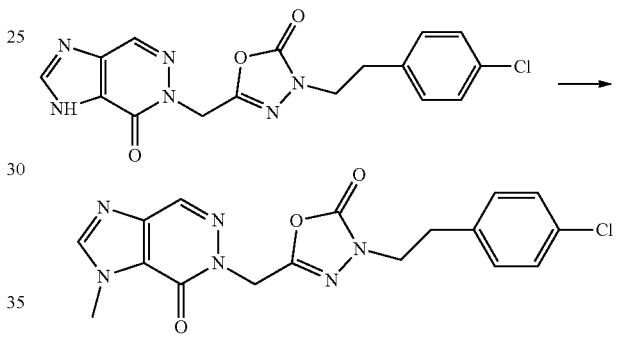

A mixture of 3-[2-(4-chlorophenyl)ethyl]-5-([7-oxo-1H, 6H,7H-imidazo[4,5-d]pyridazin-6-yl]methyl)-2,3-dihydro-1,3,4-oxadiazol-2-one (390 mg, 1.05 mmol), N,N-dimethylformamide (5 mL, 64.61 mmol), potassium carbonate (288 mg, 2.08 mmol), and $CH_3I$ (148 mg, 1.04 mmol) was stirred for 1 h at room temperature. The solids were filtered out. The filtrate was purified on a C18 silica gel column eluting with $CH_3CN/H_2O$ (10 mmol/L $NH_4HCO_3$, 5% to 95%, over 30 min). This resulted in the title compound (101.1 mg, 25%) as a white solid. LCMS [M+H$^+$] 387. $^1$H NMR (300 MHz, DMSO-d$_6$) δ 8.51 (d, J=1.2 Hz, 1H), 8.40 (s, 1H), 7.33-7.14 (m, 4H), 5.31 (s, 2H), 4.05 (s, 3H), 3.86 (t, J=6.8 Hz, 2H), 2.92 (t, J=6.8 Hz, 2H).

Example Compound 36: Preparation of 7-[2-[5-[(7-methyl-6-oxo-purin-1-yl)methyl]-2-oxo-1,3,4-oxadiazol-3-yl] ethyl]naphthalene-2-carbonitrile The overall Example Compound 36 reaction scheme is as follows:

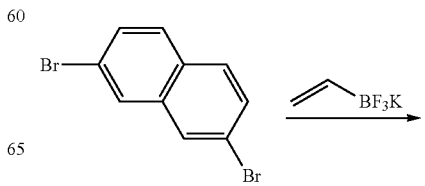

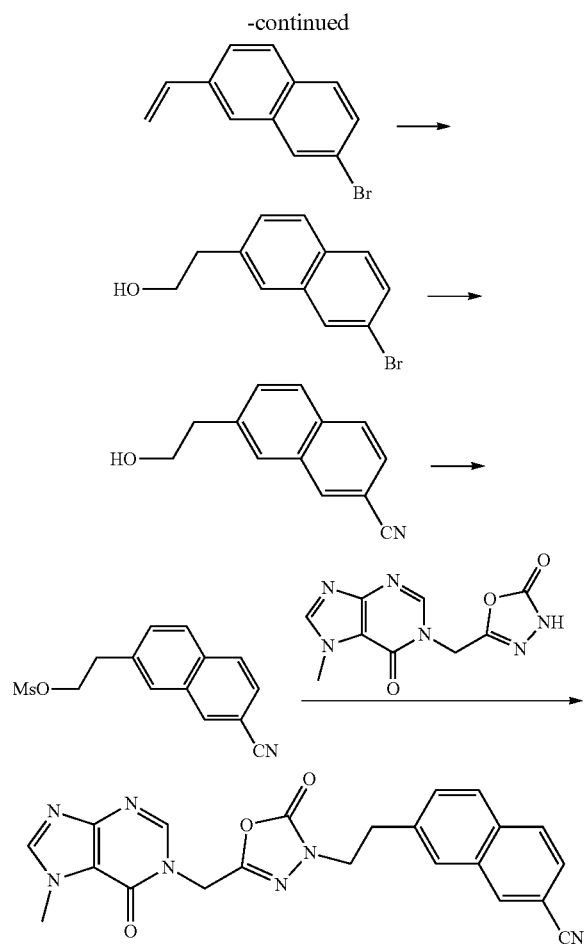

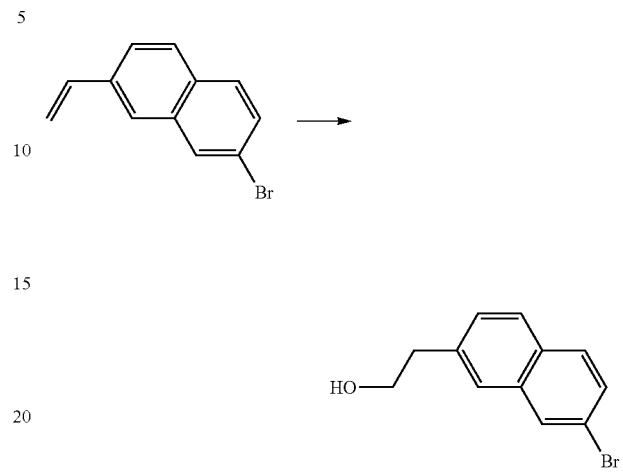

Step 2: Preparation of 2-(7-bromonaphthalen-2-yl)ethanol

BH$_3$-THF (12 mL, 12.1 mmol, 1M in THF) was added dropwise into a mixture of 2-bromo-7-ethenylnaphthalene (0.56 g, 2.41 mmol) in tetrahydrofuran (10 mL) at 0° C. The reaction mixture was stirred for 5 hours at room temperature. To this was added sodium hydroxide aqueous (10M, 2 mL) and H$_2$O$_2$(30%, 10 mL). The resulting solution was warmed to 60° C. and stirred overnight. The reaction was diluted with water, extracted with ethyl acetate, dried over anhydrous sodium sulfate, and concentrated under vacuum. The residue was applied onto a silica gel column eluted with ethyl acetate/petroleum ether (1:2) to afford the title compound (0.6 g, 48%) as an off-white solid.

Step 1: Preparation of 2-bromo-7-vinylnaphthalene

Step 3: Preparation of 7-(2-hydroxyethyl)-2-naphthonitrile

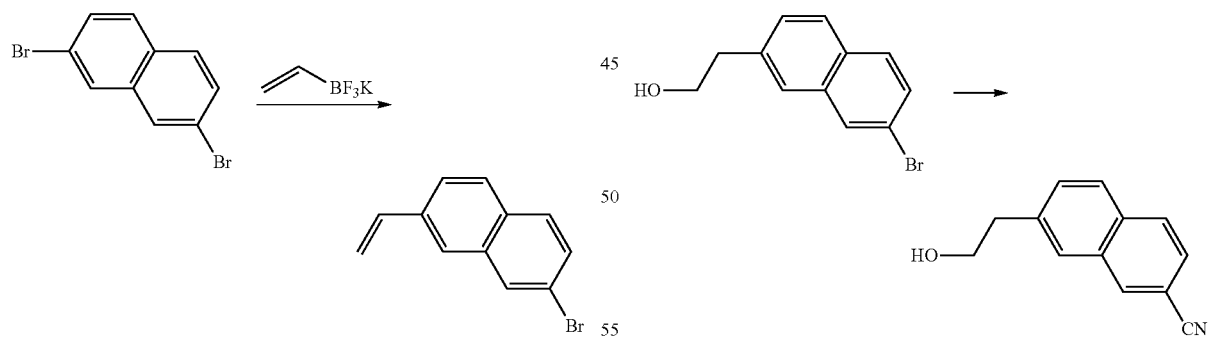

A mixture of 2,7-dibromonaphthalene (1 g, 3.49 mmol), potassium vinyltrifluoroborate (391 mg, 2.92 mmol), Pd(PPh$_3$)$_4$(335 mg, 0.29 mmol), sodium carbonate (922 mg, 8.69 mmol), dioxane (20 mL), and water (4 ml) was stirred for 3 h at 80° C. under nitrogen. The solids were filtered out. The filtrate was diluted with ethyl acetate, washed with water, dried with anhydrous Na$_2$SO$_4$, and concentrated under vacuum. The residue was purified by a silica gel column eluting with ethyl acetate/hexane (1:90) to afford the title compound (0.56 g, 82%) as a white solid.

A mixture of 2-(7-bromonaphthalen-2-yl)ethan-1-ol (300 mg, 1.2 mmol), Pd$_2$(dba)$_3$.CHCl$_3$ (248 mg, 0.24 mmol), dppf (133 mg, 0.2 mmol), Zn(CN)$_2$ (278 mg, 2.40 mmol), N,N-dimethylformamide (10 mL) was stirred overnight at 120° C. under nitrogen. The solids were filtered out. The resulting mixture was concentrated under vacuum. The residue was purified by a silica gel column eluting with ethyl acetate/petroleum ether (2:3) to afford the title compound (123 mg, 52%) as an off-white solid.

Step 4: Preparation of 2-(7-cyanonaphthalen-2-yl)ethyl methanesulfonate

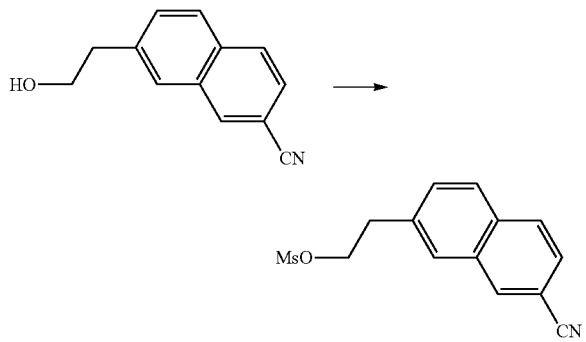

MsCl (87 mg, 0.76 mmol) was added dropwise into a solution of 7-(2-hydroxyethyl)naphthalene-2-carbonitrile (100 mg, 0.51 mmol), TEA (154 mg, 1.52 mmol), and dichloromethane (10 mL) at 0° C. The resulting solution was stirred for 2 h at room temperature and concentrated under vacuum. The crude was used directly for the next step.

Step 5: Preparation of 7-[2-[5-[(7-methyl-6-oxo-purin-1-yl)methyl]-2-oxo-1,3,4-oxadiazol-3-yl]ethyl]naphthalene-2-carbonitrile

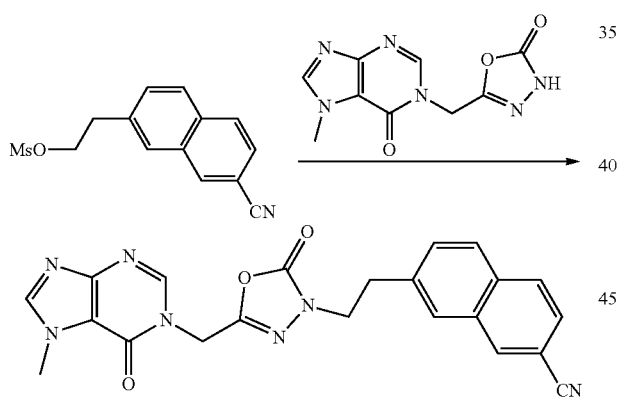

A mixture of 2-(7-cyanonaphthalen-2-yl)ethyl methanesulfonate (130 mg, 0.47 mmol), 7-methyl-1-[(5-oxo-4,5-dihydro-1,3,4-oxadiazol-2-yl)methyl]-6,7-dihydro-1H-purin-6-one (116 mg, 0.46 mmol), potassium carbonate (194 mg, 1.40 mmol), TBAI (10 mg), and N,N-dimethylformamide (10 g, 136.81 mmol) was stirred for 12 h at room temperature. The solids were filtered out. The resulting mixture was concentrated under vacuum. The crude product was purified on a C18 silica gel column eluting with $CH_3CN/H_2O$ (10 mmol/L $NH_4HCO_3$) increasing from 5% to 95% over 30 min. This resulted in the title compound (71.7 mg, 35.9%) as a white solid. LCMS [M+H$^+$] 428. $^1$H NMR (400 MHz, DMSO-d$_6$) δ 8.46 (s, 1H), 8.35 (s, 1H), 8.24 (s, 1H), 8.06 (d, J=8.5 Hz, 1H), 7.95 (d, J=8.4 Hz, 1H), 7.79 (s, 1H), 7.74 (d, J=8.4 Hz, 1H), 7.60 (d, J=8.4 Hz, 1H), 5.23 (s, 2H), 4.03-3.88 (m, 5H), 3.12 (t, J=6.6 Hz, 2H).

Example Compounds 37 ad 38: Preparation of 5-[(7-methyl-6-oxo-purin-1-yl)methyl]-3-[rac-(2S)-2-fluoro-2-(2-naphthyl)ethyl]-1,3,4-oxadiazol-2-one and 5-[(7-methyl-6-oxo-purin-1-yl)methyl]-3-[rac-(2S)-2-fluoro-2-(2-naphthyl)ethyl]-1,3,4-oxadiazol-2-one The overall Example Compounds 37 and 38 reaction scheme is as follows:

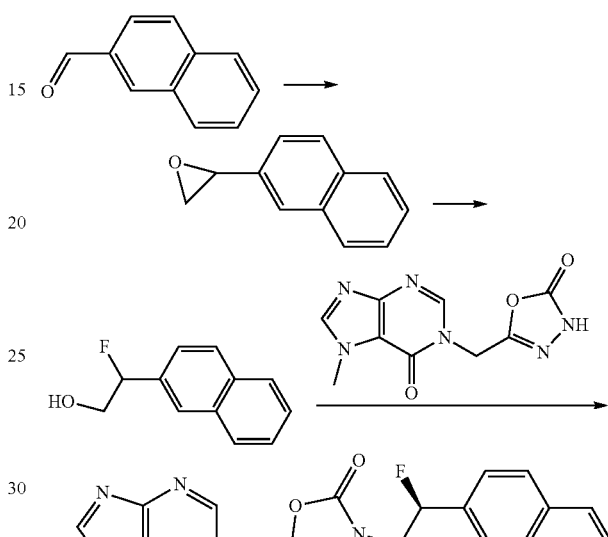

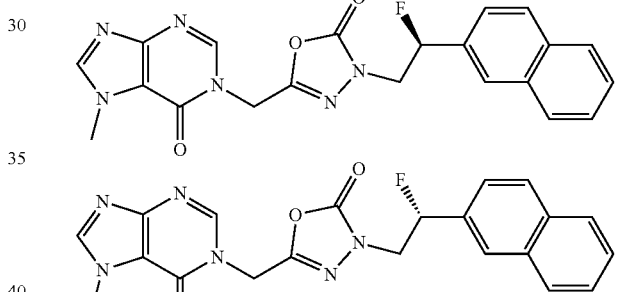

Step 1: Preparation of 2-(naphthalen-2-yl)oxirane

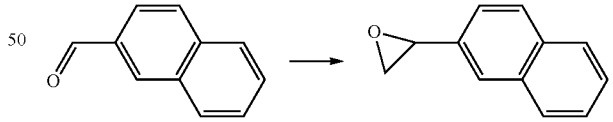

Sodium hydride (310 mg, 12.80 mmol) was added into DMSO (20 mL) under nitrogen. This was followed by the addition of trimethylsulfanium iodide (2.6 g, 12.80 mmol) in portions. The mixture was stirred for 30 min. To this was added a solution of naphthalene-2-carbaldehyde (1 g, 6.40 mmol) in tetrahydrofuran (15 mL) dropwise with stirring at 0° C. The resulting solution was stirred for 5 h at 0° C. The reaction was then quenched by water, extracted with ethyl acetate, and concentrated under vacuum. The residue was purified by a silica gel column eluting with ethyl acetate/hexane (1:5) to afford the title compound (0.78 g, 72%) as clear oil.

Step 2: Preparation of 2-fluoro-2-(naphthalen-2-yl)ethanol

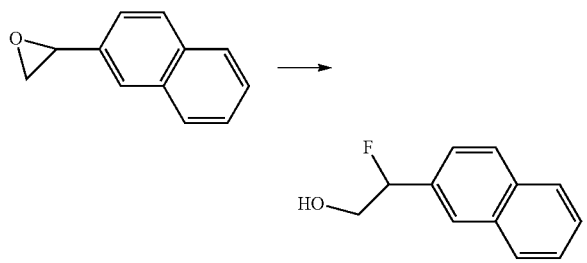

BF$_3$.Et$_2$O (327 mg, 2.3 mmol) was added dropwise into a mixture of 2-(naphthalen-2-yl)oxirane (0.78 g, 4.60 mmol), triethylamine.3HF (1.11 g, 6.90 mmol) in dichloromethane (20 mL) at 0° C. The resulting solution was stirred overnight at room temperature. The reaction was then quenched by water, extracted with dichloromethane, dried over anhydrous sodium sulfate, and concentrated under vacuum. The residue was purified by a silica gel column eluting with ethyl acetate/petroleum ether (1:3) to afford the title compound (0.4 g, 46%) as clear oil.

Step 3: Preparation of 5-[(7-methyl-6-oxo-purin-1-yl)methyl]-3-[rac-(2S)-2-fluoro-2-(2-naphthyl)ethyl]-1,3,4-oxadiazol-2-one and 5-[(7-methyl-6-oxo-purin-1-yl)methyl]-3-[rac-(2S)-2-fluoro-2-(2-naphthyl)ethyl]-1,3,4-oxadiazol-2-one

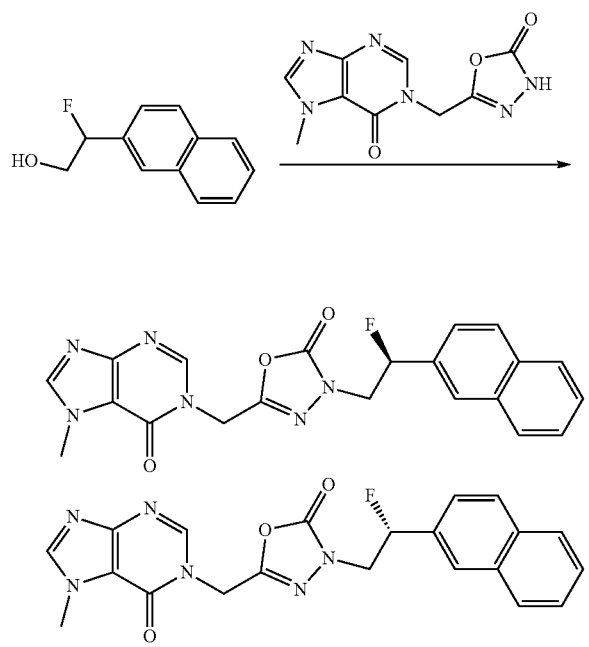

DIAD (323 mg, 1.59 mmol) was added dropwise into a mixture of 7-methyl-1-[(5-oxo-4,5-dihydro-1,3,4-oxadiazol-2-yl)methyl]-6,7-dihydro-1H-purin-6-one (150 mg, 0.60 mmol), 2-fluoro-2-(naphthalen-2-yl)ethan-1-ol (196 mg, 1.03 mmol), PPh$_3$ (419 mg, 1.59 mmol), and DMF (10 mL). The resulting solution was stirred for 1 h at room temperature. The resulting mixture was concentrated under vacuum. The crude product was purified on a C18 silica gel column eluting with CH$_3$CN/H$_2$O (10 mmol/L NH$_4$HCO$_3$) increasing from 5% to 95% over 30 min. This resulted in 80 mg of a racemic mixture. The racemic was separated by Chiral-Prep-HPLC with the following conditions (Prep-HPLC-009): Column, Chiralpak IA, 2*25 cm, 5 um; mobile phase, Hex and ethanol (hold 50.0% ethanol—in 28 min); Detector, UV 220/254 nm. This resulted in 28.3 mg of 5-[(7-methyl-6-oxo-purin-1-yl)methyl]-3-[rac-(2S)-2-fluoro-2-(2-naphthyl)ethyl]-1,3,4-oxadiazol-2-one as a white solid. LCMS [M+H$^+$] 421. t$_R$=10.702 min (Repaired IA, 0.46×10 cm, 5 μm, (Hex:DCM=5:1)(0.1% DEA):EtOH=50:50, 1.0 ml/min). $^1$H NMR (400 MHz, DMSO-d6) δ 8.37 (s, 1H), 8.25 (s, 1H), 8.02-7.89 (m, 4H), 7.62-7.51 (m, 3H), 5.97 (m, 1H), 5.27 (s, 2H), 4.37-4.23 (m, 1H), 4.14 (m, 1H), 3.99 (s, 3H). This also resulted in 29.6 mg of 5-[(7-methyl-6-oxo-purin-1-yl)methyl]-3-[rac-(2S)-2-fluoro-2-(2-naphthyl)ethyl]-1,3,4-oxadiazol-2-one as a white solid. LCMS [M+H$^+$] 421. t$_R$=10.587 min (Repaired IA, 0.46×10 cm, 5 μm, (Hex:DCM=5:1)(0.1% DEA):EtOH=50:50, 1.0 ml/min). $^1$H NMR (400 MHz, DMSO-d6) δ 8.37 (s, 1H), 8.25 (s, 1H), 8.02-7.89 (m, 4H), 7.62-7.51 (m, 3H), 5.97 (m, 1H), 5.27 (s, 2H), 4.37-4.23 (m, 1H), 4.14 (m, 1H), 3.99 (s, 3H).

Example Compound 39: Preparation of 3-(4-chloro-3-methylphenethyl)-5-((7-methyl-6-oxo-6H-purin-1(7H)-yl)methyl)-1,3,4-oxadiazol-2(3H)-one The overall Example Compound 39 reaction scheme is as follows:

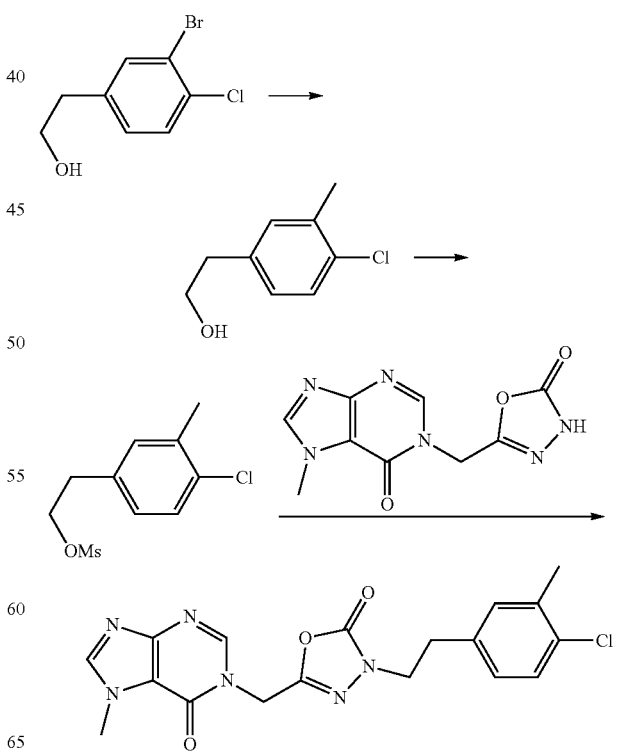

Step 1: Preparation of 2-(3-bromo-4-chlorophenyl)ethanol

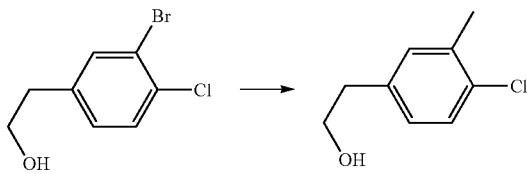

A mixture of 2-(3-bromo-4-chlorophenyl)ethan-1-ol (300 mg, 1.27 mmol), methylboronic acid (92 mg, 1.54 mmol), potassium carbonate (530 mg, 3.84 mmol), Pd(dppf)Cl$_2$ (93 mg, 0.13 mmol), and dioxane (3 mL) was stirred for 2 h at 100° C. under nitrogen. The resulting mixture was concentrated under vacuum. The residue was purified by a silica gel column eluting with ethyl acetate/petroleum ether (1/10) to afford the title compound (70 mg, 32%) as a yellow solid. GCMS m/z=170, 172.

Step 2: Preparation of 4-chloro-3-methylphenethyl methanesulfonate

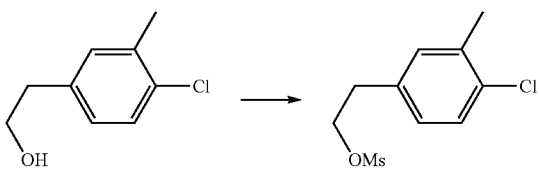

MsCl (56 mg, 0.49 mmol) was added to a mixture of 2-(4-chloro-3-methylphenyl)ethan-1-ol (70 mg, 0.41 mmol), dichloromethane (5 mL), and triethylamine (125 mg, 1.23 mmol) at 0° C. under nitrogen. The resulting solution was stirred for 1 h at 0° C. The reaction was then quenched by water, extracted with dichloromethane, dried over anhydrous sodium sulfate, and concentrated under vacuum. This resulted in the title compound (90 mg, 88%) of as a gray solid. GCMS m/z=248, 250.

Step 3: Preparation of 3-(4-chloro-3-methylphenethyl)-5-((7-methyl-6-oxo-6H-purin-1(7H)-yl)methyl)-1,3,4-oxadiazol-2(3H)-one

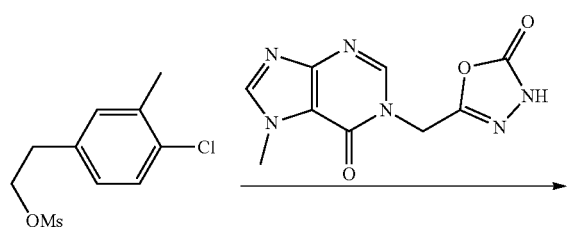

A mixture of 2-(3-chloro-4-methylphenyl)ethyl methanesulfonate (90 mg, 0.36 mmol), 7-methyl-1-[(5-oxo-4,5-dihydro-1,3,4-oxadiazol-2-yl)methyl]-6,7-dihydro-1H-purin-6-one (54 mg, 0.22 mmol), potassium carbonate (151 mg, 1.10 mmol), TBAI (13 mg, 0.04 mmol), and N,N-dimethylformamide (3 mL) was stirred for 5 h at 60° C. The solids were filtered out. The filtrate was purified on a C18 silica gel column eluting with CH$_3$CN/H$_2$O (10 mmol/L NH$_4$HCO$_3$) increasing from 5% to 90% over 30 min. This resulted in the title compound (19.1 mg, 13%) as a yellow solid. LCMS [M+H$^+$] 401. $^1$H NMR (300 MHz, CDCl$_3$) δ 8.07 (s, 1H), 7.88 (s, 1H), 7.27 (d, J=8.3 Hz, 1H), 7.07 (s, 1H), 6.96 (d, J=9.0 Hz, 1H), 5.12 (s, 2H), 4.13 (s, 3H), 3.95-3.90 (m, 2H), 3.04-2.92 (m, 2H), 2.36 (s, 3H).

Example Compound 40: Preparation of 5-((8-chloro-5-methyl-4-oxopyrido[3,4-d]pyrimidin-3(4H)-yl)methyl)-3-(4-chlorophenethyl)-1,3,4-oxadiazol-2(3H)-one

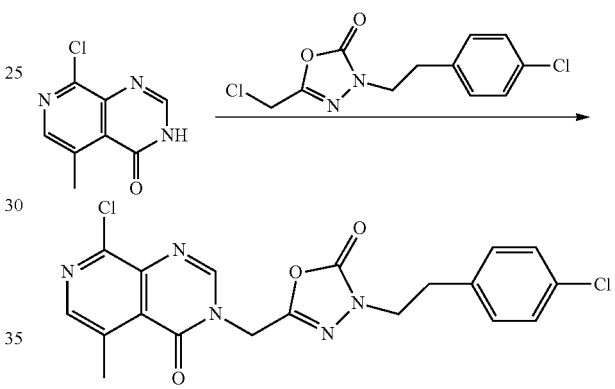

A mixture of 8-chloro-5-methyl-3H,4H-pyrido[3,4-d]pyrimidin-4-one (40 mg, 0.20 mmol), TBAI (8.12 mg, 0.02 mmol), Cs$_2$CO$_3$ (216 mg, 0.66 mmol), 5-(chloromethyl)-3-[2-(4-chlorophenyl)ethyl]-2,3-dihydro-1,3,4-oxadiazol-2-one (72.43 mg, 0.26 mmol), and N,N-dimethylformamide (2 mL) was stirred for 16 h at room temperature. The solids were filtered out. The filtrate was purified on a C18 silica gel column eluting with CH$_3$CN/H$_2$O (10 mmol/L NH$_4$HCO$_3$, 5% to 95%, 30 min). This resulted in the title compound (24.6 mg, 21%) as a white solid. LCMS [M+H$^+$]=432. $^1$H NMR (300 MHz, CDCl$_3$) δ 8.33 (s, 1H), 8.22 (s, 1H), 7.28-7.26 (m, 2H), 7.14-7.11 (m, 2H), 5.07 (s, 2H), 3.98-3.89 (m, 2H), 3.05-3.00 (m, 2H), 2.82 (s, 3H).

Example Compound 41: Preparation of 3-(4-chloro-2-fluorophenethyl)-5-((7-methyl-6-oxo-6H-purin-1(7H)-yl)methyl)-1,3,4-oxadiazol-2(3H)-one The overall Example Compound 41 reaction scheme is as follows:

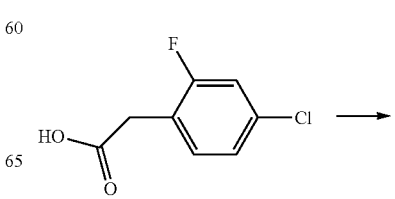

Step 1: Preparation of 2-(4-chloro-2-fluorophenyl)ethanol

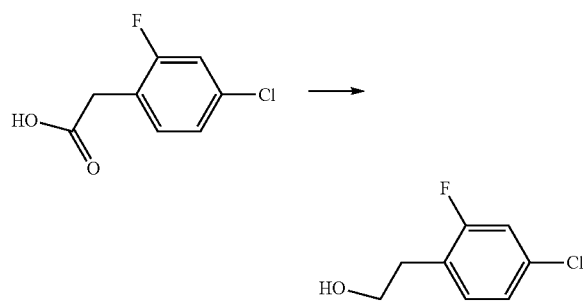

BH₃.THF (16 mL, 1 M in THF) was added dropwise into a solution of 2-(4-chloro-2-fluorophenyl)acetic acid (1 g, 5.30 mmol) in tetrahydrofuran (50 mL) at 0° C. The reaction was stirred for 1 h at 0° C., quenched by water, extracted with ethyl acetate, washed with brine, dried over anhydrous sodium sulfate, and concentrated under vacuum. The residue was purified by a silica gel column eluting with ethyl acetate/petroleum ether (1:5) to afford the title compound (934 mg) as yellow oil. GCMS m/z=174, 176.

Step 2: Preparation of 4-chloro-2-fluorophenethyl methanesulfonate

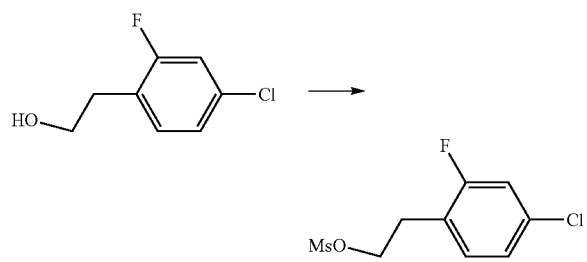

MsCl (157 mg, 1.40 mmol) was added dropwise into a mixture of 2-(4-chloro-2-fluorophenyl)ethan-1-ol (200 mg, 1.10 mmol), dichloromethane (2 mL), and triethylamine (348 mg, 3.43 mmol) at 0° C. under nitrogen. The resulting solution was stirred for 1 h at 0° C., quenched by water, extracted with dichloromethane, dried over anhydrous sodium sulfate, and concentrated under vacuum. This resulted in the title compound (500 mg) as a yellow solid. GCMS m/z=252, 254.

Step 3: Preparation of 3-(4-chloro-2-fluorophenethyl)-5-((7-methyl-6-oxo-6H-purin-1(7H)-yl)methyl)-1,3,4-oxadiazol-2(3H)-one

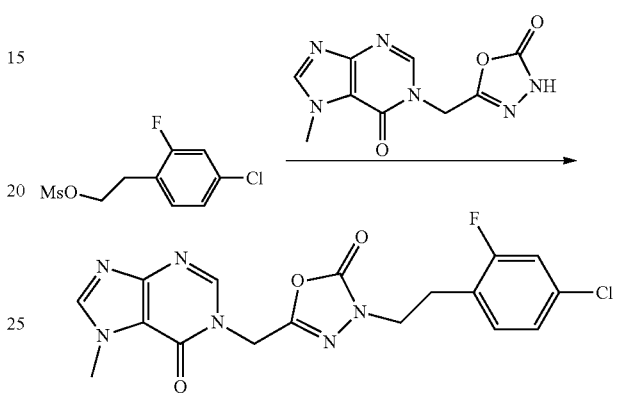

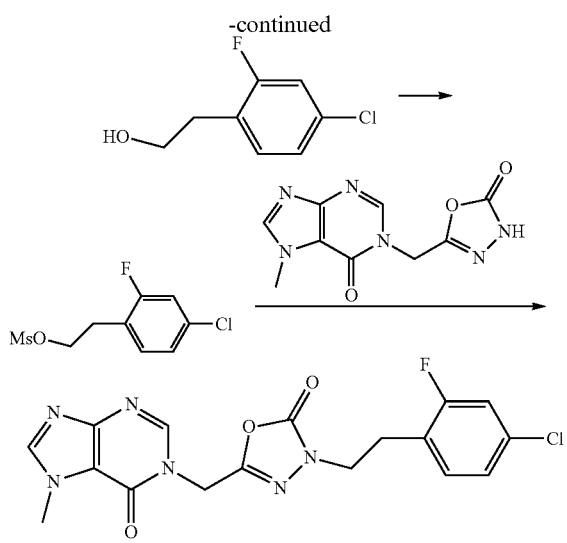

A mixture of 7-methyl-1-[(5-oxo-4,5-dihydro-1,3,4-oxadiazol-2-yl)methyl]-6,7-dihydro-1H-purin-6-one (80 mg, 0.32 mmol), TBAI (12 mg, 0.03 mmol), potassium carbonate (133.5 mg, 0.97 mmol), N,N-dimethylformamide (5 mL), and 2-(4-chloro-2-fluorophenyl)ethyl methanesulfonate (162.6 mg, 0.64 mmol) was stirred for 3 h at 50° C. in an oil bath. The solids were filtered out. The filtrate was purified on a C18 silica gel column eluting with CH₃CN/H₂O (10 mmol/L NH₄HCO₃) increasing from 5% to 95% over 30 min. This resulted in the title compound (100 mg, 38%) a white solid. LCMS [M+H+] 405. $^1$H NMR (400 MHz, CDCl₃) δ 8.05 (s, 1H), 7.87 (s, 1H), 7.11-7.05 (m, 3H), 5.11 (s, 2H), 4.13 (d, J=10.8 Hz 3H), 3.95 (t, J=7.1 Hz, 2H), 3.04 (t, J=7.1 Hz, 2H).

Example Compound 42: Preparation of 3-(2-(6-chlorobiphenyl-3-yl)ethyl)-5-((7-methyl-6-oxo-6H-purin-1(7H)-yl)methyl)-1,3,4-oxadiazol-2(3H)-one The overall Example Compound 42 reaction scheme is as follows:

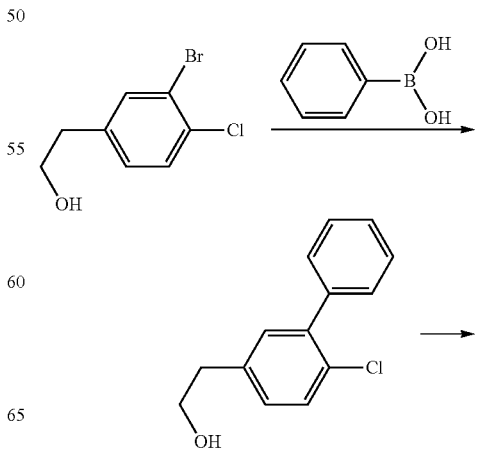

Step 1: Preparation of 2-(3-bromo-4-chlorophenyl)ethanol

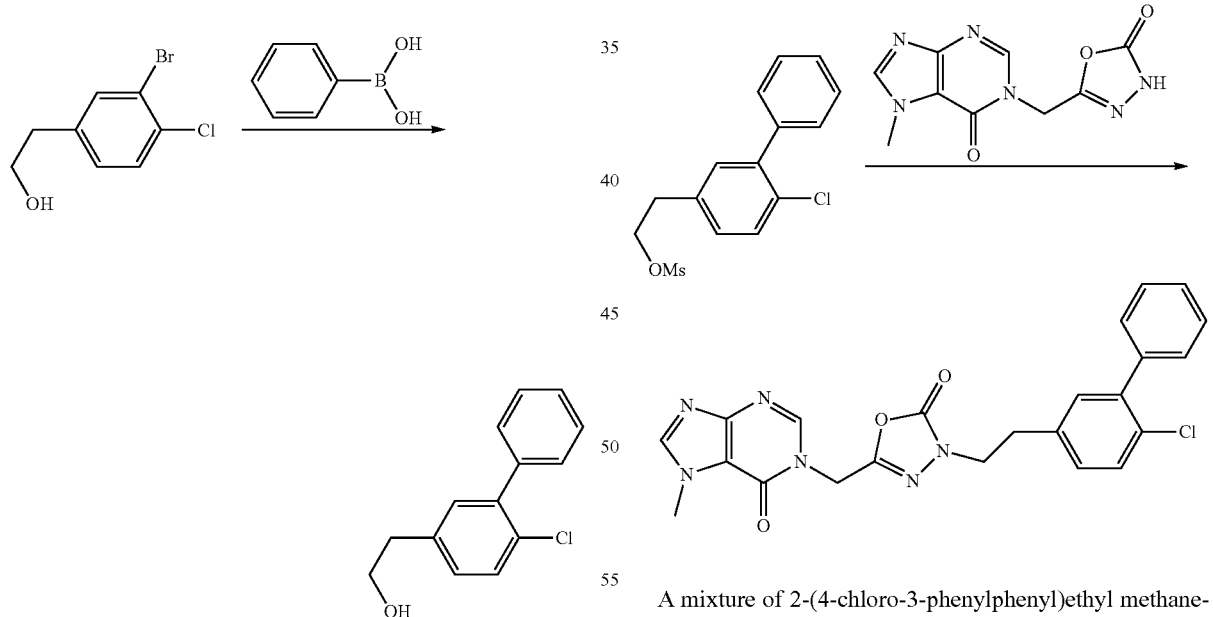

A mixture of 2-(3-bromo-4-chlorophenyl)ethan-1-ol (300 mg, 1.27 mmol), phenylboronic acid (188 mg, 1.54 mmol), potassium carbonate (535 mg, 3.87 mmol), Pd(dppf)Cl$_2$ (94 mg), and dioxane (10 mL) was stirred for 2 h at 100° C. The resulting mixture was concentrated under vacuum. The residue was purified by a silica gel column eluting with ethyl acetate/petroleum ether (1/10) to afford the title compound (150 mg, 51%) as yellow oil. GCMS m/z=232, 234.

Step 2: Preparation of 2-(6-chlorobiphenyl-3-yl)ethyl methanesulfonate

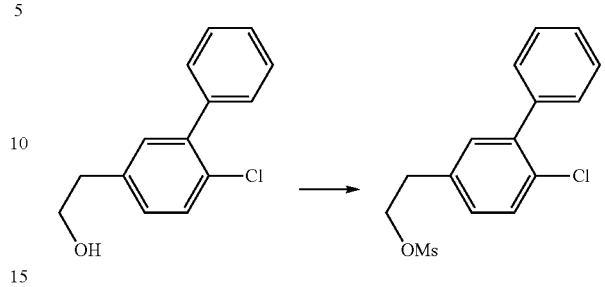

MsCl (90 mg, 0.79 mmol) was added dropwise into a mixture of 2-(4-chloro-3-phenylphenyl)ethan-1-ol (150 mg, 0.65 mmol), dichloromethane (2 mL), and triethylamine (196 mg, 1.94 mmol) at 0° C. under nitrogen. The resulting solution was stirred for 2 h at 0° C. The reaction was then quenched by water, extracted with dichloromethane, dried over anhydrous sodium sulfate, and concentrated under vacuum to afford the title compound (100 mg, 54%) as a gray solid. GCMS m/z=310, 312.

Step 3: Preparation of 3-(2-(6-chlorobiphenyl-3-yl)ethyl)-5-((7-methyl-6-oxo-6H-purin-1(7H)-yl)methyl)-1,3,4-oxadiazol-2(3H)-one

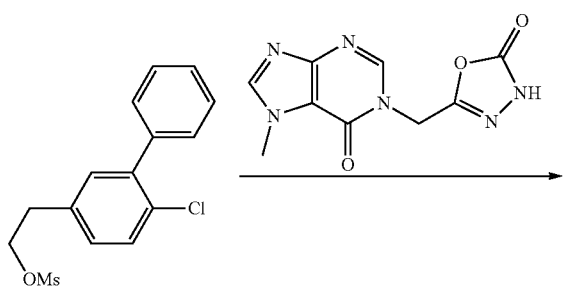

A mixture of 2-(4-chloro-3-phenylphenyl)ethyl methanesulfonate (100 mg, 0.32 mmol), 7-methyl-1-[(5-oxo-4,5-dihydro-1,3,4-oxadiazol-2-yl)methyl]-6,7-dihydro-1H-purin-6-one (80 mg, 0.32 mmol), potassium carbonate (134 mg, 0.97 mmol), TBAI (12 mg, 0.03 mmol), and N,N-dimethylformamide (3 mL) was stirred for 5 h at room temperature. The solids were filtered out. The reaction mixture was purified on a C18 silica gel column eluting with CH$_3$CN/H$_2$O (10 mmol/L NH$_4$HCO$_3$) increasing from 5% to 90% over 30 min. This resulted in the title compound (52.6 mg, 35%) as a white solid. LCMS [M+H$^+$] 463. $^1$H NMR (300 MHz, CDCl$_3$) δ 8.03 (s, 1H), 7.86 (s, 1H), 7.48-7.37 (m, 6H), 7.17 (d, J=2.0 Hz, 1H), 7.11-7.08 (m, 1H), 5.08 (s, 2H), 4.08 (s, 3H), 3.98-3.93 (m, 2H), 3.06-3.01 (m, 2H).

Example Compound 43: Preparation of 3-(4-chlorophenethyl)-5-((5,7-dimethyl-4-oxoimidazo[1,5-f][1,2,4]triazin-3(4H)-yl)methyl)-1,3,4-oxadiazol-2(3H)-one The overall Example Compound 43 reaction scheme is as follows:

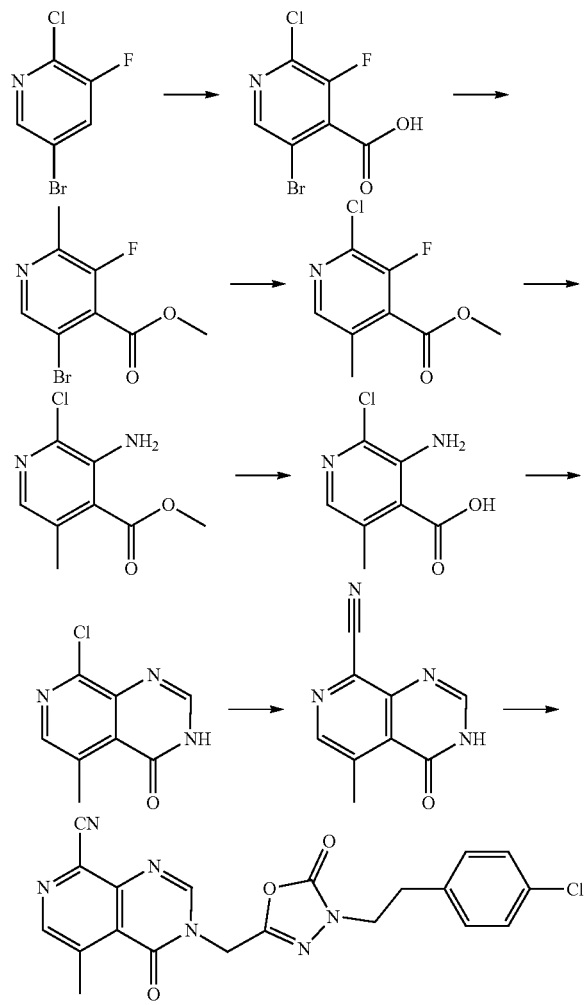

Step 1: Preparation of 5-bromo-2-chloro-3-fluoroisonicotinic acid

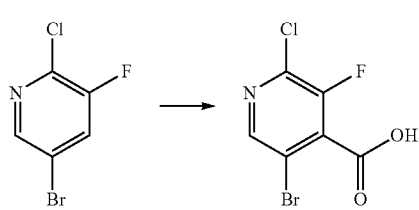 [SMILES: Fc1cc(Br)cnc1Cl ; O=C(O)c1c(Br)cnc(Cl)c1F]

LDA (47.5 mL, 2.0 mol in THF) was added dropwise into a solution of 5-bromo-2-chloro-3-fluoropyridine (10 g, 47.52 mmol) in tetrahydrofuran (300 mL) at −78° C. under nitrogen. The resulting solution was stirred for 2 h at −78° C. The resulting mixture was poured into the $CO_2$ (solid) in THF. The reaction mixture was concentrated under vacuum. The pH value of the residue was adjusted to <7 with hydrogen chloride (2 M). The resulting mixture was extracted with ethyl acetate, washed with brine, dried over anhydrous sodium sulfate, and concentrated under vacuum. This resulted in the title compound (15 g, crude) as a white solid. LCMS [M−H$^+$] 254.

Step 2: Preparation of methyl 5-bromo-3-fluoro-2-methylisonicotinate

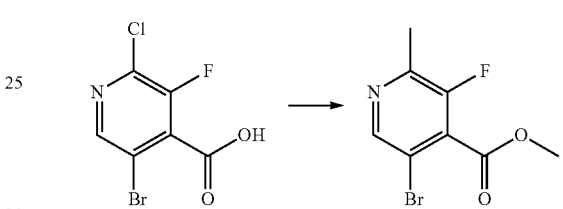

A mixture of 5-bromo-2-chloro-3-fluoropyridine-4-carboxylic acid (15 g, 59.0 mmol), tetrahydrofuran (100 mL), methanol (20 mL), TMSCHN$_2$ (60 mL, 2M in hexane) was stirred for 2 h at room temperature. The resulting mixture was concentrated under vacuum. This resulted in the title compound (12 g, crude) as oil which was used for the next step without any further purification. LCMS [M+H+] 248.

Step 3: Preparation of methyl 2-chloro-3-fluoro-5-methylisonicotinate

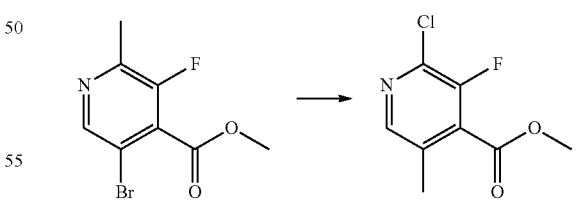

A mixture of methyl 5-bromo-2-chloro-3-fluoropyridine-4-carboxylate (5 g, 18.62 mmol), tricyclohexylphosphane (1.3 g, 4.60 mmol), palladium acetate (147 mg, 0.66 mmol), and toluene (60 mL) was stirred for 12 h at 100° C. under nitrogen. The resulting mixture was concentrated under vacuum. The residue was purified by a silica gel column eluting with ethyl acetate/petroleum ether (1:5) to afford the title compound (2.5 g, 66%) as a white solid. LCMS [M+H+] 204.

Step 4: Preparation of methyl 3-amino-2-chloro-5-methylisonicotinate

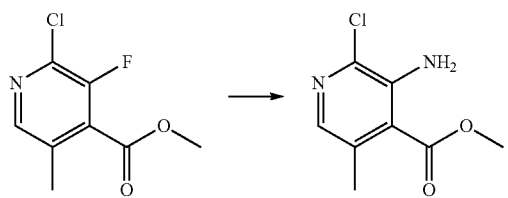

NH₃(g) (17.5 mL, 7 M in CH₃OH) was added dropwise into a solution of methyl 2-chloro-3-fluoro-5-methylpyridine-4-carboxylate (2.5 g, 12.28 mmol) in CH₃OH (50 mL). The resulting solution was stirred for 12 h at 100° C. and concentrated under vacuum. The residue was purified by a silica gel column eluting with ethyl acetate/petroleum ether (1:5) to afford the title compound (300 mg, 12%) as a white solid. LCMS [M+H⁺] 201.

Step 5: Preparation of 3-amino-2-chloro-5-methylisonicotinic acid

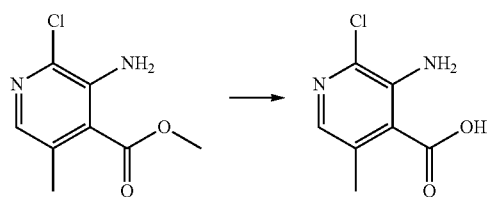

A mixture of methyl 3-amino-2-chloro-5-methylpyridine-4-carboxylate (300 mg, 1.5 mmol), water (2 mL), sodium hydroxide (200 mg, 5.00 mmol), and methanol (10 mL) was stirred for 2 h at 50° C. The resulting mixture was concentrated under vacuum. This resulted in the title compound (250 mg, crude) as a white solid which was used for the next step without any further purification. LCMS [M+H⁺] 187.

Step 6: Preparation of 8-chloro-5-methylpyrido[3,4-d]pyrimidin-4(3H)-one

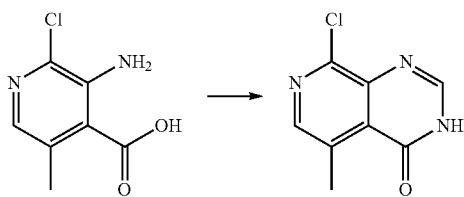

A mixture of 3-amino-2-chloro-5-methylpyridine-4-carboxylic acid (252 mg, 1.35 mmol), acetic acid; methanimidamide (600 mg, 5.80 mmol), and BuOH (15 mL) was stirred for 12 h at 120° C. The resulting mixture was concentrated under vacuum. The residue was purified by a silica gel column eluting with dichloromethane/methanol (20:1) to afford the title compound (140 mg, 53%) as a white solid. LCMS [M+H⁺] 196.

Step 7: Preparation of 5-methyl-4-oxo-3,4-dihydropyrido[3,4-d]pyrimidine-8-carbonitrile

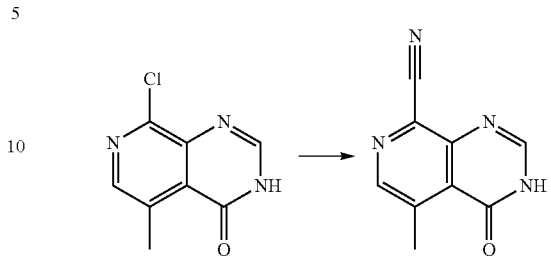

A mixture of 8-chloro-5-methyl-3H,4H-pyrido[3,4-d]pyrimidin-4-one (200 mg, 1.02 mmol), Pd₂(dba)₃ (100 mg, 0.10 mmol), dppf (200 mg, 0.36 mmol), zinc cyanide (120 mg, 1.00 mmol), and N,N-dimethylformamide (5 mL) was irradiated with microwave radiation for 1 h at 130° C. under nitrogen. The resulting mixture was concentrated under vacuum. The residue was purified by a silica gel column eluting with dichloromethane/methanol (10/1) to afford the title compound (140 mg, 74%) as a white solid. LCMS [M+H+] 187.

Step 8: Preparation of 3-((4-(4-chlorophenethyl)-5-oxo-4,5-dihydro-1,3,4-oxadiazol-2-yl)methyl)-5-methyl-4-oxo-3,4-dihydropyrido[3,4-d]pyrimidine-8-carbonitrile

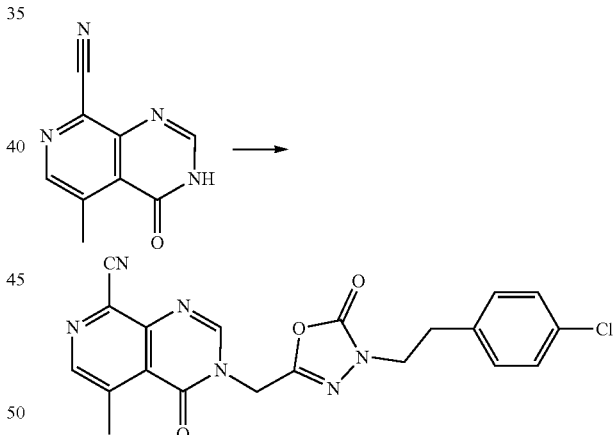

A mixture of 5-methyl-4-oxo-3H,4H-pyrido[3,4-d]pyrimidine-8-carbonitrile (100 mg, 0.54 mmol), 5-(chloromethyl)-3-[2-(4-chlorophenyl)ethyl]-2,3-dihydro-1,3,4-oxadiazol-2-one (180 mg, 0.66 mmol), TBAI (30 mg, 0.08 mmol), potassium carbonate (130 mg, 1.80 mmol), and N,N-dimethylformamide (5 mL) was stirred for 12 h at room temperature. The solids were filtered out. The reaction mixture was purified on a C18 silica gel column eluting with CH₃CN/H₂O (10 mmol/L NH₄HCO₃) increasing from 5% to 95% over 30 min. This resulted in the title compound (54.9 mg, 24%) as a white solid. LCMS [M+H+] 423. ¹H NMR (300 MHz, CDCl₃) δ 8.69 (s, 1H), 7.28-7.24 (m, 2H), 7.20-7.18 (m, 2H), 5.20 (s, 2H), 3.89-3.84 (m, 2H), 2.93-2.89 (m, 2H), 2.81 (s, 3H).

Example Compounds 44 and 45: Preparation of (S)-3-(2-(4-bromophenyl)-2-fluoroethyl)-5-((7-methyl-6-oxo-6H-purin-1 (7H)-yl)methyl)-1,3,4-oxadiazol-2(3H)-one and (R)-3-(2-(4-bromophenyl)-2-fluoroethyl)-5-((7-methyl-6-oxo-6H-purin-1(7H)-yl)methyl)-1,3,4-oxadiazol-2(3H)-one The overall Example Compounds 44 and 45 reaction scheme is as follows:

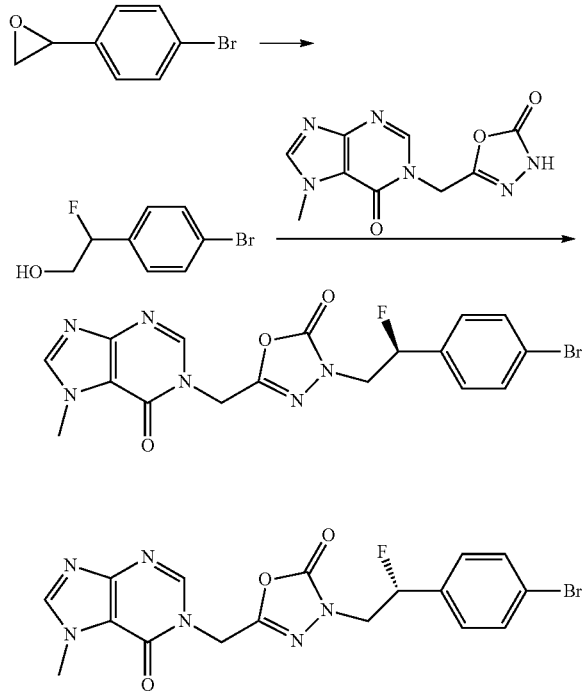

Step 1 Preparation of 2-(4-bromophenyl)-2-fluoroethanol

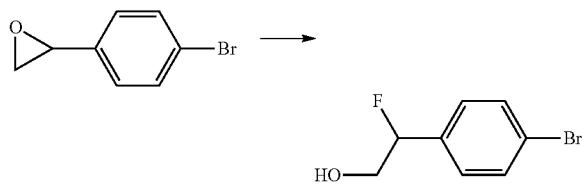

A mixture of 2-(4-bromophenyl)oxirane (800 mg, 4.00 mmol), dichloromethane (20 mL), triethylamine.3HF (1.95 g, 12.01 mmol), and BF$_3$.Et$_2$O (573.4 mg, 4.00 mmol) was stirred for 32 h at room temperature. The reaction was quenched by water. The pH value of the reaction mixture was adjusted to 8 with NH$_3$.H$_2$O. The resulting mixture was extracted with ethyl acetate, washed with brine, dried over anhydrous sodium sulfate, and concentrated under vacuum. The residue was purified by a silica gel column eluting with ethyl acetate/petroleum ether (1:2) to afford the title compound (260 mg, 30%) as light yellow oil. GCMS m/z=218, 220.

Step 2 Preparation of (S)-3-(2-(4-bromophenyl)-2-fluoroethyl)-5-((7-methyl-6-oxo-6H-purin-1 (7H)-yl) methyl)-1,3,4-oxadiazol-2(3H)-one and (R)-3-(2-(4-bromophenyl)-2-fluoroethyl)-5-((7-methyl-6-oxo-6H-purin-1 (7H)-yl)methyl)-1,3,4-oxadiazol-2(3H)-one

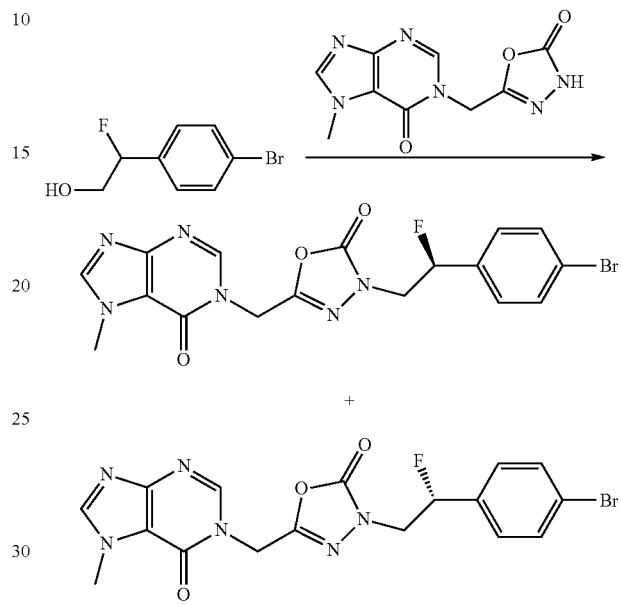

DIAD (556 mg, 2.75 mmol) was added dropwise into a mixture of 2-(4-bromophenyl)-2-fluoroethan-1-ol (240 mg, 1.10 mmol), 7-methyl-1-[(5-oxo-4,5-dihydro-1,3,4-oxadiazol-2-yl)methyl]-6,7-dihydro-1H-purin-6-one (272.8 mg, 1.10 mmol), N,N-dimethylformamide (3 mL), and PPh3 (866.3 mg, 3.30 mmol) at 0° C. under nitrogen. After being stirred for 2 h at room temperature the resulting mixture was concentrated under vacuum. The residue was purified on a C18 silica gel column eluting with CH$_3$CN/H$_2$O (10 mmol/L NH$_4$HCO$_3$) increasing from 5% to 95% over 30 min. This resulted in 110 mg of a racemic mixture. The racemic was separated by Chiral-Prep-HPLC with the following conditions (Prep-HPLC-009): Column, Chiralpak IA, 2*25 cm, 5 um; mobile phase, Hex and ethanol (hold 50.0% ethanol—in 28 min); Detector, UV 220/254 nm. This resulted in (S)-3-(2-(4-bromophenyl)-2-fluoroethyl)-5-((7-methyl-6-oxo-6H-purin-1(7H)-yl)methyl)-1,3,4-oxadiazol-2(3H)-one 37.5 mg (4%) as a white solid. LCMS [M+H+] 449. t$_R$=5.54 min (CHIRALPAK IE-3, 0.46×10 cm, 3 μm, MtBE (0.1% DEA): EtOH=50:50, 1.0 ml/min). $^1$H NMR (300 MHz, CDCl$_3$) δ 8.08 (s, 1H), 7.87 (s, 1H), 7.56 (d, J=9 Hz, 2H), 7.27-7.26 (m, 2H), 5.81-5.61 (m, 1H), 5.14 (s, 2H), 4.26-4.11 (m, 4H), 3.97-3.81 (m, 1H). This further resulted in (R)-3-(2-(4-bromophenyl)-2-fluoroethyl)-5-((7-methyl-6-oxo-6H-purin-1(7H)-yl)methyl)-1,3,4-oxadiazol-2(3H)-one (31.2 mg, 3%) as a white solid. LCMS [M+H$^+$] 449. t$_R$=6.22 min CHIRALPAK IE-3, 0.46×10 cm, 3 μm, MtBE (0.1% DEA): EtOH=50:50, 1.0 ml/min). $^1$H NMR (300 MHz, CDCl$_3$) δ 8.08 (s, 1H), 7.86 (s, 1H), 7.57-7.54 (m, 2H), 7.27-7.24 (m, 2H), 5.81-5.61 (m, 1H), 5.14 (s, 2H), 4.23-4.11 (m, 4H), 3.97-3.81 (m, 1H).

Example Compound 46: Preparation of 3-(4-chloro-phenethyl)-5-((5-methyl-4-oxopyrimido[4,5-d]pyrimidin-3(4H)-yl)methyl)-1,3,4-oxadiazol-2(3H)-one The overall Example Compound 46 reaction scheme is as follows:

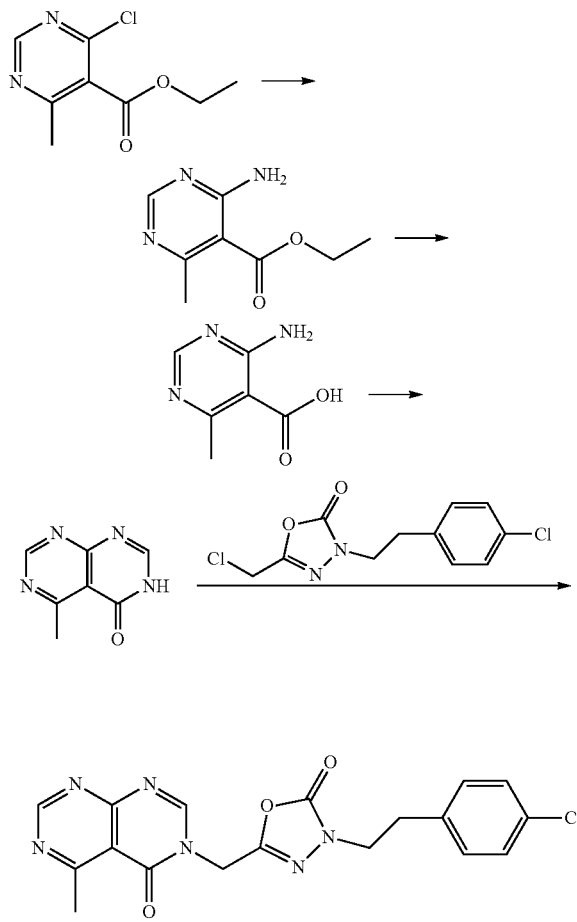

Step 1: Preparation of ethyl 4-amino-6-methylpyrimidine-5-carboxylate

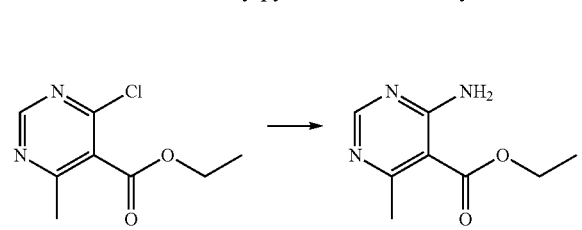

NH$_3$ (g) (8 mL, ~14% in ethanol) was added dropwise into a solution of ethyl 4-chloro-6-methylpyrimidine-5-carboxylate (800 mg, 4.00 mmol) in ethanol (10 mL). The resulting solution was stirred for 16 h at 120° C. The resulting mixture was concentrated under vacuum. The residue was purified by a silica gel column eluting with ethyl acetate/petroleum ether (1:5) to afford the title compound (700 mg, 97%) as a white solid. LCMS [M+H$^+$] 182.

Step 2: Preparation of 4-amino-6-methylpyrimidine-5-carboxylic acid

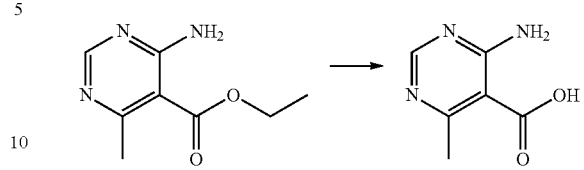

A mixture of ethyl 4-amino-6-methylpyrimidine-5-carboxylate (700 mg, 3.90 mmol), sodium hydroxide (464.4 mg, 11.60 mmol), water (6 mL), and methanol (30 mL) was stirred for 3 h at 50° C. The pH value of the solution was adjusted to 3 with hydrogen chloride (2M). The resulting mixture was concentrated under vacuum to afford the title compound (700 mg, crude) as a white solid. LCMS [M+H$^+$] 154.

Step 3: Preparation of 5-methylpyrimido[4,5-d]pyrimidin-4(3H)-one

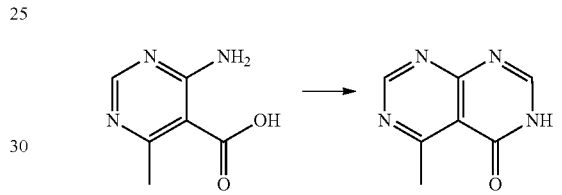

A mixture of 4-amino-6-methylpyrimidine-5-carboxylic acid (700 mg, 4.6 mmol), formamidine acetate (2 g, 19.40 mmol), and butan-1-ol (35 mL) was stirred for 3 days at 130° C. The reaction was diluted with water, extracted with ethyl acetate, washed with brine, dried over anhydrous sodium sulfate, and concentrated under vacuum. The residue was purified by a silica gel column eluting with dichloromethane/methanol (20/1) to afford the title compound (300 mg) as a light yellow solid. LCMS [M+H$^+$] 163.

Step 4: Preparation of 3-(4-chlorophenethyl)-5-((5-methyl-4-oxopyrimido[4,5-d] pyrimidin-3(4H)-yl)methyl)-1,3,4-oxadiazol-2(3H)-one

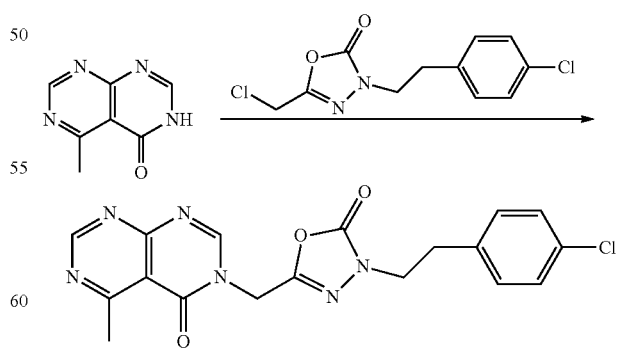

A mixture of 5-methyl-3H,4H-[1,3]diazino[4,5-d]pyrimidin-4-one (150 mg, 0.93 mmol), 5-(chloromethyl)-3-[2-(4-chlorophenyl)ethyl]-2,3-dihydro-1,3,4-oxadiazol-2-one (300 mg, 1.10 mmol), TBAI (34.15 mg, 0.09 mmol), potassium carbonate (335 mg, 2.42 mmol), and N,N-dimethylformamide (2 mL) was stirred for 2 h at room temperature. The solids were filtered out. The filtrate was purified on a C18 silica gel column eluting with $CH_3CN/H_2O$ (10 mmol/L $NH_4HCO_3$) increasing from 5% to 95% over 30 min. This resulted in the title compound (22 mg, 6%) as a white solid. LCMS [M+H$^+$] 339. $^1$H NMR (300 MHz, DMSO-d$_6$) δ 9.22 (s, 1H), 8.81 (s, 1H), 7.28 (d, J=8.4 Hz, 2H), 7.20 (d, J=8.4 Hz, 2H), 5.20 (s, 2H), 3.87 (t, J=6.8 Hz, 2H), 2.99-2.85 (m, 5H).

Example Compound 47: Preparation of 3-(4-chlorophenethyl)-5-((3-methyl-5-oxo-5H-thiazolo[3,2-a]pyrimidin-6-yl)methyl)-1,3,4-oxadiazol-2(3H)-one The overall Example Compound 47 reaction scheme is as follows:

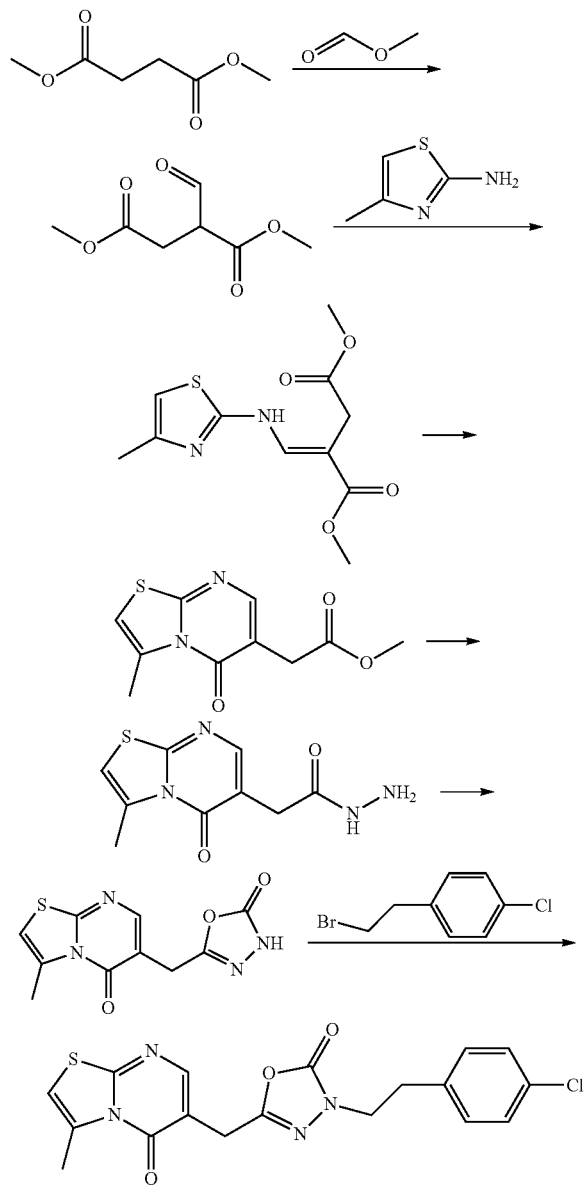

Step 1: Preparation of dimethyl 2-formylsuccinate

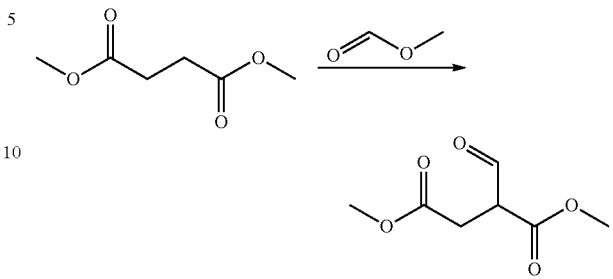

Methanol (122 mg, 3.80 mmol) was added dropwise into a mixture of sodium hydride (2.3 g, 57.50 mmol, 60%) and THF (50 mL) at 0° C. To the mixture was added a mixture of methyl formate (15 mL, 244.80 mmol) and 1,4-dimethyl butanedioate (5 mL, 38.20 mmol) dropwise with stirring at 0° C. The resulting solution was stirred for 12 h at 25° C. The resulting mixture was concentrated under vacuum. The pH value of the resulting solution was adjusted to 2 with hydrogen chloride (3M). The resulting solution was extracted with dichloromethane, washed with brine, dried over anhydrous sodium sulfate, and concentrated under vacuum. The residue was purified by a silica gel column eluting with dichloromethane/ethyl acetate (10/1) to afford the title compound (8 g crude) as yellow oil. LCMS [M+H$^+$] 175.

Step 2: Preparation of (E)-dimethyl 2-((4-methylthiazol-2-ylamino)methylene)succinate

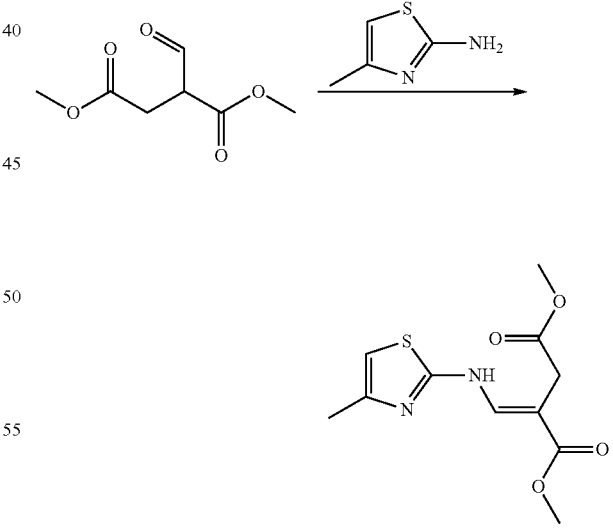

A mixture of 1,4-dimethyl 2-formylbutanedioate (8 g, 46.00 mmol), 4-methyl-1,3-thiazol-2-amine (4 g, 35.00 mmol), methanol (50 mL) was stirred for 12 h at 60° C. The resulting mixture was concentrated under vacuum. This resulted in the title compound (8 g crude) as yellow oil, which was used for the next step without any further purification. LCMS [M+H$^+$] 271

Step 3: Preparation of methyl 2-(3-methyl-5-oxo-5H-thiazolo[3,2-a]pyrimidin-6-yl)acetate

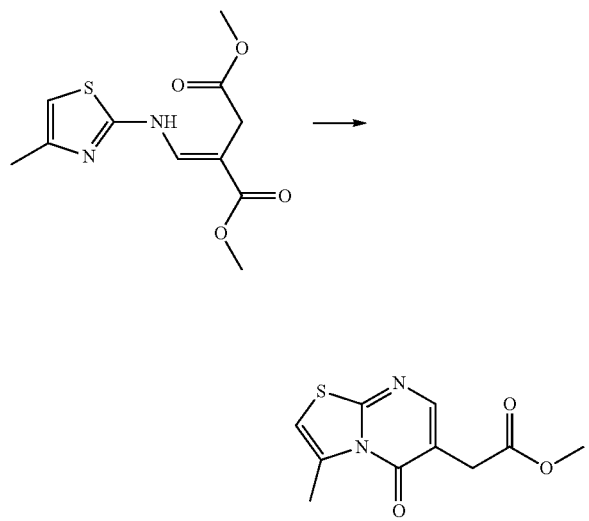

A mixture of 1,4-dimethyl (2E)-2-[[(4-methyl-1,3-thiazol-2-yl)amino]methylidene]butanedioate (8 g, 29.60 mmol) and Eaton's reagent (10 mL) was stirred for 2 h at 60° C. The resulting solution was diluted with saturated NaHCO$_3$/H$_2$O, extracted with ethyl acetate, washed with brine, dried over anhydrous sodium sulfate, and concentrated under vacuum. The residue was purified by a silica gel column eluting with dichloromethane/ethyl acetate (1/1) to afford the title compound (1.2 g, 17%) as a white solid. LCMS [M+H$^+$] 239.

Step 4: Preparation of 2-(3-methyl-5-oxo-5H-thiazolo[3,2-a]pyrimidin-6-yl)acetohydrazide

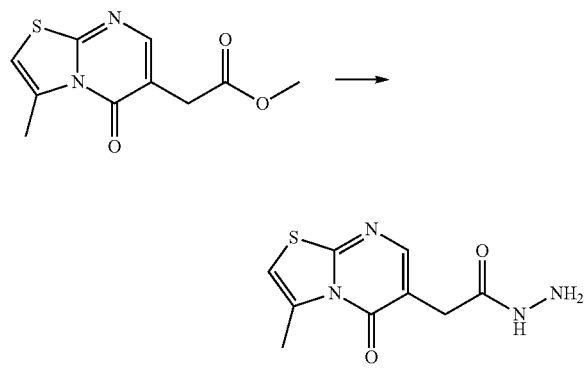

A mixture of methyl 2-[3-methyl-5-oxo-5H-[1,3]thiazolo[3,2-a]pyrimidin-6-yl]acetate (300 mg, 1.26 mmol), methanol (50 mL), and hydrazine hydrate (2 mL, 32.00 mmol) was stirred for 2 h at room temperature. The resulting mixture was concentrated under vacuum. This resulted in the title compound (260 mg, 87%)) as a white solid which was used for the next step without any further purification. [M+H$^+$] 239.

Step 5: Preparation of 5-((3-methyl-5-oxo-5H-thiazolo[3,2-a]pyrimidin-6-yl)methyl)-1,3,4-oxadiazol-2(3H)-one

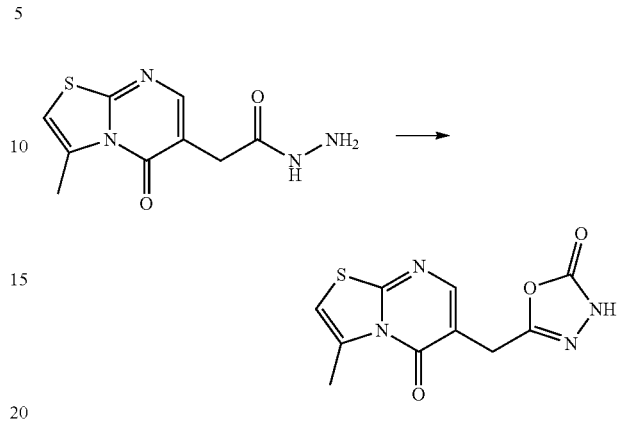

A mixture of 2-[3-methyl-5-oxo-5H-[1,3]thiazolo[3,2-a]pyrimidin-6-yl]acetohydrazide (250 mg, 1.049 mmol), N,N-dimethylformamide (10 mL), and CDI (300 mg, 1.850 mmol) was stirred for 1 h at room temperature. The reaction mixture was purified on a C18 silica gel column eluting with CH$_3$CN/H$_2$O (10 mmol/L NH$_4$HCO$_3$) increasing from 5% to 95% over 30 min. This resulted in the title compound (200 mg, 72%) as a white solid. LCMS [M+H$^+$] 264.

Step 6: Preparation of 3-(4-chloro-2-fluorophenethyl)-5-((7-methyl-6-oxo-6H-purin-1(7H)-yl)methyl)-1,3,4-oxadiazol-2(3H)-one

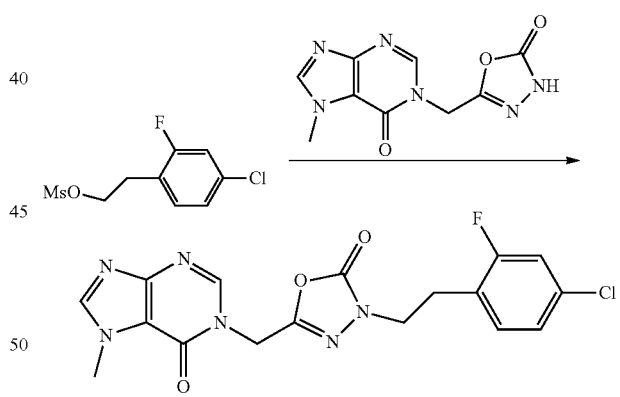

A mixture of 5-([3-methyl-5-oxo-5H-[1,3]thiazolo[3,2-a]pyrimidin-6-yl]methyl)-2,3-dihydro-1,3,4-oxadiazol-2-one (100 mg, 0.38 mmol), potassium carbonate (160 mg, 1.20 mmol), TBAI (10 mg, 0.03 mmol), 1-(2-bromoethyl)-4-chlorobenzene (90 mg, 0.41 mmol), and N,N-dimethylformamide (5 mL) was stirred for 2 h at room temperature. The reaction mixture was purified on a C18 silica gel column eluting with CH$_3$CN/H$_2$O (10 mmol/L NH$_4$HCO$_3$) increasing from 5% to 95% over 30 min. This resulted in the title compound (60 mg, 39%) as a white solid. LCMS [M+H$^+$] 405. $^1$H NMR (400 MHz, CDCl$_3$) δ 7.92 (s, 1H), 7.32-7.24 (m, 2H), 7.19-7.11 (m, 2H), 6.53-6.52 (m, 1H), 3.96-3.87 (m, 2H), 3.78 (s, 2H), 3.07-2.98 (m, 2H), 2.85 (s, 3H).

Example Compound 48: Preparation of (R)-3-((6-chloro-2,3-dihydro-1H-inden-1-yl)methyl)-5-((7-methyl-6-oxo-6,7-dihydro-1H-purin-1-yl)methyl)-1,3,4-oxadiazol-2(3H)-one The overall Example Compound 48 reaction scheme is as follows:

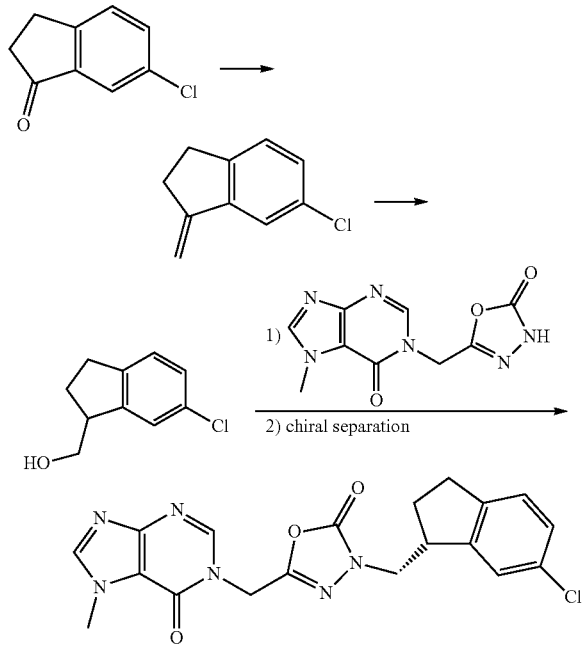

Step 1: Preparation of methyl 6-chloro-1-methylene-2,3-dihydro-1H-indene

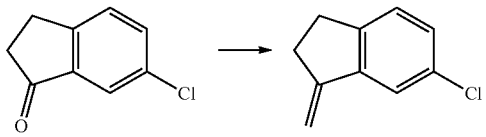

n-Butyllithium (2.4 M in hexanes, 3.00 mL, 7.2 mmol) was added to a solution of methyltriphenylphosphonium iodide (3.15 g, 7.8 mmol) in THF (24 mL) at 0° C. The reaction mixture was stirred at that temperature for 10 min and was cooled to −78° C. A solution of 6-chloro-1-methylene-2,3-dihydro-1H-indene (1.00 g, 6.00 mmol) in THF (5 mL) was then slowly added, the reaction mixture was allowed to warm to 20° C. over 2 h and stirred for 2 h. Water and ethyl acetate were added and the phases were separated. The layers were separated, the aqueous layer was extracted with ethyl acetate, the combined organic layers were dried with sodium sulfate, filtered and evaporated. The residue was purified by a silica gel column eluting with ethyl acetate/hexanes (gradient 0% to 20%) to afford the title compound (233 mg, 24%) as a colorless oil. $^1$H NMR (500 MHz, CDCl$_3$) δ 7.44 (s, 1H), 7.17 (d, J=1.3 Hz, 2H), 5.44 (t, J=2.6 Hz, 1H), 5.07 (t, J=2.2 Hz, 1H), 2.98-2.89 (m, 2H), 2.86-2.78 (m, 2H).

Step 2: Preparation of (6-chloro-2,3-dihydro-1H-inden-1-yl)methanol

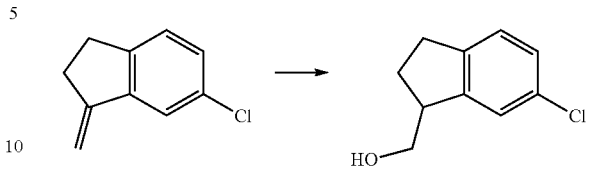

To a solution of 6-chloro-1-methylene-2,3-dihydro-1H-indene (133 mg, 0.810 mmol) in THF (8.0 mL) was slowly added BH$_3$-THF (1.0 M in THF, 1.05 mL, 1.05 mmol). The reaction mixture was stirred at 20° C. for 2.5 h. Aqueous NaOH (2.0 M, 0.81 mL, 1.62 mmol) and hydrogen peroxide (30% in water, 0.17 mL, 1.62 mmol) were successively added at 0° C. The reaction mixture was warmed to 20° C. and stirred vigorously for 30 min. Water was added and the mixture was extracted with ethyl acetate (2×). The combined organic layers were washed with an aqueous saturated solution of Na$_2$S$_2$O$_3$, dried with sodium sulfate, filtered and evaporated. The residue was purified by a silica gel column eluting with ethyl acetate/hexanes (gradient 0% to 30%) to afford the title compound (109 mg, 74%) as a colorless oil. $^1$H NMR (500 MHz, CDCl$_3$) δ 7.28-7.27 (m, 1H), 7.15 (d, J=1.2 Hz, 2H), 3.80 (t, J=5.9 Hz, 2H), 3.38-3.30 (m, 1H), 2.98-2.77 (m, 2H), 2.33-2.23 (m, 1H), 1.95 (ddt, J=12.8, 8.8, 6.4 Hz, 1H), 1.38 (t, J=5.7 Hz, 1H).

Step 3: (R)-3-((6-chloro-2,3-dihydro-1H-inden-1-yl)methyl)-5-((7-methyl-6-oxo-6,7-dihydro-1H-purin-1-yl)methyl)-1,3,4-oxadiazol-2(3H)-one

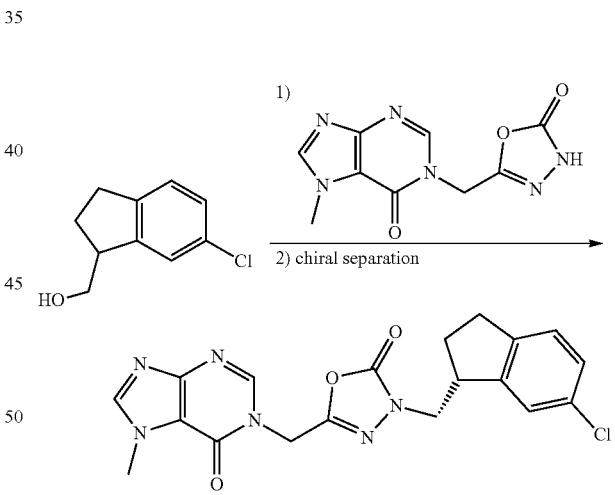

Diisopropyl azodicarboxylate (0.14 mL, 0.71 mmol) was added dropwise to a solution of 5-[(7-methyl-6-oxo-purin-1-yl)methyl]-3H-1,3,4-oxadiazol-2-one (190 mg, 0.770 mmol), (6-chloro-2,3-dihydro-1H-inden-1-yl)methanol (100 mg, 0.550 mmol) and triphenylphosphine (187 mg, 0.71 mmol) in DMF (3.6 mL) at 0° C. The reaction mixture was stirred at 20° C. for 18 h. Ethyl acetate was added and the mixture was washed 3× with water. The organic layer was dried with sodium sulfate, filtered and evaporated. The residue was purified by a silica gel column eluting with methanol/dichloromethane (gradient 0% to 4%) to afford the title compound (167 mg, 74%) as a racemic mixture. This mixture was separated by chiral HPLC (Chiralpak IA column (Daicel corporation), 5 μm, 20×250 mm, 12 mL/min, 20:20:60 MeOH:DCM:hexanes, 7.0 mg/injection). Fractions containing the first eluting enantiomer (@15.1 min) were concentrated to afford the title compound (77 mg) as a white solid. LCMS [M+H⁺] 413. ¹H NMR (500 MHz, DMSO-d6) δ 8.34 (s, 1H), 8.21 (s, 1H), 7.24-7.12 (m, 3H), 5.23 (s, 2H), 3.96 (d, J=6.6 Hz, 3H), 3.91 (dd, J=14.2, 6.3 Hz, 1H), 3.73 (dd, J=14.2, 7.6 Hz, 1H), 3.53-3.48 (m, 1H), 2.89-2.80 (m, 1H), 2.80-2.70 (m, 1H), 2.17 (dtd, J=12.9, 8.4, 6.4 Hz, 1H), 1.85-1.76 (m, 1H).

Example Compound 49: Preparation of (R)-3-((5-chloro-2,3-dihydro-1H-inden-1-yl)methyl)-5-((7-methyl-6-oxo-6,7-dihydro-1H-purin-1-yl)methyl)-1,3,4-oxadiazol-2(3H)-one The overall Example Compound 49 reaction scheme is as follows:

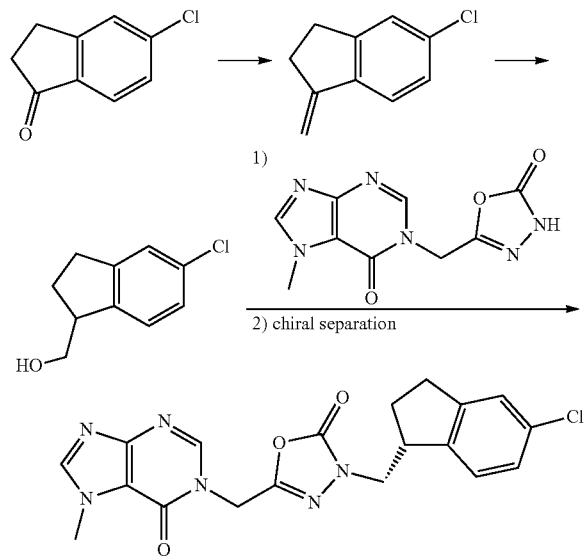

Step 1: Preparation of methyl 5-chloro-1-methylene-2,3-dihydro-1H-indene

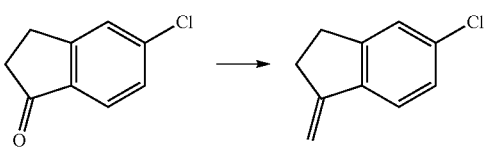

n-Butyllithium (2.5 M in hexanes, 2.88 mL, 7.2 mmol) was added to a solution of methyltriphenylphosphonium iodide (2.91 g, 7.2 mmol) in THF (24 mL) at 0° C. The reaction mixture was stirred at that temperature for 10 min and was cooled to −78° C. A solution of 5-chloro-1-methylene-2,3-dihydro-1H-indene (1.00 g, 6.00 mmol) in THF (5 mL) was then slowly added, the reaction mixture was allowed to warm to 20° C. over 2 h and stirred for 3 days. Water and ethyl acetate were added and the phases were separated. The layers were separated, the aqueous layer was extracted with ethyl acetate, the combined organic layers were dried with sodium sulfate, filtered and evaporated. The residue was purified by a silica gel column eluting with ethyl acetate/hexanes (gradient 5% to 10%) to afford the title compound (304 mg, 31%) as an orange oil. ¹H NMR (500 MHz, CDCl₃) δ 7.39 (d, J=8.2 Hz, 1H), 7.23 (d, J=1.2 Hz, 1H), 7.18-7.13 (m, 1H), 5.42 (t, J=2.6 Hz, 1H), 5.04 (t, J=2.2 Hz, 1H), 2.95 (dd, J=8.7, 5.4 Hz, 2H), 2.83-2.78 (m, 2H).

Step 2: Preparation of (5-chloro-2,3-dihydro-1H-inden-1-yl)methanol

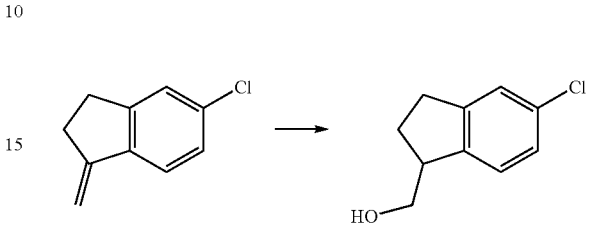

To a solution of 5-chloro-1-methylene-2,3-dihydro-1H-indene (188 mg, 1.14 mmol) in THF (4.6 mL) was slowly added BH₃-THF (0.5 M in THF, 2.85 mL, 1.43 mmol). The reaction mixture was stirred at 20° C. for 2.5 h. Aqueous NaOH (2.0 M, 2.85 mL, 5.71 mmol) and hydrogen peroxide (30% in water, 0.16 mL, 1.52 mmol) were successively added at 0° C. The reaction mixture was warmed to 20° C. and stirred vigorously for 30 min. Water was added and the mixture was extracted with ethyl acetate (2×). The combined organic layers were washed with an aqueous saturated solution of Na₂S₂O₃, dried with sodium sulfate, filtered and evaporated. The residue was purified by a silica gel column eluting with ethyl acetate/hexanes (gradient 20% to 30%) to afford the title compound (161 mg, 61%) as a colorless oil. ¹H NMR (500 MHz, CDCl₃) δ 7.22-7.18 (m, 2H), 7.15-7.12 (m, 1H), 3.77 (d, J=6.1 Hz, 2H), 3.34-3.27 (m, 1H), 2.99-2.90 (m, 1H), 2.91-2.82 (m, 1H), 2.32-2.22 (m, 1H), 1.98-1.90 (m, 1H), 1.61 (s, 1H).

Step 3: (R)-3-((5-chloro-2,3-dihydro-1H-inden-1-yl)methyl)-5-((7-methyl-6-oxo-6,7-dihydro-1H-purin-1-yl)methyl)-1,3,4-oxadiazol-2(3H)-one

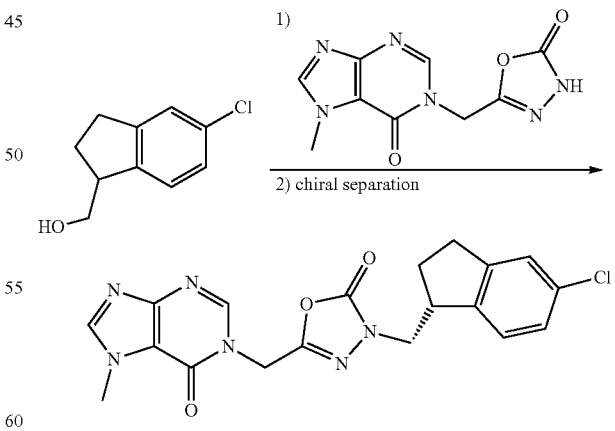

Diisopropyl azodicarboxylate (0.26 mL, 1.32 mmol) was added dropwise to a solution of 5-[(7-methyl-6-oxo-purin-1-yl)methyl]-3H-1,3,4-oxadiazol-2-one (352 mg, 1.42 mmol), (5-chloro-2,3-dihydro-1H-inden-1-yl)methanol (185 mg, 1.01 mmol) and triphenylphosphine (345 mg, 1.32 mmol) in DMF (6.7 mL) at 0° C. The reaction mixture was stirred at 20° C. for 15 h. Ethyl acetate was added and the mixture was washed 3× with water. The organic layer was dried with sodium sulfate, filtered and evaporated. The residue was purified by a silica gel column eluting with methanol/dichloromethane (gradient 2% to 5%) to afford the title compound (294 mg, 70%) as a racemic mixture. 100 mg of this mixture was separated by chiral HPLC (Chiralpak IB column (Daicel corporation), 5 μm, 20×250 mm, 12 mL/min, 20:20:60 MeOH:DCM:hexanes, 3.5 mg/injection). Fractions containing the second eluting enantiomer (@8.8 min) were concentrated to afford the title compound (36 mg) as a white solid. LCMS [M+H$^+$] 413. $^1$H NMR (500 MHz, DMSO-d6) δ 8.35 (s, 1H), 8.23 (d, J=0.5 Hz, 1H), 7.27 (s, 1H), 7.15 (d, J=8.2 Hz, 1H), 7.11 (dd, J=8.1, 2.0 Hz, 1H), 5.24 (s, 2H), 3.97 (s, 3H), 3.86 (dd, J=14.2, 6.7 Hz, 1H), 3.72 (dd, J=14.2, 7.6 Hz, 1H), 3.49-3.42 (m, 1H), 2.95-2.87 (m, 1H), 2.84-2.75 (m, 1H), 2.23-2.13 (m, 1H), 1.85-1.77 (m, 1H).

Example Compound 50: Preparation of 3-[3-(4-chlorophenyl)cyclobutyl]-5-[(7-methyl-6-oxo-purin-1-yl)methyl]-1,3,4-oxadiazol-2-one The overall Example Compound 50 reaction scheme is as follows:

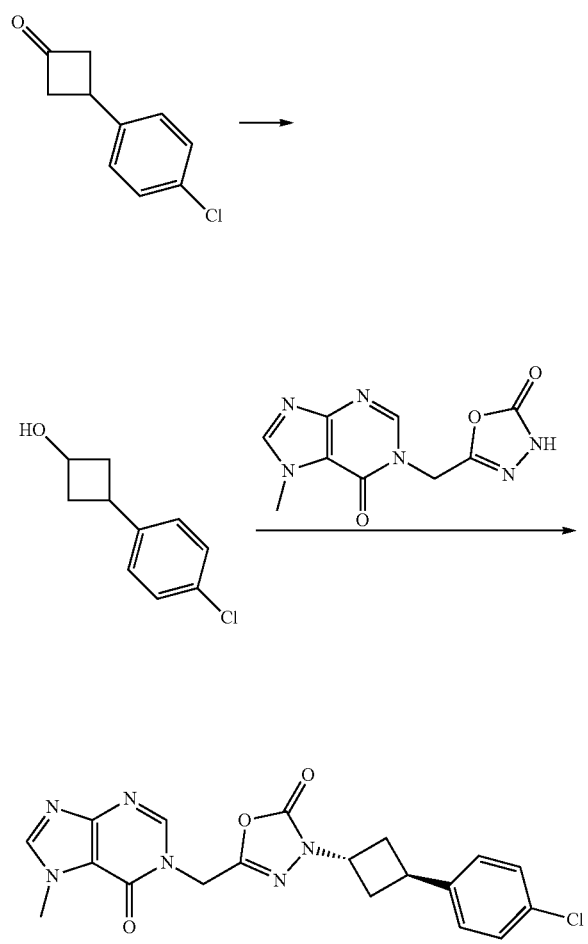

Step 1: Preparation of 3-(4-chlorophenyl)cyclobutanol

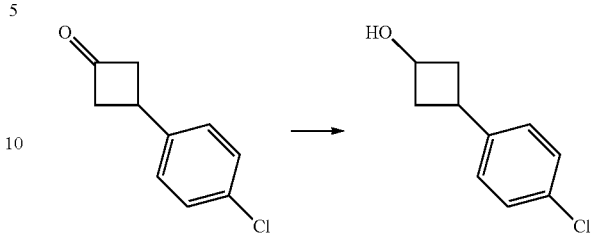

Sodium borohydride (66.4 mg, 1.76 mmol) was added to a solution of 3-(4-chlorophenyl)cyclobutanone (317 mg, 1.76 mmol) in methanol (5 mL). The reaction was stirred at room temperature for 2 h. The reaction was quenched with water at 0° C. and extracted with iPrOAc (3×). The combined organic extracts were washed with brine, dried with MgSO$_4$, filtered and concentrated. The crude mixture was adsorbed on silica gel and purified by silica gel column with 0-70% iPOAc/Heptane to afford the title compound (280 mg, 87%) as a clear oil.

Step 2: Preparation of 3-[3-(4-chlorophenyl)cyclobutyl]-5-[(7-methyl-6-oxo-purin-1-yl)methyl]-1,3,4-oxadiazol-2-one

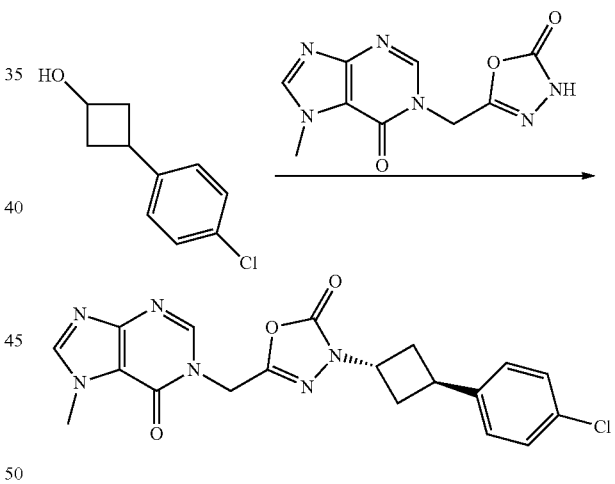

DIAD (162 μL, 0.81 mmol) was added to a solution of 5-[(7-methyl-6-oxo-purin-1-yl)methyl]-3H-1,3,4-oxadiazol-2-one (100 mg, 0.40 mmol), 3-(4-chlorophenyl)cyclobutanol (147 mg, 0.81 mmol) and triphenylphosphine resin bound (2.25 mmol/g) (358 mg, 0.81 mmol) in THF (2.7 mL) at 0° C. The mixture was stirred at room temperature overnight. The reaction was filtered through celite and concentrated on the rotavap. The crude product was purified by SFC using a Chiralpak IA column with 45% of 0.1% ammonium hydroxide in methanol in CO$_2$. This resulted in the titled compound (41.9 mg, 25% Yield) as a white solid. LCMS [M+H$^+$]: 413.1. 1H NMR (400 MHz, DMSO-d6) δ 8.37 (s, 1H), 8.23 (d, J=0.7 Hz, 1H), 7.37 (s, 4H), 5.27 (s, 2H), 4.65 (ddt, J=8.4, 6.5, 1.6 Hz, 1H), 3.98 (s, 3H), 3.63 (ddt, J=11.3, 8.5, 5.0 Hz, 1H), 2.85-2.67 (m, 2H), 2.56-2.44 (m, 2H).

155

Example Compound 51: Preparation of 5-[(7-methyl-6-oxo-purin-1-yl)methyl]-3-(3-phenylcyclobutyl)-1,3,4-oxadiazol-2-one The overall Example Compound 51 reaction scheme is as follows:

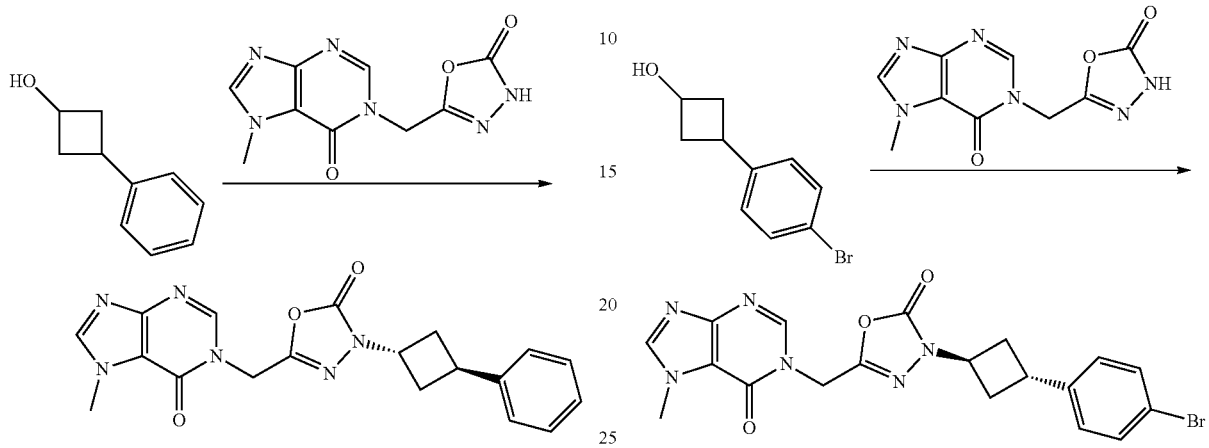

Step 1: Preparation of 5-[(7-methyl-6-oxo-purin-1-yl)methyl]-3-(3-phenylcyclobutyl)-1,3,4-oxadiazol-2-one DIAD (243 µL, 1.21 mmol) was added to a solution of 5-[(7-methyl-6-oxo-purin-1-yl)methyl]-3H-1,3,4-oxadiazol-2-one (150 mg, 0.60 mmol), 3-phenylcyclobutanol (189 mg, 1.21 mmol) and triphenylphosphine resin bound (2.25 mmol/g) (537 mg, 1.21 mmol) in THF (4 mL) at 0° C. The mixture was stirred at room temperature overnight. The reaction was filtered through celite and concentrated on the rotavap. The product was purified by SFC using a pyridyl amide column with 15% of 0.1% ammonium hydroxide in methanol in $CO_2$. This resulted in the titled compound (35.7 mg, 16% Yield) as a white solid. LCMS [M+H$^+$]: 379.1. 1H NMR (400 MHz, DMSO-d6) δ 8.38 (s, 1H), 8.23 (s, 1H), 7.33 (d, J=4.3 Hz, 4H), 7.27-7.15 (m, 1H), 5.27 (s, 2H), 4.71-4.58 (m, 1H), 3.98 (s, 3H), 3.69-3.57 (m, 1H), 2.85-2.72 (m, 2H), 2.58-2.45 (m, 2H).

156

Example Compound 52: Preparation of 3-[3-(4-bromophenyl)cyclobutyl]-5-[(7-methyl-6-oxo-purin-1-yl)methyl]-1,3,4-oxadiazol-2-one The overall Example Compound 52 reaction scheme is as follows:

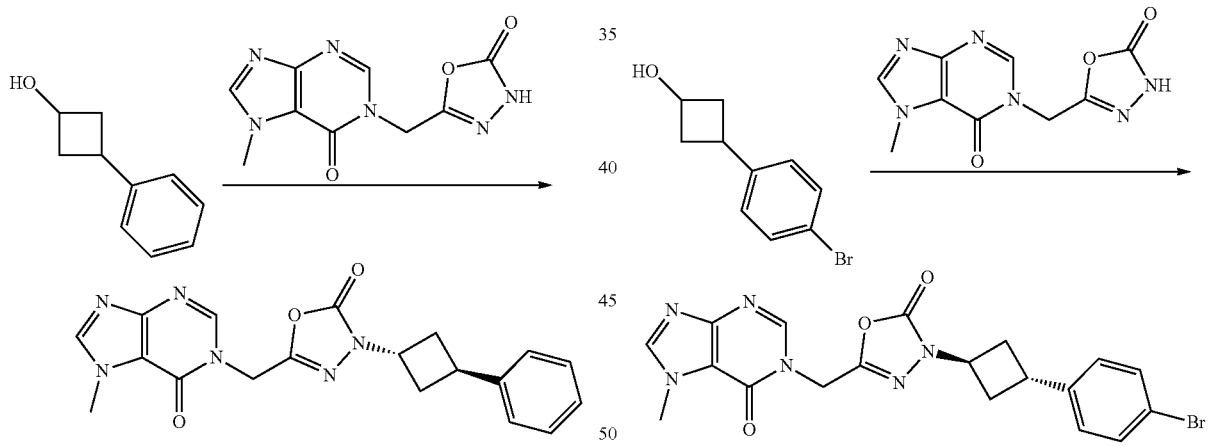

Step 1: Preparation of 3-[3-(4-bromophenyl)cyclobutyl]-5-[(7-methyl-6-oxo-purin-1-yl)methyl]-1,3,4-oxadiazol-2-one To a vial containing a solution of 5-[(7-methyl-6-oxo-purin-1-yl)methyl]-3H-1,3,4-oxadiazol-2-one (100 mg, 0.40 mmol), 3-(4-bromophenyl)cyclobutanol (193 mg, 0.81 mmol) and triphenylphosphine resin bound (2.4 mmol/g) (336 mg, 0.81 mmol) in THF (4 mL) was added di-ter-butyl azidocarboxylate (189 mg, 0.81 mmol) and the solution was heated to 70° C. overnight. The reaction mixture was diluted with DCM, filtered through celite, eluting with DCM and the filtrate was concentrated in vacuo. The residue was taken up in DCM (5 mL) and TFA (5 mL) was added and the reaction mixture was stirred for 1 h then concentrated in vacuo. The residue was taken up in DCM and washed with saturated aqueous sodium bicarbonate. The aqueous layer was back-extracted with DCM (2×) and the combined organic layers were dried over sodium sulfate, filtered and concentrated in vacuo. The residue was adsorbed onto silica and purified by flash column chromatography with 0-100% EtOAc in heptane to afford the desired compound as a brown oil. The product was purified by SFC using a Chiralpak IA column with 45% of 0.1% ammonium hydroxide in methanol in CO$_2$. This resulted in the titled compound (73.6 mg, 40% Yield) as a white solid. LCMS [M+H$^+$]: 457.0. 1H NMR (400 MHz, DMSO-d6) δ 8.37 (s, 1H), 8.22 (s, 1H), 7.54-7.47 (m, 2H), 7.34-7.27 (m, 2H), 5.27 (s, 2H), 4.71-4.58 (m, 1H), 3.98 (s, 3H), 3.67-3.55 (m, 1H), 3.29 (d, J=2.2 Hz, 1H), 2.84-2.72 (m, 2H), 2.49-2.43 (m, 1H).

Example Compound 53: Preparation of 3-[3-(3-chlorophenyl)cyclobutyl]-5-[(7-methyl-6-oxo-purin-1-yl)methyl]-1,3,4-oxadiazol-2-one The overall Example Compound 53 reaction scheme is as follows:

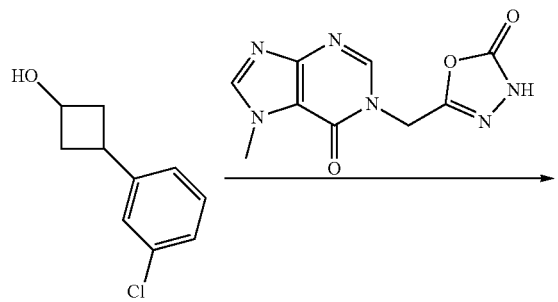

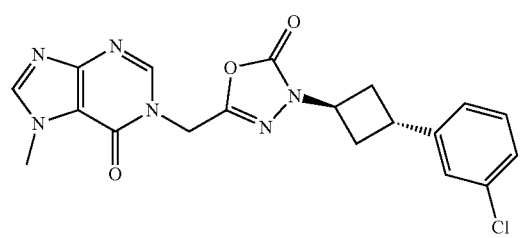

Step 1: Preparation of 3-[3-(3-chlorophenyl)cyclobutyl]-5-[(7-methyl-6-oxo-purin-1-yl)methyl]-1,3,4-oxadiazol-2-one

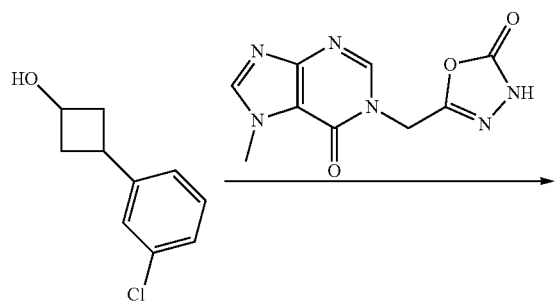

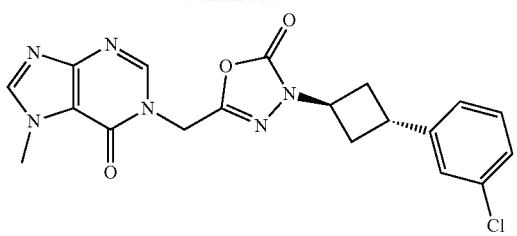

To a vial containing a solution of 5-[(7-methyl-6-oxo-purin-1-yl)methyl]-3H-1,3,4-oxadiazol-2-one (100 mg, 0.40 mmol), 3-(3-chlorophenyl)cyclobutanol (155 mg, 0.81 mmol) and triphenylphosphine resin bound (2.4 mmol/g) (336 mg, 0.81 mmol) in THF (4 mL) was added di-tert-butyl azidocarboxylate (189 mg, 0.81 mmol) and the solution was heated to 70° C. overnight. The reaction mixture was diluted with DCM, filtered through celite, eluting with DCM and the filtrate was concentrated in vacuo. The residue was taken up in DCM (5 mL) and TFA (5 mL) was added and the reaction mixture was stirred for 1 h then concentrated in vacuo. The residue was taken up in DCM and washed with saturated aqueous sodium bicarbonate. The aqueous layer was back-extracted with DCM (2×) and the combined organic layers were dried over sodium sulfate, filtered and concentrated in vacuo. The residue was adsorbed onto silica and purified by flash column chromatography with 0-100% EtOAc in heptane to afford the desired compound as a brown oil. The product was purified by SFC using a Chiralpak AS column with 35% of 0.1% ammonium hydroxide in methanol in CO$_2$. This resulted in the titled compound (82.4 mg, 50% Yield) as a white solid. LCMS [M+H$^+$]: 413.1. 1H NMR (400 MHz, DMSO-d6) δ 8.38 (s, 1H), 8.23 (d, J=0.7 Hz, 1H), 7.41 (t, J=1.9 Hz, 1H), 7.38-7.33 (m, 1H), 7.32-7.25 (m, 2H), 5.27 (s, 2H), 4.72-4.60 (m, 1H), 3.98 (s, 3H), 3.72-3.59 (m, 1H), 2.85-2.72 (m, 2H), 2.58-2.51 (m, 2H).

Example Compound 54: Preparation of 3-(3-(4-methoxyphenyl)cyclobutyl)-5-((7-methyl-6-oxo-6,7-dihydro-1H-purin-1-yl)methyl)-1,3,4-oxadiazol-2(3H)-one The overall Example Compound 54 reaction scheme is as follows:

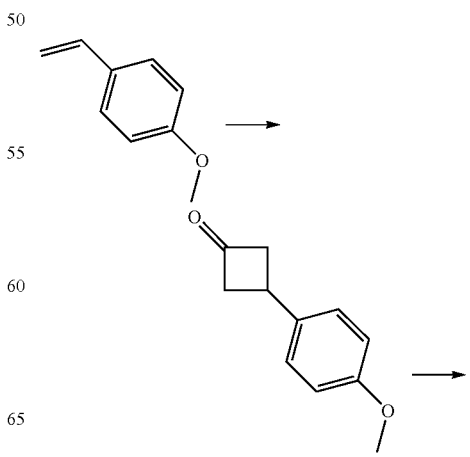

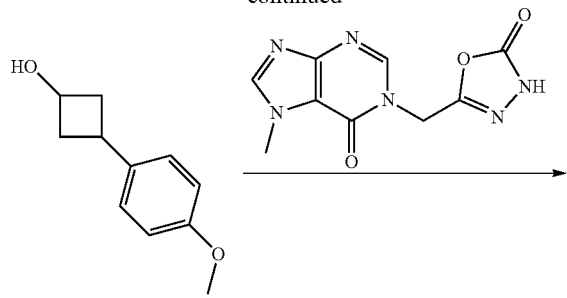

Step 1: Preparation of 3-(4-methoxyphenyl)cyclobutanone

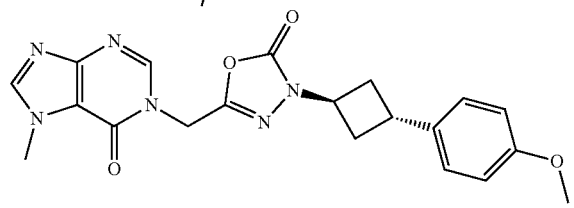

To a flame-dry flask was added dropwise a mixture of 4-methoxystyrene (1.0 g, 7.45 mmol) and 2,4,6-trimethylpyridine (1.8 mL, 13.41 mmol) in dichloroethane (25 mL) to a solution of N,N-dimethylacetamide (1.0 mL, 11.18 mmol) and trifluoromethanesulfonic anhydride (2.3 mL, 13.42 mmol) in dichloroethane (1.5 mL) at −15° C. under nitrogen. The mixture was stirred at reflux overnight. Water was added and the reaction was stirred at reflux for 4 h. The mixture was poured in saturated aqueous NaHCO$_3$/DCM and extracted with DCM (3×). The organics were washed with brine, dried with MgSO$_4$, filtered and concentrated. The crude mixture was adsorbed on silica gel and purified by silica gel column with 0-40% iPrOAc/Heptane to afford the titled compound (457 mg, 35% Yield) as a yellow oil.

Step 2: Preparation of 3-(4-methoxyphenyl)cyclobutanol

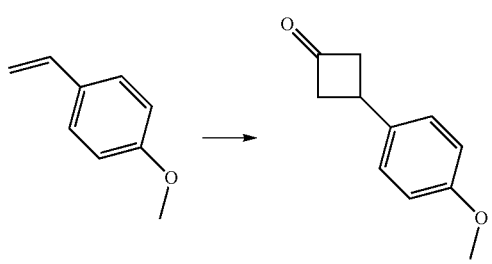

Sodium borohydride (93.0 mg, 2.46 mmol) was added to a solution of 3-(4-methoxyphenyl)cyclobutanone (456 mg, 2.46 mmol) in methanol (8 mL). The reaction was stirred at room temperature for 2 h. The reaction was quenched with water at 0° C. and extracted with iPrOAc (3×). The combined organic extracts were washed with brine, dried with MgSO$_4$, filtered and concentrated. The crude mixture was adsorbed on silica gel and purified by silica gel column with 0-70% iPOAc/Heptane to afford the title compound (382 mg, 87%) as a clear oil.

Step 3: Preparation of 3-(3-(4-methoxyphenyl)cyclobutyl)-5-((7-methyl-6-oxo-6,7-dihydro-1H-purin-1-yl)methyl)-1,3,4-oxadiazol-2(3H)-one

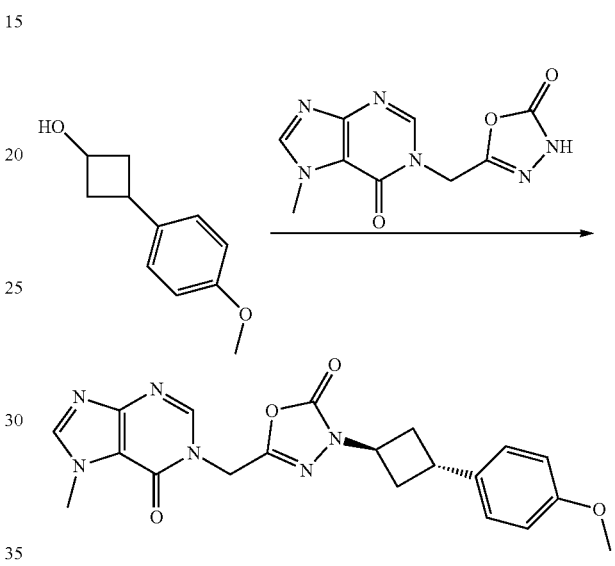

DIAD (162 µL, 0.81 mmol) was added to a solution of 5-[(7-methyl-6-oxo-purin-1-yl)methyl]-3H-1,3,4-oxadiazol-2-one (100 mg, 0.40 mmol), Preparation of 3-(4-methoxyphenyl)cyclobutanol (144 mg, 0.81 mmol) and triphenylphosphine (211 mg, 0.81 mmol) in THF (4 mL) at 0° C. The mixture was stirred at room temperature overnight. The crude mixture was adsorbed on silica gel and purified by silica gel column with 30-80% (3:1 iPOAc:MeOH)/Heptane. The cis/trans mixture was purified by SFC using a Chiralpak IA column with 5-60% of 0.1% ammonium hydroxide in methanol in CO$_2$. This resulted in the titled compound (83.1 mg, 51% Yield) as a white solid. LCMS [M+H$^+$]: 409.1. H NMR (400 MHz, DMSO-d6) δ 8.37 (s, 1H), 8.22 (s, 1H), 7.29-7.20 (m, 2H), 6.95-6.84 (m, 2H), 5.27 (s, 2H), 4.62 (s, 1H), 3.98 (s, 3H), 3.73 (s, 3H), 3.62-3.50 (m, 1H), 2.81-2.67 (m, 2H), 2.49-2.41 (m, 2H).

Example Compound 55: Preparation of 5-[(7-methyl-6-oxo-purin-1-yl)methyl]-3-[2-(4-phenylphenyl)ethyl]-1,3,4-oxadiazol-2-one The overall Example Compound 55 reaction scheme is as follows:

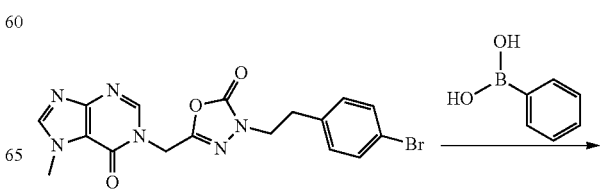

-continued

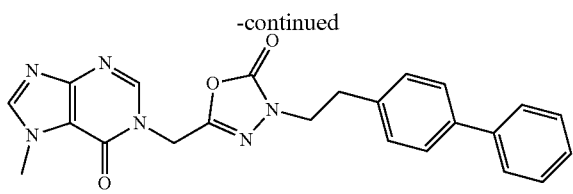

Step 1: Preparation of 5-[(7-methyl-6-oxo-purin-1-yl)methyl]-3-[2-(4-phenylphenyl)ethyl]-1,3,4-oxadiazol-2-one

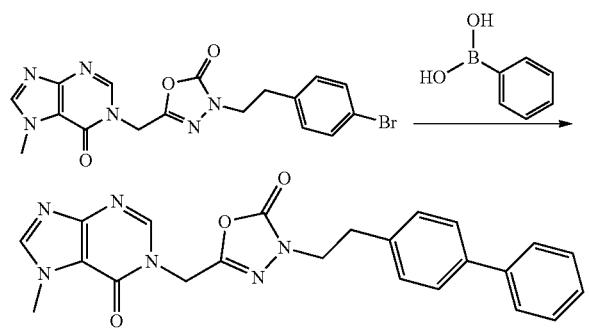

To a vial containing a solution of 3-[2-(4-bromophenyl)ethyl]-5-[(7-methyl-6-oxo-purin-1-yl)methyl]-1,3,4-oxadiazol-2-one (40.0 mg, 0.0928 mmol), phenylboronic acid (14.3 mg, 0.117 mmol) in toluene (2.5 mL) was added a solution of potassium carbonate (276 mg, 2.00 mmol) in water (0.63 mL). Then tetrakis(triphenylphosphine)palladium(0) (11.5 mg, 9.95 mol) was added and the headspace of the reaction vial was flushed with $N_2$ for 10 seconds and sealed. The solution was heated to 80° C. for 16 hours. The reaction mixture was diluted with i-PrOAc, washed with water, and extracted with i-PrOAc (3×). The combined organic layers were dried over sodium sulfate, filtered and concentrated in vacuo. The residue was adsorbed onto silica and purified by flash column chromatography with 0-100% EtOAc in heptane to afford the titled compound as a white crystalline solid (17.6 mg, 44% Yield). LCMS [M+H$^+$]: 429.1. 1H NMR (400 MHz, DMSO-d6) δ 8.35 (s, 1H), 8.22 (s, 1H), 7.64 (d, J=4.9 Hz, 2H), 7.58-7.49 (m, 2H), 7.45 (t, J=7.6 Hz, 2H), 7.35 (t, J=7.3 Hz, 1H), 7.26 (d, J=8.2 Hz, 2H), 5.23 (s, 2H), 3.97 (s, 3H), 3.90 (t, J=7.0 Hz, 2H), 2.96 (t, J=7.0 Hz, 2H).

Example Compound 57: Preparation of trans-3-[3-(4-chlorophenyl)cyclobutyl]-5-[[6-oxo-7-(trideuteriomethyl)purin-1-yl]methyl]-1,3,4-oxadiazol-2-one The overall Example Compound 57 reaction scheme is as follows;

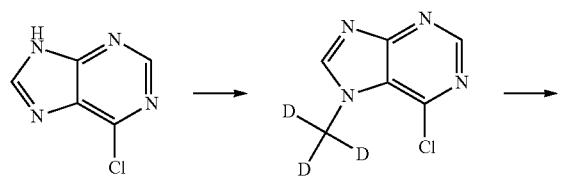

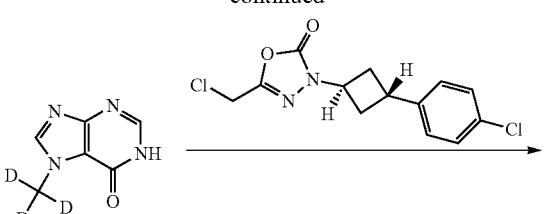

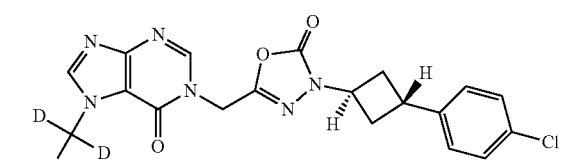

Step 1: Preparation of 6-chloro-7-(trideuteriomethyl)purine

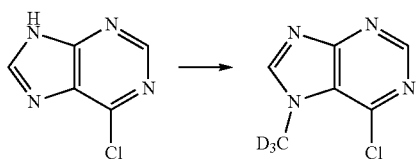 [SMILES: Clc1ncnc2[nH]cnc12 ; [2H]C([2H])([2H])n1cnc2ncnc(Cl)c21]

A solution of 6-chloro-9H-purine (3.0 g, 19.41 mmol) in tetrahydrofuran (30 mL) was added MeMgCl (3M in THF) (7.5 mL, 21.35 mmol) at 0° C. under nitrogen. The resulting solution was stirred for 1 hour at 0° C. Then MeI (8.44 g, 58.23 mmol) was added and the resulting mixture was stirred at 60° C. for 3 hours. The reaction was quenched with MeOH and concentrated under vacuum. The residue was adsorbed onto silica gel and purified by flash column chromatography eluted with DCM/MeOH (9:1) to afford the title compound (2.10 g, 63% yield) as a light yellow solid.

Step 2: Preparation of 7-(trideuteriomethyl)-1H-purin-6-one

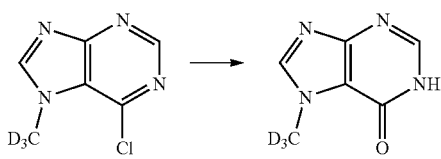 [SMILES: [2H]C([2H])([2H])n1cnc2ncnc(Cl)c21 ; [2H]C([2H])([2H])n1cnc2nc[nH]c(=O)c21]

A solution of [6-chloro-7-(trideuteriomethyl)purine (2.10 g, 12.24 mmol) and NaOH (2.00 g, 50 mmol) in water (20 mL) was stirred at 100° C. for 2 hours. The pH value of the reaction mixture was adjusted to 6 with HCl. The solvent was removed under vacuum. The residue was adsorbed onto silica gel and purified by flash column chromatography eluted with DCM/MeOH (4:1) to afford the title compound (257 mg, 13.7% yield)] as a white solid.

Step 3: Preparation of trans-3-[3-(4-chlorophenyl)
cyclobutyl]-5-[[6-oxo-7-(trideuteriomethyl)purin-1-
yl] methyl]-1,3,4-oxadiazol-2-one

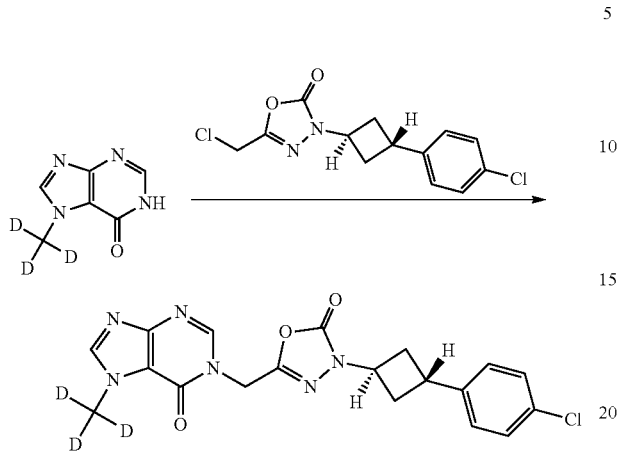

The title compound was prepared from 7-(trideuteriomethyl)-1H-purin-6-one (40 mg, 0.26 mmol) and 5-(chloromethyl)-3-[3-(4-chlorophenyl)cyclobutyl]-1,3,4-oxadiazol-2-one (78 mg, 0.26 mmol) as a white solid (40 mg, 37% yield), in a manner analogous to Example 58, Step 3. LCMS [M+H$^+$]: 416. $^1$H NMR (400 MHz, DMSO-d$_6$) δ 8.38 (s, 1H), 8.23 (s, 1H), 7.37 (s, 4H), 5.27 (s, 2H), 4.72-4.56 (m, 1H), 3.65-3.60 (m, 1H), 2.81-2.74 (m, 2H), 2.53 (s, 1H), 2.49-2.44 (m, 1H).

Example Compound 59: Preparation of trans-3-[3-(4-chlorophenyl)cyclobutyl]-5-[(8-deuterio-7-methyl-6-oxo-purin-1-yl)methyl]-1,3,4-oxadiazol-2-one The overall Example Compound 59 reaction scheme is as follows:

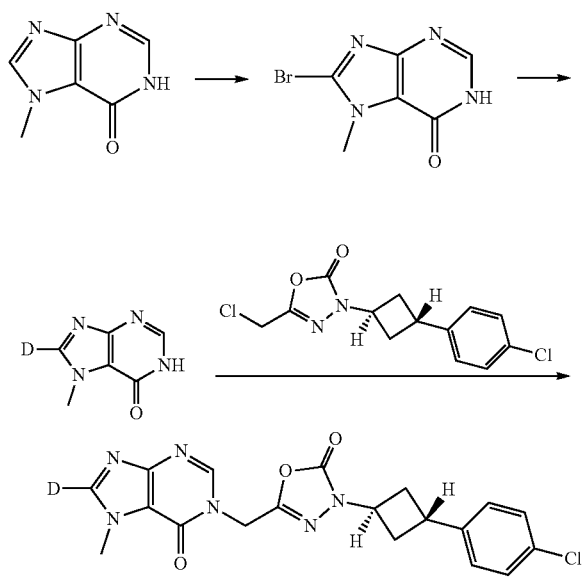

Step 1: Preparation of
8-bromo-7-methyl-1H-purin-6(7H)-one

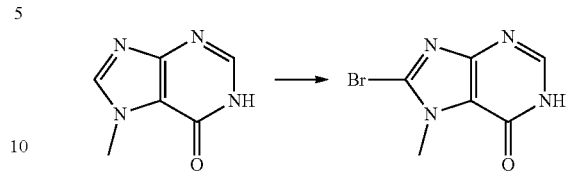

A mixture of 7-methyl-1H-purin-6-one (200 mg, 1.33 mmol) and NBS (284 mg, 1.60 mmol) in acetonitrile (8 mL) was stirred overnight at 80° C. The solvent was removed under vacuum. The residue was mixture with silica gel and purified by flash column chromatography eluted with CH$_2$Cl$_2$/MeOH (10:1) to afford the title compound (50 mg, 16%) as a white solid.

Step 2: Preparation of
8-deuterio-7-methyl-1H-purin-6-one

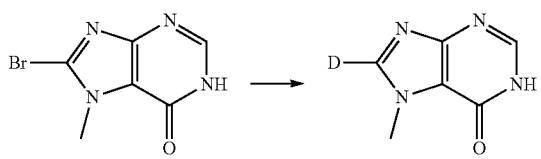

A mixture of 8-bromo-7-methyl-1H-purin-6-one (1.40 g, 6.11 mmol), D$_2$O (5 mL), CD$_3$OD (10 mL), Zn (3.91 g, 61.13 mmol), and DCOOD (2.93 g, 61.13 mmol) was stirred at room temperature for one hour. The solids were filtered out and the filtrate was purified by HPLC to yield the title compound (510 mg, 55%) as a white solid.

Step 3: Preparation of trans-3-[3-(4-chlorophenyl)
cyclobutyl]-5-[(8-deuterio-7-methyl-6-oxo-purin-1-
yl)methyl]-1,3,4-oxadiazol-2-one

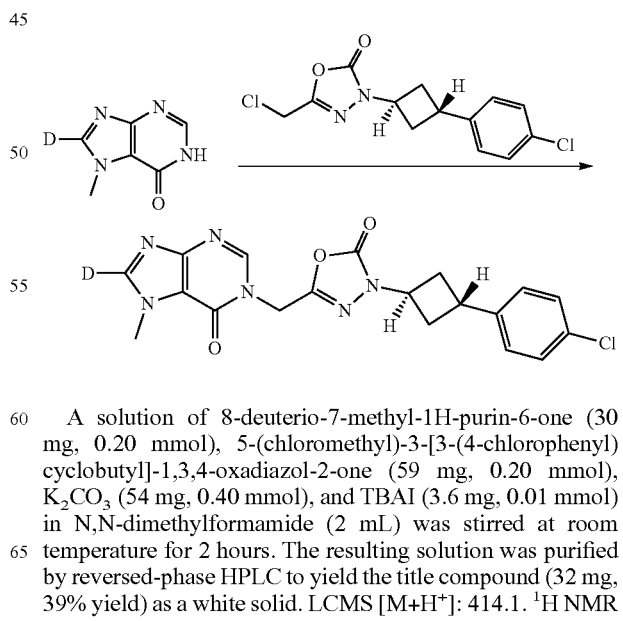

A solution of 8-deuterio-7-methyl-1H-purin-6-one (30 mg, 0.20 mmol), 5-(chloromethyl)-3-[3-(4-chlorophenyl)cyclobutyl]-1,3,4-oxadiazol-2-one (59 mg, 0.20 mmol), K$_2$CO$_3$ (54 mg, 0.40 mmol), and TBAI (3.6 mg, 0.01 mmol) in N,N-dimethylformamide (2 mL) was stirred at room temperature for 2 hours. The resulting solution was purified by reversed-phase HPLC to yield the title compound (32 mg, 39% yield) as a white solid. LCMS [M+H$^+$]: 414.1. $^1$H NMR (400 MHz, DMSO-d$_6$) δ 8.38 (s, 1H), 7.38 (s, 4H), 5.27 (s, 2H), 4.65 (m, 1H), 3.97 (s, 3H), 3.63 (m, 1H), 2.53-3.25 (m, 2H), 2.23-2.46 (m, 2H).

Example Compound 60: Preparation of trans-3-[3-(4-chlorophenyl)cyclobutyl]-5-[(2-deuterio-7-methyl-6-oxo-purin-1-yl)methyl]-1,3,4-oxadiazol-2-one

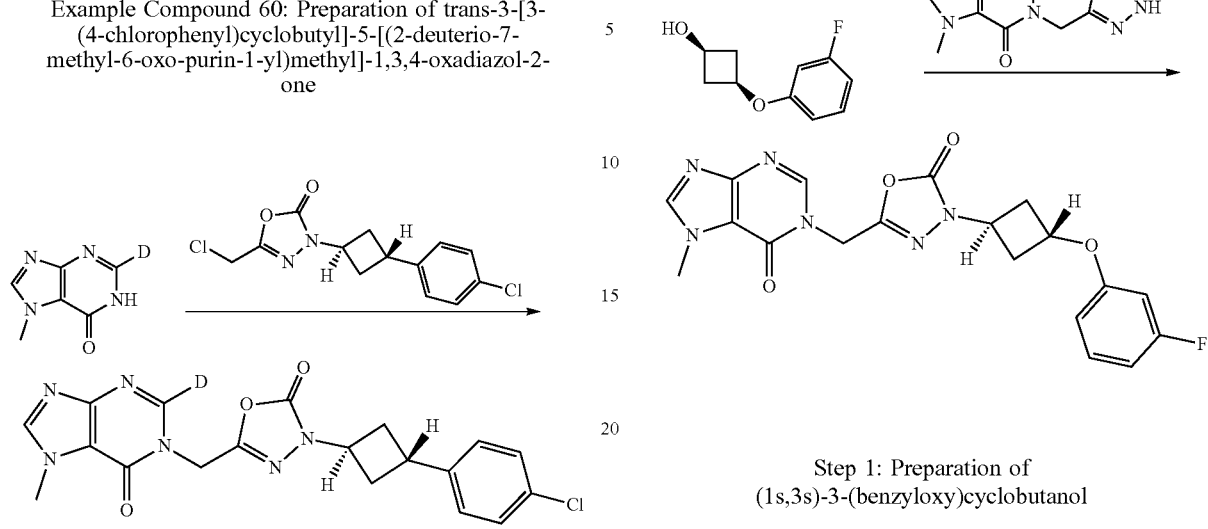

The title compound was prepared from 5-(chloromethyl)-3-[3-(4-chlorophenyl)cyclobutyl]-1,3,4-oxadiazol-2-one (119 mg, 0.40 mmol) and 2-deuterio-7-methyl-1H-purin-6-one (60 mg, 0.40 mmol) as a white solid (24 mg, 15% yield), in a manner analogous to Example 58, Step 3. LCMS [M+H$^+$] 413. $^1$H NMR (400 MHz, CDCl$_3$) δ 7.84 (s, 1H), 7.31-7.26 (m, 2H), 7.22-7.17 (m, 2H), 5.15 (s, 2H), 4.77-4.70 (m, 1H), 4.10 (s, 3H), 3.67-3.60 (m, 1H), 2.94-2.86 (m, 2H), 2.56-2.50 (m, 2H).

Example Compound 63: Preparation of trans-3-[3-(3-fluorophenoxy)cyclobutyl]-5-[(7-methyl-6-oxo-purin-1-yl)methyl]-1,3,4-oxadiazol-2-one The overall Example Compound 63 reaction scheme is as follows:

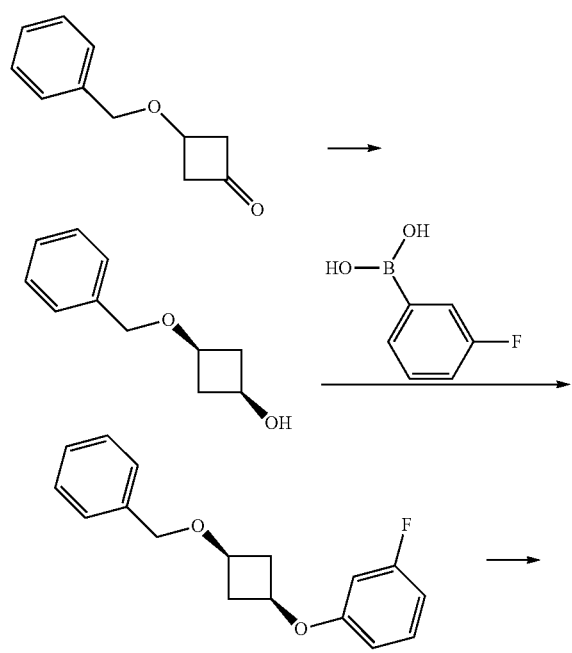

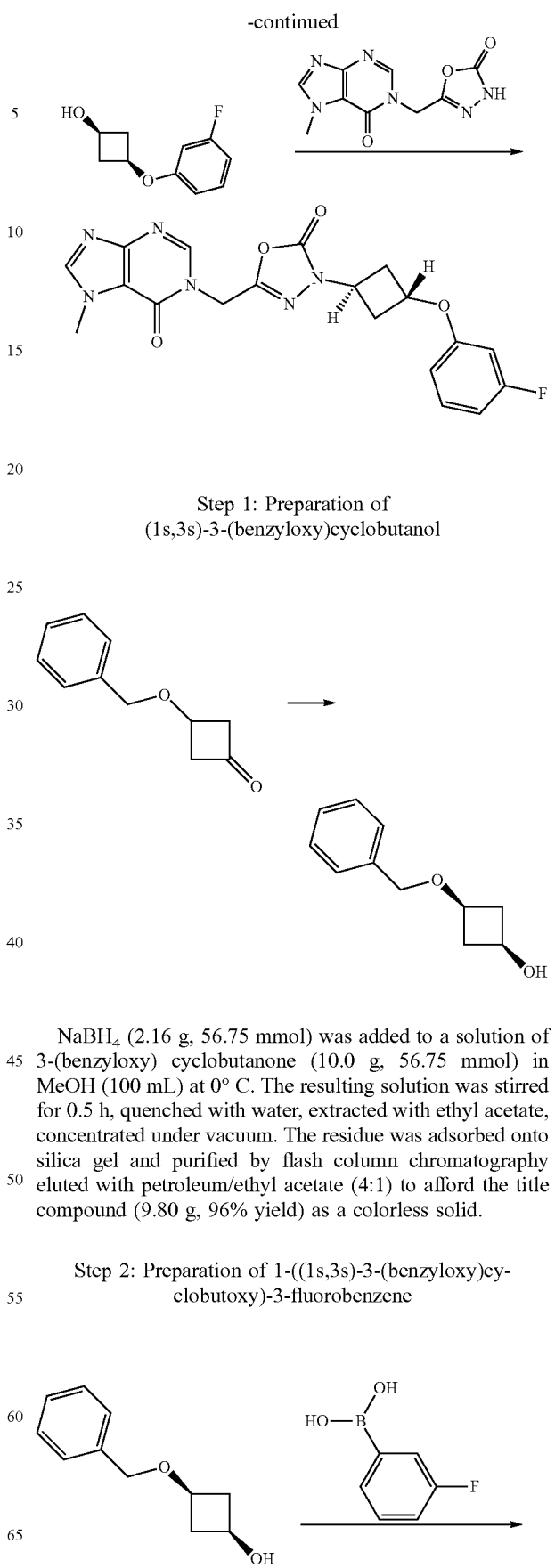

Step 1: Preparation of (1s,3s)-3-(benzyloxy)cyclobutanol

NaBH$_4$ (2.16 g, 56.75 mmol) was added to a solution of 3-(benzyloxy) cyclobutanone (10.0 g, 56.75 mmol) in MeOH (100 mL) at 0° C. The resulting solution was stirred for 0.5 h, quenched with water, extracted with ethyl acetate, concentrated under vacuum. The residue was adsorbed onto silica gel and purified by flash column chromatography eluted with petroleum/ethyl acetate (4:1) to afford the title compound (9.80 g, 96% yield) as a colorless solid.

Step 2: Preparation of 1-((1s,3s)-3-(benzyloxy)cyclobutoxy)-3-fluorobenzene

167

-continued

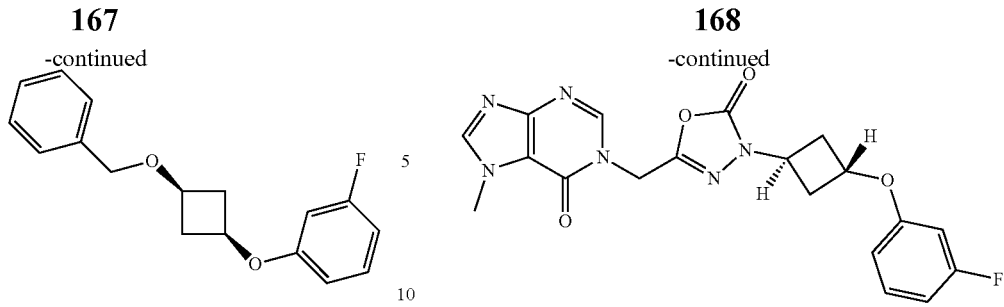

A mixture of 3-benzyloxycyclobutanol (6.3 g, 35.35 mmol), 3-fluorophenylboronic acid (7.42 g, 53.02 mmol), DMAP (17.25 g, 141.39 mmol), 4A molecular sieve (10 g), and Cu(OAc)$_2$ (14.14 g, 70.70 mmol) in DCM (60 mL) was stirred at room temperature under oxygen for 12 h. The reaction mixture was diluted with DCM, washed with water and concentrated under vacuum. The residue was adsorbed onto silica gel and purified by flash column chromatography eluted with petroleum/ethyl acetate (9:1) to afford the title compound (1.70 g, 17% yield) as yellow oil.

Step 3: Preparation of (1s,3s)-3-(3-fluorophenoxy)cyclobutanol

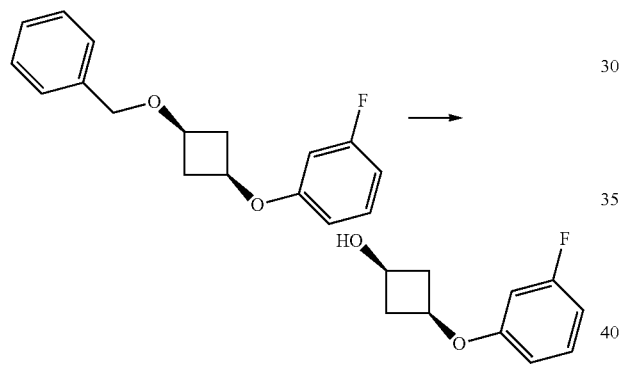

A mixture of Pd/C (10%) (0.17 g) and 1-(3-benzyloxycyclobutoxy)-3-fluorobenzene (1.70 g, 6.24 mmol) in ethanol (10 mL) was stirred under hydrogen at 25° C. for 12 h. The reaction mixture was diluted with ethanol and the solid was filtered out. The filtrate was concentrated under vacuum. The residue was adsorbed onto silica gel and purified by flash column chromatography eluted with petroleum/ethyl acetate (84:16). This resulted in the title compound (980 mg, 86% yield) as a white solid.

Step 4: Preparation of trans-3-[3-(3-fluorophenoxy)cyclobutyl]-5-[(7-methyl-6-oxo-purin-1-yl)methyl]-1,3,4-oxadiazol-2-one

168

-continued

DIAD (665 mg, 3.29 mmol) was added to a solution of 3-(3-fluorophenoxy) cyclobutanol (200 mg, 1.10 mmol), 5-[(7-methyl-6-oxo-purin-1-yl)methyl]-3H-1,3,4-oxadiazol-2-one (326 mg, 1.32 mmol) and PPh$_3$ (862.84 mg, 3.29 mmol) in tetrahydrofuran (5 mL) at 25° C. for 1 h. The reaction mixture was concentrated under vacuum. The residue was adsorbed onto silica gel and purified by flash column chromatography eluted with EtOH/DCM (20:1) to afford the title compound (150 mg, 33% yield). LCMS [M+H$^+$]: 413.1. $^1$H NMR (400 MHz, DMSO-d$_6$): δ 8.38 (s, 1H), 8.24 (s, 1H), 7.32-7.30 (m, 1H), 6.78-6.68 (m, 3H), 5.27 (s, 2H), 4.89 (m, 1H), 4.75-4.64 (m, 1H), 3.98 (s, 3H), 2.86-2.75 (m, 2H), 2.55 (m, 2H).

Example Compound 64: Preparation of trans-3-[3-(4-chlorophenyl)cyclobutyl]-5-[(1-methyl-7-oxo-triazolo[4,5-d]pyrimidin-6-yl)methyl]-1,3,4-oxadiazol-2-one The overall Example Compound 64 reaction scheme is as follows:

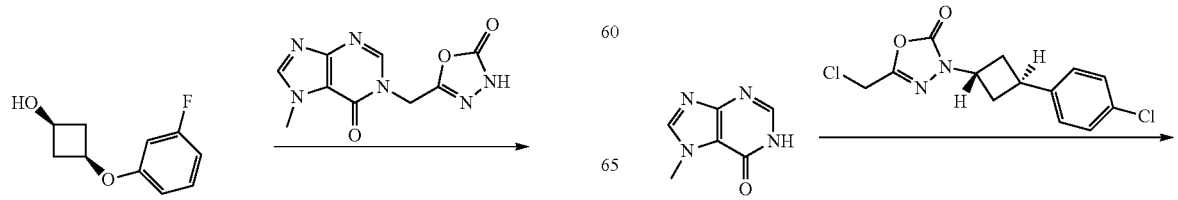

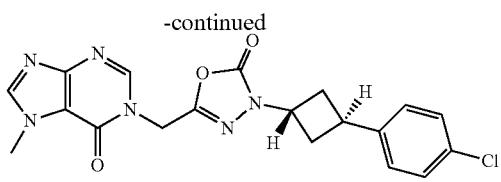

Step 1: Preparation of 4-amino-3-benzyl-5-carbamoyl-1-methyl-1H-1,2,3-triazol-3-ium 4-methylbenzenesulfonate

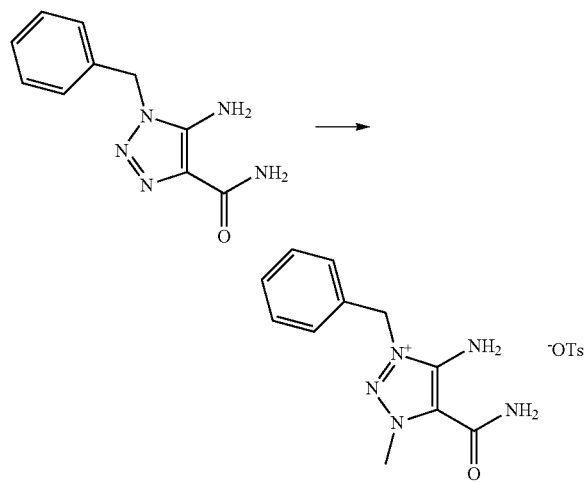

To a vial was added a suspension of 5-amino-1-benzyl-triazole-4-carboxamide (10.1 g, 46.5 mmol) and methyl 4-methylbenzenesulfonate (10.5 mL, 69.7 mmol) in dimethyl sulfoxide (5.0 mL) and the vial was placed in a heating block pre-heated to 150° C. for 5 min. The homogeneous solution was then cooled to room temperature, 100 mL of ethanol was added and the mixture was cooled in an ice bath. The mixture was filtered through a fritted funnel and the precipitate was rinsed with 25 mL of cold ethanol. The precipitate was collected and dried under vacuum to yield the title compound as a beige solid (6.33 g, 34%). LCMS [M+]: 232.1.

Step 2: Preparation of 4-amino-1-methyl-1H-1,2,3-triazole-5-carboxamide

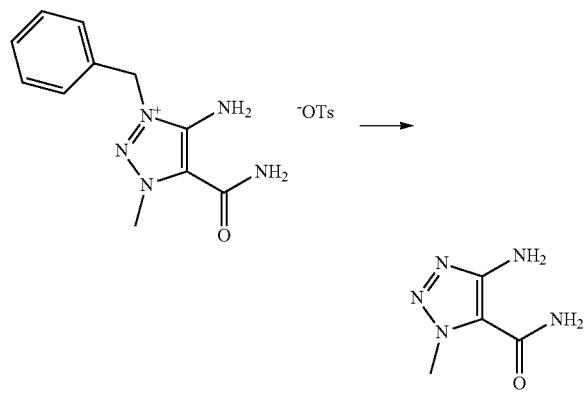

To a suspension of 5-amino-1-benzyl-3-methyl-triazol-1-ium-4-carboxamide; 4-methylbenzenesulfonate (6.29 g, 15.6 mmol) and ammonium formate (2.95 g, 46.8 mmol) in ethanol (250 mL), purged with nitrogen was added palladium on Carbon (10 wt %) (1.66 g, 1.56 mmol) and the reaction mixture was heated to 60° C. for 2 h. The reaction mixture was filtered through a fritted funnel and the solids were washed hot ethanol. The filtrate was concentrated in vacuo, the residue was taken up in ~500 mL of EtOAc and filtered, washing with ~200 mL of EtOAc and the filtrate was concentrated in vacuo to give the title compound as a white solid (1.28 g, 58%). 1H NMR (400 MHz, DMSO-d6) δ 5.76 (s, 3H), 5.35 (s, 2H), 4.05 (s, 2H).

Step 3: Preparation of 1-methyl-1,6-dihydro-7H-[1,2,3]triazolo[4,5-d]pyrimidin-7-one

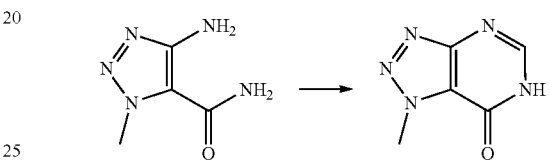

To a microwave vial was added 4-amino-1-methyl-1H-1,2,3-triazole-5-carboxamide (1.26 g, 8.48 mmol) followed by formamide (2.36 mL, 59.4 mmol) and the reaction was heated to 200° C. under microwave irradiation for 45 min. The mixture was diluted with EtOH causing precipitation. The mixture was chilled in an ice bath and the solid collected by vacuum filtration. The precipitate was washed with a small amount of chilled EtOH, collected and dried under vacuum to give a beige solid (915 mg, 71%). 1H NMR (400 MHz, DMSO-d6) δ 12.69 (s, 1H), 8.09 (s, 1H), 4.34 (s, 3H).

Step 4: Preparation of trans-3-[3-(4-chlorophenyl)cyclobutyl]-5-[(1-methyl-7-oxo-triazolo[4,5-d]pyrimidin-6-yl)methyl]-1,3,4-oxadiazol-2-one

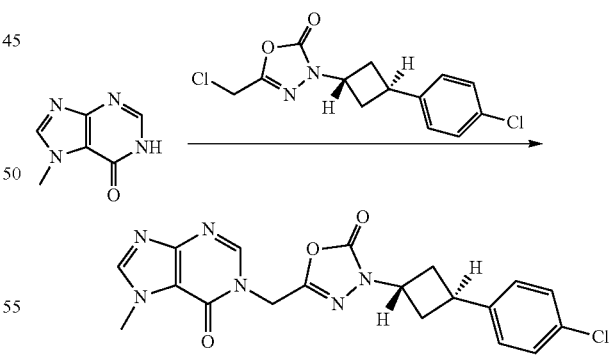

The title compound was prepared from 1-methyl-6H-triazolo[4,5-d]pyrimidin-7-one (25 mg, 0.17 mmol) and 5-(chloromethyl)-3-((1r,3r)-3-(4-chlorophenyl) cyclobutyl)-1,3,4-oxadiazol-2(3H)-one ((50 mg, 0.17 mmol) in a manner analogous to Example 58, Step 3 as a white solid (40 mg, 58% yield). LCMS [M+H⁺]: 414.0. ¹H NMR (300 MHz, DMSO-d6) δ 8.52 (s, 1H), 7.40-7.34 (s, 4H), 5.31 (s, 2H), 4.68-4.63 (m, 1H), 4.38 (s, 3H), 3.67-3.56 (m, 1H), 2.84-2.74 (m, 2H), 2.58-2.46 (m, 2H).

Example Compound 65: Preparation of trans-2-[[4-[3-(4-chlorophenyl)cyclobutyl]-5-oxo-1,3,4-oxadiazol-2-yl] methyl] pyrido[1,2-a] pyrazine-1,6-dione The overall Example Compound 65 reaction scheme is as follows:

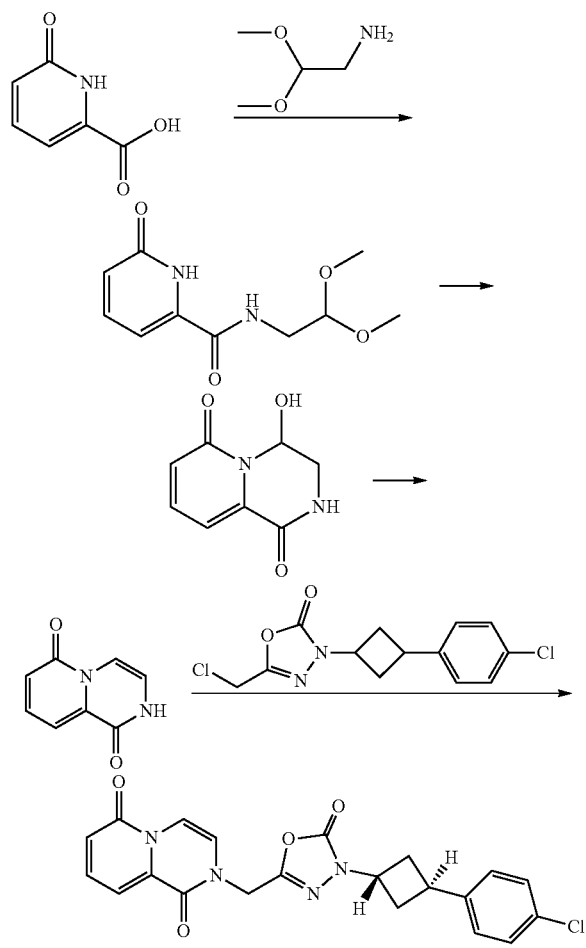

Step 1: Preparation of N-(2,2-dimethoxyethyl)-6-oxo-1,6-dihydropyridine-2-carboxamide

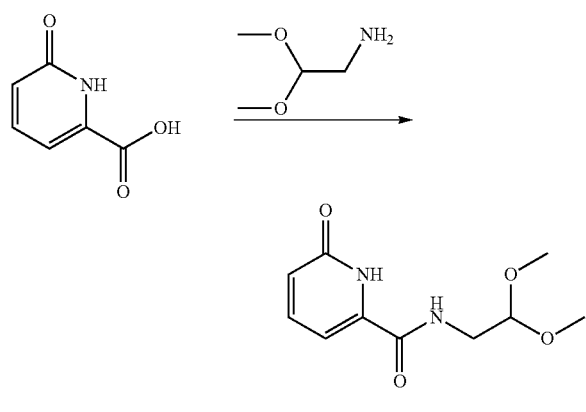

HATU (4.10 g, 10.78 mmol) was added to a solution of 6-oxo-1H-pyridine-2-carboxylic acid (1.0 g, 7.19 mmol), 2,2-dimethoxyethanamine (1.51 g, 14.38 mmol) and DIEA (4.64 g, 35.94 mmol) in N,N-dimethylformamide (10 mL) at room temperature. The mixture was stirred at room temperature for 12 hours. The reaction mixture was purified by reversed phase HPLC to yield the title compound (1 g, 61% yield) as a white solid.

Step 2: Preparation of 4-hydroxy-3,4-dihydro-2H-pyrido[1,2-a]pyrazine-1,6-dione

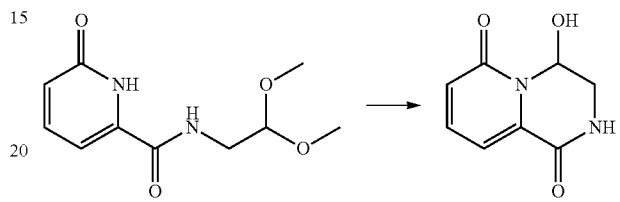

HCl (1 M, 20 mL) was added to a solution of N-(2,2-dimethoxyethyl)-6-oxo-1H-pyridine-2-carboxamide (1.00 g, 1.77 mmol) in water (7 mL) at 25° C. The reaction mixture was stirred at room temperature for 3 h. The solids were collected by filtration to afford the title compound (420 mg, 52% yield) as a white solid.

Step 3: Preparation of 2H-pyrido[1,2-a]pyrazine-1,6-dione

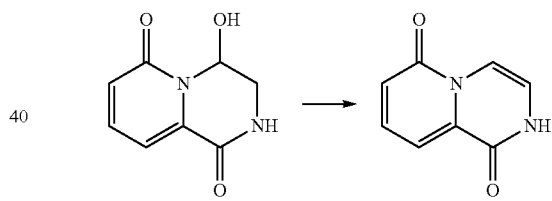

A mixture of 4-hydroxy-3,4-dihydro-2H-pyrido[1,2-a]pyrazine-1,6-dione (420 mg, 2.33 mmol) and TsOH (201 mg, 1.17 mmol) in toluene (5 mL) was stirred at 100° C. for 12 h. The solvent was concentrated under vacuum. The reaction mixture was purified by reversed phase HPLC to yield the title compound (100 mg, 26% yield) as a yellow solid.

Step 4: Preparation of trans-2-[[4-[3-(4-chlorophenyl)cyclobutyl]-5-oxo-1,3,4-oxadiazol-2-yl] methyl] pyrido[1,2-a] pyrazine-1,6-dione

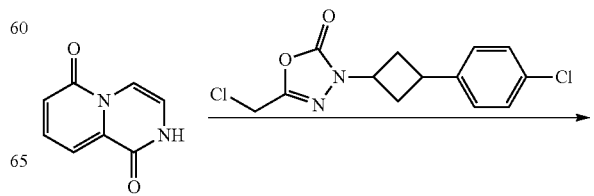

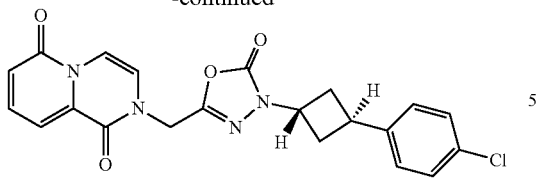

The title compound was prepared from 2H-pyrido[1,2-a]pyrazine-1,6-dione (90 mg, 0.56 mmol) and 5-(chloromethyl)-3-[3-(4-chlorophenyl)cyclobutyl]-1,3,4-oxadiazol-2-one (199 mg, 0.67 mmol) in a manner analogous to Example 58, Step 3 as a white solid (24 mg, 10% yield). LCMS [M+H$^+$]: 425.1. $^1$H NMR (400 MHz, CDCl$_3$): δ 7.86 (d, J=6.5 Hz, 1H), 7.64 (dd, J=9.2, 7.2 Hz, 1H), 7.45 (dd, J=7.0, 1.1 Hz, 1H), 7.37-7.29 (m, 2H), 7.26-7.18 (m, 2H), 6.92 (dd, J=9.2, 1.2 Hz, 1H), 6.64 (d, J=6.5 Hz, 1H), 5.01 (s, 2H), 4.84-4.71 (m, 1H), 3.68-3.66 (m, 1H), 3.01-2.89 (m, 2H), 2.61-2.50 (m, 2H).

Example Compound 70: trans-3-[3-(3-chlorophenoxy)cyclobutyl]-5-[(7-methyl-6-oxo-purin-1-yl)methyl]-1,3,4-oxadiazol-2-one The overall Example Compound 70 reaction scheme is as follows:

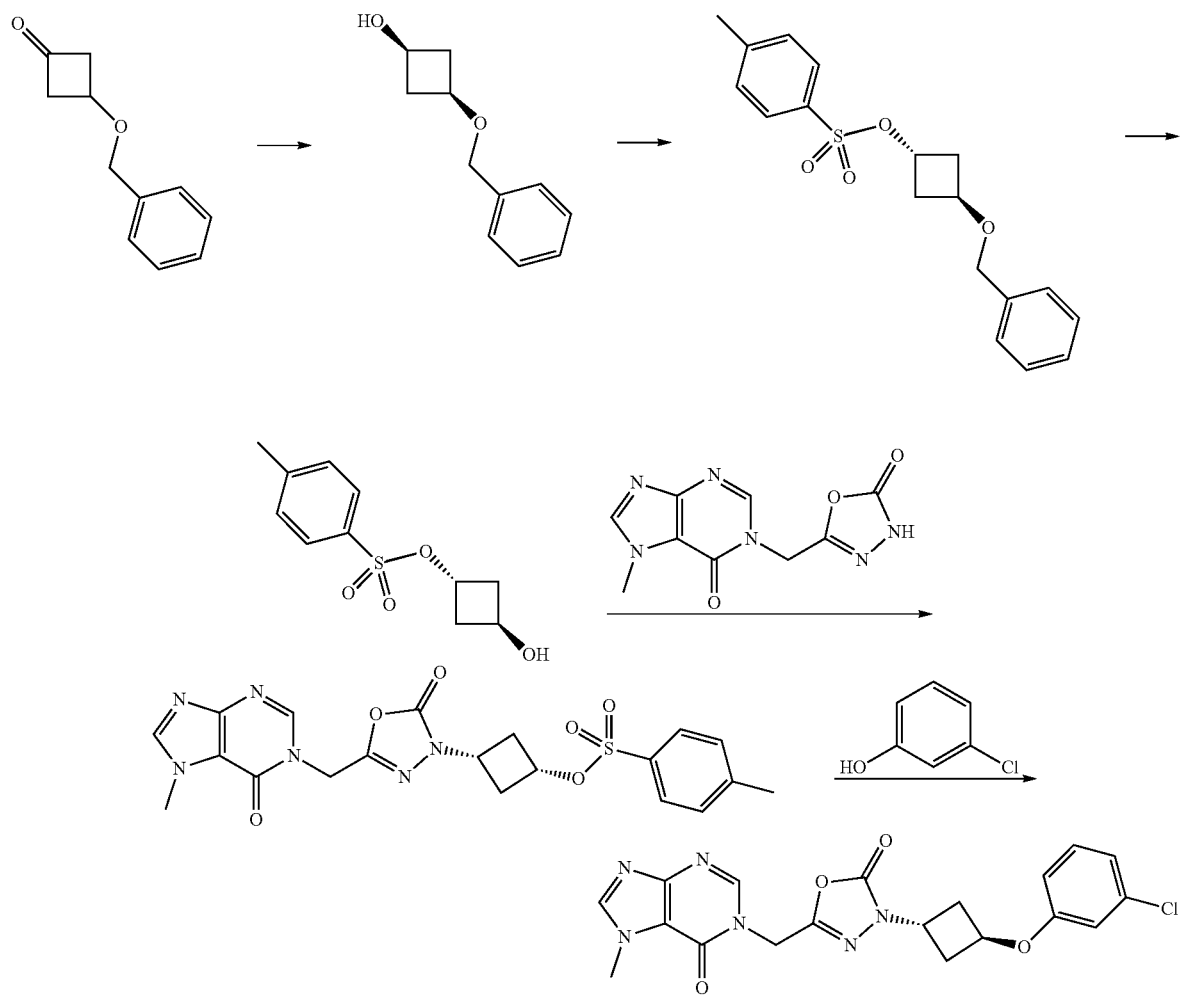

Step 1: Preparation of (1s,3s)-3-(benzyloxy)cyclobutanol

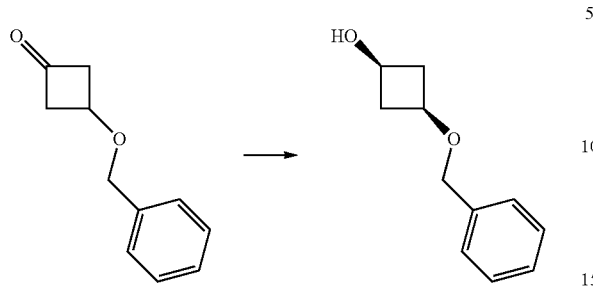

Sodium borohydride (215 mg, 5.68 mmol) was added to a solution of 3-benzyloxycyclobutanone (1.00 g, 5.68 mmol) in methanol (19 mL). The reaction was stirred at room temperature for 4 h. The reaction was quenched with water and was extracted with iPrOAc (3×). The combined organic extracts were washed with brine, dried with $MgSO_4$, filtered and concentrated. The crude mixture was adsorbed on silica gel and by silica gel column with 0-80% iPOAc/Heptane to afford the title compound (880 mg, 87%) as clear oil.

Step 2: Preparation of (1r,3r)-3-(benzyloxy)cyclobutyl 4-methylbenzenesulfonate

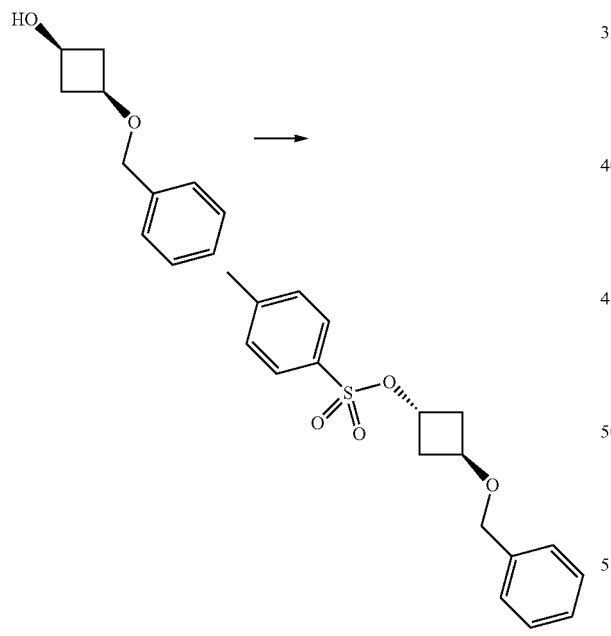

DIAD (1.69 mL, 8.53 mmol) was added to a solution of 3-(benzyloxy)cyclobutanol (800 mg, 4.26 mmol), pyridinium p-toluenesulfonate (2.14 g, 8.53 mmol) and triphenylphosphine (2.24 g, 8.53 mmol) in THF (43 mL). The mixture was stirred at 50° C. for 2 days. The crude mixture was adsorbed on silica gel and purified by silica gel column with 0-50% iPrOAc/heptane to afford the title compound (1.25 g, 88% Yield) as a clear oil.

Step 3: Preparation of (1r,3r)-3-hydroxycyclobutyl 4-methylbenzenesulfonate

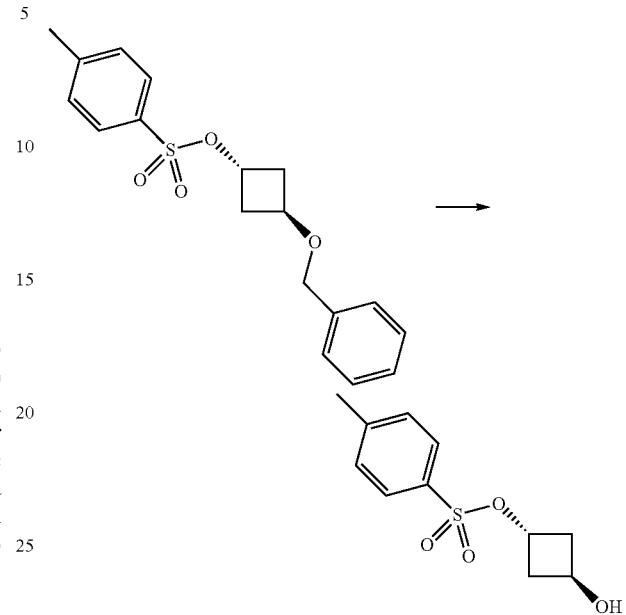

A mixture of (3-benzyloxycyclobutyl) 4-methylbenzenesulfonate (1.11 g, 3.34 mmol) and Pd on carbon (10% wt) (533 mg, 0.50 mmol) in EtOH (33 mL) under N2 was backfilled with $H_2$ (3×) using a balloon and stirred overnight. The reaction mixture was filtered through diatomaceous earth and the cake was washed with MeOH. The filtrate was concentrated on the rotavap. The crude mixture was adsorbed on silica gel and purified by silica gel column with 30-100% iPrOAc/heptane to afford the title compound (597 mg, 74% Yield) was obtained as a clear oil.

Step 4: Preparation of (1s,3s)-3-(5-((7-methyl-6-oxo-6,7-dihydro-1H-purin-1-yl)methyl)-2-oxo-1,3,4-oxadiazol-3(2H)-yl)cyclobutyl 4-methylbenzenesulfonate

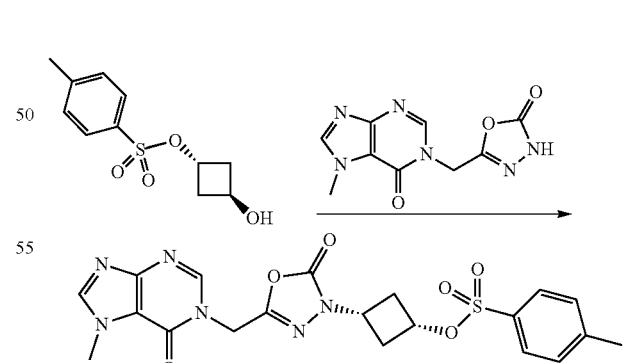

DIAD (449 μL, 2.27 mmol) was added to a solution of 5-[(7-methyl-6-oxo-purin-1-yl)methyl]-3H-1,3,4-oxadiazol-2-one (375 mg, 1.51 mmol), (3-hydroxycyclobutyl) 4-methylbenzenesulfonate (476 mg, 1.96 mmol) and triphenylphosphine (594 mg, 2.27 mmol) in THF (10 mL) at 0° C. The mixture was stirred at room temperature overnight.

The same amount of DIAD and triphenylphosphine was added and the reaction was stirred at 50° C. for 7 h. The crude mixture was adsorbed on silica gel and purified by silica gel column with 30-80% (3:1 iPrOAc/MeOH)/heptane to afford the title compound (547 mg, 77% Yield) as a white solid.

Step 5: Preparation of trans-3-[3-(3-chlorophenoxy)cyclobutyl]-5-[(7-methyl-6-oxo-purin-1-yl)methyl]-1,3,4-oxadiazol-2-one

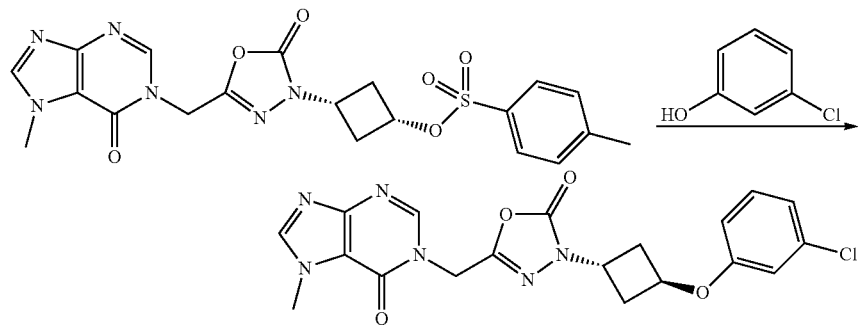

A mixture of [3-[5-[(7-methyl-6-oxo-purin-1-yl)methyl]-2-oxo-1,3,4-oxadiazol-3-yl]cyclobutyl] 4-methylbenzenesulfonate (100 mg, 0.21 mmol), 3-chlorophenol (44 μL, 0.42 mmol) and $Cs_2CO_3$ (138 mg, 0.42 mmol) in DMSO (1.1 mL) was stirred at 80° C. overnight. The reaction mixture was partitioned in water/iPrOAc and extracted with iPrOAc (3×). The combined organic extracts were washed with brine, dried over $MgSO_4$, filtered and concentrated. The crude mixture was adsorbed on silica gel and purified by silica gel column with 30-80% (3:1 iPrOAc/MeOH)/Heptane. The compound was further purified by chiral SFC using a Chiralpak OJ column with 40% of 0.1% ammonium hydroxide in methanol in $CO_2$. This resulted in the title compound (10.9 mg, 12% Yield) as a white solid. LCMS [M+H$^+$]: 429.1. 1H NMR (400 MHz, DMSO-d6) δ 8.36 (s, 1H), 8.22 (s, 1H), 7.30 (t, J=8.1 Hz, 1H), 7.00 (ddd, J=8.0, 2.0, 0.9 Hz, 1H), 6.89 (t, J=2.2 Hz, 1H), 6.81 (ddd, J=8.4, 2.5, 0.9 Hz, 1H), 5.26 (s, 2H), 4.90 (tt, J=7.0, 3.6 Hz, 1H), 4.69 (tt, J=8.5, 6.2 Hz, 1H), 3.97 (s, 3H), 2.85-2.74 (m, 2H), 2.58-2.50 (m, 2H).

Example Compound 83: 3-((4-((trans)-3-(4-chlorophenyl)cyclobutyl)-5-oxo-4,5-dihydro-1,3,4-oxadiazol-2-yl)methyl)-5-methylpyrido[3,2-d]pyrimidine-4,6(3H,5H)-dione The overall Example Compound 83 reaction scheme is as follows:

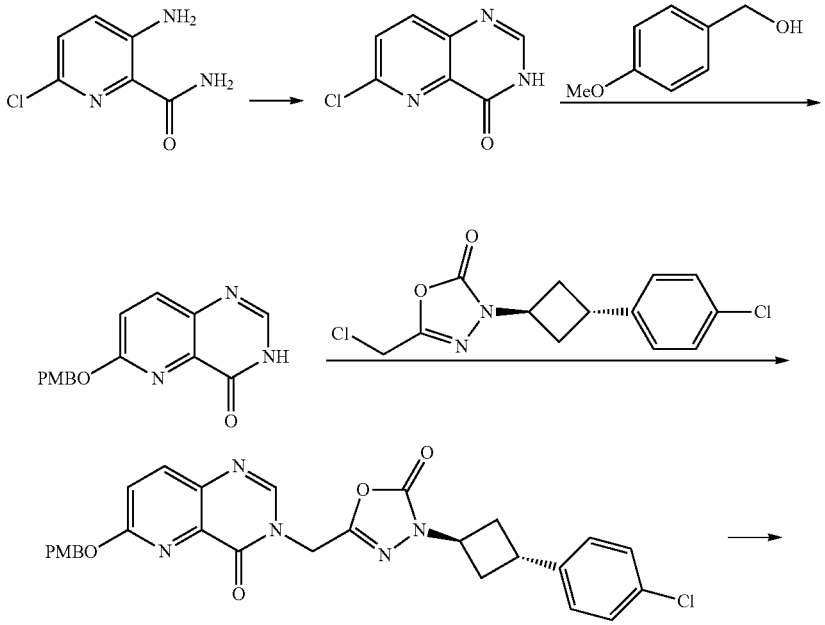

-continued

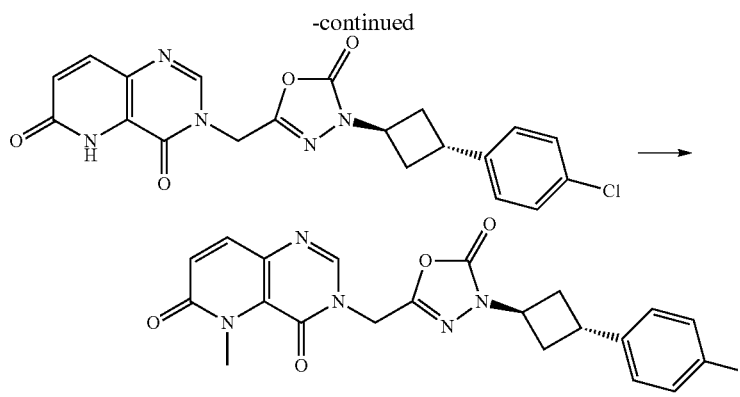

Step 1: Preparation of 6-chloropyrido[3,2-d]pyrimidin-4(3H)-one

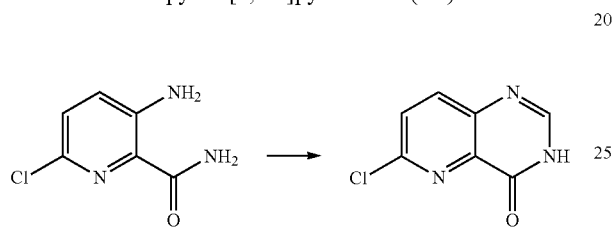

Acetic anhydride (15.1 mL, 160 mmol) was added to a mixture of 3-amino-6-chloro-pyridine-2-carboxamide (2.50 g, 14.6 mmol) and triethyl orthoformate (15.1 mL, 90.7 mmol). The reaction mixture was refluxed for 2 hours and it was cooled down to 20° C. which caused the formation of a precipitate. Isopropanol (20 mL) was added and the solid was filtered, washed with isopropanol and dried under vacuum to afford 6-chloropyrido[3,2-d]pyrimidin-4(3H)-one (1.10 g, 6.06 mmol, 42% yield) as a beige solid. LCMS [M+H$^+$] 182.0.

Step 2: Preparation of 6-((4-methoxybenzyl)oxy)pyrido[3,2-d]pyrimidin-4(3H)-one

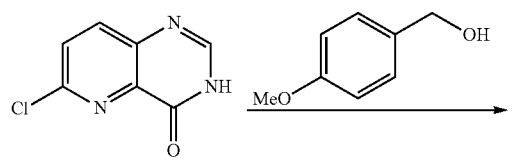

-continued 4-methoxybenzyl alcohol (0.39 mL, 3.17 mmol) was added to a suspension of sodium hydride 60% in mineral oil (1.03 g, 25.8 mmol) in DMF (13 mL). The reaction mixture was stirred for 30 min. at 20° C. 6-Chloro-3H-pyrido[3,2-d]pyrimidin-4-one (2.34 g, 12.9 mmol) was added and the reaction mixture was heated at 85° C. for 1 hour. A second solution of sodium (4-methoxyphenyl)methanolate (3.17 mmol) in DMF (13 mL) was made as mentioned above and it was added to the reaction mixture at 20° C. The resulting mixture was stirred at 85° C. for 1 more hour. The reaction mixture was splitted in three portions and each of them was purified by reverse chromatography on C-18 column using a solution of MeCN in 10 mM of ammonium formate in water, pH=3.8 (5 to 40% gradient). Pure fractions of the three purifications were combined. Most of MeCN was evaporated and the resulting mixture was lyophilized to give 6-((4-methoxybenzyl)oxy)pyrido[3,2-d]pyrimidin-4(3H)-one (1.42 g, 5.01 mmol, 39% yield) as a pale brown solid. LCMS [M−H$^-$] 282.1.

Step 3: Preparation of 3-((trans)-3-(4-chlorophenyl)cyclobutyl)-5-((6-((4-methoxybenzyl)oxy)-4-oxopyrido[3,2-d]pyrimidin-3(4H)-yl)methyl)-1,3,4-oxadiazol-2(3H)-one

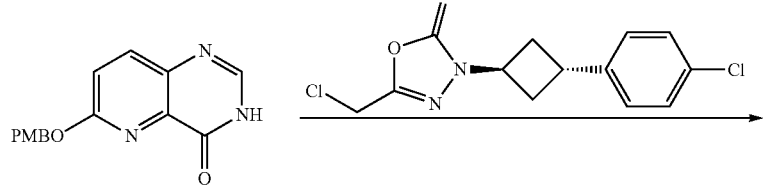

-continued

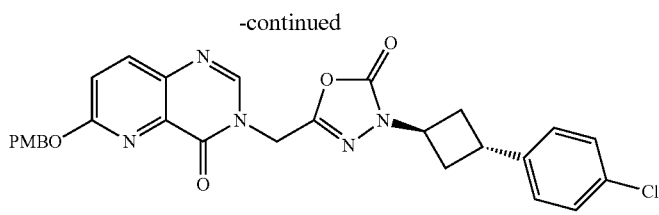

DMF (11 mL) was added to a mixture of 6-((4-methoxybenzyl)oxy)pyrido[3,2-d] pyrimidin-4(3H)-one (165 mg, 0.580 mmol), 5-(chloromethyl)-3-((trans)-3-(4-chlorophenyl)cyclobutyl)-1,3,4-oxadiazol-2(3H)-one (174 mg, 0.580 mmol, prepared in Example 92, step 3), tetrabutylammonium iodide (43 mg, 0.12 mmol) and cesium carbonate (569 mg, 1.75 mmol). The reaction mixture was stirred at 20° C. for 2 hours. Ethyl acetate was added and the mixture was washed with brine (3×). The organic layer was dried over anhydrous $Na_2SO_4$, filtered and evaporated under reduced pressure. The crude product was purified by flash chromatography on silica gel using a solution of MeOH in DCM (1 to 4% gradient). The obtained product was re-purified by flash chromatography on silica gel using a solution of EtOAc in hexanes (50%) to give 3-((trans)-3-(4-chlorophenyl)cyclobutyl)-5-((6-((4-methoxybenzyl)oxy)-4-oxopyrido[3,2-d]pyrimidin-3(4H)-yl)methyl)-1,3,4-oxadiazol-2(3H)-one (90 mg, 0.16 mmol, 28% yield) as a pale purple solid. $^1$H NMR (500 MHz, CDCl$_3$) δ 8.09 (s, 1H), 7.96 (d, J=8.9 Hz, 1H), 7.48-7.45 (m, 2H), 7.32-7.28 (m, 2H), 7.22-7.17 (m, 3H), 6.94-6.90 (m, 2H), 5.51 (s, 2H), 5.19 (s, 2H), 4.77-4.70 (m, 1H), 3.81 (s, 3H), 3.68-3.60 (m, 1H), 2.96-2.87 (m, 2H), 2.57-2.49 (m, 2H).

Step 4: Preparation of 3-((4-((trans)-3-(4-chlorophenyl)cyclobutyl)-5-oxo-4,5-dihydro-1,3,4-oxadiazol-2-yl)methyl)pyrido[3,2-d]pyrimidine-4,6(3H,5H)-dione

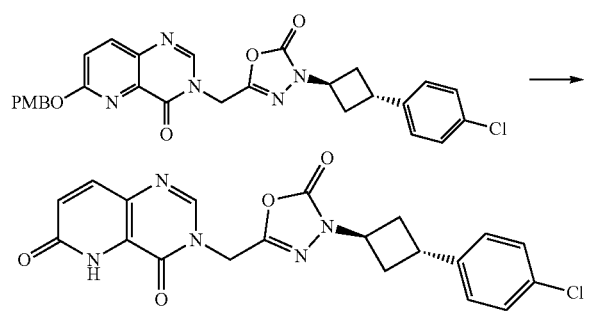

Trifluoroacetic acid (0.30 mL, 3.9 mmol) was added to 3-((trans)-3-(4-chlorophenyl)cyclobutyl)-5-((6-((4-methoxybenzyl)oxy)-4-oxopyrido[3,2-d] pyrimidin-3(4H)-yl)methyl)-1,3,4-oxadiazol-2(3H)-one (33 mg, 0.060 mmol). The reaction mixture was stirred for 1 min. and the solvent was evaporated. The residue was co-evaporated twice with DCM to give 3-((4-((trans)-3-(4-chlorophenyl)cyclobutyl)-5-oxo-4,5-dihydro-1,3,4-oxadiazol-2-yl)methyl)pyrido[3,2-d]pyrimidine-4,6(3H,5H)-dione (26 mg, 0.060 mmol, 100% yield) which was used directly in the next step. LCMS [M+H$^+$] 426.0.

Step 5: Preparation of 3-((4-((trans)-3-(4-chlorophenyl)cyclobutyl)-5-oxo-4,5-dihydro-1,3,4-oxadiazol-2-yl)methyl)-5-methylpyrido[3,2-d]pyrimidine-4,6(3H,5H)-dione

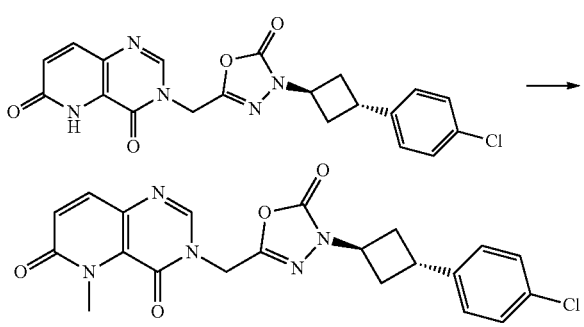

A solution of iodomethane (4.1 μL, 0.070 mmol) in DMF (0.3 mL) was added to 3-((4-((trans)-3-(4-chlorophenyl)cyclobutyl)-5-oxo-4,5-dihydro-1,3,4-oxadiazol-2-yl)methyl)pyrido[3,2-d]pyrimidine-4,6(3H,5H)-dione (26 mg, 0.060 mmol). Potassium carbonate (25 mg, 0.18 mmol) was added and the reaction mixture was stirred for 30 min. Cesium carbonate (59 mg, 0.18 mmol) was then added and the reaction mixture was stirred for another 30 min. The resulting mixture was directly purified by semi-prep HPLC-MS (column X-Bridge 30×50) using a solution of MeCN in 10 mM of ammonium formate in water, pH=3.8 (35 to 55% gradient). Pure fractions were combined, frozen and lyophilized to give 3-((4-((trans)-3-(4-chlorophenyl)cyclobutyl)-5-oxo-4,5-dihydro-1,3,4-oxadiazol-2-yl)methyl)-5-methylpyrido[3,2-d]pyrimidine-4,6(3H,5H)-dione (5.0 mg, 0.011 mmol, 19% yield) as a white solid. LCMS [M+H$^+$] 440.0; $^1$H NMR (500 MHz, DMSO-d6) δ 8.41 (s, 1H), 7.74 (d, J=9.6 Hz, 1H), 7.40-7.35 (m, 4H), 6.96 (d, J=9.6 Hz, 1H), 5.24 (s, 2H), 4.69-4.61 (m, 1H), 3.90 (s, 3H), 3.68-3.59 (m, 1H), 2.83-2.75 (m, 2H), 2.54-2.50 (m, 2H).

Example Compound 85: Preparation of 3-(3-(3-chlorophenoxy)propyl)-5-((5-methyl-4-oxopyrido[2,3-d]pyrimidin-3(4H)-yl)methyl)-1,3,4-oxadiazol-2(3H)-one

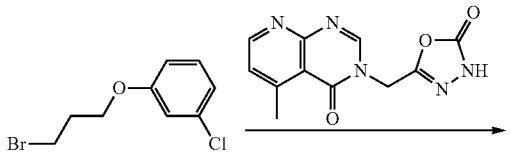

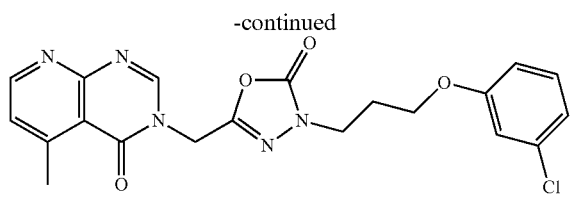

The title compound was prepared from 5-(5-methyl-4-oxo-3H,4H-pyrido[2,3-d]pyrimidin-3-ylmethyl)-2,3-dihydro-1,3,4-oxadiazol-2-one (50 mg, 0.19 mmol) and 1-(3-bromopropoxy)-3-chlorobenzene (48 mg, 0.19 mmol) as a white solid (14 mg, 17% yield), in a manner analogous to Example 85, step 2. LCMS [M+H$^+$] 427. $^1$H NMR (400 MHz, DMSO-d$_6$) δ 8.77 (d, J=4.8 Hz, 1H), 8.60 (s, 1H), 7.39 (d, J=4.8 Hz, 1H), 7.27-7.25 (m, 1H), 6.97-6.94 (m, 2H), 6.88-6.83 (m, 1H), 5.19 (s, 2H), 4.02 (t, J=6.0 Hz, 2H), 3.81 (t, J=6.4 Hz, 2H), 2.77 (m, 3H), 2.08-2.02 (m, 2H).

Example Compound 86: Preparation of 1-([4-[3-(3-chlorophenoxy)propyl]-5-oxo-4,5-dihydro-1,3,4-oxadiazol-2-yl]methyl)-7-methyl-6,7-dihydro-1H-purin-6-one The overall Example Compound 86 reaction scheme is as follows:

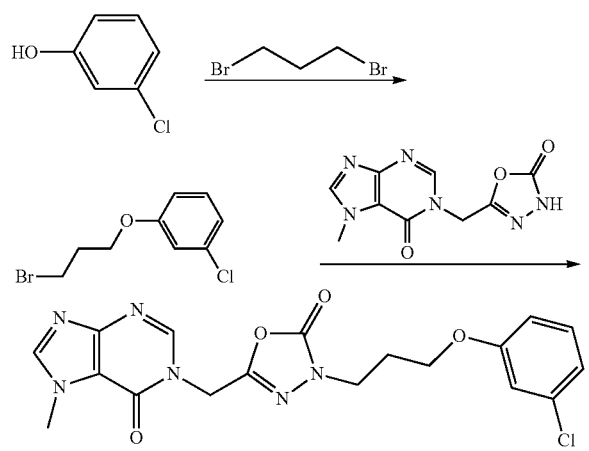

Step 1: Preparation of 1-(3-bromopropoxy)-3-chloro-benzene

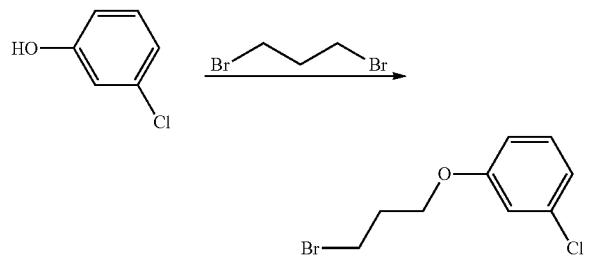

A mixture of 3-chlorophenol (0.03 mL, 23.34 mmol), 1,3-dibromopropane (9.4 g, 46.56 mmol) and K$_2$CO$_3$ (9.66 g, 70.01 mmol) in acetonitrile (15 mL) was stirred at 80° C. for 24 hours. The solids were filtered out and the filtrate was concentrated under vacuum. The residue was adsorbed onto silica gel and purified by flash column chromatography eluted with petroleum/ethyl acetate (4/1) to afford the title compound (4 g, 16.03 mmol, 68.7% yield) as yellow oil.

Step 2: Preparation of 1-([4-[3-(3-chlorophenoxy)propyl]-5-oxo-4,5-dihydro-1,3,4-oxadiazol-2-yl]methyl)-7-methyl-6,7-dihydro-1H-purin-6-one

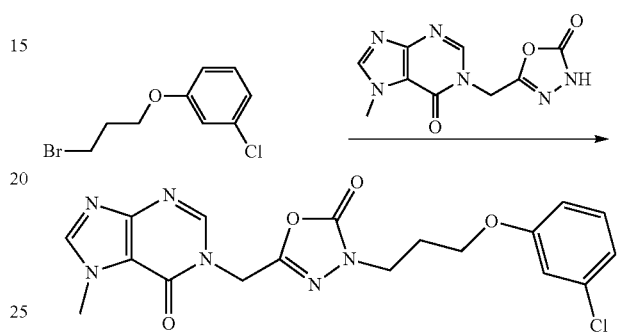

A mixture of 7-methyl-1-[(5-oxo-4,5-dihydro-1,3,4-oxadiazol-2-yl)methyl]-6,7-dihydro-1H-purin-6-one (50 mg, 0.20 mmol, TBAI (7.4 mg, 0.02 mmol), potassium carbonate (83.5 mg, 0.60 mmol), and 1-(3-bromopropoxy)-3-chlorobenzene (50.4 mg, 0.20 mmol) in N,N-dimethylformamide (3 mL) was stirred for 2 h at 25° C. The solids were filtered out and concentrated in vacuo. The residue was purified by reversed phase HPLC to afford the title compound (51.4 mg, 61%) as a white solid. LCMS [M+H$^+$] 416. $^1$H NMR (400 MHz, DMSO-d$_6$) δ 8.34 (s, 1H), 8.22 (s, 1H), 7.27 (t, J=8.0 Hz, 1H), 6.99-6.95 (m, 2H), 6.86-6.84 (m, 1H), 5.22 (s, 2H), 4.03 (t, J=6.0 Hz, 2H), 3.96 (s, 3H), 3.80 (t, J=6.7 Hz, 2H), 2.08-2.01 (m, 2H).

Example Compound 92: 5-[(7-methyl-6-oxo-purin-1-yl)methyl]-3-[(1R,3R)-3-(4-fluorophenyl)cyclopentyl]-1,3,4-oxadiazol-2-one The overall Example Compound 92 reaction scheme is as follows:

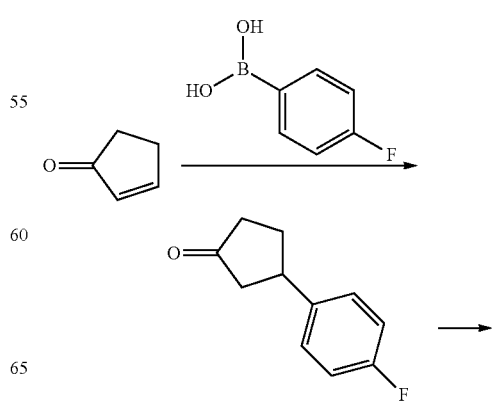

Step 2: Preparation of 3-(4-fluorophenyl)cyclopentanol

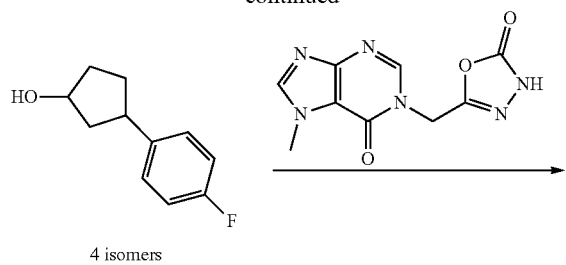

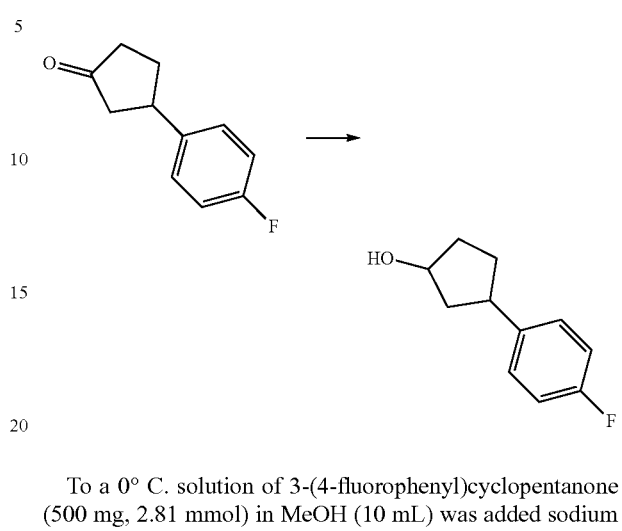

To a 0° C. solution of 3-(4-fluorophenyl)cyclopentanone (500 mg, 2.81 mmol) in MeOH (10 mL) was added sodium borohydride (159 mg, 4.21 mmol). After 30 min., a saturated aqueous solution of NH$_4$Cl was slowly added and the mixture was stirred for 20 min. at 20° C. The aqueous layer was extracted with DCM (3×) and the combined organic layers were washed with brine, dried over anhydrous MgSO$_4$, filtered and concentrated under reduced pressure to give a 1.5:1 diastereomeric mixture of 3-(4-fluorophenyl) cyclopentanol (459 mg, 2.55 mmol, 91% yield) as colorless oil. The crude material was used directly in the next step.

Step 3: Preparation of 5-[(7-methyl-6-oxo-purin-1-yl)methyl]-3-[(1R,3R)-3-(4-fluorophenyl)cyclopentyl]-1,3,4-oxadiazol-2-one

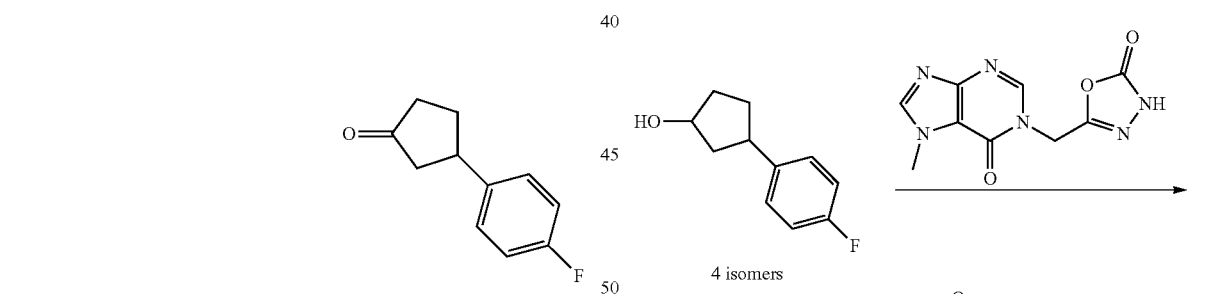

Step 1: Preparation of 3-(4-fluorophenyl)cyclopentanone

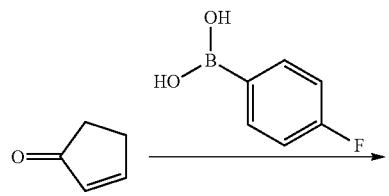

To a 150 mL pressure vessel charged with acetylacetonatobis(ethylene)rhodium (I) (157 mg, 0.610 mmol), (rac)-BINAP (379 mg, 0.610 mmol) and 4-fluorophenylboronic acid (6.1 mL, 42.6 mmol) was added 1,4-Dioxane (32 mL), water (3.2 mL) and 2-cyclopenten-1-one (1.00 g, 12.2 mmol). The reaction mixture was bubbled with nitrogen for 10 min. and it was stirred at 110° C. for 16 hours. The reaction mixture was concentrated under reduced pressure and the crude product was purified by flash chromatography on silica gel (50 g column) using a solution of EtOAc in hexanes (10 to 15% gradient) to afford 3-(4-fluorophenyl) cyclopentanone (1.88 g, 10.6 mmol, 87% yield) as a colorless oil. $^1$H NMR (500 MHz, CDCl$_3$) δ 7.24-7.19 (m, 2H), 7.05-7.00 (m, 2H), 3.45-3.34 (m, 1H), 2.70-2.62 (m, 1H), 2.51-2.40 (m, 2H), 2.37-2.25 (m, 2H), 2.00-1.89 (m, 1H).

The title compound was prepared from a 1.5:1 diastereomeric mixture of 3-(4-fluorophenyl)cyclopentanol and 5-[(7-methyl-6-oxo-purin-1-yl)methyl]-3H-1,3,4-oxadiazol-2-one (prepared according to Example Compound 1, Step 5) in a manner analogous to Example 71, Step 4. The resulting 4 isomers were separated by SFC with the following conditions: Column: IA, 10×250 mm, 5 um, Isocratic 35% MeOH, 10 mL/min, 100 Bar, Column temperature: 35° C., Run time: 20 min. The title compound, 5-[(7-methyl-6-oxo-purin-1-yl)methyl]-3-[(1R,3R)-3-(4-fluorophenyl)cyclopentyl]-1,3,4-oxadiazol-2-one, was obtained as a white solid as the second eluting compound (Rt=10.5 min.); LCMS [M+H⁺] 411.1; ¹H NMR (500 MHz, DMSO-d6) δ 8.35 (s, 1H), 8.22 (s, 1H), 7.30-7.26 (m, 2H), 7.13-7.07 (m, 2H), 5.24 (s, 2H), 4.65-4.58 (m, 1H), 3.97 (s, 3H), 3.31-3.22 (m, 1H), 2.26-2.09 (m, 3H), 2.04-1.95 (m, 1H), 1.94-1.85 (m, 1H), 1.65-1.54 (m, 1H).

Example Compound 93: trans-3-[[4-[3-(4-chlorophenyl)cyclobutyl]-5-oxo-1,3,4-oxadiazol-2-yl]methyl]-5-methyl-4-oxo-pyrido[2,3-d]pyrimidine-7-carbonitrile The overall Example Compound 93 reaction scheme is as follows:

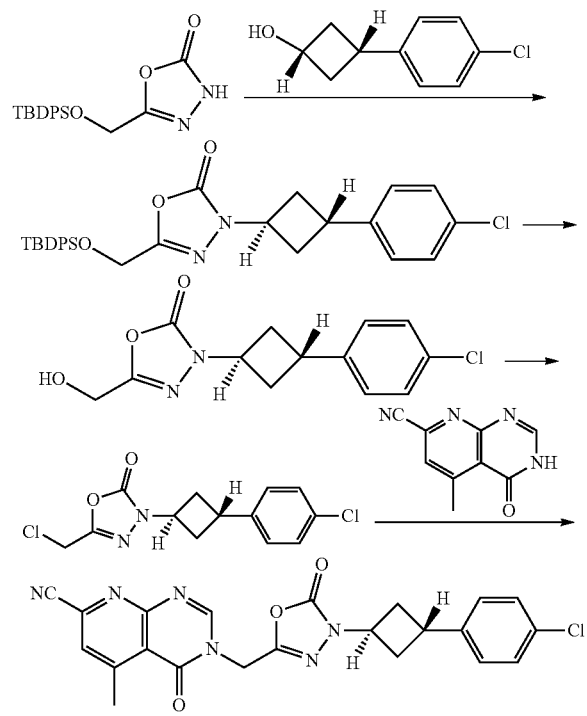

Step 1: Preparation of 5-[[(tert-butyldiphenylsilyl)oxy]methyl]-3-[(1r,3r)-3-(4-chlorophenyl)cyclobutyl]-2,3-dihydro-1,3,4-oxadiazol-2-one

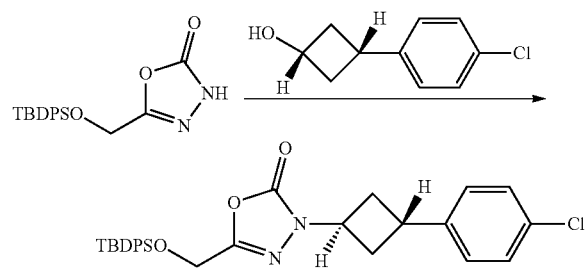

DIAD (3.32 g, 16.41 mmol) was added dropwise into a solution of 5-[[(tert-butyldiphenylsilyl)oxy] methyl]-2,3-dihydro-1,3,4-oxadiazol-2-one (1.94 g, 5.47 mmol), (1s,3s)-3-(4-chlorophenyl)cyclobutan-1-ol (1.30 g, 7.11 mmol), tetrahydrofuran (100 mL), PPh₃ (4.31 g, 16.43 mmol) under N₂(g). The resulting solution was stirred overnight at room temperature and concentrated under vacuum. The crude product was purified by reversed phase HPLC to yield the title compound (1.20 g, 42%) as a brown solid.

Step 2: Preparation of 5-(hydroxymethyl)-3-[(1r,3r)-3-(4-chlorophenyl) cyclobutyl]-2,3-dihydro-1,3,4-oxadiazol-2-one

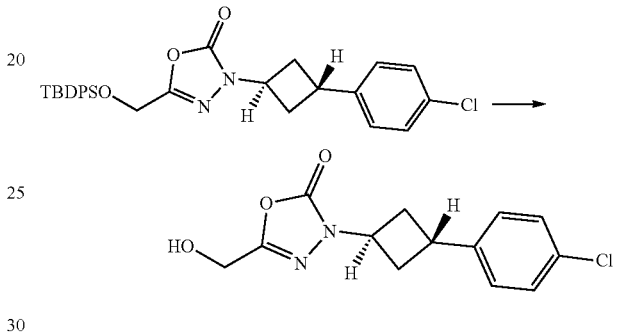

A mixture of 5-[[(tert-butyldiphenylsilyl)oxy]methyl]-3-[(1r,3r)-3-(4-chlorophenyl)cyclobutyl]-2,3-dihydro-1,3,4-oxadiazol-2-one (1.20 g, 2.31 mmol), tetrahydrofuran (30 mL), TBAF (1 M) (2.54 mL, 2.54 mmol) was stirred for 1 h at room temperature. The resulting mixture was concentrated under vacuum. The crude product was purified by reversed phase HPLC to yield the title compound (600 mg, 92%) as a brown solid.

Step 3: Preparation of 5-(chloromethyl)-3-[(1r,3r)-3-(4-chlorophenyl) cyclobutyl]-2,3-dihydro-1,3,4-oxadiazol-2-one

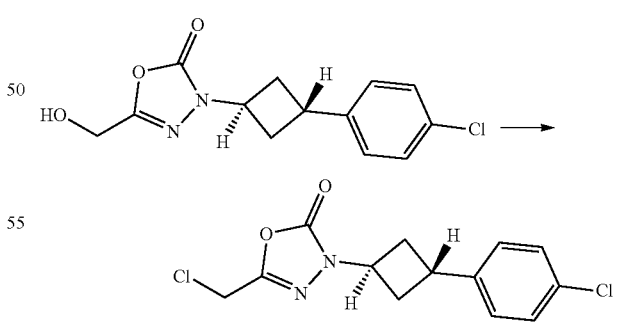

A mixture of 5-(hydroxymethyl)-3-[(1r,3r)-3-(4-chlorophenyl)cyclobutyl]-2,3-dihydro-1,3,4-oxadiazol-2-one (200 mg, 0.71 mmol), dichloromethane (20 mL), thionyl chloride (423.82 mg, 3.56 mmol) was stirred overnight at room temperature. The resulting mixture was concentrated to afford the title compound (210 mg, 99%) as brown oil.

189

Step 4: Preparation of trans-3-[[4-[3-(4-chlorophenyl)cyclobutyl]-5-oxo-1,3,4-oxadiazol-2-yl]methyl]-5-methyl-4-oxo-pyrido[2,3-d]pyrimidine-7-carbonitrile

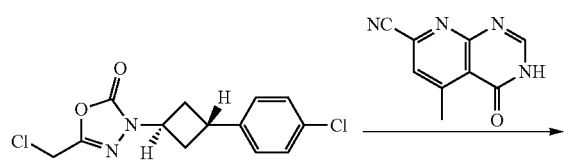

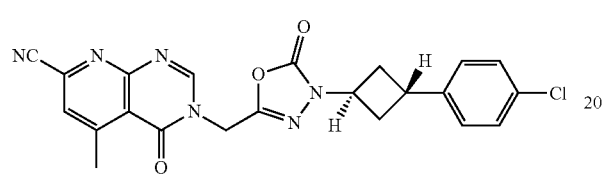

The title compound was prepared from 5-methyl-4-oxo-3H,4H-pyrido[2,3-d]pyrimidine-7-carbonitrile (24 mg, 0.13 mmol) and 5-(chloromethyl)-3-[(1r,3r)-3-(4-chlorophenyl)cyclobutyl]-2,3-dihydro-1,3,4-oxadiazol-2-one (40 mg, 0.13 mmol) in a manner analogous to Example 58, Step 3 as a white solid (27 mg, 45% yield). LCMS [M+H$^+$]: 449.1. $^1$H NMR (300 MHz, DMSO-d$_6$) δ 8.75 (s, 1H), 8.05 (s, 1H), 7.40-7.34 (m, 4H), 5.25 (s, 2H), 4.68-4.63 (m, 1H), 3.67-3.60 (m, 1H), 2.85 (s, 3H), 2.81-2.74 (m, 2H), 2.55-2.46 (m, 2H).

Example Compound 94: Preparation of trans-3-[3-(4-chlorophenyl)-3-fluoro-cyclobutyl]-5-[(4-oxopyrido[2,3-d]pyrimidin-3-yl)methyl]-1,3,4-oxadiazol-2-one The overall Example Compound 94 reaction scheme is as follows:

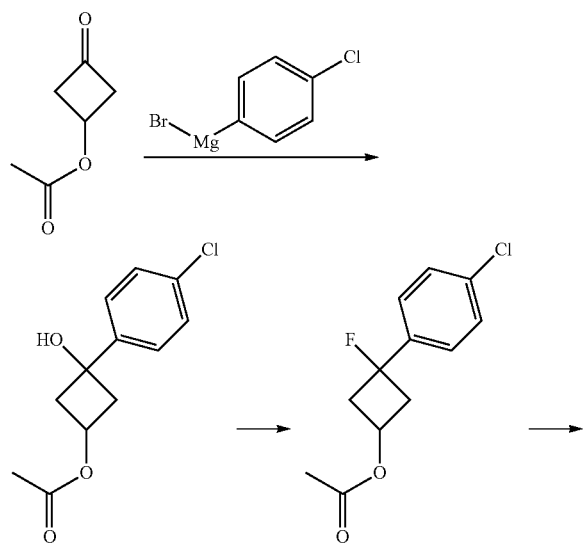

190

-continued

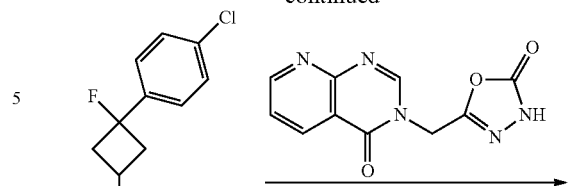

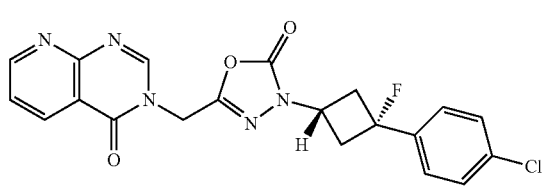

Step 1: Preparation of 3-(4-chlorophenyl)-3-hydroxycyclobutyl acetate

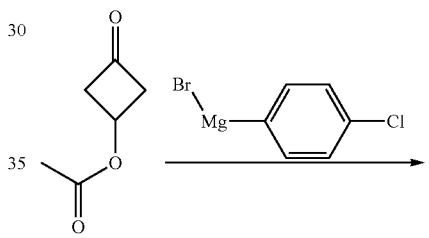

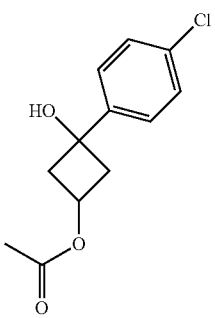

Bromo(4-chlorophenyl)magnesium (12 mL, 55.61 mmol) was added dropwise to a solution of 3-oxocyclobutyl acetate (1.28 g, 9.99 mmol) in tetrahydrofuran (60 mL) at −78° C. under nitrogen. The resulting solution was stirred for 2 h at −78° C. The reaction was then quenched with saturated aqueous NH$_4$Cl, extracted with ethyl acetate, washed with brine, dried over anhydrous sodium sulfate, and concentrated under vacuum. The residue was adsorbed onto silica gel and purified by flash column chromatography eluted with ethyl acetate/petroleum ether (1:5) to afford the title compound 9.60 g, 25%) as colorless oil.

Step 2: Preparation of 3-(4-chlorophenyl)-3-fluorocyclobutyl acetate

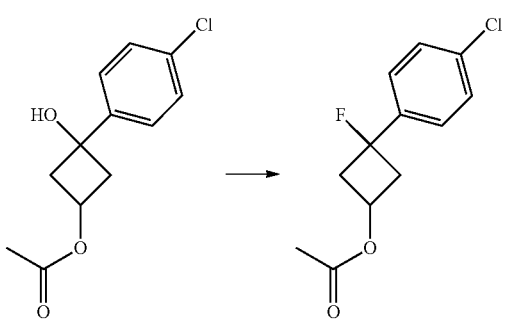 [SMILES: CC(=O)OC1CC(O)(c2ccc(Cl)cc2)C1 ; CC(=O)OC1CC(F)(c2ccc(Cl)cc2)C1]

DAST (770 mg, 4.77 mmol) was added dropwise to a solution of 3-(4-chlorophenyl)-3-hydroxycyclobutyl acetate (900 mg, 3.73 mmol) in DCM (30 mL). The resulting solution was stirred for 2 h at −10° C. The reaction was then quenched with saturated aqueous sodium bicarbonate, extracted with dichloromethane, dried over anhydrous sodium sulfate, and concentrated under vacuum. The residue was adsorbed onto silica gel and purified by flash column chromatography eluted with ethyl acetate/petroleum ether (1:10) to afford the title compound (600 mg, 66%) as colorless oil.

Step 3: Preparation of 3-(4-chlorophenyl)-3-fluorocyclobutan-1-ol

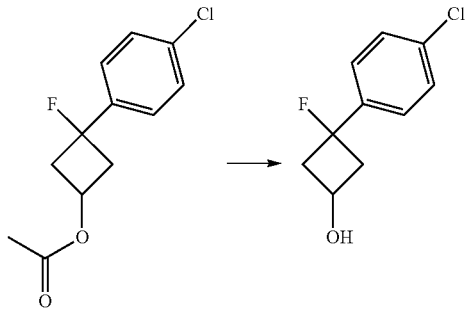 [SMILES: CC(=O)OC1CC(F)(c2ccc(Cl)cc2)C1 ; OC1CC(F)(c2ccc(Cl)cc2)C1]

A mixture of 3-(4-chlorophenyl)-3-fluorocyclobutyl acetate (600 mg, 2.47 mmol), methanol (10 mL), and sodium methylate (5.4 M) in MeOH (0.5 mL, 2.7 mmol) was stirred for 1 h at 0° C. The reaction was then quenched with 30 mg of AcOH, diluted with water, extracted with ethyl acetate, dried over anhydrous sodium sulfate, and concentrated under vacuum. This resulted in 400 mg (81%) of the title compound as a yellow solid.

Step 4 Preparation of trans-3-[3-(4-chlorophenyl)-3-fluoro-cyclobutyl]-5-[(4-oxopyrido[2,3-d]pyrimidin-3-yl)methyl]-1,3,4-oxadiazol-2-one

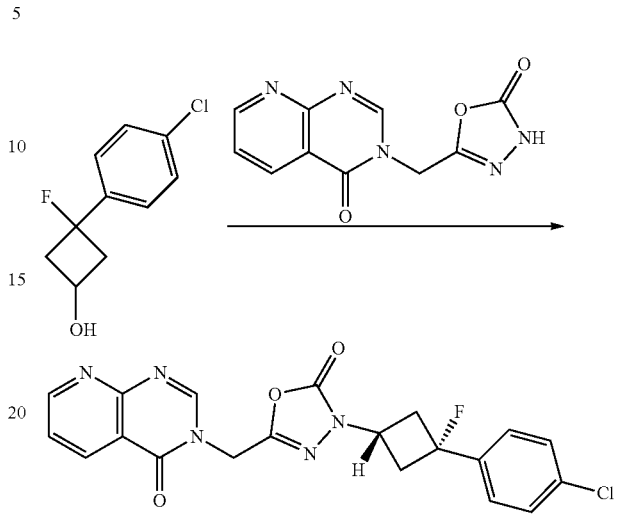

DIAD (884 mg, 4.37 mmol) was added dropwise to a solution of 3-(4-chlorophenyl)-3-fluorocyclobutan-1-ol (350 mg, 1.74 mmol), 5-(4-oxo-3H,4H-pyrido[2,3-d]pyrimidin-3-ylmethyl)-2,3-dihydro-1,3,4-oxadiazol-2-one (429 mg, 1.75 mmol), and PPh$_3$ (1.40 g, 5.24 mmol) in N,N-dimethylformamide (10 mL) at 0° C. The resulting solution was stirred for 12 h at 25° C. The resulting mixture was concentrated under vacuum. The crude product was further purified by reversed phase HPLC to afford the title compound (29 mg, 4%) as a white solid. LCMS [M+H$^+$] 428. $^1$H NMR (300 MHz, DMSO-d$_6$) δ 9.02-9.01 (m, 1H), 8.69 (s, 1H), 8.61-8.57 (m, 1H), 7.65-7.57 (m, 3H), 7.52-7.51 (m, 2H), 5.29 (s, 2H), 4.41-4.29 m, 1H), 3.08-2.94 (m, 4H).

Example Compound 98: trans-3-[3-(4-chlorophenyl) cyclobutyl]-5-[(4-oxopyrido[2,3-d]pyrimidin-3-yl) methyl]-1,3,4-oxadiazol-2-one The overall Example Compound 98 reaction scheme is as follows:

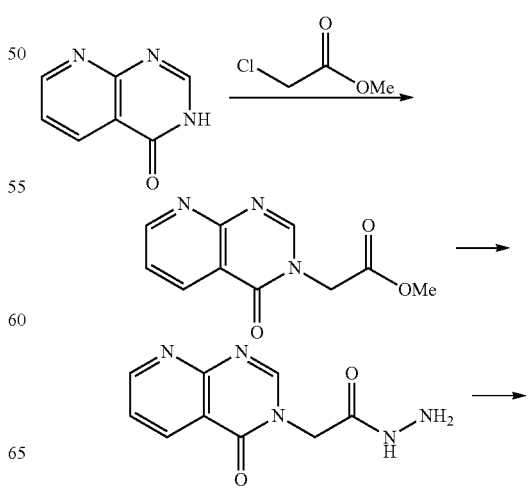

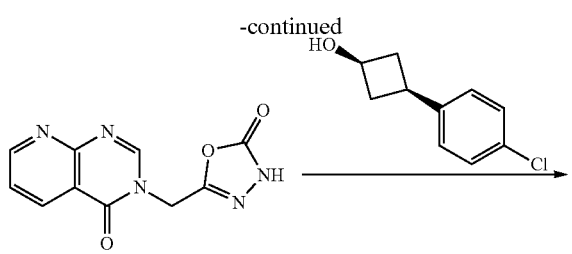

Step 1: Preparation of methyl 2-(4-oxopyrido[2,3-d]pyrimidin-3(4H)-yl)acetate

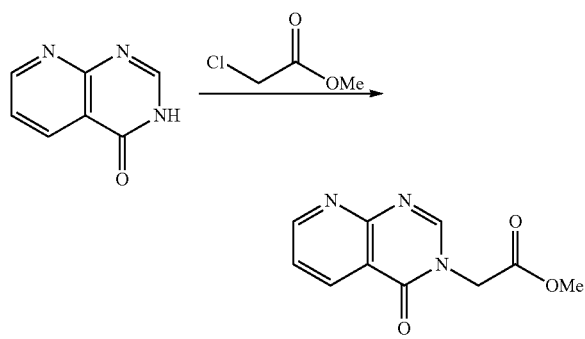

Methyl 2-chloroacetate (1.0 mL, 12.0 mmol) was added dropwise to a mixture of pyrido[2,3-d]pyrimidin-4(3H)-one (1.50 g, 9.70 mmol), $K_2CO_3$ (2.70 g, 19.0 mmol) and TBAI (180 mg, 0.48 mmol) in DMF (39 mL). The reaction was stirred at room temperature for 4 h. The crude mixture was diluted with iPrOAc and filtered through diatomaceous earth. The filtrated was concentrated on the rotavap. The crude mixture was adsorbed on silica gel and purified by silica gel column with 30-70% (3:1 iPrOAc/MeOH)/Heptane to afford the title compound (1.89 g, 89% Yield) as a white solid.

Step 2: Preparation of 2-(4-oxopyrido[2,3-d]pyrimidin-3(4H)-yl)acetohydrazide

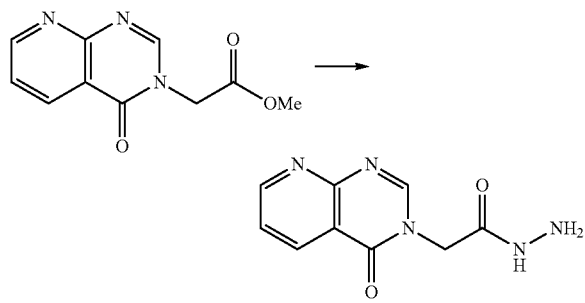

A mixture of methyl 2-(4-oxopyrido[2,3-d]pyrimidin-3-yl)acetate (2.40 g, 11.0 mmol) and hydrazine monohydrate (5.3 mL, 110 mmol) in MeOH (55 mL) was stirred at room temperature for 2 days. The reaction mixture was cooled in an ice bath and the white solid was recovered by filtration. The solid was washed with cold MeOH and dried under vacuum to afford the title compound (1.13 g, 47% Yield) as a white solid.

Step 3: Preparation of 5-((4-oxopyrido[2,3-d]pyrimidin-3(4H)-yl)methyl)-1,3,4-oxadiazol-2(3H)-one

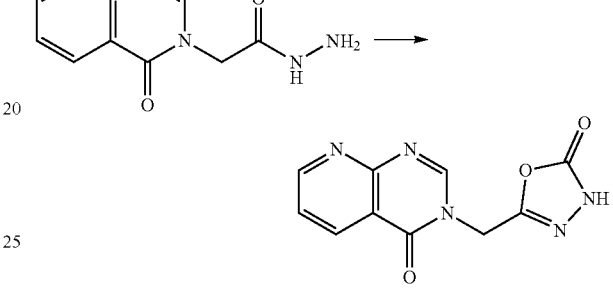

A mixture of 2-(4-oxopyrido[2,3-d]pyrimidin-3-yl)acetohydrazide (1.13 g, 5.16 mmol) and 1,1'-carbonyldiimidazole (1.29 g, 7.73 mmol) in DMF (13 mL) was stirred at room temperature overnight. The mixture was concentrated on the rotavap. The white solid was triturated with MeOH and recovered by filtration to afford the title compound (818 mg, 65% Yield) as a white solid.

Step 4: Preparation of 3-((1r,3r)-3-(4-chlorophenyl)cyclobutyl)-5-((4-oxopyrido[2,3-d]pyrimidin-3(4H)-yl)methyl)-1,3,4-oxadiazol-2(3H)-one

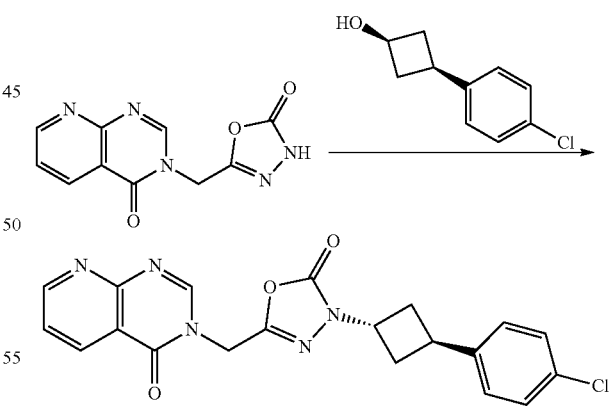

DIAD (129 µL, 0.65 mmol) was added to a solution of 5-[(4-oxopyrido[2,3-d]pyrimidin-3-yl)methyl]-3H-1,3,4-oxadiazol-2-one (80.0 mg, 0.33 mmol), 3-(4-chlorophenyl)cyclobutanol (119 mg, 0.65 mmol) and triphenylphosphine (171 mg, 0.65 mmol) in THF (40 mL) at 0° C. The mixture was stirred at room temperature overnight. The crude mixture was adsorbed on silica gel and purified by silica gel column with 30-80% (3:1 iPrOAc/MeOH)/heptane. The compound was further purified by chiral SFC using a Cellulose-3 column with 35% of 0.1% ammonium hydroxide in methanol in $CO_2$. This resulted in the titled compound (68.7 mg, 51% Yield) as a white solid. LCMS [M+H$^+$]: 410.1. 1H NMR (400 MHz, DMSO-d6) δ 9.01 (dd, J=4.7, 2.0 Hz, 1H), 8.68 (s, 1H), 8.59 (dd, J=8.0, 2.0 Hz, 1H), 7.63 (dd, J=7.9, 4.6 Hz, 1H), 7.41-7.31 (m, 4H), 5.28 (s, 2H), 4.71-4.58 (m, 1H), 3.63 (dddd, J=10.0, 8.7, 5.9, 4.8 Hz, 1H), 2.84-2.71 (m, 2H), 2.58-2.43 (m, 2H).

Example Compound 100: 5-[(7-methyl-6-oxo-purin-1-yl)methyl]-3-[(1R,3R)-3-(4-chlorophenyl)cyclopentyl]-1,3,4-oxadiazol-2-one The overall Example Compound 100 reaction scheme is as follows:

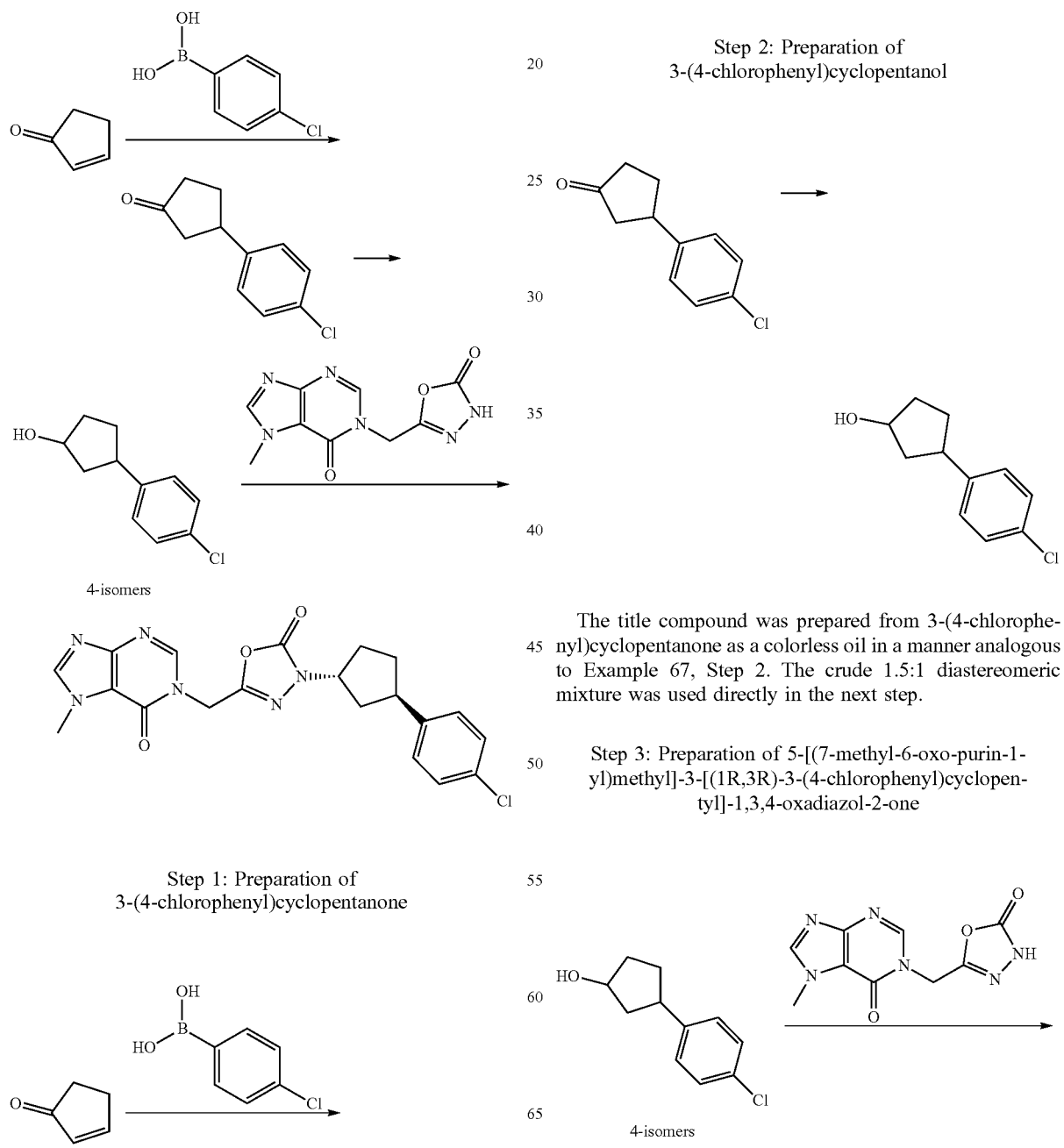

Step 1: Preparation of 3-(4-chlorophenyl)cyclopentanone

The title compound was prepared from 4-chlorophenylboronic acid and 2-cyclopenten-1-one as a colorless oil in a manner analogous to Examples 91, Step 1. $^1$H NMR (500 MHz, CDCl$_3$) δ 7.30-7.20 (m, 3H), 7.15-7.11 (m, 1H), 3.45-3.34 (m, 1H), 2.67 (dd, J=18.1, 7.6 Hz, 1H), 2.51-2.41 (m, 2H), 2.35-2.26 (m, 2H), 2.04-1.92 (m, 1H).

Step 2: Preparation of 3-(4-chlorophenyl)cyclopentanol

The title compound was prepared from 3-(4-chlorophenyl)cyclopentanone as a colorless oil in a manner analogous to Example 67, Step 2. The crude 1.5:1 diastereomeric mixture was used directly in the next step.

Step 3: Preparation of 5-[(7-methyl-6-oxo-purin-1-yl)methyl]-3-[(1R,3R)-3-(4-chlorophenyl)cyclopentyl]-1,3,4-oxadiazol-2-one -continued

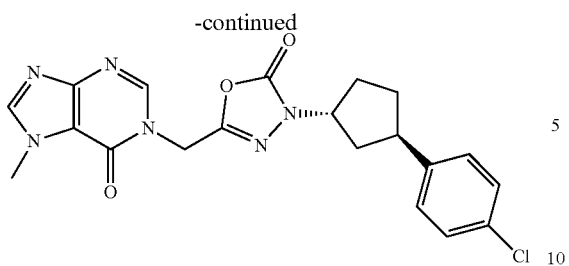

The title compound was prepared from a 1.5:1 diastereomeric mixture of 3-(4-chlorophenyl)cyclopentanol and 5-[(7-methyl-6-oxo-purin-1-yl)methyl]-3H-1,3,4-oxadiazol-2-one (prepared according to Example Compound 1, Step 5) in a manner analogous to Example 71, Step 4. The resulting 4 isomers were separated by SFC with the following conditions: Column: AD 10×250 mm, 5 um Isocratic 55% MeOH, 10 mL/min 100 Bar, Column temperature: 35° C., Run time: 15 min. The title compound, 5-[(7-methyl-6-oxo-purin-1-yl)methyl]-3-[(1R,3R)-3-(4-chlorophenyl)cyclopentyl]-1,3,4-oxadiazol-2-one, was obtained as a white solid as the fourth eluting compound (Rt=12.7 min.); LCMS [M+H$^+$] 427.0; $^1$H NMR (500 MHz, DMSO-d6) δ 8.35 (s, 1H), 8.22 (s, 1H), 7.34 (d, J=8.1 Hz, 2H), 7.27 (d, J=8.1 Hz, 2H), 5.24 (s, 2H), 4.67-4.57 (m, 1H), 3.97 (s, 3H), 3.30-3.18 (m, 1H), 2.29-2.08 (m, 3H), 2.07-1.96 (m, 1H), 1.96-1.83 (m, 1H), 1.69-1.51 (m, 1H).

Example Compound 103: Preparation of 3-[3-[(trans)-4-(difluoromethoxy)phenyl]cyclobutyl]-5-[(7-methyl-6-oxo-purin-1-yl)methyl]-1,3,4-oxadiazol-2-one The overall Example Compound 103 reaction scheme is as follows:

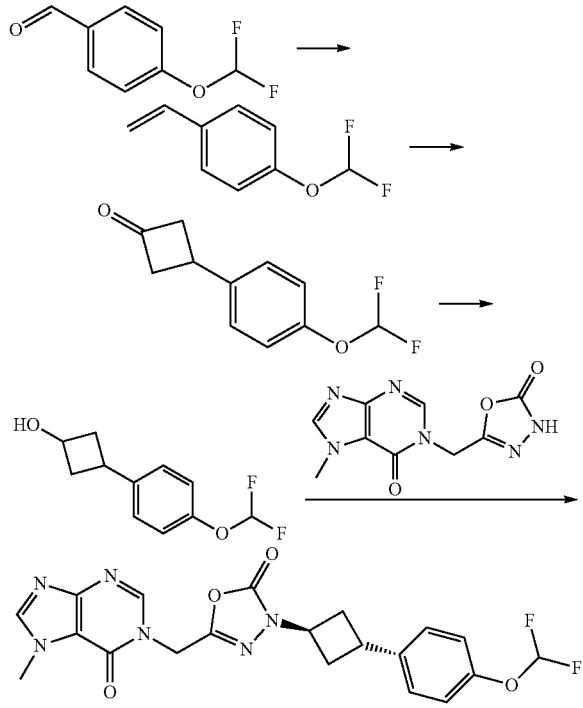

Step 1: Preparation of 1-(difluoromethoxy)-4-vinyl-benzene

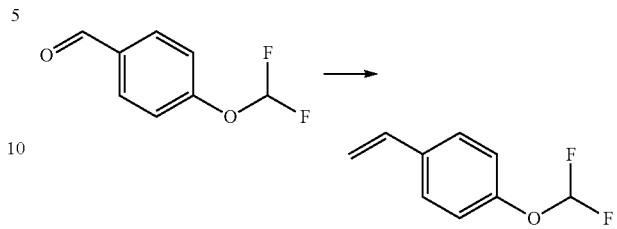

Methyltriphenylphosphonium iodide (9.16 g, 22.7 mmol) was added slowly to a suspension of potassium tertbutoxide (2.54 g, 22.7 mmol) in tetrahydrofuran (35 mL) at 0° C. After 30 min., a solution of 4-(difluoromethoxy)benzaldehyde (2.3 mL, 17.4 mmol) in tetrahydrofuran (9 mL) was added. The resulting mixture was allowed to stir at 20° C. for 1 h 30. The resulting solution was diluted with diethyl ether, washed with water and brine. The organic layer was dried over anhydrous MgSO4, filtered and concentrated under vacuum. The residue was purified by a silica gel column eluting with hexanes to afford 1-(difluoromethoxy)-4-vinyl-benzene (2.72 g, 92% yield) as yellow oil. $^1$H NMR (500 MHz, CDCl$_3$) δ 7.42-7.37 (m, 2H), 7.10-7.05 (m, 2H), 6.69 (dd, J=17.6, 10.9 Hz, 1H), 6.50 (t, J=74.0 Hz, 1H), 5.70 (dd, J=17.6, 0.7 Hz, 1H), 5.28-5.23 (m, 1H).

Step 2: Preparation of 3-[4-(difluoromethoxy)phenyl]cyclobutanone

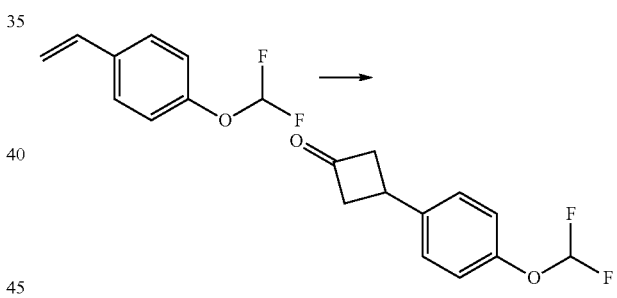

To a flame dried RBF under nitrogen containing a solution of N,N-dimethylacetamide (2.22 mL, 23.9 mmol) in 1,2-dichloroethane (53 mL) at −15° C. was added trifluoromethanesulfonic anhydride (4.8 mL, 28.7 mmol). A solution of 1-(difluoromethoxy)-4-vinyl-benzene (2.71 g, 15.9 mmol) and 2,4,6-trimethylpyridine (3.8 mL, 28.7 mmol) in 1,2-dichloroethane (3 mL) was then added dropwise. The resulting mixture was refluxed overnight. Water (15 mL) was added and the resulting mixture was refluxed for an additional 4 hours. The reaction mixture was cooled to 20° C. and it was poured in an aqueous saturated solution of NaHCO$_3$ and DCM. The organic layer was washed with water and brine, dried over anhydrous MgSO$_4$ and concentrated under vacuum. The residue was purified by a silica gel column eluting with ethyl acetate and hexanes (0 to 30% gradient) to afford two fractions. The first fraction afforded 3-[4-(difluoromethoxy)phenyl]cyclobutanone (752 mg, 22% yield) as a yellow oil. The second fraction was contaminated with residual 2,4,6-trimethylpyridine. It was then dissolved in ethyl acetate, washed with 1N hydrochloric acid, water, brine, dried over anhydrous MgSO$_4$ and concentrated under vacuum to afford a second crop of the title compound (700 mg, 21% yield) as a yellow oil. $^1$H NMR (500 MHz, CDCl$_3$) δ 7.32-7.27 (m, 2H), 7.14-7.09 (m, 2H), 6.49 (t, J=73.9 Hz, 1H), 3.72-3.64 (m, 1H), 3.56-3.47 (m, 2H), 3.27-3.17 (m, 2H).

Step 3: Preparation of 3-[4-(difluoromethoxy)phenyl]cyclobutanol

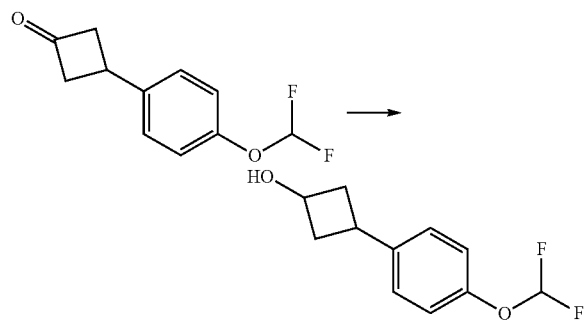

To a 0° C. solution of 3-[4-(difluoromethoxy)phenyl] cyclobutanone (750 mg, 3.53 mmol) in methanol (12 mL) was added sodium borohydride (134 mg, 3.53 mmol). The reaction mixture was stirred at 20° C. for 40 min. Methanol was evaporated and the residue was diluted with ethyl acetate, washed with water and brine, dried over anhydrous MgSO$_4$ and concentrated under vacuum. The product was purified by a silica gel column eluting with ethyl acetate and hexanes (0 to 40% gradient) to afford the title compound (575 mg, 76% yield) as a yellowish oil. $^1$H NMR (500 MHz, CDCl$_3$) δ 7.24-7.18 (m, 2H), 7.07-7.03 (m, 2H), 6.48 (t, J=74.2 Hz, 1H), 4.33-4.24 (m, 1H), 2.99-2.90 (m, 1H), 2.81-2.72 (m, 2H), 2.03-1.95 (m, 2H), 1.77 (d, J=6.3 Hz, 1H); A 12:1 cis:trans ratio is observed.

Step 4: Preparation of 3-[3-[(trans)-4-(difluoromethoxy)phenyl]cyclobutyl]-5-[(7-methyl-6-oxo-purin-1-yl)methyl]-1,3,4-oxadiazol-2-one

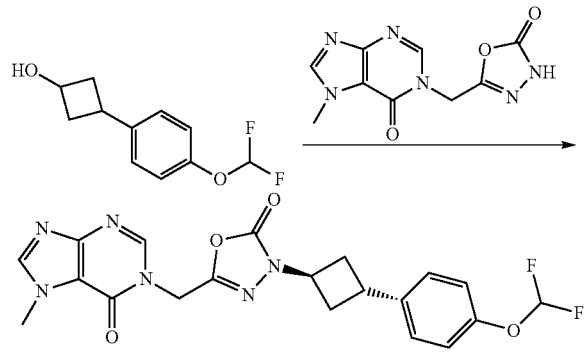

The title compound was prepared from 3-[4-(difluoromethoxy)phenyl]cyclobutanol (12:1 cis:trans ratio) and 5-[(7-methyl-6-oxo-purin-1-yl)methyl]-3H-1,3,4-oxadiazol-2-one (prepared according to Example Compound 1, Step 5) in a manner analogous to Example 71, Step 4. The obtained isomeric mixture was purified by chiral HPLC using Chiralpak IA, 5 um, 20×250 mm, 12 mL/min, 15:15: 70 methanol: dichloromethane: hexane, 5-40 mg/injection to afford 3-[3-[(trans)-4-(difluoromethoxy)phenyl]cyclobutyl]-5-[(7-methyl-6-oxo-purin-1-yl)methyl]-1,3,4-oxadiazol-2-one as a white solid. LCMS [M+H$^+$] 445.0. $^1$H NMR (500 MHz, DMSO-d6) δ 8.38 (s, 1H), 8.23 (d, J=0.4 Hz, 1H), 7.41-7.36 (m, 2H), 7. 19 (t, J=74.3 Hz, 1H), 7.16-7.10 (m, 2H), 5.27 (s, 2H), 4.68-4.59 (m, 1H), 3.97 (s, 3H), 3.68-3.59 (m, 1H), 2.82-2.73 (m, 2H), 2.54-2.45 (m, 2H).

Example Compound 105: trans-3-[3-(4-chlorophenyl)-3-fluoro-cyclobutyl]-5-[(7-methyl-6-oxo-purin-1-yl)methyl]-1,3,4-oxadiazol-2-one The overall Example Compound 105 reaction scheme is as follows:

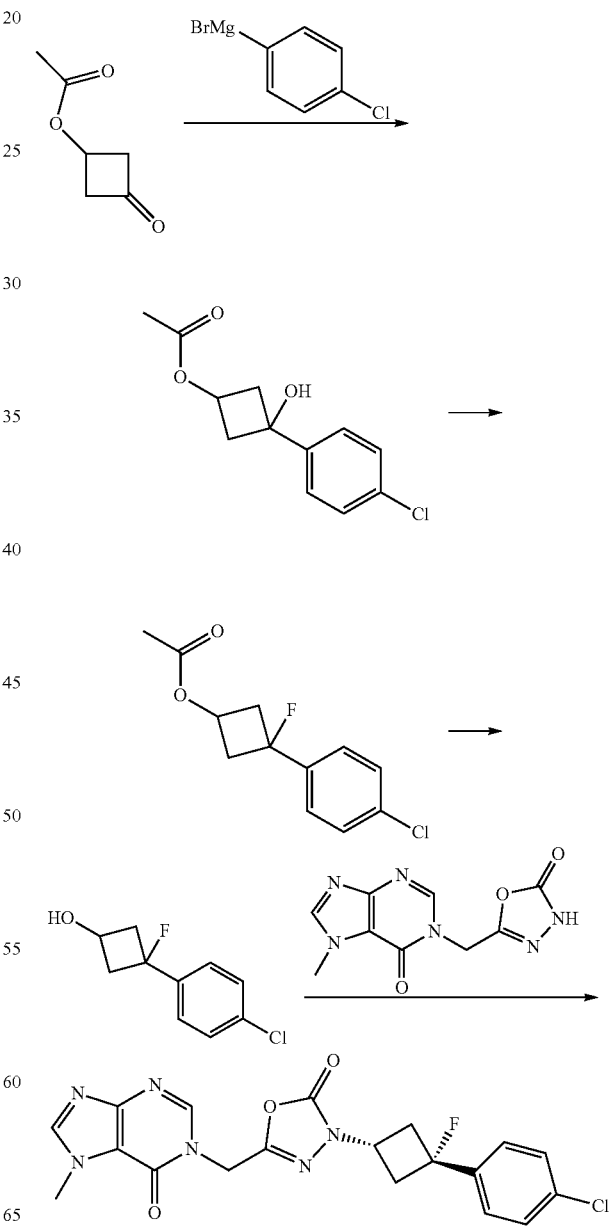

Step 1: Preparation of 3-(4-chlorophenyl)-3-hydroxycyclobutyl acetate

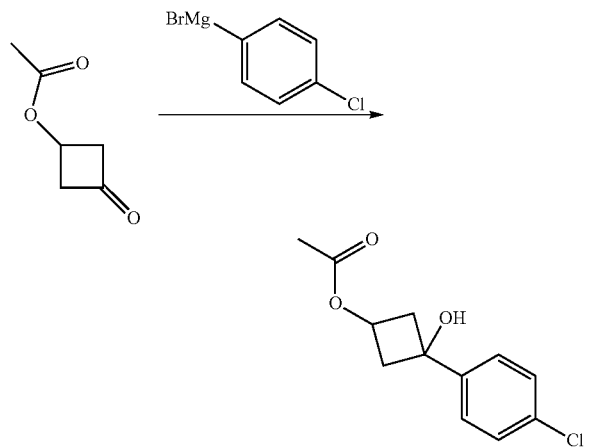

Bromo-(4-chlorophenyl)magnesium (1M in 2-Me-THF) (13.7 mL, 13.4 mmol) was added dropwise to a solution of (3-oxocyclobutyl) acetate (1.72 g, 13.4 mmol) in THF (17 mL) at −78° C. under $N_2$. The reaction was stirred at −78° C. for 2 h. The reaction was quenched with saturated $NH_4Cl$, partitioned in water/iPrOAc and extracted with iPrOAc (3×). The combined organic extracts were washed with water and brine and they were dried over $MgSO_4$, filtered and concentrated. The crude mixture was adsorbed on silica and purified by silica gel column with 0-50% iPrOAc/heptane to afford the title compound (1.19 g, 37% Yield) as a clear oil.

Step 2: Preparation of 3-(4-chlorophenyl)-3-fluorocyclobutyl acetate

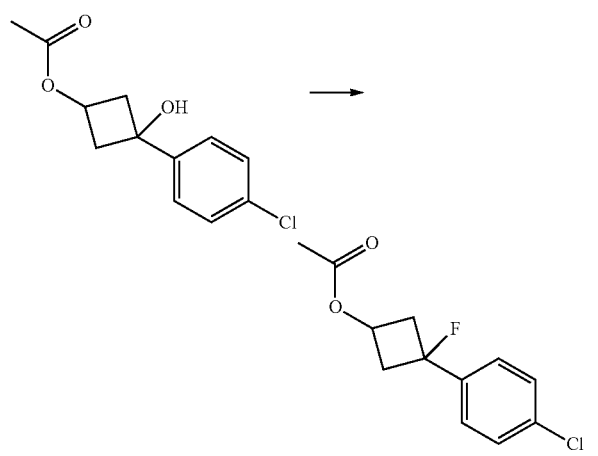

Deoxo-Fluor (1.10 mL, 5.44 mmol) was added to a solution of [3-(4-chlorophenyl)-3-hydroxy-cyclobutyl] acetate (1.19 g, 4.94 mmol) in DCM (49 mL) at 0° C. under $N_2$. The reaction was stirred at room temperature for 4 h. The reaction mixture was partitioned in saturate $NaHCO_3$/DCM and extracted with DCM (3×). The combined organic extracts were washed with brine, dried over $MgSO_4$, filtered and concentrated. The crude mixture was adsorbed on silica gel and purified by silica gel column with 0-40% iPrOAc/ Heptane to afford the title compound (869 mg, 73% Yield) as a clear oil.

Step 3: Preparation of 3-(4-chlorophenyl)-3-fluorocyclobutanol

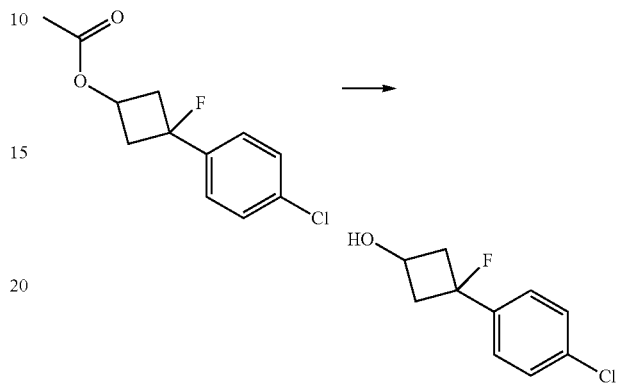

Sodium methoxide (0.5M in MeOH) (1.0 mL, 0.72 mmol) was added to a solution of [3-(4-chlorophenyl)-3-fluorocyclobutyl] acetate (869 mg, 3.58 mmol) in MeOH (14 mL) at 0° C. The mixture was stirred at 0° C. for 1 h. The reaction was quenched with AcOH (41 µL, 0.72 mmol) at 0° C. and concentrated on the rotavap. The residue was poured in water/iPrOAc and extracted with iPrOAc (3×). The combined organic extracts were washed with saturated $NaHCO_3$ and brine and they were dried with $MgSO_4$, filtered and concentrated. The crude mixture was adsorbed on silica gel and purified by silica gel column with 0-60% iPrOAc/ Heptane to afford the tile compound (664 mg, 92% Yield) as an orange-ish solid. The compound was used right away in the next step as it tends to be unstable upon standing.

Step 4: Preparation of 3-((1s,3s)-3-(4-chlorophenyl)-3-fluorocyclobutyl)-5-((7-methyl-6-oxo-6,7-dihydro-1H-purin-1-yl)methyl)-1,3,4-oxadiazol-2(3H)-one

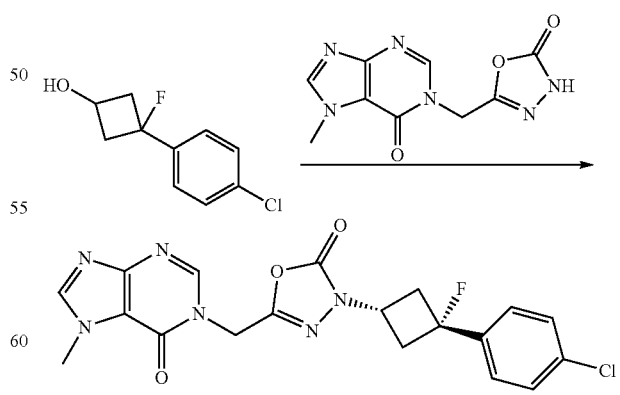

DIAD (659 µL, 3.32 mmol) was added to a solution of 5-[(7-methyl-6-oxo-purin-1-yl)methyl]-3H-1,3,4-oxadiazol-2-one (550 mg, 2.22 mmol), 3-(4-chlorophenyl)-3-fluorocyclobutanol (667 mg, 3.32 mmol) and triphenylphosphine (872 mg, 3.32 mmol) in THF (15 mL) at 0° C. The mixture was stirred at room temperature overnight. The crude mixture was adsorbed on silica gel and purified by silica gel column with 30-80% (3:1 iPrOAc/MeOH)/heptane. The compound was further purified by chiral SFC using a Cellulose-3 column with 30% of 0.1% ammonium hydroxide in methanol in $CO_2$. This resulted in the titled compound (266 mg, 28% Yield) as a white solid. LCMS [M+H$^+$]: 431.1. 1H NMR (400 MHz, DMSO-d6) δ 8.37 (s, 1H), 8.22 (s, 1H), 7.62-7.54 (m, 2H), 7.56-7.46 (m, 2H), 5.27 (s, 2H), 4.34 (pd, J=8.2, 3.7 Hz, 1H), 3.98 (s, 3H), 3.12-2.93 (m, 4H).

Example 2: $IC_{50}$ Determinations of Exemplified Compounds

The $IC_{50}$ (effective concentration) of compounds on the human and rat TRPA1 channels were determined using a FLIPR Tetra instrument. CHO cells expressing TRPA1 were plated into 384-well plates, incubated overnight at 37° C., and loaded with BD calcium indicator dye for 1 hr at 37° C. followed by 15 minutes at room temperature. The assay buffer was Hank's Balanced Salt Solution (HBSS) containing 20 mM HEPES (pH readjusted to 7.4) along with 0.02% BSA.

Following dye load and plate cool down, compounds were added to the cells using FLIPR Tetra. Plates were then incubated with compounds for 20 minutes at room temperature prior to adding agonist. Following this incubation, about an $EC_{50}$ concentration of cinnamaldehyde (75 uM for human TRPA1 and 45 uM for rat TRPA1) was added to active the channels and block of cinnamaldehyde induced calcium influx was measured.

The $IC_{50}$ results were fit with a standard Hill function, keeping the Hill coefficient (n) fixed to 1.5. Fixing the Hill coefficient will generally reduce variability of the $IC_{50}$ determination. The $IC_{50}$ results were individually examined to make sure the MIN and MAX points were set correctly prior to validation of the results.

The $IC_{50}$ (hTRPA1 $IC_{50}$ (micromolar)) results for compounds of the present disclosure are shown in Table 1 below where "hTRPA1" refers to hTRPA1 CHO Ca2+ MAX EVO ($IC_{50}$).

TABLE 1

| Ex. | Structure | Name | hTRPA1 |
|---|---|---|---|
| 1 | 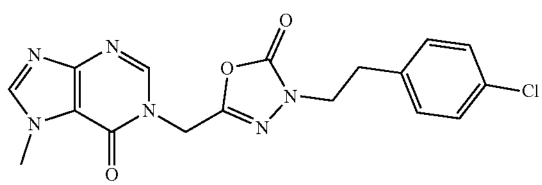 [SMILES: Cn1cnc2ncn(Cc3nn(CCc4ccc(Cl)cc4)c(=O)o3)c(=O)c21] | 3-[2-(4-chlorophenyl)ethyl]-5-[(7-methyl-6-oxo-purin-1-yl)methyl]-1,3,4-oxadiazol-2-one | 0.095 |
| 2 | 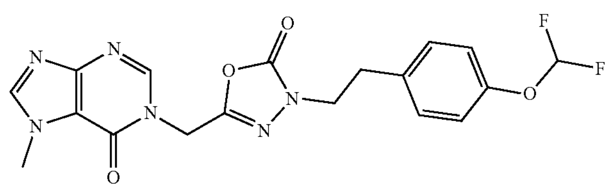 [SMILES: Cn1cnc2ncn(Cc3nn(CCc4ccc(OC(F)F)cc4)c(=O)o3)c(=O)c21] | 3-(4-(difluoromethoxy)phenethyl)-5-((7-methyl-6-oxo-6H-purin-1(7H)-yl)methyl)-1,3,4-oxadiazol-2(3H)-one | 0.211 |
| 3 | 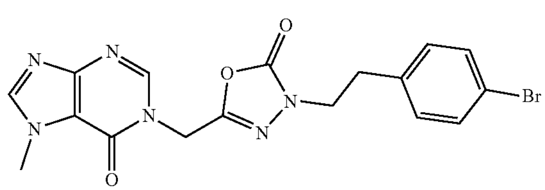 [SMILES: Cn1cnc2ncn(Cc3nn(CCc4ccc(Br)cc4)c(=O)o3)c(=O)c21] | 3-(4-bromophenethyl)-5-((7-methyl-6-oxo-6H-purin-1(7H)-yl)methyl)-1,3,4-oxadiazol-2(3H)-one | 0.044 |
| 4 | 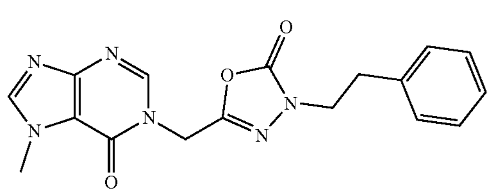 [SMILES: Cn1cnc2ncn(Cc3nn(CCc4ccccc4)c(=O)o3)c(=O)c21] | 5-((7-methyl-6-oxo-6H-purin-1(7H)-yl)methyl)-3-phenethyl-1,3,4-oxadiazol-2(3H)-one | 1.055 |
| 5 | 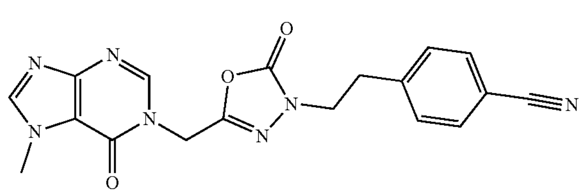 [SMILES: Cn1cnc2ncn(Cc3nn(CCc4ccc(C#N)cc4)c(=O)o3)c(=O)c21] | 4-(2-(5-((7-methyl-6-oxo-6H-purin-1(7H)-yl)methyl)-2-oxo-1,3,4-oxadiazol-3(2H)-yl)ethyl)benzonitrile | 1.172 |

TABLE 1-continued

| Ex. | Structure | Name | hTRPA1 |
|---|---|---|---|
| 6 | 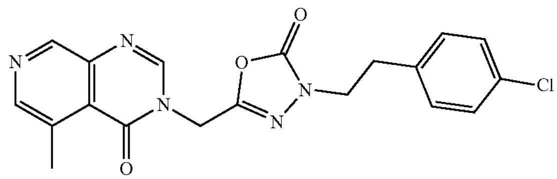 [SMILES: Cc1cncc2ncn(Cc3nn(CCc4ccc(Cl)cc4)c(=O)o3)c(=O)c12] | 3-(4-chlorophenethyl)-5-((5-methyl-4-oxopyrido[3,4-d]pyrimidin-3(4H)-yl)methyl)-1,3,4-oxadiazol-2(3H)-one | 0.013 |
| 7 | 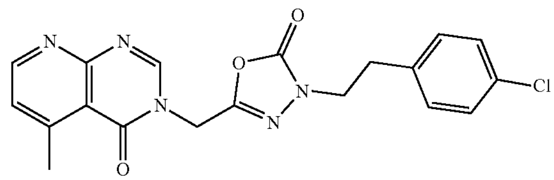 [SMILES: Cc1ccnc2ncn(Cc3nn(CCc4ccc(Cl)cc4)c(=O)o3)c(=O)c12] | 3-[2-(4-chlorophenyl)ethyl]-5-[(5-methyl-4-oxo-pyrido[2,3-d]pyrimidin-3-yl)methyl]-1,3,4-oxadiazol-2-one | 0.012 |
| 8 | 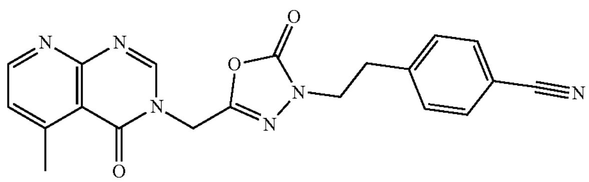 [SMILES: Cc1ccnc2ncn(Cc3nn(CCc4ccc(C#N)cc4)c(=O)o3)c(=O)c12] | 4-[2-[5-[(5-methyl-4-oxo-pyrido[2,3-d]pyrimidin-3-yl)methyl]-2-oxo-1,3,4-oxadiazol-3-yl]ethyl]benzonitrile | 0.166 |
| 9 | 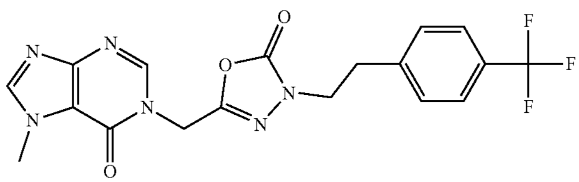 [SMILES: Cn1cnc2ncn(Cc3nn(CCc4ccc(C(F)(F)F)cc4)c(=O)o3)c(=O)c21] | 5-((7-methyl-6-oxo-6H-purin-1(7H)-yl)methyl)-3-(4-(trifluoromethyl)phenethyl)-1,3,4-oxadiazol-2(3H)-one | 0.582 |
| 10 | 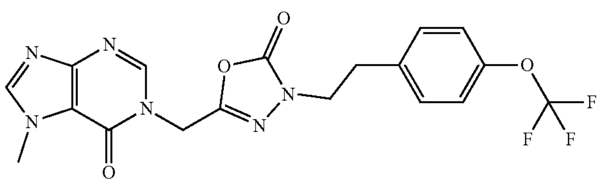 [SMILES: Cn1cnc2ncn(Cc3nn(CCc4ccc(OC(F)(F)F)cc4)c(=O)o3)c(=O)c21] | 5-((7-methyl-6-oxo-6H-purin-1(7H)-yl)methyl)-3-(4-(trifluoromethoxy)phenethyl)-1,3,4-oxadiazol-2(3H)-one | 0.086 |
| 11 | 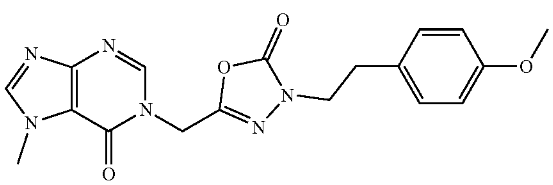 [SMILES: COc1ccc(CCn2nc(Cn3cnc4ncn(C)c4c3=O)oc2=O)cc1] | 3-(4-methoxyphenethyl)-5-((7-methyl-6-oxo-6H-purin-1(7H)-yl)methyl)-1,3,4-oxadiazol-2(3H)-one | 0.278 |
| 12 | 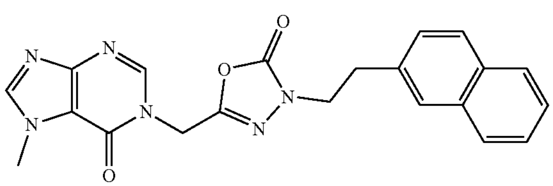 [SMILES: Cn1cnc2ncn(Cc3nn(CCc4ccc5ccccc5c4)c(=O)o3)c(=O)c21] | 5-((7-methyl-6-oxo-6H-purin-1(7H)-yl)methyl)-3-(2-(naphthalen-2-yl)ethyl)-1,3,4-oxadiazol-2(3H)-one | 0.041 |
| 13 | 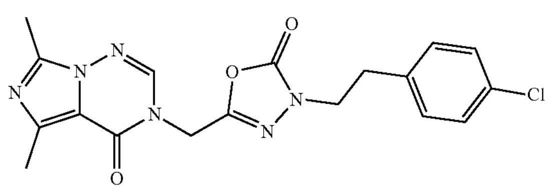 [SMILES: Cc1nc(C)n2ncn(Cc3nn(CCc4ccc(Cl)cc4)c(=O)o3)c(=O)c12] | 3-(4-chlorophenethyl)-5-((5,7-dimethyl-4-oxoimidazo[1,5-f][1,2,4]triazin-3(4H)-yl)methyl)-1,3,4-oxadiazol-2(3H)-one | 0.265 |

TABLE 1-continued

| Ex. | Structure | Name | hTRPA1 |
|---|---|---|---|
| 14 | 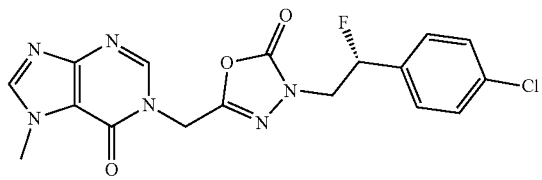 | (R)-3-(2-(4-chlorophenyl)-2-fluoroethyl)-5-((7-methyl-6-oxo-6H-purin-1(7H)-yl)methyl)-1,3,4-oxadiazol-2(3H)-one | 0.034 |
| 15 | 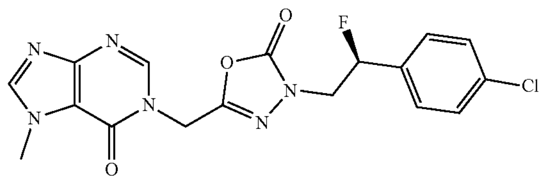 [SMILES: Cn1cnc2ncn(Cc3nn(C[C@@H](F)c4ccc(Cl)cc4)c(=O)o3)c(=O)c21] | (S)-3-(2-(4-chlorophenyl)-2-fluoroethyl)-5-((7-methyl-6-oxo-6H-purin-1(7H)-yl)methyl)-1,3,4-oxadiazol-2(3H)-one | 3.831 |
| 16 | 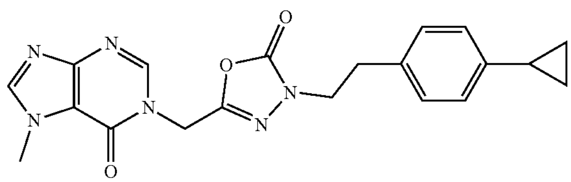 [SMILES: Cn1cnc2ncn(Cc3nn(CCc4ccc(C5CC5)cc4)c(=O)o3)c(=O)c21] | 3-(4-cyclopropylphenethyl)-5-((7-methyl-6-oxo-6H-purin-1(7H)-yl)methyl)-1,3,4-oxadiazol-2(3H)-one | 0.356 |
| 17 | 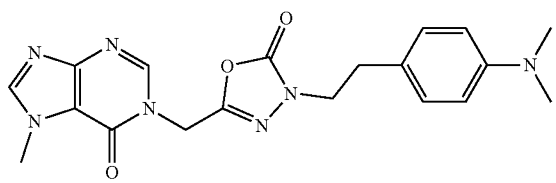 [SMILES: CN(C)c1ccc(CCn2nc(Cn3cnc4ncn(C)c4c3=O)oc2=O)cc1] | 3-(4-(dimethylamino)phenethyl)-5-((7-methyl-6-oxo-6H-purin-1(7H)-yl)methyl)-1,3,4-oxadiazol-2(3H)-one | 0.164 |
| 18 | 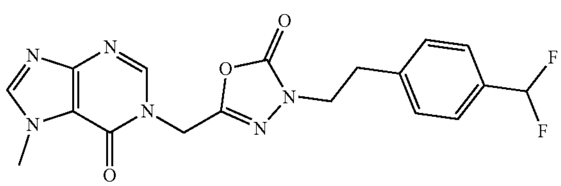 [SMILES: Cn1cnc2ncn(Cc3nn(CCc4ccc(C(F)F)cc4)c(=O)o3)c(=O)c21] | 3-(4-(difluoromethyl)phenethyl)-5-((7-methyl-6-oxo-6H-purin-1(7H)-yl)methyl)-1,3,4-oxadiazol-2(3H)-one | 0.509 |
| 19 | 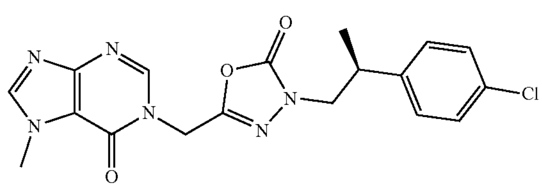 [SMILES: C[C@H](Cn1nc(Cn2cnc3ncn(C)c3c2=O)oc1=O)c1ccc(Cl)cc1] | (S)-3-(2-(4-chlorophenyl)propyl)-5-((7-methyl-6-oxo-6H-purin-1(7H)-yl)methyl)-1,3,4-oxadiazol-2(3H)-one | 0.034 |
| 20 | 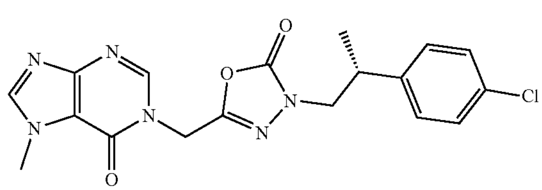 [SMILES: C[C@@H](Cn1nc(Cn2cnc3ncn(C)c3c2=O)oc1=O)c1ccc(Cl)cc1] | (R)-3-(2-(4-chlorophenyl)propyl)-5-((7-methyl-6-oxo-6H-purin-1(7H)-yl)methyl)-1,3,4-oxadiazol-2(3H)-one | 0.812 |
| 21 | 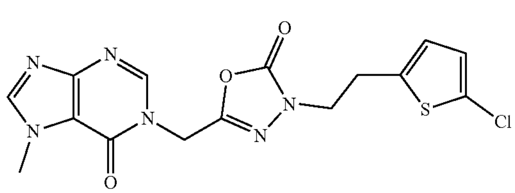 [SMILES: Cn1cnc2ncn(Cc3nn(CCc4ccc(Cl)s4)c(=O)o3)c(=O)c21] | 3-(2-(5-chlorothiophen-2-yl)ethyl)-5-((7-methyl-6-oxo-6H-purin-1(7H)-yl)methyl)-1,3,4-oxadiazol-2(3H)-one | 0.286 |

TABLE 1-continued

| Ex. | Structure | Name | hTRPA1 |
|---|---|---|---|
| 22 | 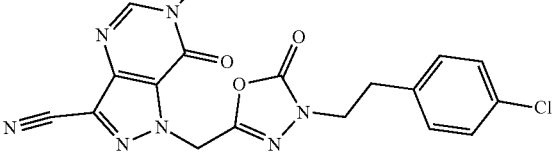 | 1-([4-[2-(4-chlorophenyl)ethyl]-5-oxo-4,5-dihydro-1,3,4-oxadiazol-2-yl]methyl)-6-methyl-7-oxo-1H,6H,7H-pyrazolo[4,3-d]pyrimidine-3-carbonitrile | 0.014 |
| 23 | 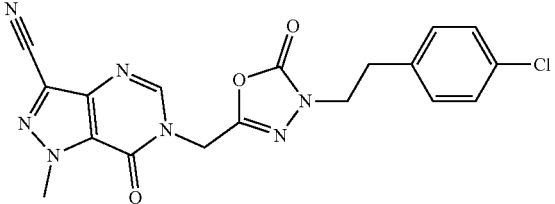 | 6-([4-[2-(4-chlorophenyl)ethyl]-5-oxo-4,5-dihydro-1,3,4-oxadiazol-2-yl]methyl)-1-methyl-7-oxo-1H,3aH,6H,7H,7aH-pyrazolo[4,3-d]pyrimidine-3-carbonitrile | 0.100 |
| 24 | 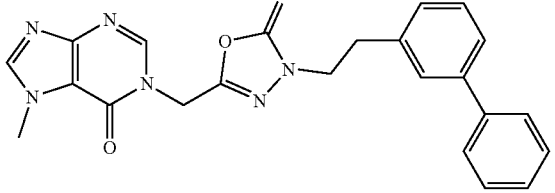 | 7-methyl-1-([5-oxo-4-[2-(3-phenylphenyl)ethyl]-4,5-dihydro-1,3,4-oxadiazol-2-yl]methyl)-6,7-dihydro-1H-purin-6-one | 0.338 |
| 25 | 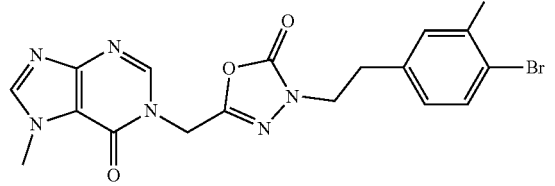 | 1-([4-[2-(4-bromo-3-chlorophenyl)ethyl]-5-oxo-4,5-dihydro-1,3,4-oxadiazol-2-yl]methyl)-7-methyl-6,7-dihydro-1H-purin-6-one | 0.132 |
| 26 | 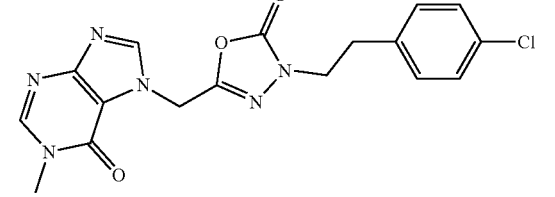 | 7-([4-[2-(4-chlorophenyl)ethyl]-5-oxo-4,5-dihydro-1,3,4-oxadiazol-2-yl]methyl)-1-methyl-6,7-dihydro-1H-purin-6-one | 0.737 |
| 27 | 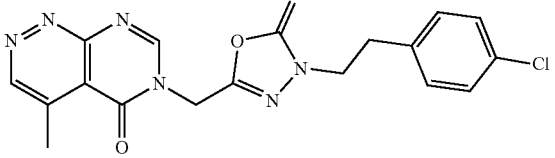 | 3-(4-chlorophenethyl)-5-((4-methyl-5-oxopyridazino[3,4-d]pyrimidin-6(5H)-yl)methyl)-1,3,4-oxadiazol-2(3H)-one | 0.049 |
| 28 | 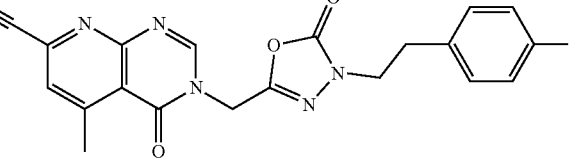 | 3-((4-(4-chlorophenethyl)-5-oxo-4,5-dihydro-1,3,4-oxadiazol-2-yl)methyl)-5-methyl-4-oxo-3,4-dihydropyrido[2,3-d]pyrimidine-7-carbonitrile | 0.009 |

TABLE 1-continued

| Ex. | Structure | Name | hTRPA1 |
|---|---|---|---|
| 29 | 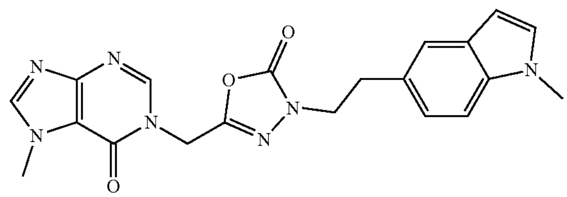 [SMILES: Cn1ccc2cc(CCn3nc(Cn4cnc5ncn(C)c5c4=O)oc3=O)ccc21] | 3-[2-(1-methylindol-5-yl)ethyl]-5-[(7-methyl-6-oxo-purin-1-yl)methyl]-1,3,4-oxadiazol-2-one | 0.087 |
| 30 | 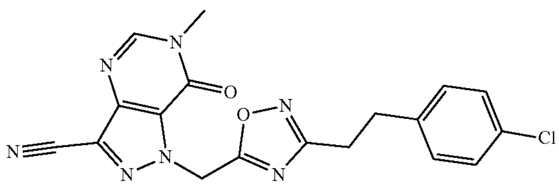 [SMILES: Cn1cnc2c(C#N)nn(Cc3nc(CCc4ccc(Cl)cc4)no3)c2c1=O] | 1-[[3-[2-(4-chlorophenyl)ethyl]-1,2,4-oxadiazol-5-yl]methyl]-6-methyl-7-oxo-pyrazolo[4,3-d]pyrimidine-3-carbonitrile | 0.0266 |
| 31 | 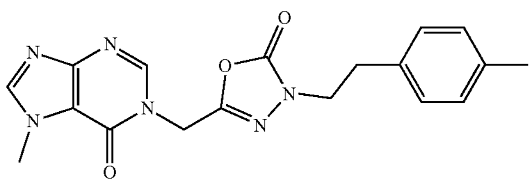 [SMILES: Cc1ccc(CCn2nc(Cn3cnc4ncn(C)c4c3=O)oc2=O)cc1] | 5-[(7-methyl-6-oxo-purin-1-yl)methyl]-3-[2-(p-tolyl)ethyl]-1,3,4-oxadiazol-2-one | 0.126 |
| 32 | 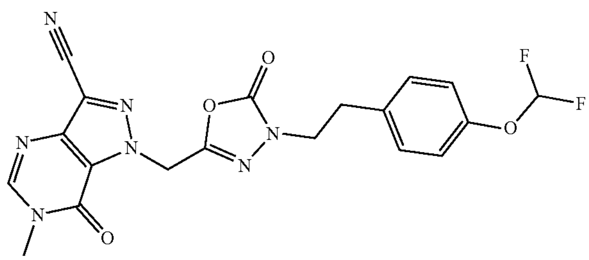 [SMILES: Cn1cnc2c(C#N)nn(Cc3nn(CCc4ccc(OC(F)F)cc4)c(=O)o3)c2c1=O] | 1-[(4-[2-[4-(difluoromethoxy)phenyl]ethyl]-5-oxo-4,5-dihydro-1,3,4-oxadiazol-2-yl)methyl]-6-methyl-7-oxo-1H,6H,7H-pyrazolo[4,3-d]pyrimidine-3-carbonitrile | 0.036 |
| 33 | 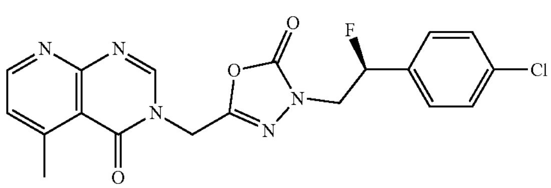 [SMILES: Cc1ccnc2ncn(Cc3nn(C[C@@H](F)c4ccc(Cl)cc4)c(=O)o3)c(=O)c12] | 5-[(5-methyl-4-oxo-pyrido[2,3-d]pyrimidin-3-yl)methyl]-3-[(2R)-2-(4-chlorophenyl)-2-fluoro-ethyl]-1,3,4-oxadiazol-2-one | 0.180 |
| 34 | 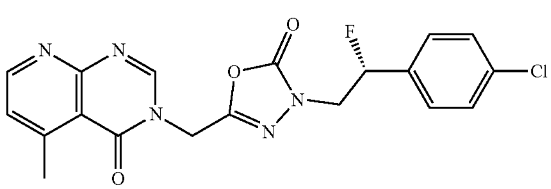 [SMILES: Cc1ccnc2ncn(Cc3nn(C[C@H](F)c4ccc(Cl)cc4)c(=O)o3)c(=O)c12] | 5-[(5-methyl-4-oxo-pyrido[2,3-d]pyrimidin-3-yl)methyl]-3-[(2S)-2-(4-chlorophenyl)-2-fluoro-ethyl]-1,3,4-oxadiazol-2-one | 0.005 |
| 35 | 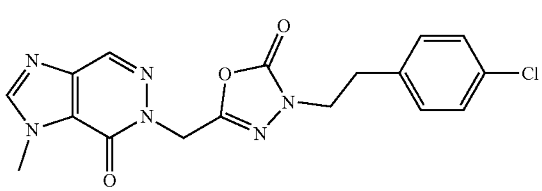 [SMILES: Cn1cnc2cnn(Cc3nn(CCc4ccc(Cl)cc4)c(=O)o3)c(=O)c21] | 3-[2-(4-chlorophenyl)ethyl]-5-[(3-methyl-4-oxo-imidazo[4,5-d]pyridazin-5-yl)methyl]-1,3,4-oxadiazol-2-one | 0.096 |

TABLE 1-continued

| Ex. | Structure | Name | hTRPA1 |
|---|---|---|---|
| 36 | 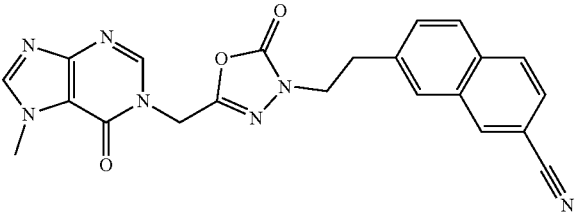 [SMILES: Cn1cnc2ncn(Cc3nn(CCc4ccc5ccc(C#N)cc5c4)c(=O)o3)c(=O)c21] | 7-[2-[5-[(7-methyl-6-oxo-purin-1-yl)methyl]-2-oxo-1,3,4-oxadiazol-3-yl]ethyl]naphthalene-2-carbonitrile | 0.120 |
| 37 | 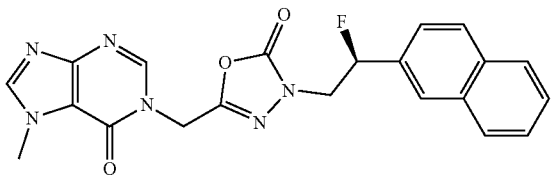 [SMILES: Cn1cnc2ncn(Cc3nn(C[C@@H](F)c4ccc5ccccc5c4)c(=O)o3)c(=O)c21] | 5-[(7-methyl-6-oxo-purin-1-yl)methyl]-3-[(2S)-2-fluoro-2-(2-naphthyl)ethyl]-1,3,4-oxadiazol-2-one | 0.332 |
| 38 | 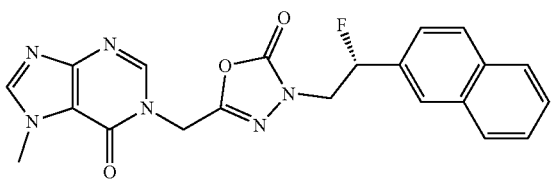 [SMILES: Cn1cnc2ncn(Cc3nn(C[C@H](F)c4ccc5ccccc5c4)c(=O)o3)c(=O)c21] | 5-[(7-methyl-6-oxo-purin-1-yl)methyl]-3-[(2S)-2-fluoro-2-(2-naphthyl)ethyl]-1,3,4-oxadiazol-2-one | 0.007 |
| 39 | 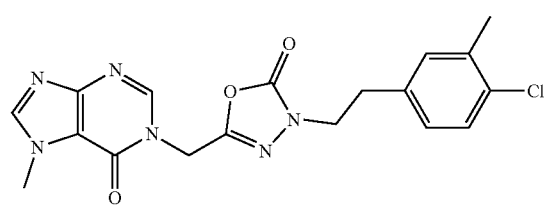 [SMILES: Cc1cc(CCn2nc(Cn3cnc4ncn(C)c4c3=O)oc2=O)ccc1Cl] | 3-(4-chloro-3-methylphenethyl)-5-((7-methyl-6-oxo-6H-purin-1(7H)-yl)methyl)-1,3,4-oxadiazol-2(3H)-one | 0.113 |
| 40 | 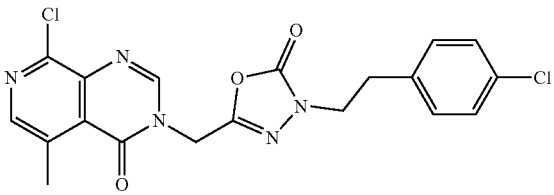 [SMILES: Cc1cnc(Cl)c2ncn(Cc3nn(CCc4ccc(Cl)cc4)c(=O)o3)c(=O)c12] | 5-((8-chloro-5-methyl-4-oxopyrido[3,4-d]pyrimidin-3(4H)-yl)methyl)-3-(4-chlorophenethyl)-1,3,4-oxadiazol-2(3H)-one | 0.018 |
| 41 | 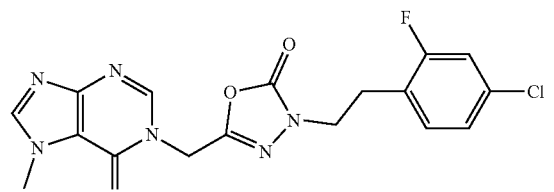 | 3-(4-chloro-2-fluorophenethyl)-5-((7-methyl-6-oxo-6H-purin-1(7H)-yl)methyl)-1,3,4-oxadiazol-2(3H)-one | 0.492 |
| 42 | 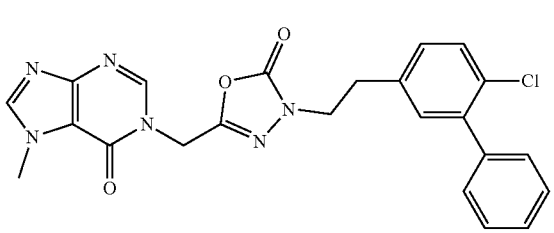 [SMILES: Cn1cnc2ncn(Cc3nn(CCc4ccc(Cl)c(-c5ccccc5)c4)c(=O)o3)c(=O)c21] | 3-(2-(6-chlorobiphenyl-3-yl)ethyl)-5-((7-methyl-6-oxo-6H-purin-1(7H)-yl)methyl)-1,3,4-oxadiazol-2(3H)-one | 0.098 |

TABLE 1-continued

| Ex. | Structure | Name | hTRPA1 |
|---|---|---|---|
| 43 | 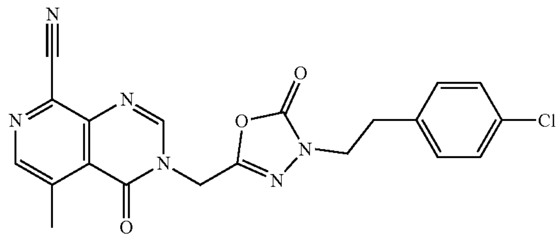 [SMILES: Cc1cnc(C#N)c2ncn(Cc3nn(CCc4ccc(Cl)cc4)c(=O)o3)c(=O)c12] | 3-(4-chlorophenethyl)-5-((5,7-dimethyl-4-oxoimidazo[1,5-f][1,2,4]triazin-3(4H)-yl)methyl)-1,3,4-oxadiazol-2(3H)-one | 0.018 |
| 44 | 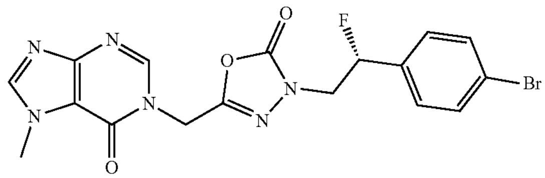 [SMILES: Cn1cnc2ncn(Cc3nn(C[C@H](F)c4ccc(Br)cc4)c(=O)o3)c(=O)c21] | (R)-3-(2-(4-bromophenyl)-2-fluoroethyl)-5-((7-methyl-6-oxo-6H-purin-1(7H)-yl)methyl)-1,3,4-oxadiazol-2(3H)-one | 0.010 |
| 45 | 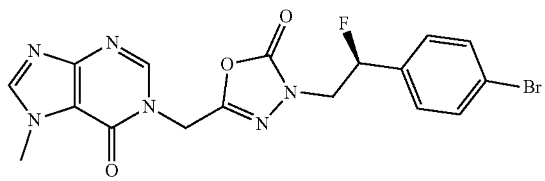 [SMILES: Cn1cnc2ncn(Cc3nn(C[C@@H](F)c4ccc(Br)cc4)c(=O)o3)c(=O)c21] | (S)-3-(2-(4-bromophenyl)-2-fluoroethyl)-5-((7-methyl-6-oxo-6H-purin-1(7H)-yl)methyl)-1,3,4-oxadiazol-2(3H)-one | 1.20 |
| 46 | 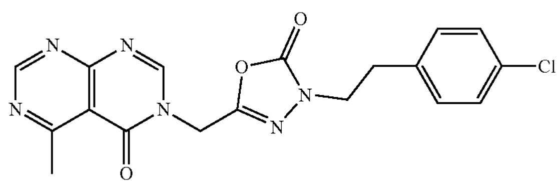 [SMILES: Cc1ncnc2ncn(Cc3nn(CCc4ccc(Cl)cc4)c(=O)o3)c(=O)c12] | 3-(4-chlorophenethyl)-5-((5-methyl-4-oxopyrimido[4,5-d]pyrimidin-3(4H)-yl)methyl)-1,3,4-oxadiazol-2(3H)-one | 0.107 |
| 47 | 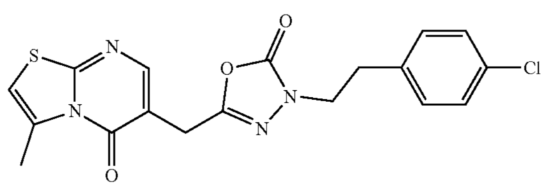 [SMILES: Cc1csc2ncc(Cc3nn(CCc4ccc(Cl)cc4)c(=O)o3)c(=O)n12] | 3-(4-chlorophenethyl)-5-((3-methyl-5-oxo-5H-thiazolo[3,2-a]pyrimidin-6-yl)methyl)-1,3,4-oxadiazol-2(3H)-one | 0.065 |
| 48 | 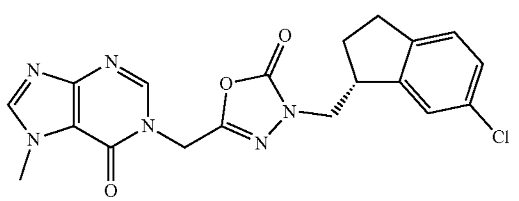 [SMILES: Cn1cnc2ncn(Cc3nn(C[C@@H]4CCc5ccc(Cl)cc54)c(=O)o3)c(=O)c21] | (R)-3-((6-chloro-2,3-dihydro-1H-inden-1-yl)methyl)-5-((7-methyl-6-oxo-6,7-dihydro-1H-purin-1-yl)methyl-1,3,4-oxadiazol-2(3H)-one | 0.196 |
| 49 | 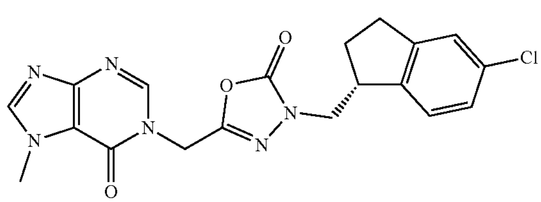 [SMILES: Cn1cnc2ncn(Cc3nn(C[C@@H]4CCc5cc(Cl)ccc54)c(=O)o3)c(=O)c21] | (R)-3-((5-chloro-2,3-dihydro-1H-inden-1-yl)methyl)-5-((7-methyl-6-oxo-6,7-dihydro-1H-purin-1-yl)methyl)-1,3,4-oxadiazol-2(3H)-one | 0.061 |
| 50 | 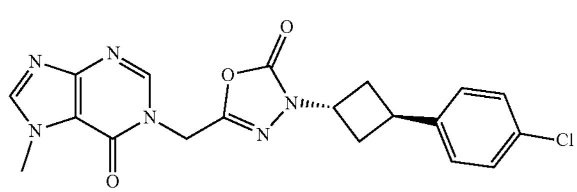 [SMILES: Cn1cnc2ncn(Cc3nn([C@H]4C[C@H](c5ccc(Cl)cc5)C4)c(=O)o3)c(=O)c21] | 3-[3-(4-chlorophenyl)cyclobutyl]-5-[(7-methyl-6-oxo-purin-1-yl)methyl]-1,3,4-oxadiazol-2-one | 0.014 |

TABLE 1-continued

| Ex. | Structure | Name | hTRPA1 |
|-----|-----------|------|--------|
| 51 | 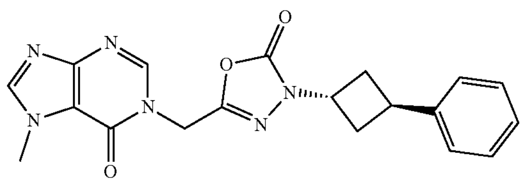 [SMILES: Cn1cnc2ncn(Cc3nn([C@H]4C[C@H](c5ccccc5)C4)c(=O)o3)c(=O)c21] | 5-[(7-methyl-6-oxo-purin-1-yl)methyl]-3-(3-phenylcyclobutyl)-1,3,4-oxadiazol-2-one | 0.168 |
| 52 | 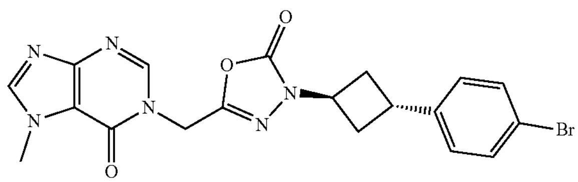 [SMILES: Cn1cnc2ncn(Cc3nn([C@H]4C[C@H](c5ccc(Br)cc5)C4)c(=O)o3)c(=O)c21] | 3-[3-(4-bromophenyl)cyclobutyl]-5-[(7-methyl-6-oxo-purin-1-yl)methyl]-1,3,4-oxadiazol-2-one | 0.020 |
| 53 | 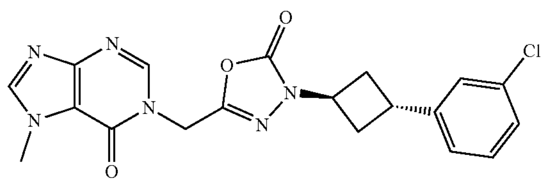 [SMILES: Cn1cnc2ncn(Cc3nn([C@H]4C[C@H](c5cccc(Cl)c5)C4)c(=O)o3)c(=O)c21] | 3-[3-(3-chlorophenyl)cyclobutyl]-5-[(7-methyl-6-oxo-purin-1-yl)methyl]-1,3,4-oxadiazol-2-one | 0.044 |
| 54 | 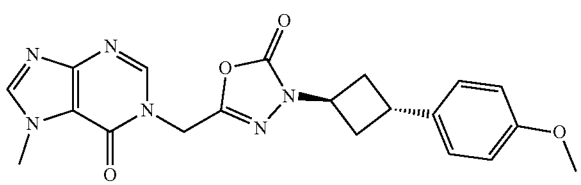 [SMILES: COc1ccc([C@H]2C[C@H](n3nc(Cn4cnc5ncn(C)c5c4=O)oc3=O)C2)cc1] | 3-(3-(4-methoxyphenyl)cyclobutyl)-5-((7-methyl-6-oxo-6,7-dihydro-1H-purin-1-yl)methyl)-1,3,4-oxadiazol-2(3H)-one | 0.105 |
| 55 | 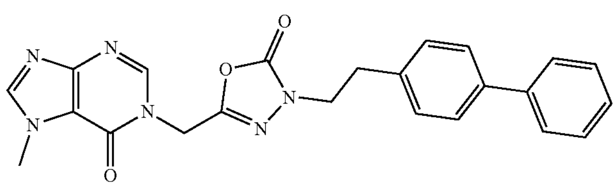 [SMILES: Cn1cnc2ncn(Cc3nn(CCc4ccc(-c5ccccc5)cc4)c(=O)o3)c(=O)c21] | 5-[(7-methyl-6-oxo-purin-1-yl)methyl]-3-[2-(4-phenylphenyl)ethyl]-1,3,4-oxadiazol-2-one | 0.251 |
| 56 | 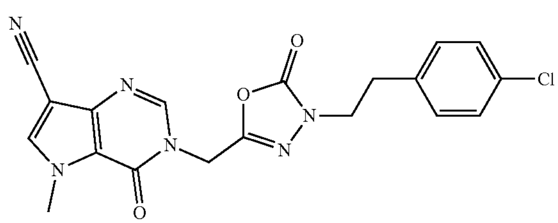 [SMILES: Cn1cc(C#N)c2ncn(Cc3nn(CCc4ccc(Cl)cc4)c(=O)o3)c(=O)c21] | 3-((4-(4-chlorophenethyl)-5-oxo-4,5-dihydro-1,3,4-oxadiazol-2-yl)methyl)-5-methyl-4,5-dihydro-3H-pyrrolo[3,2-d]pyrimidine-7-carbonitrile | 0.168 |
| 57 | 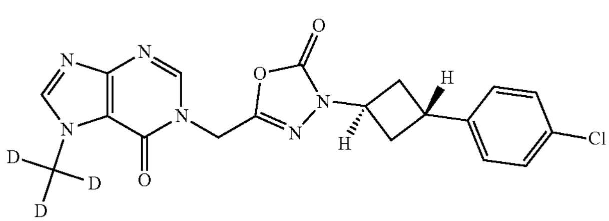 [SMILES: [2H]C([2H])([2H])n1cnc2ncn(Cc3nn([C@H]4C[C@H](c5ccc(Cl)cc5)C4)c(=O)o3)c(=O)c21] | trans-3-[3-(4-chlorophenyl)cyclobutyl]-5-[[6-oxo-7-(trideuteriomethyl)purin-1-yl]methyl]-1,3,4-oxadiazol-2-one | — |
| 58 | 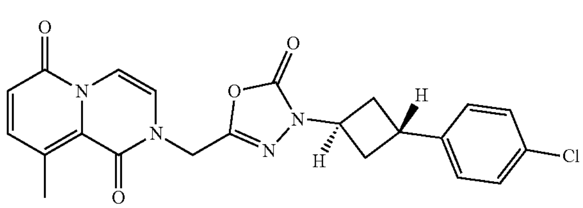 [SMILES: Cc1ccc(=O)n2ccn(Cc3nn([C@H]4C[C@H](c5ccc(Cl)cc5)C4)c(=O)o3)c(=O)c12] | 2-[[4-[3-(4-chlorophenyl)cyclobutyl]-5-oxo-1,3,4-oxadiazol-2-yl]methyl]-9-methyl-pyrido[1,2-a]pyrazine-1,6-dione | 0.0403 |

TABLE 1-continued

| Ex. | Structure | Name | hTRPA1 |
|---|---|---|---|
| 59 | 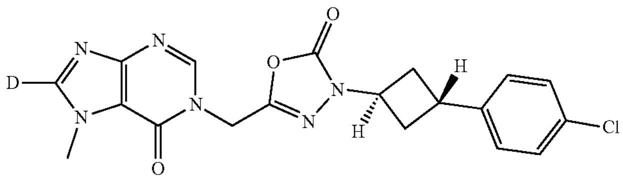 [SMILES: [2H]c1nc2ncn(Cc3nn([C@H]4C[C@H](c5ccc(Cl)cc5)C4)c(=O)o3)c(=O)c2n1C] | trans-3-[3-(4-chlorophenyl)cyclobutyl]-5-[(8-deuterio-7-methyl-6-oxo-purin-1-yl)methyl]-1,3,4-oxadiazol-2-one | 0.0226 |
| 60 | 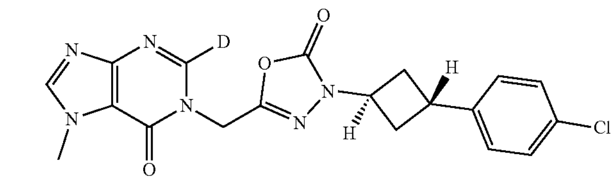 [SMILES: [2H]c1nc2ncn(C)c2c(=O)n1Cc1nn([C@H]2C[C@H](c3ccc(Cl)cc3)C2)c(=O)o1] | trans-3-[3-(4-chlorophenyl)cyclobutyl]-5-[(2-deuterio-7-methyl-6-oxo-purin-1-yl)methyl]-1,3,4-oxadiazol-2-one | 0.0284 |
| 61 | 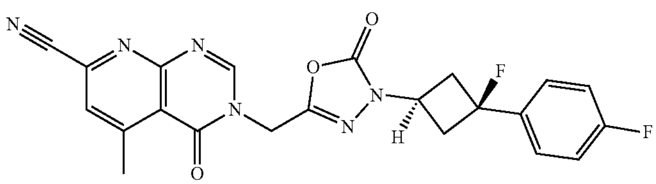 [SMILES: Cc1cc(C#N)nc2ncn(Cc3nn([C@H]4C[C@](F)(c5ccc(F)cc5)C4)c(=O)o3)c(=O)c12] | 3-[[4-[3-fluoro-3-(4-fluorophenyl)cyclobutyl]-5-oxo-1,3,4-oxadiazol-2-yl]methyl]-5-methyl-4-oxo-pyrido[2,3-d]pyrimidine-7-carbonitrile | 0.0112 |
| 62 | 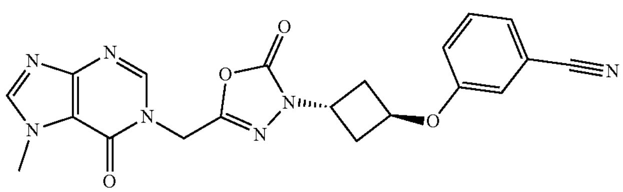 [SMILES: Cn1cnc2ncn(Cc3nn([C@H]4C[C@H](Oc5cccc(C#N)c5)C4)c(=O)o3)c(=O)c21] | 3-[3-[5-[(7-methyl-6-oxo-purin-1-yl)methyl]-2-oxo-1,3,4-oxadiazol-3-yl]cyclobutoxy]benzonitrile | 0.0455 |
| 63 | 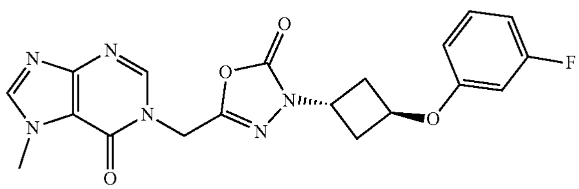 [SMILES: Cn1cnc2ncn(Cc3nn([C@H]4C[C@H](Oc5cccc(F)c5)C4)c(=O)o3)c(=O)c21] | trans-3-[3-(3-fluorophenoxy)cyclobutyl]-5-[(7-methyl-6-oxo-purin-1-yl)methyl]-1,3,4-oxadiazol-2-one | 0.0115 |
| 64 | 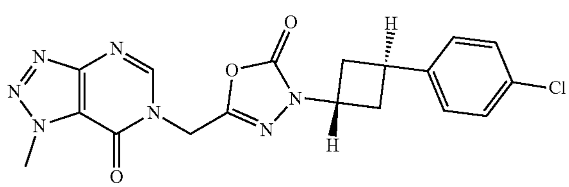 [SMILES: Cn1nnc2ncn(Cc3nn([C@H]4C[C@H](c5ccc(Cl)cc5)C4)c(=O)o3)c(=O)c21] | trans-3-[3-(4-chlorophenyl)cyclobutyl]-5-[(1-methyl-7-oxo-triazolo[4,5-d]pyrimidin-6-yl)methyl]-1,3,4-oxadiazol-2-one | 0.0769 |
| 65 | 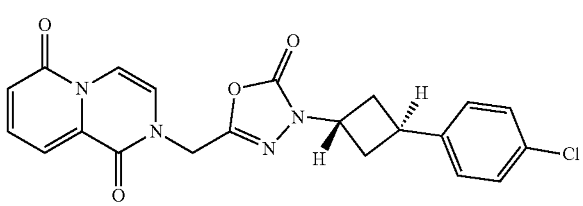 [SMILES: O=c1c2cccc(=O)n2ccn1Cc1nn([C@H]2C[C@H](c3ccc(Cl)cc3)C2)c(=O)o1] | trans-2-[[4-[3-(4-chlorophenyl)cyclobutyl]-5-oxo-1,3,4-oxadiazol-2-yl]methyl]pyrido[1,2-a]pyrazine-1,6-dione | 0.0211 |
| 66 | 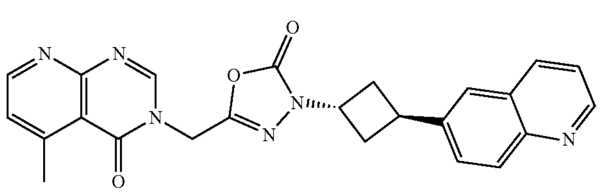 [SMILES: Cc1ccnc2ncn(Cc3nn([C@H]4C[C@H](c5ccc6ncccc6c5)C4)c(=O)o3)c(=O)c12] | 5-[(5-methyl-4-oxo-pyrido[2,3-d]pyrimidin-3-yl)methyl]-3-[3-(6-quinolyl)cyclobutyl]-1,3,4-oxadiazol-2-one | 0.0125 |

TABLE 1-continued

| Ex. | Structure | Name | hTRPA1 |
|---|---|---|---|
| 67 | 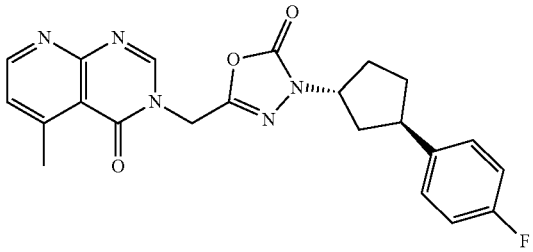 [SMILES: Cc1ccnc2ncn(Cc3nn([C@@H]4CC[C@@H](c5ccc(F)cc5)C4)c(=O)o3)c(=O)c12] | 5-[(5-methyl-4-oxo-pyrido[2,3-d]pyrimidin-3-yl)methyl]-3-[rac-(1R,3R)-3-(4-fluorophenyl)cyclopentyl]-1,3,4-oxadiazol-2-one | 0.00476 |
| 68 | 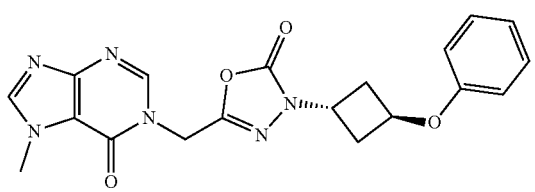 [SMILES: Cn1cnc2ncn(Cc3nn([C@H]4C[C@H](Oc5ccccc5)C4)c(=O)o3)c(=O)c21] | 3-[3-(4-chlorophenoxy)cyclobutyl]-5-[(7-methyl-6-oxo-purin-1-yl)methyl]-1,3,4-oxadiazol-2-one | 0.0569 |
| 69 | 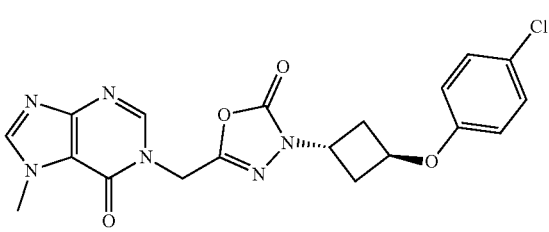 [SMILES: Cn1cnc2ncn(Cc3nn([C@H]4C[C@H](Oc5ccc(Cl)cc5)C4)c(=O)o3)c(=O)c21] | 3-[3-(4-chlorophenoxy)cyclobutyl]-5-[(7-methyl-6-oxo-purin-1-yl)methyl]-1,3,4-oxadiazol-2-one | 0.785 |
| 70 | 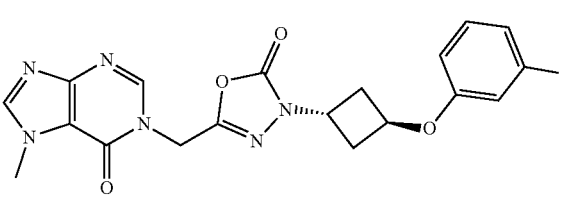 | trans-3-[3-(3-chlorophenoxy)cyclobutyl]-5-[(7-methyl-6-oxo-purin-1-yl)methyl]-1,3,4-oxadiazol-2-one | 0.0177 |
| 71 | 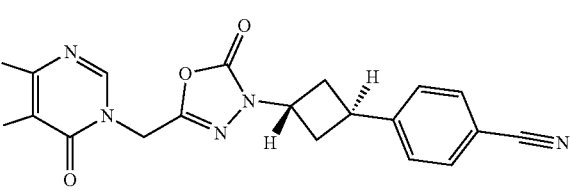 | 4-[3-[5-[(7-methyl-6-oxo-purin-1-yl)methyl]-2-oxo-1,3,4-oxadiazol-3-yl]cyclobutyl]benzonitrile | 0.0597 |
| 73 | 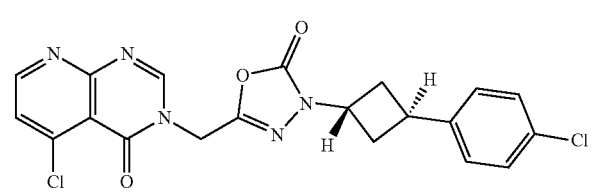 [SMILES: O=c1c2c(Cl)ccnc2ncn1Cc1nn([C@H]2C[C@H](c3ccc(Cl)cc3)C2)c(=O)o1] | 5-[(5-chloro-4-oxo-pyrido[2,3-d]pyrimidin-3-yl)methyl]-3-[3-(4-chlorophenyl)cyclobutyl]-1,3,4-oxadiazol-2-one | 0.00588 |
| 74 | 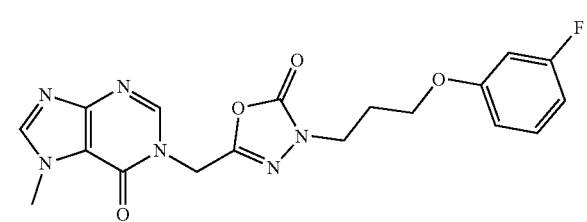 [SMILES: Cn1cnc2ncn(Cc3nn(CCCOc4cccc(F)c4)c(=O)o3)c(=O)c21] | 3-[3-(3-fluorophenoxy)propyl]-5-[(7-methyl-6-oxo-purin-1-yl)methyl]-1,3,4-oxadiazol-2-one | 0.0775 |

TABLE 1-continued

| Ex. | Structure | Name | hTRPA1 |
|---|---|---|---|
| 75 | 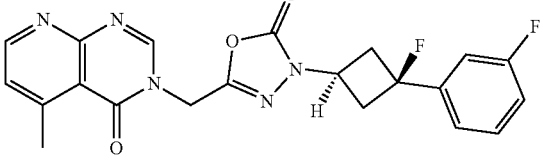 | 3-[3-fluoro-3-(3-fluorophenyl)cyclobutyl]-5-[(5-methyl-4-oxo-pyrido[2,3-d]pyrimidin-3-yl)methyl]-1,3,4-oxadiazol-2-one | 0.0405 |
| 76 | 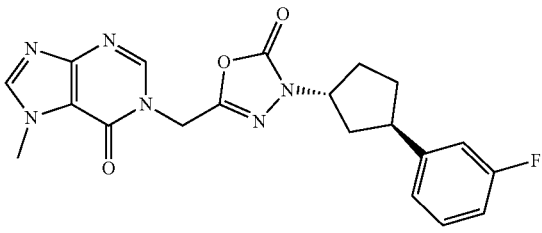 [SMILES: Cn1cnc2ncn(Cc3nn([C@@H]4CC[C@@H](c5cccc(F)c5)C4)c(=O)o3)c(=O)c21] | 5-[(7-methyl-6-oxo-purin-1-yl)methyl]-3-[rac-(1R,3R)-3-(3-fluorophenyl)cyclopentyl]-1,3,4-oxadiazol-2-one | 0.0758 |
| 77 | 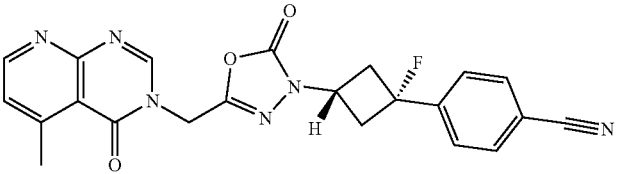 [SMILES: Cc1ccnc2ncn(Cc3nn([C@H]4C[C@](F)(c5ccc(C#N)cc5)C4)c(=O)o3)c(=O)c12] | 4-[1-fluoro-3-[5-[(5-methyl-4-oxo-pyrido[2,3-d]pyrimidin-3-yl)methyl]-2-oxo-1,3,4-oxadiazol-3-yl]cyclobutyl]benzonitrile | 0.0214 |
| 78 | 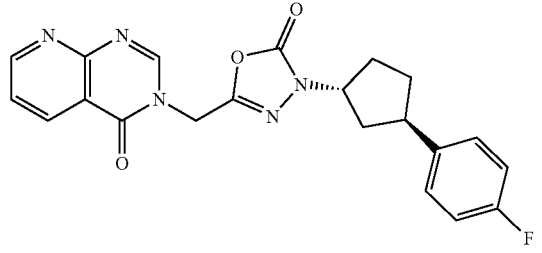 [SMILES: O=c1c2cccnc2ncn1Cc1nn([C@@H]2CC[C@@H](c3ccc(F)cc3)C2)c(=O)o1] | 5-[(4-oxopyrido[2,3-d]pyrimidin-3-yl)methyl]-3-[rac-(1R,3R)-3-(4-fluorophenyl)cyclopentyl]-1,3,4-oxadiazol-2-one | 0.0406 |
| 79 | 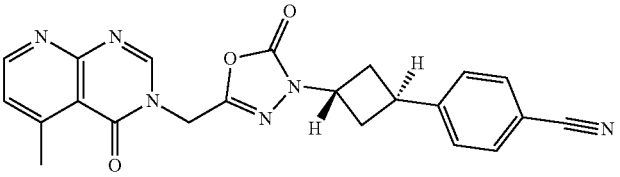 | 4-[3-[5-[(5-methyl-4-oxo-pyrido[2,3-d]pyrimidin-3-yl)methyl]-2-oxo-1,3,4-oxadiazol-3-yl]cyclobutyl]benzonitrile | 0.00258 |
| 80 | 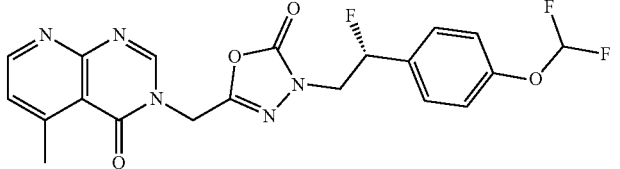 [SMILES: Cc1ccnc2ncn(Cc3nn(C[C@H](F)c4ccc(OC(F)F)cc4)c(=O)o3)c(=O)c12] | 5-[(5-methyl-4-oxo-pyrido[2,3-d]pyrimidin-3-yl)methyl]-3-[rac-(2R)-2-[4-(difluoromethoxy)phenyl]-2-fluoro-ethyl]-1,3,4-oxadiazol-2-one | 0.0119 |
| 81 | 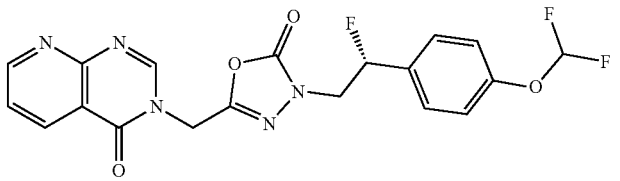 [SMILES: O=c1c2cccnc2ncn1Cc1nn(C[C@H](F)c2ccc(OC(F)F)cc2)c(=O)o1] | 5-[(4-oxopyrido[2,3-d]pyrimidin-3-yl)methyl]-3-[rac-(2R)-2-[4-(difluoromethoxy)phenyl]-2-fluoro-ethyl]-1,3,4-oxadiazol-2-one | 0.05 |

TABLE 1-continued

| Ex. | Structure | Name | hTRPA1 |
|---|---|---|---|
| 82 | 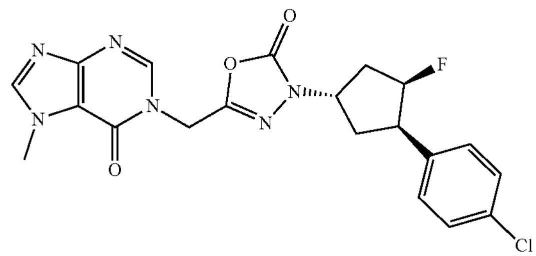 [SMILES: Cn1cnc2ncn(Cc3nn([C@@H]4C[C@@H](F)[C@@H](c5ccc(Cl)cc5)C4)c(=O)o3)c(=O)c21] | 5-[(7-methyl-6-oxo-purin-1-yl)methyl]-3-[rac-(1S,3R,4R)-3-(4-chlorophenyl)-4-fluoro-cyclopentyl]-1,3,4-oxadiazol-2-one | 0.0439 |
| 83 | 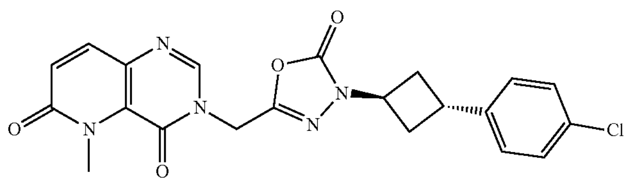 [SMILES: Cn1c(=O)ccc2ncn(Cc3nn([C@H]4C[C@H](c5ccc(Cl)cc5)C4)c(=O)o3)c(=O)c21] | 3-((4-((trans)-3-(4-chlorophenyl)cyclobutyl)-5-oxo-4,5-dihydro-1,3,4-oxadiazol-2-yl)methyl)-5-methylpyrido[3,2-d]pyrimidine-4,6(3H,5H)-dione | 0.0152 |
| 84 | 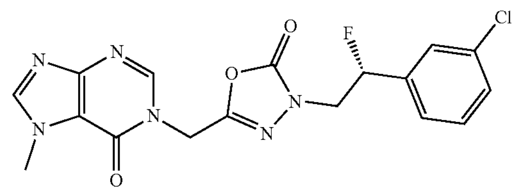 [SMILES: Cn1cnc2ncn(Cc3nn(C[C@H](F)c4cccc(Cl)c4)c(=O)o3)c(=O)c21] | 5-[(7-methyl-6-oxo-purin-1-yl)methyl]-3-[rac-(2R)-2-(3-chlorophenyl)-2-fluoro-ethyl]-1,3,4-oxadiazol-2-one | 0.166 |
| 85 | 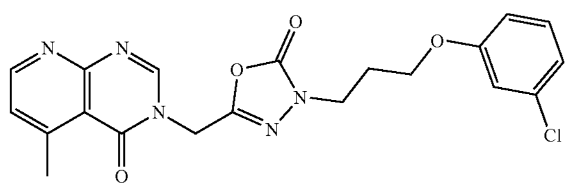 [SMILES: Cc1ccnc2ncn(Cc3nn(CCCOc4cccc(Cl)c4)c(=O)o3)c(=O)c12] | 3-(3-(3-chlorophenoxy)propyl)-5-((5-methyl-4-oxopyrido[2,3-d]pyrimidin-3(4H)-yl)methyl)-1,3,4-oxadiazol-2(3H)-one | 0.00634 |
| 86 | 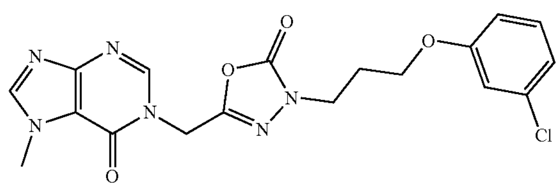 [SMILES: Cn1cnc2ncn(Cc3nn(CCCOc4cccc(Cl)c4)c(=O)o3)c(=O)c21] | 1-([4-[3-(3-chlorophenoxy)propyl]-5-oxo-4,5-dihydro-1,3,4-oxadiazol-2-yl]methyl)-7-methyl-6,7-dihydro-1H-purin-6-one | 0.0226 |
| 87 | 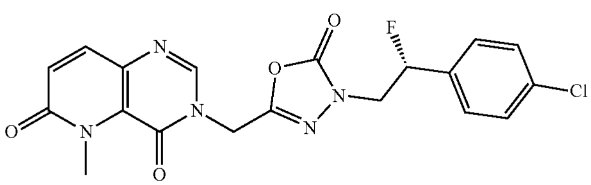 [SMILES: Cn1c(=O)ccc2ncn(Cc3nn(C[C@H](F)c4ccc(Cl)cc4)c(=O)o3)c(=O)c21] | 5-methyl-3-[[5-oxo-4-[rac-(2R)-2-(4-chlorophenyl)-2-fluoro-ethyl]-1,3,4-oxadiazol-2-yl]methyl]pyrido[3,2-d]pyrimidine-4,6-dione | 0.0438 |
| 88 | 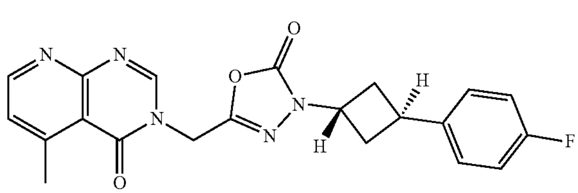 [SMILES: Cc1ccnc2ncn(Cc3nn([C@H]4C[C@H](c5ccc(F)cc5)C4)c(=O)o3)c(=O)c12] | 3-[3-(4-fluorophenyl)cyclobutyl]-5-[(5-methyl-4-oxo-pyrido[2,3-d]pyrimidin-3-yl)methyl]-1,3,4-oxadiazol-2-one | 0.00576 |
| 89 | 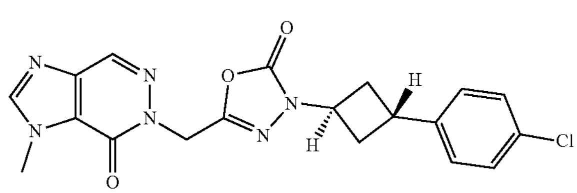 [SMILES: Cn1cnc2cnn(Cc3nn([C@H]4C[C@H](c5ccc(Cl)cc5)C4)c(=O)o3)c(=O)c21] | 3-[3-(4-chlorophenyl)cyclobutyl]-5-[(3-methyl-4-oxo-imidazo[4,5-d]pyridazin-5-yl)methyl]-1,3,4-oxadiazol-2-one | 0.0457 |

TABLE 1-continued

| Ex. | Structure | Name | hTRPA1 |
|---|---|---|---|
| 90 | 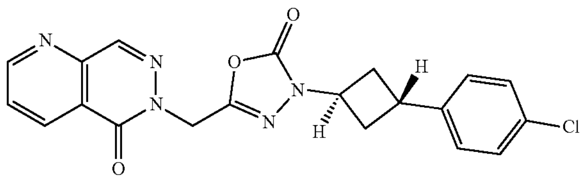 [SMILES: O=c1c2cccnc2cnn1Cc1nn([C@H]2C[C@H](c3ccc(Cl)cc3)C2)c(=O)o1] | 3-[3-(4-chlorophenyl)cyclobutyl]-5-[(5-oxopyrido[2,3-d]pyridazin-6-yl)methyl]-1,3,4-oxadiazol-2-one | 0.0799 |
| 91 | 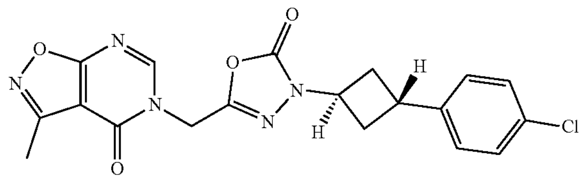 [SMILES: Cc1noc2ncn(Cc3nn([C@H]4C[C@H](c5ccc(Cl)cc5)C4)c(=O)o3)c(=O)c12] | 5-[[4-[3-(4-chlorophenyl)cyclobutyl]-5-oxo-1,3,4-oxadiazol-2-yl]methyl]-3-methyl-isoxazolo[5,4-d]pyrimidin-4-one | 0.0362 |
| 92 | 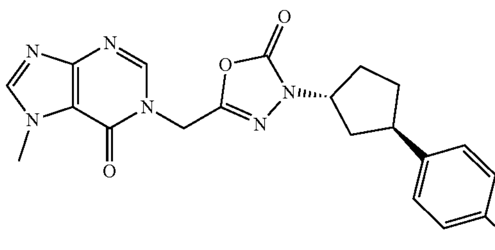 | 5-[(7-methyl-6-oxo-purin-1-yl)methyl]-3-[(1R,3R)-3-(4-fluorophenyl)cyclopentyl]-1,3,4-oxadiazol-2-one | 0.00826 |
| 93 | 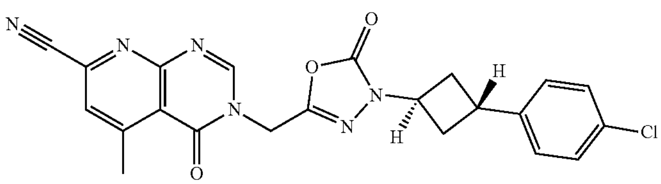 [SMILES: Cc1cc(C#N)nc2ncn(Cc3nn([C@H]4C[C@H](c5ccc(Cl)cc5)C4)c(=O)o3)c(=O)c12] | trans-3-[[4-[3-(4-chlorophenyl)cyclobutyl]-5-oxo-1,3,4-oxadiazol-2-yl]methyl]-5-methyl-4-oxo-pyrido[2,3-d]pyrimidine-7-carbonitrile | 0.00484 |
| 94 | 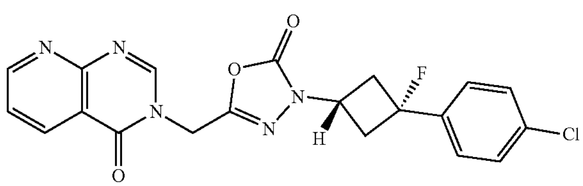 [SMILES: O=c1c2cccnc2ncn1Cc1nn([C@H]2C[C@](F)(c3ccc(Cl)cc3)C2)c(=O)o1] | trans-3-[3-(4-chlorophenyl)-3-fluoro-cyclobutyl]-5-[(4-oxopyrido[2,3-d]pyrimidin-3-yl)methyl]-1,3,4-oxadiazol-2-one | 0.0168 |
| 95 | 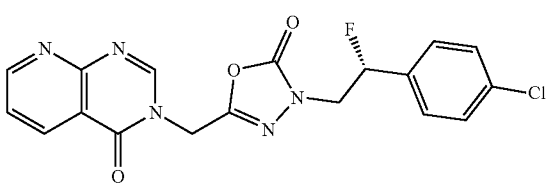 [SMILES: O=c1c2cccnc2ncn1Cc1nn(C[C@H](F)c2ccc(Cl)cc2)c(=O)o1] | 5-[(4-oxopyrido[2,3-d]pyrimidin-3-yl)methyl]-3-[rac-(2R)-2-(4-chlorophenyl)-2-fluoro-ethyl]-1,3,4-oxadiazol-2-one | 0.0485 |
| 96 | 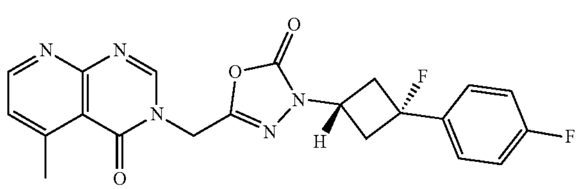 [SMILES: Cc1ccnc2ncn(Cc3nn([C@H]4C[C@](F)(c5ccc(F)cc5)C4)c(=O)o3)c(=O)c12] | 3-[3-fluoro-3-(4-fluorophenyl)cyclobutyl]-5-[(5-methyl-4-oxo-pyrido[2,3-d]pyrimidin-3-yl)methyl]-1,3,4-oxadiazol-2-one | 0.018 |
| 97 | 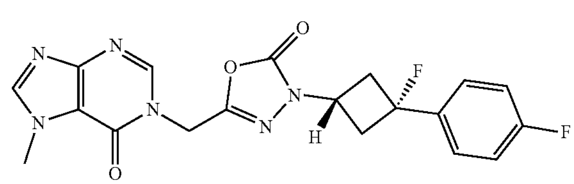 [SMILES: Cn1cnc2ncn(Cc3nn([C@H]4C[C@](F)(c5ccc(F)cc5)C4)c(=O)o3)c(=O)c21] | 3-[3-fluoro-3-(4-fluorophenyl)cyclobutyl]-5-[(7-methyl-6-oxo-purin-1-yl)methyl]-1,3,4-oxadiazol-2-one | 0.0802 |

TABLE 1-continued

| Ex. | Structure | Name | hTRPA1 |
|---|---|---|---|
| 98 | 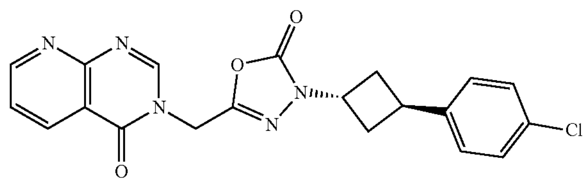 [SMILES: O=c1c2cccnc2ncn1Cc1nn([C@H]2C[C@H](c3ccc(Cl)cc3)C2)c(=O)o1] | trans-3-[3-(4-chlorophenyl)cyclobutyl]-5-[(4-oxopyrido[2,3-d]pyrimidin-3-yl)methyl]-1,3,4-oxadiazol-2-one | 0.0162 |
| 99 | 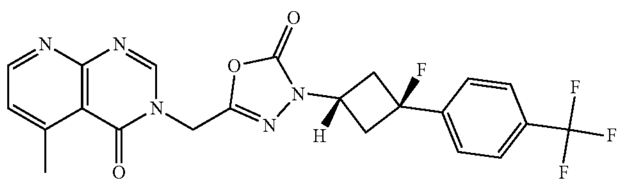 [SMILES: Cc1ccnc2ncn(Cc3nn([C@H]4C[C@@](F)(c5ccc(C(F)(F)F)cc5)C4)c(=O)o3)c(=O)c12] | 3-[3-fluoro-3-[4-(trifluoromethyl)phenyl]cyclobutyl]-5-[(5-methyl-4-oxo-pyrido[2,3-d]pyrimidin-3-yl)methyl]-1,3,4-oxadiazol-2-one | 0.0573 |
| 100 | 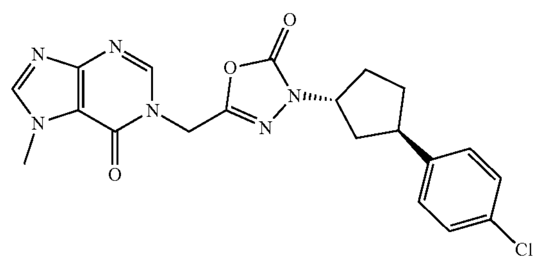 [SMILES: Cn1cnc2ncn(Cc3nn([C@@H]4CC[C@@H](c5ccc(Cl)cc5)C4)c(=O)o3)c(=O)c21] | 5-[(7-methyl-6-oxo-purin-1-yl)methyl]-3-[(1R,3R)-3-(4-chlorophenyl)cyclopentyl]-1,3,4-oxadiazol-2-one | 0.00959 |
| 101 | 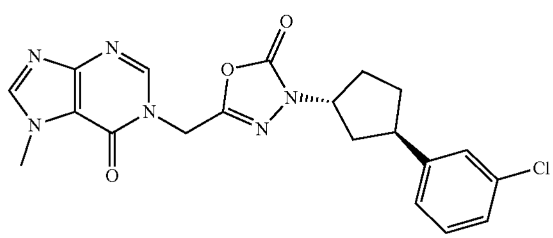 [SMILES: Cn1cnc2ncn(Cc3nn([C@@H]4CC[C@@H](c5cccc(Cl)c5)C4)c(=O)o3)c(=O)c21] | 5-[(7-methyl-6-oxo-purin-1-yl)methyl]-3-[rac-(1R,3R)-3-(3-chlorophenyl)cyclopentyl]-1,3,4-oxadiazol-2-one | 0.0361 |
| 103 | 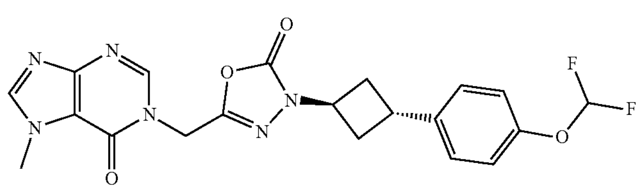 [SMILES: Cn1cnc2ncn(Cc3nn([C@H]4C[C@H](c5ccc(OC(F)F)cc5)C4)c(=O)o3)c(=O)c21] | 3-[3-[(trans)-4-(difluoromethoxy)phenyl]cyclobutyl]-5-[(7-methyl-6-oxo-purin-1-yl)methyl]-1,3,4-oxadiazol-2-one | 0.026 |
| 104 | 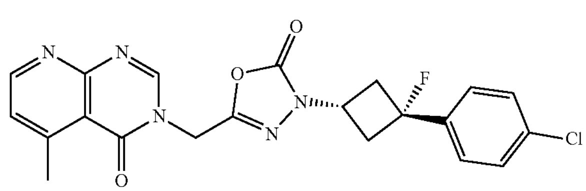 [SMILES: Cc1ccnc2ncn(Cc3nn([C@H]4C[C@](F)(c5ccc(Cl)cc5)C4)c(=O)o3)c(=O)c12] | 3-[3-(4-chlorophenyl)-3-fluoro-cyclobutyl]-5-[(5-methyl-4-oxo-pyrido[2,3-d]pyrimidin-3-yl)methyl]-1,3,4-oxadiazol-2-one | 0.0296 |
| 105 | 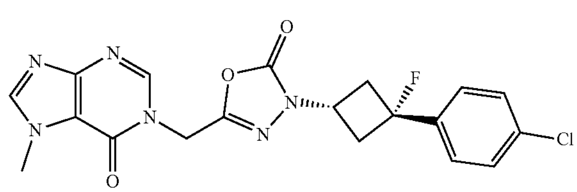 [SMILES: Cn1cnc2ncn(Cc3nn([C@H]4C[C@](F)(c5ccc(Cl)cc5)C4)c(=O)o3)c(=O)c21] | trans-3-[3-(4-chlorophenyl)-3-fluoro-cyclobutyl]-5-[(7-methyl-6-oxo-purin-1-yl)methyl]-1,3,4-oxadiazol-2-one | 0.064 |

TABLE 1-continued

| Ex. | Structure | Name | hTRPA1 |
|---|---|---|---|
| 106 | 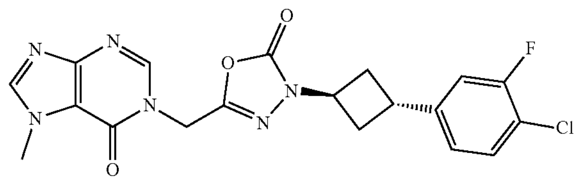 [SMILES: Cn1cnc2ncn(Cc3nn([C@H]4C[C@H](c5ccc(Cl)c(F)c5)C4)c(=O)o3)c(=O)c21] | 3-[3-(4-chloro-3-fluoro-phenyl)cyclobutyl]-5-[(7-methyl-6-oxo-purin-1-yl)methyl]-1,3,4-oxadiazol-2-one | 0.0299 |
| 107 | 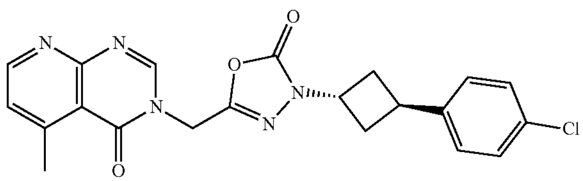 [SMILES: Cc1ccnc2ncn(Cc3nn([C@H]4C[C@H](c5ccc(Cl)cc5)C4)c(=O)o3)c(=O)c12] | 3-[3-(4-chlorophenyl)cyclobutyl]-5-[(5-methyl-4-oxo-pyrido[2,3-d]pyrimidin-3-yl)methyl]-1,3,4-oxadiazol-2-one | 0.0063 |
| 108 | 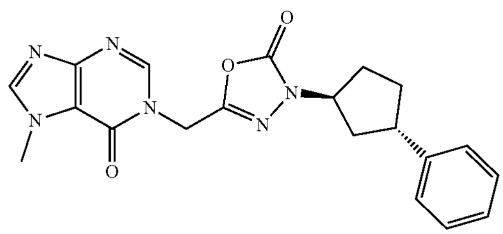 [SMILES: Cn1cnc2ncn(Cc3nn([C@H]4CC[C@H](c5ccccc5)C4)c(=O)o3)c(=O)c21] | 5-[(7-methyl-6-oxo-purin-1-yl)methyl]-3-[rac-(1S,3S)-3-phenylcyclopentyl]-1,3,4-oxadiazol-2-one | 0.156 |
| 109 | 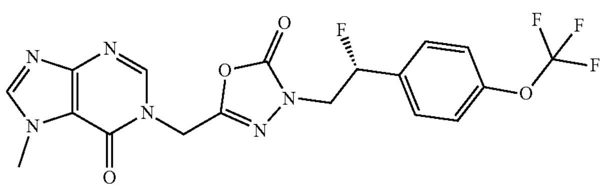 [SMILES: Cn1cnc2ncn(Cc3nn(C[C@H](F)c4ccc(OC(F)(F)F)cc4)c(=O)o3)c(=O)c21] | 5-[(7-methyl-6-oxo-purin-1-yl)methyl]-3-[rac-(2R)-2-fluoro-2-[4-(trifluoromethoxy)phenyl]ethyl]-1,3,4-oxadiazol-2-one | 0.0191 |
| 110 | 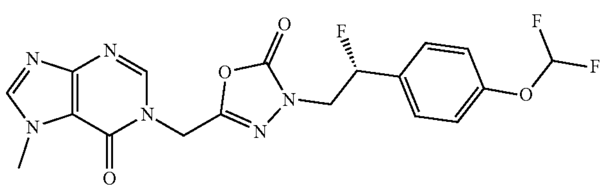 [SMILES: Cn1cnc2ncn(Cc3nn(C[C@H](F)c4ccc(OC(F)F)cc4)c(=O)o3)c(=O)c21] | 5-[(7-methyl-6-oxo-purin-1-yl)methyl]-3-[rac-(2R)-2-[4-(difluoromethoxy)phenyl]-2-fluoro-ethyl]-1,3,4-oxadiazol-2-one | 0.0813 |
| 111 | 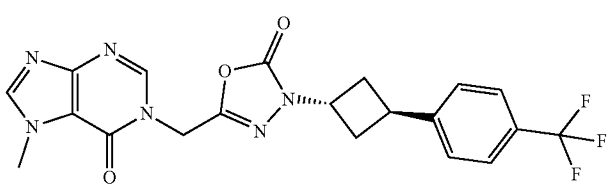 [SMILES: Cn1cnc2ncn(Cc3nn([C@H]4C[C@H](c5ccc(C(F)(F)F)cc5)C4)c(=O)o3)c(=O)c21] | 5-[(7-methyl-6-oxo-purin-1-yl)methyl]-3-[3-[4-(trifluoromethyl)phenyl]cyclobutyl]-1,3,4-oxadiazol-2-one | 0.09 |
| 112 | 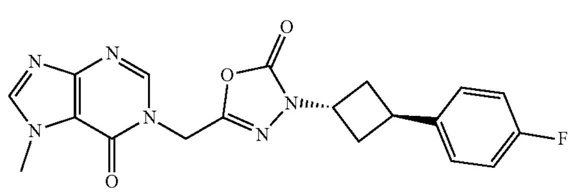 [SMILES: Cn1cnc2ncn(Cc3nn([C@H]4C[C@H](c5ccc(F)cc5)C4)c(=O)o3)c(=O)c21] | 3-[3-(4-fluorophenyl)cyclobutyl]-5-[(7-methyl-6-oxo-purin-1-yl)methyl]-1,3,4-oxadiazol-2-one | 0.0648 |
| 113 | 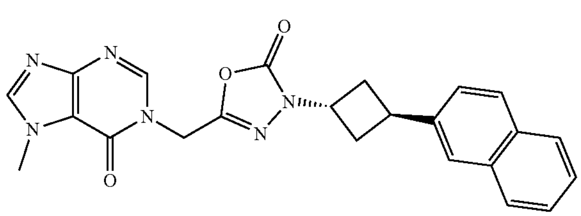 [SMILES: Cn1cnc2ncn(Cc3nn([C@H]4C[C@H](c5ccc6ccccc6c5)C4)c(=O)o3)c(=O)c21] | 5-[(7-methyl-6-oxo-purin-1-yl)methyl]-3-[3-(2-naphthyl)cyclobutyl]-1,3,4-oxadiazol-2-one | 0.0178 |

Example 3: Pharmacokinetic Analysis

Certain pharmacokinetic attributes were evaluated for some compounds of the present disclosure. The results are shown in Table 2 below where: "RLM-CL$_{hep}$" refers to rat liver microsome clearance in mL/min/kg; "HLM-CL$_{hep}$" refers to human liver microsome clearance in mL/min/kg; and "Rat IV PK" refers to hepatic clearance in mL/min/kg for a rat IV dose of 1 mg/kg. hTRPA1 IC$_{50}$ data reported in table 1 is repeated in Table 2 below. The compounds of the present disclosure were discovered to provide for an unexpected combination of high potency as measured by hTRPA1 IC$_{50}$ and high stability as measured by RLM-CL$_{hep}$, HLM-CL$_{hep}$ and Rat IV PK.

Human liver microsome clearance (mL/min/kg) and rat liver microsome clearance (mL/min/kg) may be measured according to the method described by Ackley et al, "Metabolic Stability Assessed by Liver Microsomes and Hepatocytes", in "Optimization in Drug Discovery" in the "Methods in Pharmacology and Toxicology" series (ISSN 1557-2153), pp. 151-162 (Yan, Ed., Print ISBN 978-1-58829-332-9, Springer (2004), as well as by using commercially available assay kits by Cerep, Cyprotex, Bd Bioscience and others. RLM-CL$_{hep}$ and HLM-CL$_{hep}$ microsome stability reactions for the results reported in Table 2 below were performed in 100 mM KPi with 0.5 mg/ml protein, 1 mM NADPH and a final compound concentration of 1 µM. The reactions were incubated at 37° C. for 0, 20, 40 and 60 minutes and at each allotted time point an aliquot of the reaction mixture was added to ice-cold acetonitrile with internal standard. The samples were subsequently centrifuged at 3000×g for 10 minutes and supernatant was diluted in water before LC-MS/MS analysis.

TABLE 2

| Compound | hTRPA1 IC$_{50}$ | RLM-CL$_{hep}$ | HLM-CL$_{hep}$ | Rat IV PK |
|---|---|---|---|---|
| Example Compound 1 | 0.095 µm | 34 mL/min/kg | 11 mL/min/kg | 48 mL/min/kg |
| Example Compound 14 | 0.034 µm | 28 mL/min/kg | 6 mL/min/kg | 17 mL/min/kg |
| Example Compound 50 | 0.014 µm | 12 mL/min/kg | 5 mL/min/kg | 10 mL/min/kg |

Example 4: Proton NMR and LCMS Identification of Example Compounds

Proton NMR and LCMS M+1 data for the compounds of Table 1 are shown below in Table 3. Proton NMR and LCMS M+1 was done according to methods described elsewhere herein.

TABLE 3

| Ex. | 1H NMR (ppm) | M + H |
|---|---|---|
| 1 | $^1$H NMR (400 MHz, DMSO) δ 8.34 (s, 1H), 8.23 (s, 1H), 7.29 (d, J = 8.4 Hz,2 H), 7.20 (d, J = 8.4 Hz, 2H), 5.22 (s, 2H), 3.98 (s, 3H), 3.85 (t, J = 6.8 Hz, 2H), 2.91 (t, J = 6.8 Hz, 2H). | 387 |
| 2 | $^1$H NMR (300 MHz, DMSO-d6) δ 8.35 (s, 1H), 8.24 (s, 1H), 7.44-6.90 (m, 4H), 5.23 (s, 2H), 3.99 (s, 3H), 3.85 (t, J = 6.9 Hz, 2H), 2.92 (t, J = 6.9 Hz, 2H). | 419 |
| 3 | $^1$H NMR (400 MHz, DMSO-d$_6$) δ 8.35 (s, 1H), 8.25 (s, 1H), 7.46-7.38 (m, 2H), 7.22-7.10 (m, 2H), 5.22 (s, 2H), 3.99 (s, 3H), 3.86 (t, J = 6.8 Hz, 2H), 2.89 (t, J = 6.8 Hz, 2H). | 431 |
| 4 | $^1$H NMR (400 MHz, DMSO-d6) δ 8.35 (s, 1H), 8.25 (s, 1H), 7.29-7.13(m, 5H), 5.23 (s, 2H), 3.99 (s, 3H), 3.86 (t, J = 7.0 Hz, 2H), 2.91 (t, J = 7.0 Hz, 2H). | 353 |
| 5 | $^1$H NMR (400 MHz, DMSO-d6) δ 8.34 (s, 1H), 8.25 (s, 1H), 7.75-7.67 (m, 2H), 7.46-7.36 (m, 2H), 5.21 (s, 2H), 4.03 (s, 3H), 3.93 (t, J = 6.8 Hz, 2H), 3.02 (t, J = 6.8 Hz, 2H). | 378 |
| 6 | $^1$H-NMR (400 MHz, DMSO-d$_6$) δ 8.93 (s, 1H), 8.54 (d, J = 4.3 Hz, 2H), 7.32-7.15 (m, 4H), 5.19 (s, 2H), 3.87 (t, J = 6.8 Hz, 2H), 2.92 (t, J = 6.7 Hz, 2H), 2.75 (s, 3H). | 398 |
| 7 | $^1$H NMR (400 MHz, DMSO-d$_6$) δ 8.79 (d, J = 4.8 Hz, 1H), 8.62 (s, 1H), 7.42 (d, J = 4.8 Hz, 1H), 7.32-7.15 (m, 4H), 5.19 (s, 2H), 3.87 (t, J = 6.8 Hz, 2H), 2.92 (t, J = 6.8 Hz, 2H), 2.82 (s, 3H). | 398 |
| 8 | $^1$H NMR δ 8.84 (d, J = 4.8 Hz, 1H), 8.28 (s, 1H), 7.64-7.55 (m, 2H), 7.34-7.29 (m, 3H), 5.05 (s, 2H), 3.96 (t, J = 7.2 Hz, 2H), 3.11 (t, J = 7.3 Hz, 2H), 2.95-2.90 (m, 3H) | 389 |
| 9 | $^1$H NMR (400 MHz, DMSO) δ 8.35 (s, 1H), 8.25 (s, 1H), 7.60 (d, J = 8.0 Hz, 2H), 7.42 (d, J = 8.0 Hz, 2H), 5.23 (s, 2H), 3.99 (s, 3H), 3.92 (t, J = 6.8 Hz, 2H), 3.02 (t, J = 6.8 Hz, 2H). | 421 |
| 10 | $^1$H NMR (400 MHz,DMSO) δ 8.35 (s, 1H), 8.24 (s, 1H), 7.32 (d, J = 8.7 Hz, 2H), 7.23 (d, J = 8.0 Hz, 2H), 5.23 (s, 2H), 3.98 (s, 3H), 3.88 (t, J = 6.9 Hz, 2H), 2.95 (t, J = 6.9 Hz, 2H). | 437 |
| 11 | $^1$H NMR (400 MHz, DMSO) δ 8.36 (s, 1H), 8.24 (s, 1H), 7.15-7.01 (m, 2H), 6.86-6.73 (m, 2H), 5.23 (s, 2H), 3.99 (s, 3H), 3.81 (t, J = 7.0 Hz, 2H), 3.69 (s, 3H), 2.84 (t, J = 6.9 Hz, 2H). | 383 |
| 12 | $^1$H NMR(400 MHz, DMSO) δ 8.37 (s, 1H), 8.26 (s, 1H), 7.86 (dd, J = 6.0, 3.4 Hz, 1H), 7.80 (dd, J = 7.0, 4.4 Hz, 2H), 7.64 (s, 1H), 7.50-7.42 (m, 2H), 7.37 (dd, J = 8.4, 1.6 Hz, 1H), 5.24 (s, 2H), 4.00 (s, 3H), 3.96 (t, J = 6.9 Hz, 2H), 3.09 (t, J = 6.8 Hz, 2H). | 403 |
| 13 | $^1$H NMR(400 MHz, DMSO-d6) δ 8.11 (s, 1H), 7.36-7.13 (m, 4H), 5.04 (s, 2H), 3.87 (t, J = 6.8 Hz, 2H), 2.92 (t, J = 6.8 Hz, 2H), 2.48 (s, 2H), 2.47 (s, 2H). | 401 |
| 14 | $^1$H NMR (400 MHz, CD$_3$CN) δ 8.09 (s, 1H), 7.91 (s, 1H), 7.45-7.39 (m, 4H), 8.86-5.72 (m, 1H), 5.11 (s, 2H), 4.20-4.10 (m, 1H), 4.05-3.93 (m, 4H). | 405 |
| 15 | $^1$H NMR (400 MHz, CD$_3$CN) δ 8.09 (s, 1H), 7.91 (s, 1H), 7.45-7.39 (m, 4H), 8.86-5.72 (m, 1H), 5.11 (s, 2H), 4.20-4.10 (m, 1H), 4.05-3.93 (m, 4H). | 405 |
| 16 | $^1$H NMR (400 MHz, DMSO-d6) δ 8.35 (s, 1H), 8.24 (s, 1H), 7.04-6.91 (m, 4H), 5.23 (s, 2H), 3.99 (s, 3H), 3.81 (t, J = 7.0 Hz, 2H), 2.85 (t, J = 7.0 Hz, 2H), 1.86-1.82 (m, 1H), 0.93-0.86 (m, 2H), 0.61-0.59 (m, 2H). | 393 |
| 17 | $^1$H NMR (400 MHz, DMSO-d6) δ 8.36 (s, 1H), 8.24 (s, 1H), 6.96 (d, J = 8.2 Hz, 2H), 6.61-6.53 (m, 2H), 5.24 (s, 2H), 3.99 (s, 3H), 3.77 (t, J = 7.0 Hz, 2H), 2.82 (s, 8H). | 396 |
| 18 | $^1$H NMR (400 MHz, DMSO) δ 8.36 (s, 1H), 8.25 (s, 1H), 7.44 (d, J = 7.8 Hz, 2H), 7.32 (d, J = 7.9 Hz, 2H), 7.13-6.99 (m, 1H), 5.23 (s, 2H), 3.99 (s, 3H), 3.89 (t, J = 6.9 Hz, 2H), 2.98 (t, J = 6.9 Hz, 2H). | 403 |
| 19 | $^1$H NMR (300 MHz, DMSO-d6) δ 8.31 (s, 1H), 8.22 (s, 1H), 7.32-7.17 (m, 4H), 5.17 (s, 2H), 3.96 (s, 3H), 3.75 (d, J = 7.6 Hz, 2H), 3.13 (q, J = 7.4 Hz, 1H), 1.18 (d, J = 7.0 Hz, 3H). | 401 |
| 20 | $^1$H NMR (300 MHz, DMSO-d6) δ 8.30 (s, 1H), 8.22 (s, 1H), 7.31-7.16 (m, 4H), 5.17 (s, 2H), 3.96 (s, 3H), 3.75 (d, J = 7.5 Hz, 2H), 3.12 (q, J = 7.2 Hz, 1H), 1.18 (d, J = 7.0 Hz, 3H). | 401 |

TABLE 3-continued

| Ex. | 1H NMR (ppm) | M + H |
|---|---|---|
| 21 | ¹H NMR (400 MHz, CDCl₃) δ 8.07 (s, 1H), 7.87 (s, 1H), 6.74 (d, J = 3.7 Hz, 1H), 6.62 (dt, J = 3.7, 0.9 Hz, 1H), 5.13 (s, 2H), 4.12 (s, 3H), 3.94 (t, J = 7.1 Hz, 2H), 3.16 (t, J = 7.1 Hz, 2H). | 393 |
| 22 | ¹H NMR (300 MHz, DMSO-d₆) δ 8.47 (s, 1H), 7.30-7.17 (m, 4H), 5.91 (s, 2H), 3.90-3.85 (m, 2H), 3.55 (s, 3H), 2.94-2.90 (m, 3H). | 412 |
| 23 | ¹H NMR (300 MHz, DMSO-d₆) δ 8.46 (s, 1H), 7.30-7.19 (m, 4H), 5.25 (s, 2H), 4.30 (s, 3H), 3.88-3.85 (m, 2H), 2.93-2.90 (m, 2H). | 412 |
| 24 | ¹H NMR (400 MHz, DMSO-d₆) δ 8.35 (s, 1H), 8.24 (s, 1H), 7.67-7.59 (m, 2H), 7.54-7.29 (m, 6H), 7.20-7.13 (m, 1H), 5.23 (s, 2H), 3.95-3.92 (m, 5H), 3.01-2.98 (t, J = 7.1 Hz, 2H). | 429 |
| 25 | ¹H NMR (300 MHz, DMSO-d₆) δ 8.35 (s, 1H), 8.24(s, 1H), 7.61 (d, J = 8.2 Hz, 1H), 7.49 (d, J = 2.1 Hz, 1H), 7.09-7.02 (m, 1H), 5.22 (s, 2H), 3.99 (s, 3H), 3.90-3.87 (t, J = 6.7 Hz, 2H), 2.93-2.89 (t, J = 6.7 Hz, 2H), 1.25 (s, 1H). | 466 |
| 26 | ¹H NMR(300 MHz, DMSO-d₆) δ 8.36-8.33 (d, J = 11.8 Hz, 2H), 7.31-7.23 (m, 2H), 7.22-7.13 (m, 2H), 5.65 (s, 2H), 3.86-3.82 (t, J = 6.7 Hz, 2H), 3.34 (s, 3H), 2.89-2.86 (t, J = 6.7 Hz, 2H). | 387 |
| 27 | ¹H NMR (400 MHz, DMSO-d₆) δ 9.37 (s, 1H), 8.71 (s, 1H), 7.26 (d, J = 8.4 Hz, 2H), 7.21 (d, J = 8.4 Hz, 2H), 5.19 (s, 2H), 3.86 (t, J = 6.8 Hz, 2H), 2.92 (t, J = 6.8 Hz, 2H), 2.79 (s, 3H). | 399 |
| 28 | ¹H NMR (400 MHz, DMSO-d₆) δ 8.71 (s, 1H), 8.06 (s, 1H), 7.28 (d, J = 8.4 Hz, 2H), 7.20 (d, J = 8.4 Hz, 2H), 5.19 (s, 2H), 3.86 (t, J = 6.4 Hz, 2H), 2.91 (t, J = 6.8 Hz, 2H), 2.85 (s, 3H). | 423 |
| 29 | ¹H NMR (300 MHz, DMSO-d₆) δ 8.37 (s, 1H), 8.26 (s, 1H), 7.35-7.23 (m, 3H), 6.96 (dd, J = 8.4, 1.6 Hz, 1H), 6.29 (dd, J = 3.1, 0.9 Hz, 1H), 5.25 (s, 2H), 4.00 (s, 3H), 3.87 (t, J = 7.0 Hz, 2H), 3.35 (s, 3H), 2.98 (t, J = 7.0 Hz, 2H). | 406 |
| 30 | ¹H NMR(400 MHz, DMSO-d₆) δ 8.48 (s, 1H), 7.37-7.16 (m, 4H), 6.29 (s, 2H), 3.53 (s, 3H), 3.04-2.88 (m, 4H). | 396 |
| 31 | ¹H NMR (400 MHz, DMSO-d₆) δ 8.36 (s, 1H), 8.25 (s, 1H), 7.05 (s, 4H), 5.24 (s, 2H), 4.00 (s, 3H), 3.83 (t, J = 6.9 Hz, 2H), 2.87 (t, J = 6.9 Hz, 2H), 2.24 (s, 3H). | 367 |
| 32 | ¹H NMR (400 MHz, CDCl₃) δ 8.05 (s, 1H), 7.28-7.06 (m, 4H), 6.70-6.33 (t, J = 72.0 Hz, 1H), 5.82 (s, 2H), 3.95 (t, J = 8.0 Hz, 2H), 3.67 (s, 3H), 3.04 (t, J = 8.0 Hz, 2H). | 444 |
| 33 | ¹H NMR (300 MHz, DMSO-d₆) δ 8.79 (d, J = 4.8 Hz, 1H), 8.61 (s, 1H), 7.45 (s, 5H), 5.92-5.76 (dd, J = 7.8, 3.3 Hz, 1H), 5.21 (s, 2H), 4.27-3.96 (m, 2H), 2.81 (d, J = 0.8 Hz, 3H). | 416 |
| 34 | ¹H NMR (300 MHz, DMSO-d₆) δ 8.79 (d, J = 4.8 Hz, 1H), 8.61 (s, 1H), 7.45 (s, 5H), 5.92-5.76 (dd, J = 7.8, 3.3 Hz, 1H), 5.21 (s, 2H), 4.27-3.96 (m, 2H), 2.81 (d, J = 0.8 Hz, 3H). | 416 |
| 35 | ¹H NMR (300 MHz, DMSO-d₆) δ 8.51 (d, J = 1.2 Hz, 1H), 8.40 (s, 1H), 7.33-7.14 (m, 4H), 5.31 (s, 2H), 4.05 (s, 3H), 3.86 (t, J = 6.8 Hz, 2H), 2.92 (t, J = 6.8 Hz, 2H). | 387 |
| 36 | ¹H NMR (400 MHz, DMSO-d₆) δ 8.46 (s, 1H), 8.35 (s, 1H), 8.24 (s, 1H), 8.06 (d, J = 8.5 Hz, 1H), 7.95 (d, J = 8.4 Hz, 1H), 7.79 (s, 1H), 7.74 (d, J = 8.4 Hz, 1H), 7.60 (d, J = 8.4 Hz, 1H), 5.23 (s, 2H), 4.03-3.88 (m, 5H), 3.12 (t, J = 6.6 Hz, 2H). | 428 |
| 37 | ¹H NMR (400 MHz, DMSO-d₆) δ 8.37 (s, 1H), 8.25 (s, 1H), 8.02-7.89 (m, 4H), 7.62-7.51 (m, 3H), 5.97 (m, 1H), 5.27 (s, 2H), 4.37-4.23 (m, 1H), 4.14 (m, 1H), 3.99 (s, 3H). | 421 |
| 38 | ¹H NMR (400 MHz, DMSO-d₆) δ 8.37 (s, 1H), 8.25 (s, 1H), 8.02-7.89 (m, 4H), 7.62-7.51 (m, 3H), 5.97 (m, 1H), 5.27 (s, 2H), 4.37-4.23 (m, 1H), 4.14 (m, 1H), 3.99 (s, 3H). | 421 |
| 39 | ¹H NMR (300 MHz, CDCl₃) δ 8.07 (s, 1H), 7.88 (s, 1H), 7.27 (d, J = 8.3 Hz, 1H), 7.07 (s, 1H), 6.96 (d, J = 9.0 Hz, 1H), 5.12 (s, 2H), 4.13 (s, 3H), 3.95-3.90 (m, 2H), 3.04-2.92 (m, 2H), 2.36 (s, 3H). | 401 |
| 40 | ¹H NMR (300 MHz, CDCl₃) δ 8.33 (s, 1H), 8.22 (s, 1H), 7.28-7.26 (m, 1H), 7.14-7.11 (m, 2H), 5.07 (s, 2H), 3.98-3.89 (m, 2H), 3.05-3.00 (m, 2H), 2.82 (s, 3H) | 432 |
| 41 | ¹H NMR (400 MHz, CDCl₃) δ 8.05 (s, 1H), 7.87 (s, 1H), 7.11-7.05 (m, 3H), 5.11 (s, 2H), 4.13 (d, J = 10.8 Hz 3H), 3.95 (t, J = 7.1 Hz, 2H), 3.04 (t, J = 7.1 Hz, 2H). | 405 |
| 42 | ¹H NMR (300 MHz, CDCl₃) δ 8.03 (s, 1H), 7.86 (s, 1H), 7.48-7.37 (m, 6H), 7.17 (d, J = 2.0 Hz, 1H), 7.11-7.08 (m, 1H), 5.08 (s, 2H), 4.08 (s, 3H), 3.98-3.93 (m, 2H), 3.06-3.01 (m, 2H). | 463 |
| 43 | ¹H NMR (300 MHz, CDCl₃) δ 8.69 (s, 1H), 7.28-7.24 (m, 2H), 7.20-7.18 (m, 2H), 5.20 (s, 2H), 3.89-3.84 (m, 2H), 2.93-2.89 (m, 2H), 2.81 (s, 3H). | 423 |
| 44 | ¹H NMR (300 MHz, CDCl₃) δ 8.08 (s, 1H), 7.86 (s, 1H), 7.57-7.54 (m, 2H), 7.27-7.24 (m, 2H), 5.81-5.61 (m, 1H), 5.14 (s, 2H), 4.23-4.11 (m, 4H), 3.97-3.81 (m, 1H). | 449 |
| 45 | ¹H NMR (300 MHz, CDCl₃) δ 8.08 (s, 1H), 7.87 (s, 1H), 7.56 (d, J = 9 Hz, 2H), 7.27-7.26 (m, 2H), 5.81-5.61 (s, 2H), 4.26-4.11 (m, 4H), 3.97-3.81 (m, 1H). | 449 |
| 46 | ¹H NMR (300 MHz, DMSO-d₆) δ 9.22 (s, 1H), 8.81 (s, 1H), 7.28 (d, J = 8.4 Hz, 2H), 7.20 (d, J = 8.4 Hz, 2H), 5.20 (s, 2H), 3.87 (t, J = 6.8 Hz, 2H), 2.99-2.85 (m, 5H). | 339 |
| 47 | ¹H NMR (400 MHz, CDCl₃) δ 7.92 (s, 1H), 7.32-7.24 (m, 2H), 7.19-7.11 (m, 2H), 6.53-6.52 (m, 1H), 3.96-3.87 (m, 2H), 3.78 (s, 2H), 3.07-2.98 (m, 2H), 2.85 (s, 3H). | 405 |
| 48 | ¹H NMR (500 MHz, DMSO-d6) δ 8.34 (s, 1H), 8.21 (s, 1H), 7.24-7.12 (m, 3H), 5.23 (s, 2H), 3.96 (d, J = 6.6 Hz, 3H), 3.91 (d, J = 14.2, 6.3 Hz, 1H), 3.73 (dd, J = 14.2, 7.6 Hz, 1H), 3.53-3.48 (m, 1H), 2.89-2.80 (m, 1H), 280-2.70 (m, 1H), 2.17 (dtd, J = 12.9, 8.4, 6.4 Hz, 1H), 1.85-1.76 (m, 1H). | 413 |
| 49 | ¹H NMR (500 MHz, DMSO-d6) δ 8.35 (s, 1H), 8.23 (d, J = 0.5 Hz, 1H), 7.27 (s, 1H), 7.15 (d, J = 8.2 Hz, 1H), 7.11 (dd, J = 8.1, 2.0 Hz, 1H), 5.24 (s, 2H), 3.97 (s, 3H), 3.86 (dd, J = 14.2, 6.7 Hz, 1H), 3.72 (dd, J = 14.2, 7.6 Hz, 1H), 3.49-3.42 (m, 1H), 2.95-2.87 (m, 1H), 2.84-2.75 (m, 1H), 2.23-2.13 (m, 1H), 1.85-1.77 (m, 1H). | 413 |
| 50 | ¹H NMR (400 MHz, DMSO-d6) δ 8.37 (s, 1H), 8.23 (d, J = 0.7 Hz, 1H), 7.37 (s, 4H), 5.27 (s, 2H), 4.65 (ddt, J = 8.4, 6.5, 1.6 Hz, 1H), 3.98 (s, 3H), 3.63 (ddt, J = 11.3, 8.5, 5.0 Hz, 1H), 2.85-2.67 (m, 2H), 2.56-2.44 (m, 2H). | 413.1 |
| 51 | ¹H NMR (400 MHz, DMSO-d6) δ 8.38 (s, 1H), 8.23 (s, 1H), 7.33 (d, J = 4.3 Hz, 4H), 7.27-7.15 (m, 1H), 5.27 (s, 2H), 4.71-4.58 (m, 1H), 3.98 (s, 3H), 3.69-3.57 (m, 1H), 2.85-2.72 (m, 2H), 2.58-2.45 (m, 2H) | 379.1 |
| 52 | ¹H NMR (400 MHz, DMSO-d6) δ 8.37 (s, 1H), 8.22 (s, 1H), 7.54-7.47 (m, 2H), 7.34-7.27 (m, 2H), 5.27 (s, 2H), 4.71-4.58 (m, 1H), 3.98 (s, 3H), 3.67-3.55 (m, 1H), 3.29 (d, J = 2.2 Hz, 1H), 2.84-2.72 (m, 2H), 2.49-2.43 (m, 1H). | 457 |
| 53 | ¹H NMR (400 MHz, DMSO-d6) δ 8.38 (s, 1H), 8.23 (d, J = 0.7 Hz, 1H), 7.41 (t, J = 1.9 Hz, 1H), 7.38-7.33 (m, 1H), 7.32-7.25 (m, 2H), 5.27 (s, 2H), 4.72-4.60 (m, 1H), 3.98 (s, 3H), 3.72-3.59 (m, 1H), 2.85-2.72 (m, 2H), 2.58-2.51 (m, 2H). | 413.1 |
| 54 | ¹H NMR (400 MHz ,DMSO-d6) δ 8.37 (s, 1H), 8.22 (s, 1H), 7.29-7.20 (m, 2H), 6.95-6.84 (m, 2H), 5.27 (s, 2H), 4.62 (s, 1H), 3.98 (s, 3H), 3.73 (s, 3H), 3.62-3.50 (m, 1H), 2.81-2.67 (m, 2H), 2.49-2.41 (m, 2H). | 409.1 |
| 55 | ¹H NMR (400 MHz, DMSO-d6) δ 8.35 (s, 1H), 8.22 (s, 1H), 7.64 (d, J = 4.9 Hz, 2H), 7.58-7.49 (m, 2H), 7.45 (t, J = 7.6 Hz, 2H), 7.35 (t, J = 7.3 Hz, 1H), 7.26 (d, J = 8.2 Hz, 2H), 5.23 (s, 2H), 3.97 (s, 3H), 3.90 (t, J = 7.0 Hz, 2H), 2.96 (t, J = 7.0 Hz, 2H). | 429.1 |
| 57 | ¹H NMR (400 MHz, DMSO-d₆) δ 8.38 (s, 1H), 8.23 (s, 1H), 7.37 (s, 4H), 5.27 (s, 2H), 4.72-4.56 (m, 1H), 3.65-3.60 (m, 1H), 2.81-2.74 (m, 2H), 2.53 (s, 1H), 2.49-2.44 (m, 1H) | 416 |
| 59 | ¹H NMR (400 MHz, DMSO-d₆) δ 8.38 (s, 1H), 7.38 (s, 4H), 5.27 (s, 2H), 4.65 (m, 1H), 3.97 (s, 3H), 3.63 (m, 1H), 2.53-3.25 (m, 2H), 2.23-2.46 (m, 2H) | 414.1 |
| 60 | ¹H NMR (400 MHz, CDCl₃) δ 7.84 (s, 1H), 7.31-7.26 (m, 2H), 7.22-7.17 (m, 2H), 5.15 (s, 2H), 4.77-4.70 (m, 1H),4.10 (s, 3H), 3.67-3.60 (m, 1H), 2.94-2.86 (m, 2H), 2.56-2.50 (m, 2H) | 413 |
| 63 | ¹H NMR (400 MHz, DMSO-d₆): δ 8.38 (s, 1H), 8.24 (s, 1H), 7.32-7.30 (m, 1H), 6.78-6.68 (m, 3H), 5.27 (s, 2H), 4.89 (m, 1H), 4.75-4.64 (m, 1H), 3.98 (s, 3H), 2.86-2.75 (m, 2H), 2.55 (m, 2H) | 413.1 |
| 64 | 414.0 ¹H NMR (300 MHz, DMSO-d₆) δ 8.52 (s, 1H), 7.40-7.34 (m, 4H), 5.31 (s, 2H), 4.68-4.63 (m, 1H), 4.38 (s, 3H), 3.67-3.56 (m, 1H), 2.84-2.74 (m, 2H), 2.58-2.46 (m, 2H) | 414.0 |
| 65 | ¹H NMR (400 MHz, CDCl₃): δ 7.86 (d, J = 6.5 Hz, 1H), 7.64 (d, J = 9.2, 7.2 Hz, 1H), 7.45 (dd, J = 7.0, 1.1 Hz, 1H), 7.37-7.29 (m, 2H), 7.26-7.18 (m, 2H), 6.92 (dd, J = 9.2, 1.2 Hz, 1H), 6.64 (d, J = 6.5 Hz, 1H), 5.01 (s, 2H), 4.84-4.71 (m, 1H), 3.68-3.66 (m, 1H), 3.01-2.89 (m, 2H), 2.61-2.50 (m, 2H) | 425.1 |
| 70 | ¹H NMR (400 MHz, DMSO-d6) δ 8.36 (s, 1H), 8.22 (s, 1H), 7.30 (t, J = 8.1 Hz, 1H), 7.00 (ddd, J = 8.0, 2.0, 0.9 Hz, 1H), 6.89 (t, J = 2.2 Hz, 1H), 6.81 (ddd, J = 8.4, 2.5, 0.9 Hz, 1H), 5.26 (s, 2H), 4.90 (tt, J = 7.0, 3.6 Hz, 1H), 4.69 (tt, J = 8.5, | 429.1 |

TABLE 3-continued

| Ex. | 1H NMR (ppm) | M + H |
|---|---|---|
| | 6.2 Hz, 1H), 3.97 (s, 3H), 2.85-2.74 (m, 2H), 2.58-2.50 (m, 2H) | |
| 83 | $^1$H NMR (500 MHz, DMSO-d6) δ 8.41 (s, 1H), 7.74 (d, J = 9.6 Hz, 1H), 7.40-7.35 (m, 4H), 6.96 (d, J = 9.6 Hz, 1H), 5.24 (s, 2H), 4.69-4.61 (m, 1H), 3.90 (s, 3H), 3.68-3.59 (m, 1H), 2.83-2.75 (m, 2H), 2.54-2.50 (m, 2H) | 440.0 |
| 85 | $^1$H NMR (400 MHz, DMSO-$d_6$) δ 8.77 (d, J = 4.8 Hz, 1H), 8.60 (s, 1H), 7.39 (d, J = 4.8 Hz, 1H), 7.27-7.25 (m, 1H), 6.97-6.94 (m, 2H), 6.88-6.83 (m, 1H), 5.19 (s, 2H), 4.02 (t, J = 6.0 Hz, 2H), 3.81 (t, J = 6.4 Hz, 2H), 2.77 (m, 3H), 2.08-2.02 (m, 2H) | 427 |
| 86 | $^1$HNMR (400 MHz, DMSO-$d_6$) δ 8.34 (s, 1H), 8.22 (s, 1H), 7.27 (t, J = 8.0 Hz, 1H), 6.99-6.95 (m, 2H), 6.86-6.84 (m, 1H), 5.22 (s, 2H), 4.03 (t, J = 6.0 Hz, 2H), 3.96 (s, 3H), 3.80 (t, J = 6.7 Hz, 2H), 2.08-2.01 (m, 2H) | 416 |
| 92 | $^1$H NMR (500 MHz, DMSO-d6) δ 8.35 (s, 1H), 8.22 (s, 1H), 7.30-7.26 (m, 2H), 7.13-7.07 (m, 2H), 5.24 (s, 2H), 4.65-4.58 (m, 1H), 3.97 (s, 3H), 3.31-3.22 (m, 1H), 2.26-2.09 (m, 3H), 2.04-1.95 (m, 1H), 1.94-1.85 (m, 1H), 1.65-1.54 (m, 1H) | 411.1 |
| 93 | $^1$H NMR (300 MHz, DMSO-$d_6$) δ 8.75 (s, 1H), 8.05 (s, 1H), 7.40-7.34 (m, 4H), 5.25 (s, 2H), 4.68-4.63 (m, 1H), 3.67-3.60 (m, 1H), 2.85 (s, 3H), 2.81-2.74 (m, 2H), 2.55-2.46 (m, 2H) | 449.1 |
| 94 | $^1$H NMR (300 MHz, DMSO-$d_6$) δ 9.02-9.01 (m, 1H), 8.69 (s, 1H), 8.61-8.57 (m, 1H), 7.65-7.57 (m, 3H), 7.52-7.51 (m, 2H), 5.29 (s, 2H), 4.41-4.29 (m, 1H), 3.08-2.94 (m, 4H) | 428 |
| 98 | $^1$H NMR (400 MHz, DMSO-d6) δ 9.01 (dd, J = 4.7, 2.0 Hz, 1H), 8.68 (s, 1H), 8.59 (dd, J = 8.0, 2.0 Hz, 1H), 7.63 (dd, J = 7.9, 4.6 Hz, 1H), 7.41-7.31 (m, 4H), 5.28 (s, 2H), 4.71-4.58 (m, 1H), 3.63 (dddd, J = 10.0, 8.7, 5.9, 4.8 Hz, 1H), 2.84-2.71 (m, 2H), 2.58-2.43 (m, 2H) | 410.1 |
| 100 | $^1$H NMR (500 MHz, DMSO-d6) δ 8.35 (s, 1H), 8.22 (s, 1H), 7.34 (d, J = 8.1 Hz, 2H), 7.27 (d, J = 8.1 Hz, 2H), 5.24 (s, 2H), 4.67-4.57 (m, 1H), 3.97 (s, 3H), 3.30-3.18 (m, 1H), 2.29-2.08 (m, 3H), 2.07-1.96 (m, 1H), 1.96-1.83 (m, 1H), 1.69-1.51 (m, 1H) | 427.0 |
| 103 | $^1$H NMR (500 MHz, DMSO-d6) δ 8.38 (s, 1H), 8.23 (d, J = 0.4 Hz, 1H), 7.41-7.36 (m, 2H), 7.19 (t, J = 74.3 Hz, 1H), 7.16-7.10 (m, 2H), 5.27 (s, 2H), 4.68-4.59 (m, 1H), 3.97 (s, 3H), 3.68-3.59 (m, 1H), 2.82-2.73 (m, 2H), 2.54-2.45 (m, 2H) | 445.0 |
| 105 | $^1$H NMR (400 MHz, DMSO-d6) δ 8.37 (s, 1H), 8.22 (s, 1H), 7.62-7.54 (m, 2H), 7.56-7.46 (m, 2H), 5.27 (s, 2H), 4.34 (pd, J = 8.2, 3.7 Hz, 1H), 3.98 (s, 3H), 3.12-2.93 (m, 4H) | 431.1 |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A compound of formula (I) or a pharmaceutically acceptable salt thereof

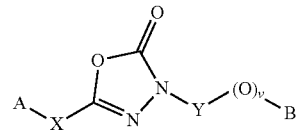
(I)

wherein:

A is

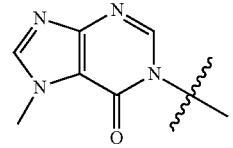 [SMILES: *n1cnc2ncn(C)c2c1=O]

X is selected from a bond, $C_{1-4}$ alkylene, —O—, —S—; —SO$_2$—, and —N(R$^1$)—, wherein R$^1$ is selected from H and $C_{1-6}$ alkyl;

Y is selected from substituted and unsubstituted $C_{1-4}$ alkylene, $C_{2-4}$ alkenylene, and $C_{3-6}$ cycloalkylene wherein one or more carbons of $C_{1-4}$ alkylene or $C_{2-4}$ alkenylene may be replaced with —O— or —C(O)—;

B is selected from substituted and unsubstituted 5-membered aryl, 6-membered aryl, 5-membered heteroaryl, 6-membered heteroaryl, 6-6 fused bicyclic aryl, 6-6 fused bicyclic heteroaryl, 6-5 fused bicyclic aryl, 6-5 fused bicyclic heteroaryl, 6-5 fused bicyclic aryl-heteroaryl, 6-5 fused bicyclic aryl-cycloalkylene, and 6-6 fused bicyclic aryl-heteroaryl; and v is 0 or 1.

2. The compound of claim 1, wherein Y is selected from substituted and unsubstituted $C_{2-3}$ alkylene, $C_2$ alkenylene, and $C_{4-8}$ cycloalkylene.

3. The compound of claim 2, wherein Y is substituted with one or more substituents independently selected from —$C_{1-4}$ alkyl, -halo$C_{1-4}$ alkyl, —CN, —OH, halogen, -cyclopropyl, deutero, and -deuterio-$C_{1-4}$ alkyl.

4. The compound of claim 3 wherein Y is substituted with at least one of halo, —$C_{1-4}$ alkyl, —OH, and -C3-4 cycloalkyl.

5. The compound of claim 4 wherein Y is substituted with F, CH$_3$, —OH or cyclopropyl.

6. The compound of claim 1, wherein Y is selected from:

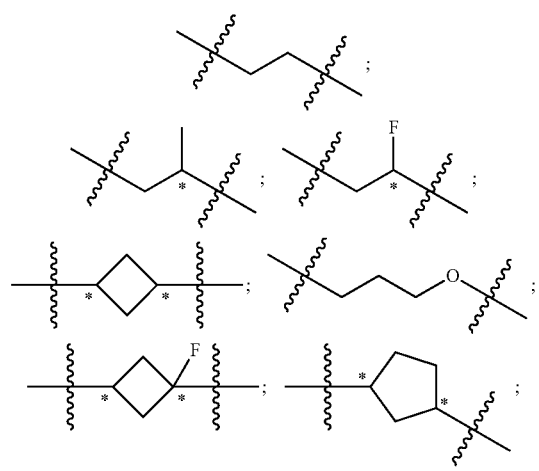

-continued

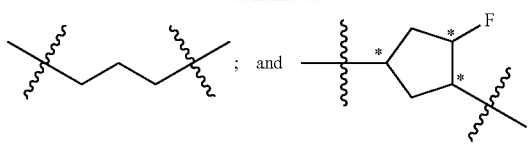

wherein * denotes a chiral center (i) in an R configuration or in an S configuration or (ii) a mixture of R and S configurations for a plurality of compounds of formula (I).

7. The compound of claim 1, wherein B is selected from:

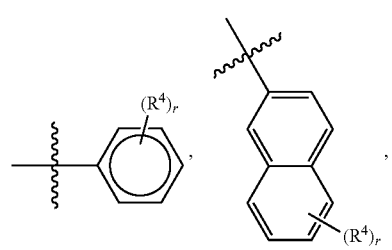

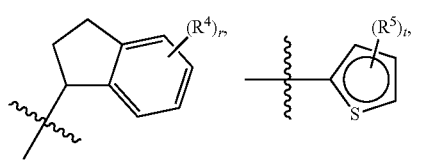

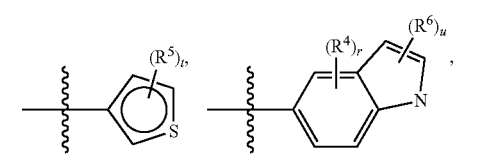

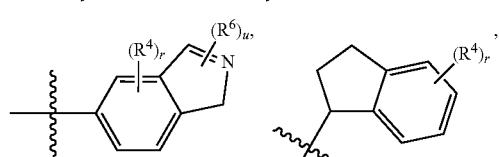

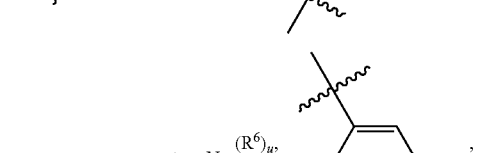

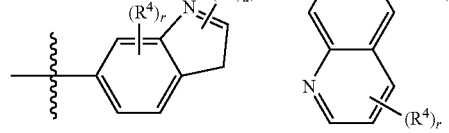

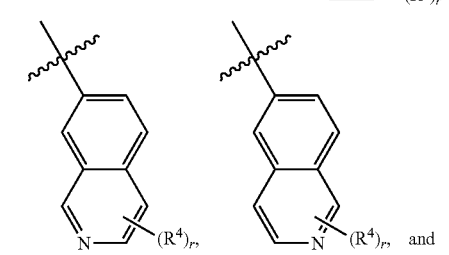

-continued

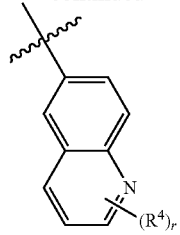

wherein
r is independently selected from 0, 1 and 2 and $R^4$ is selected from $C_{1-4}$ alkyl, halo$C_{1-4}$ alkyl, —O-halo$C_{1-4}$ alkyl, halogen, —OCHF$_2$, —CN, —CHF$_2$, —CF$_3$, —OCF$_3$, —N(CH$_3$)$_2$, —OCH$_3$, -phenyl,

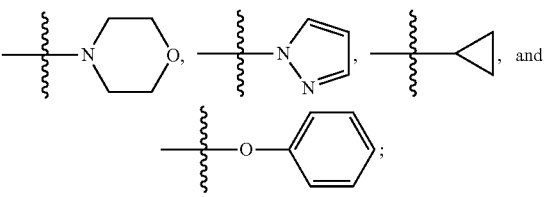

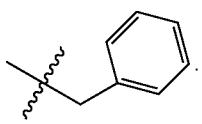 [SMILES: *Cc1ccccc1]

t is selected from 0 and 1 and $R^5$ is halogen; and
u is selected from 0 and 1 and $R^6$ is selected from $C_{1-4}$ alkyl; and

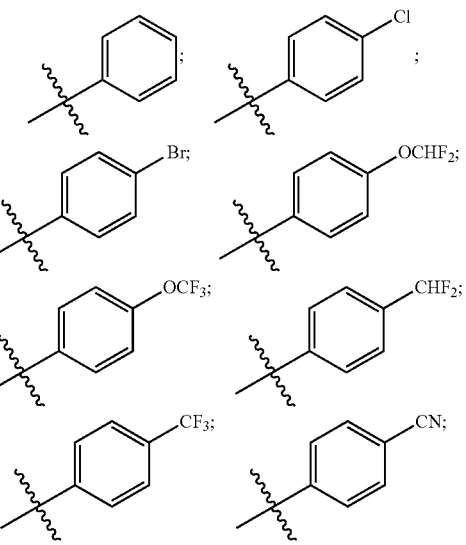

8. The compound of claim 7 wherein: —O-halo$C_{1-4}$ alkyl is selected from —OCHF$_2$ and —OCF$_3$; halo$C_{1-4}$ alkyl is selected from —CHF$_2$ and —CF$_3$; and $C_{1-4}$-alkoxy is —OCH$_3$.

9. The compound of claim 7 wherein B is selected from:

-continued
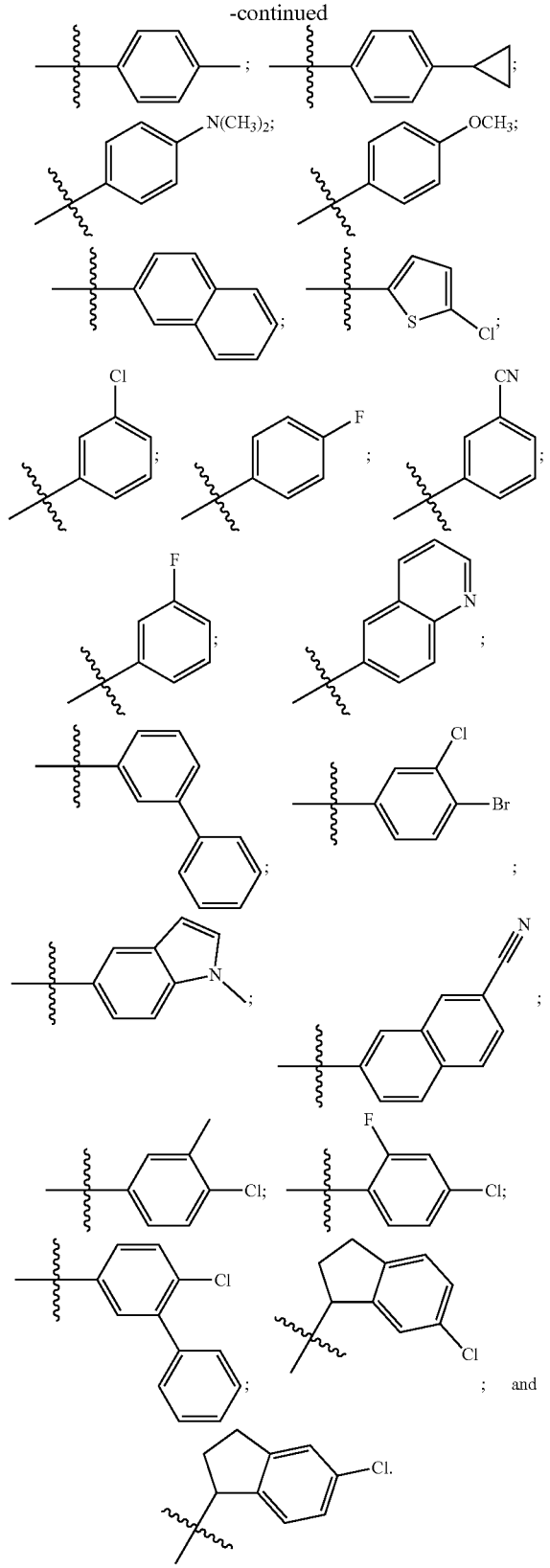
10. The compound of claim 1 wherein X is —CH$_2$—.
11. A compound, or pharmaceutically acceptable salts thereof, selected from:
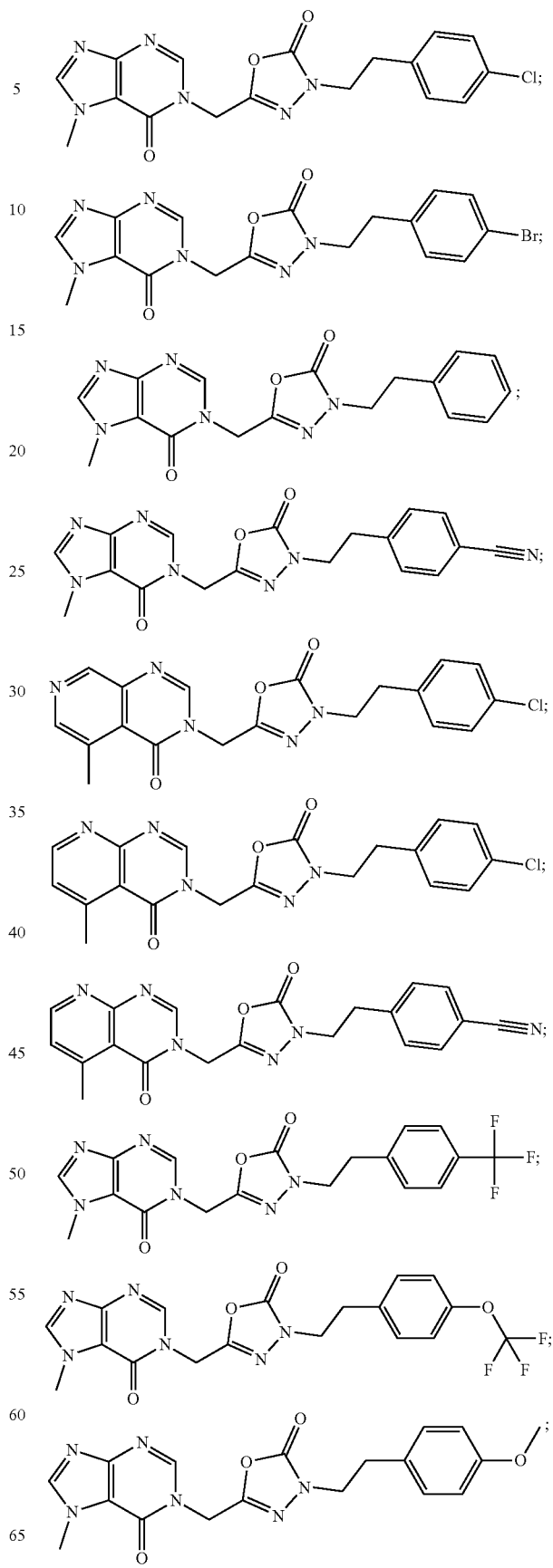

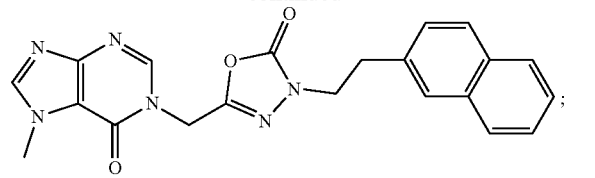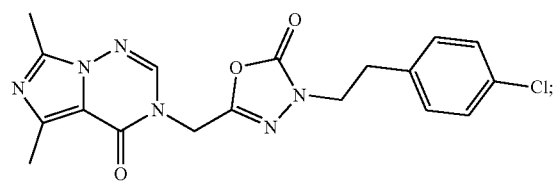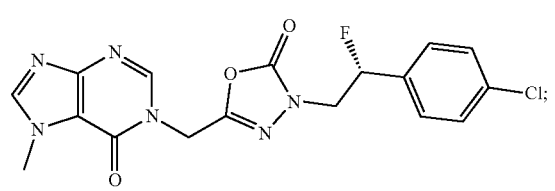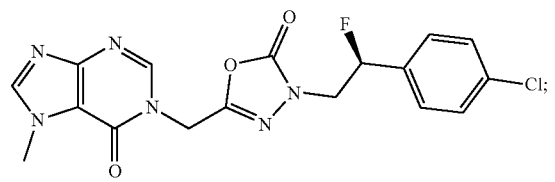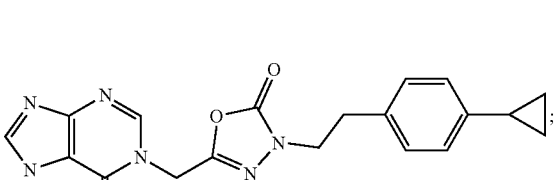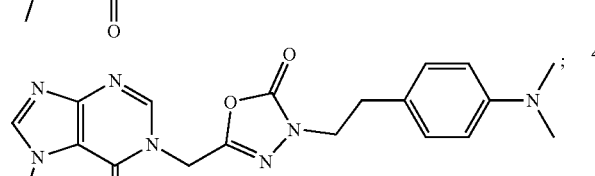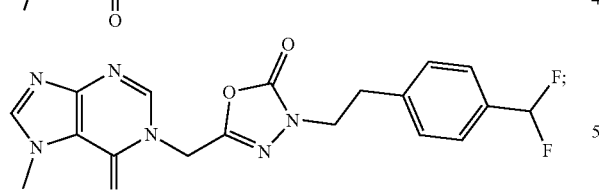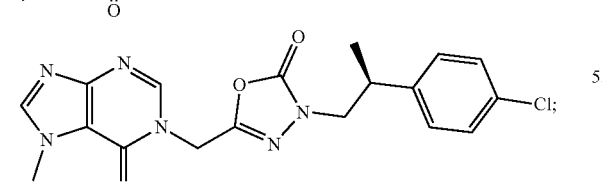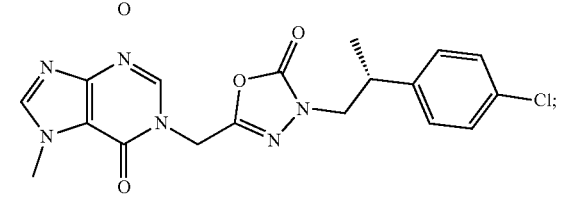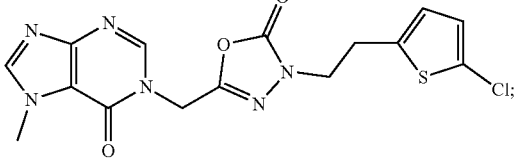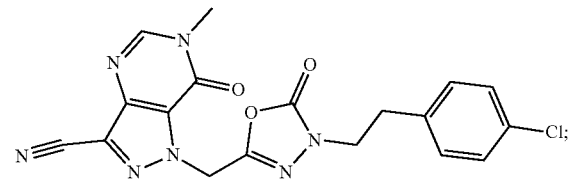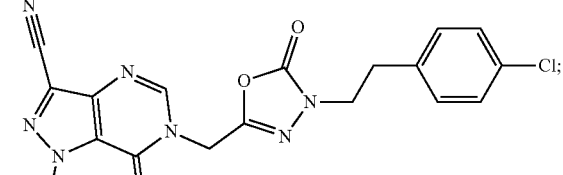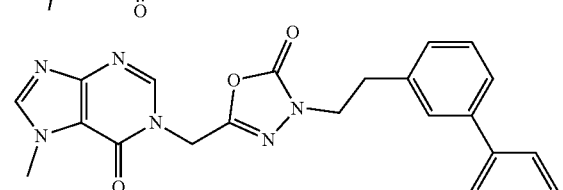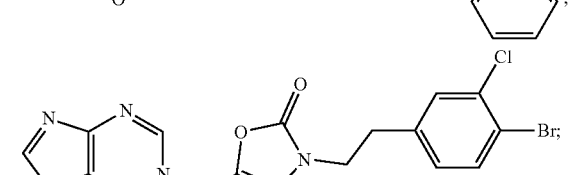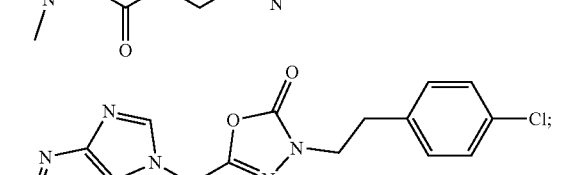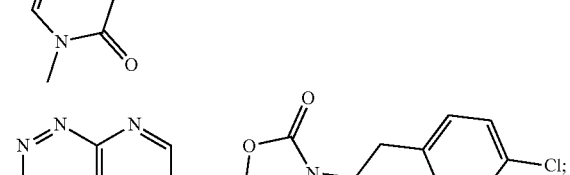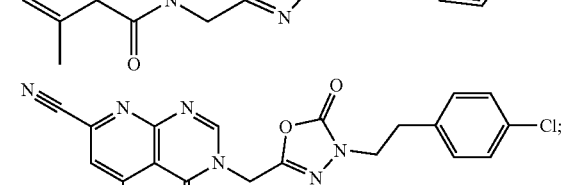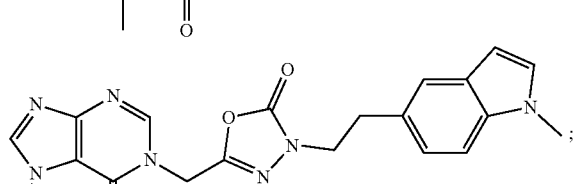

245
-continued
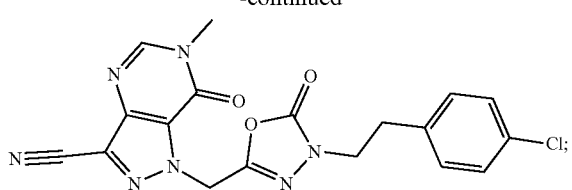
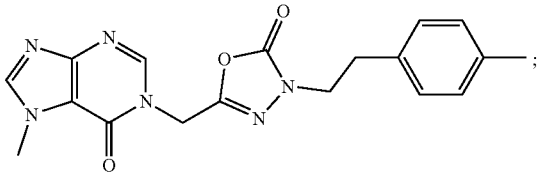
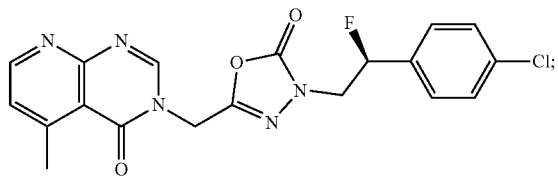
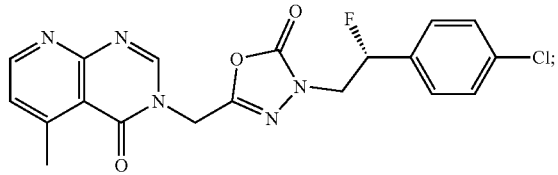
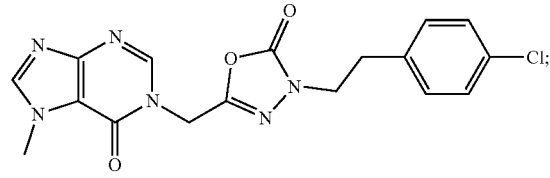
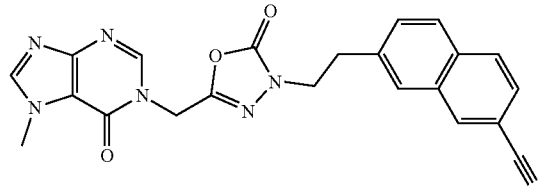
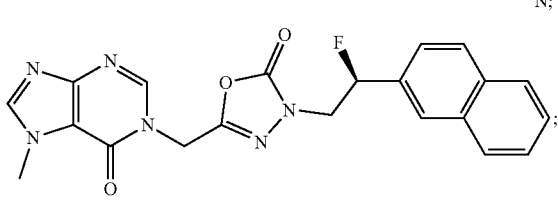
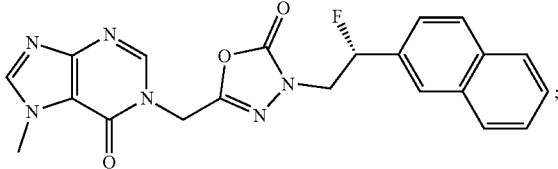
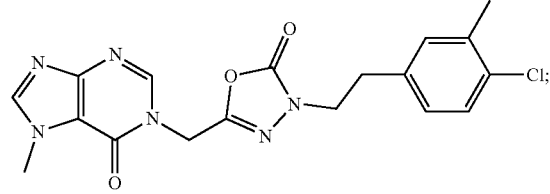
246
-continued
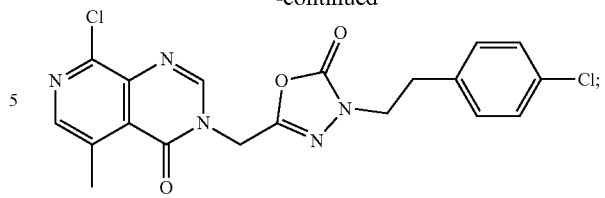
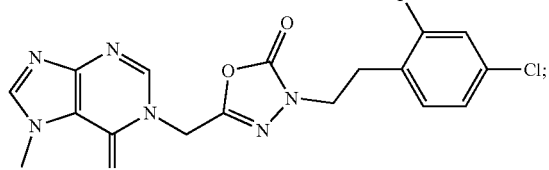
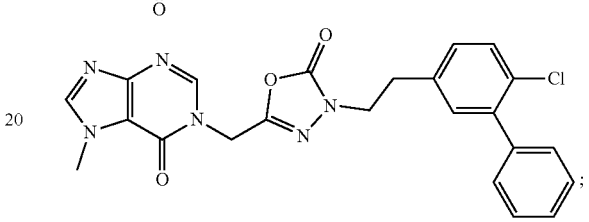
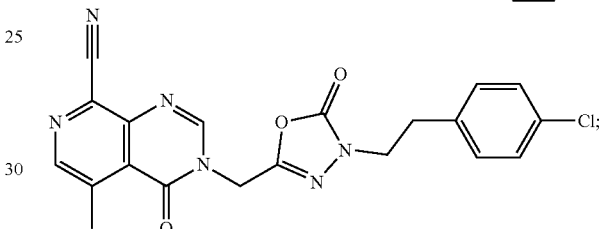
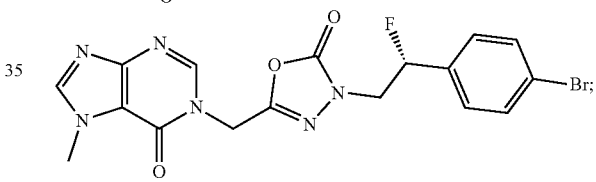
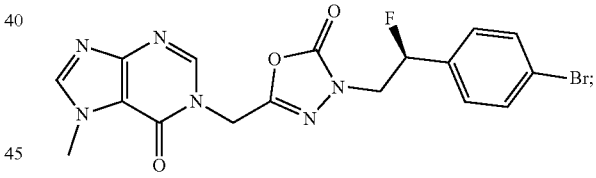
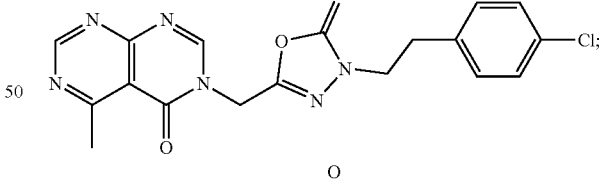
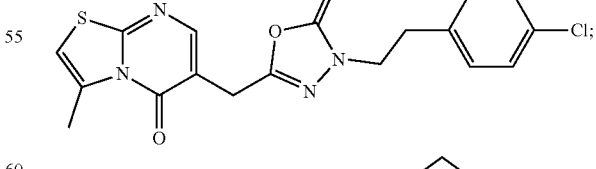
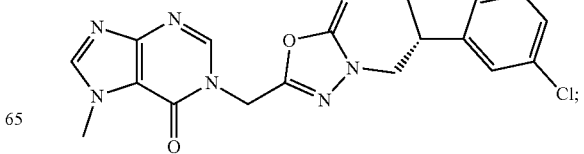

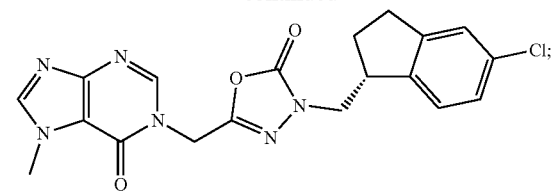
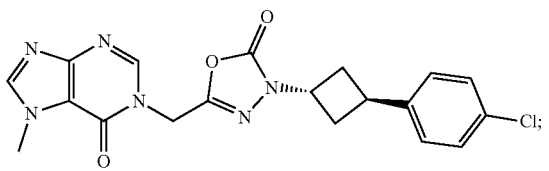
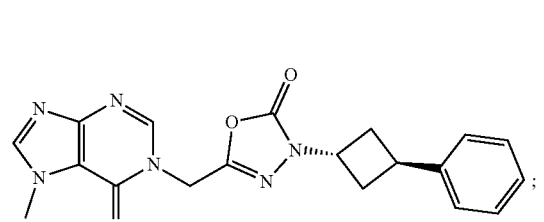
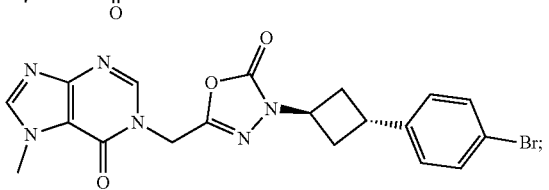
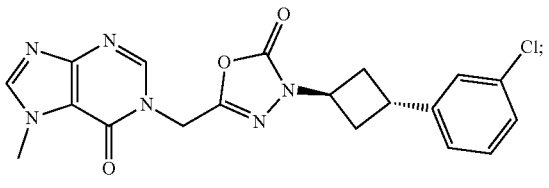
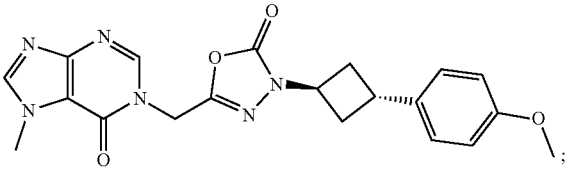
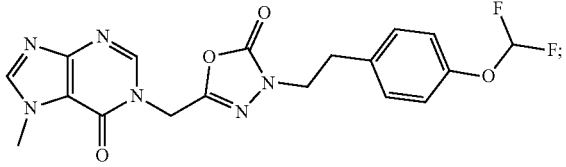
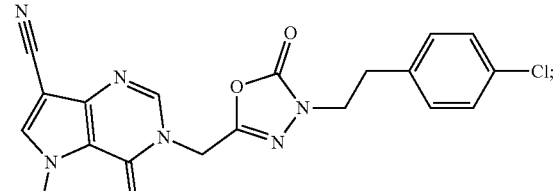
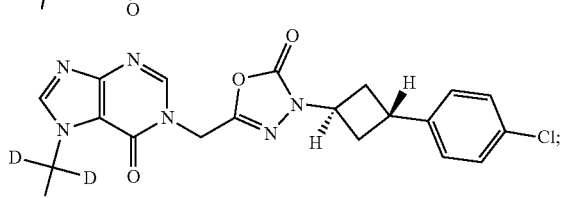
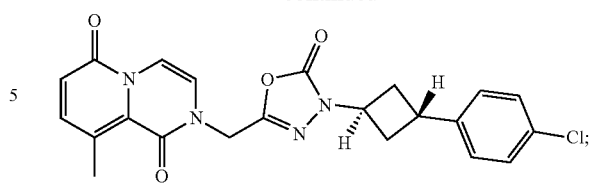
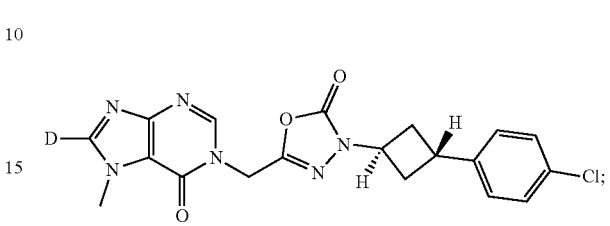
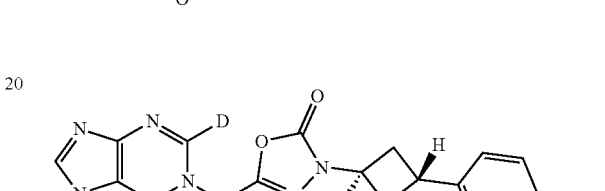
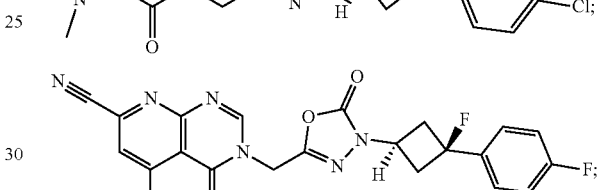
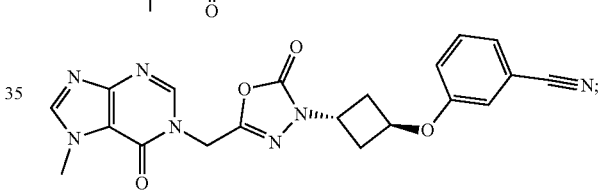
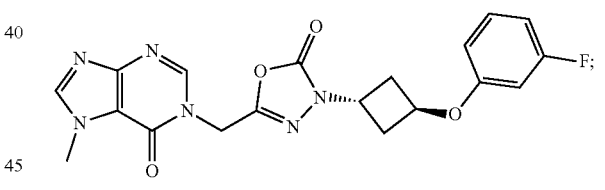
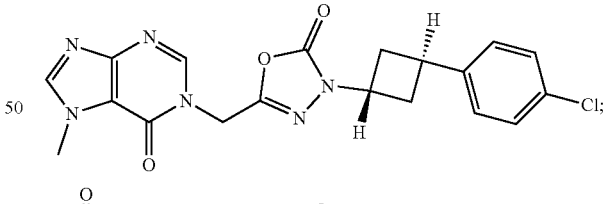
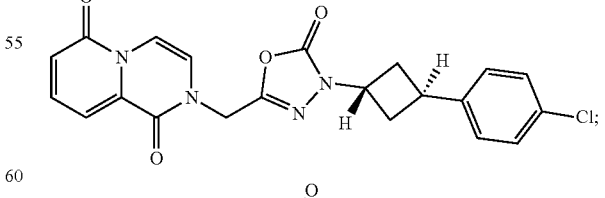
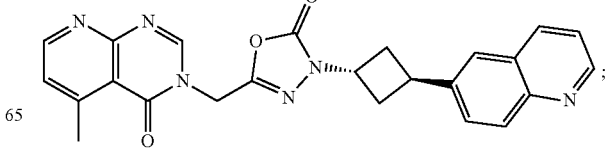

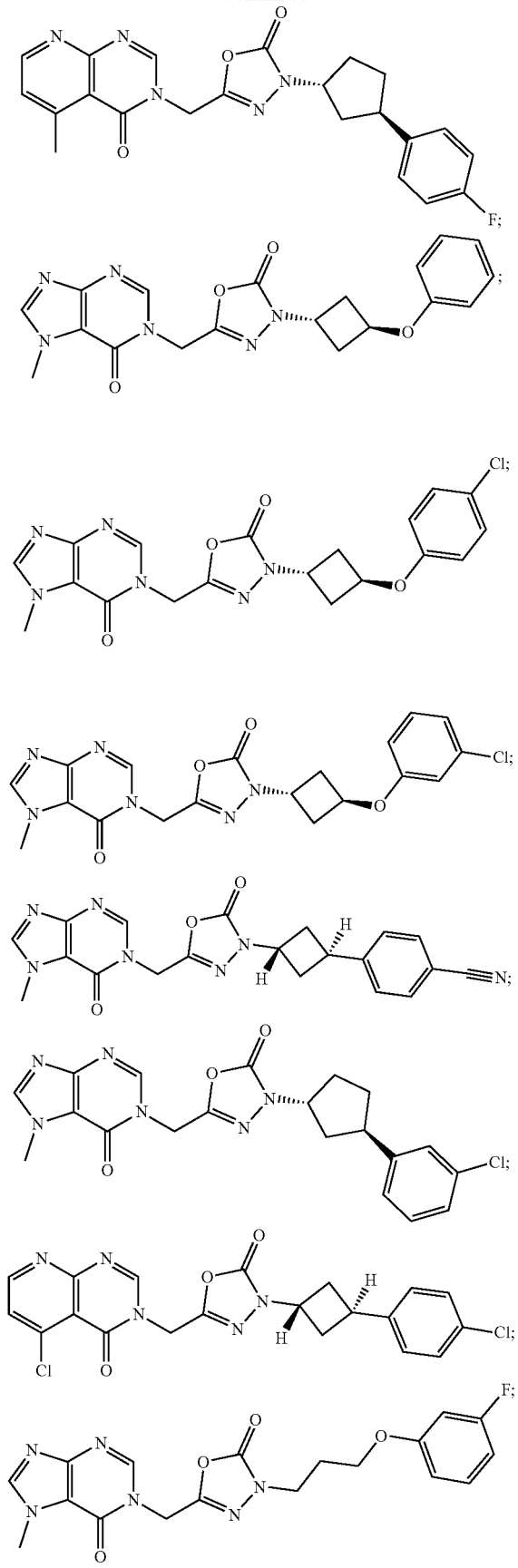
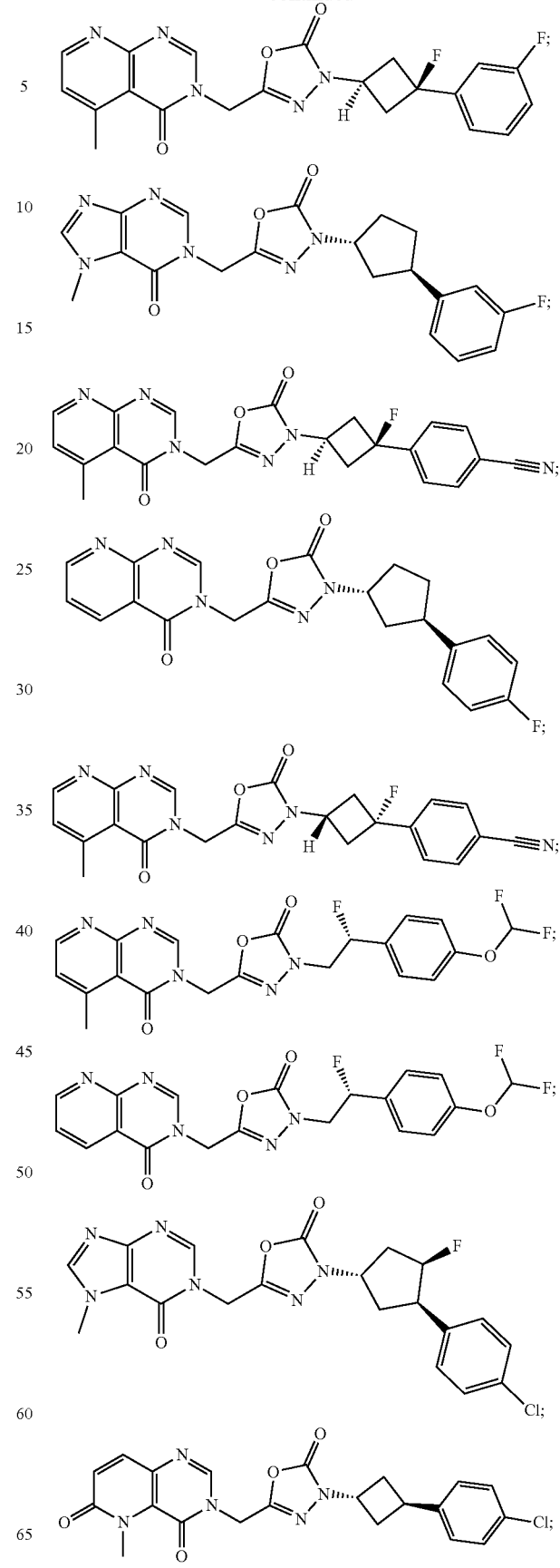

251
-continued
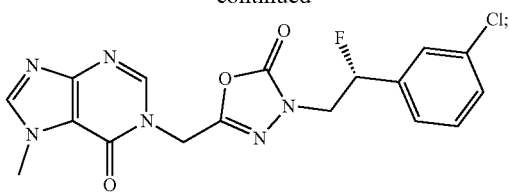
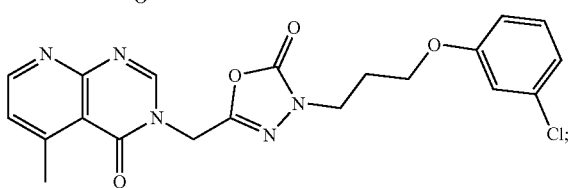
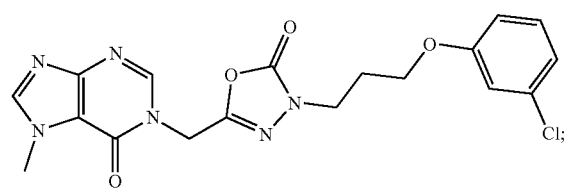
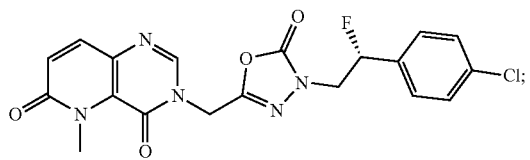
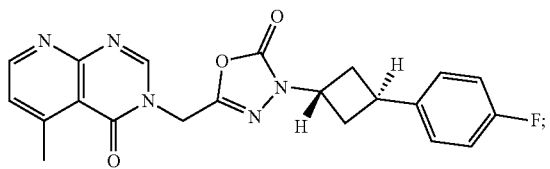
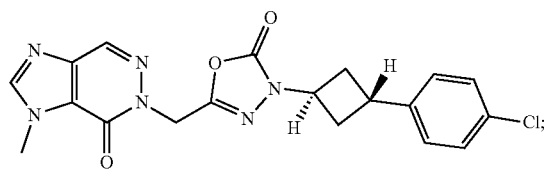
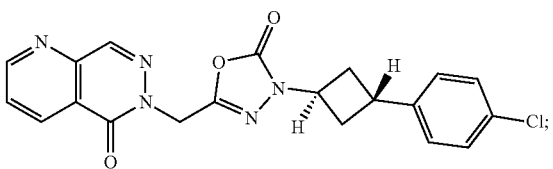
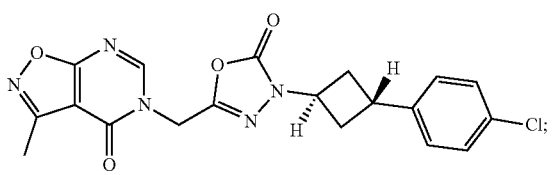
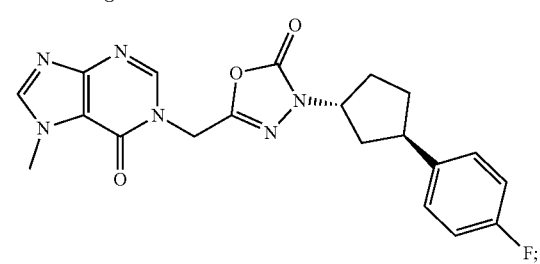
252
-continued
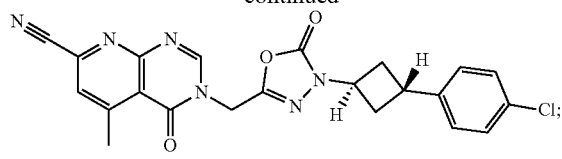
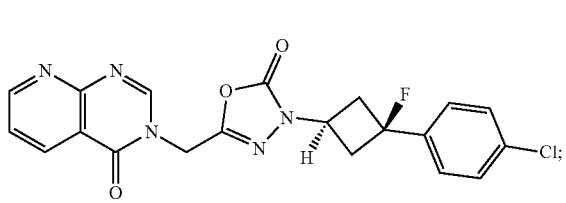
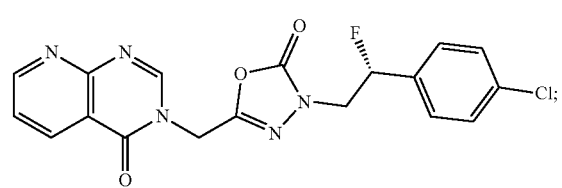
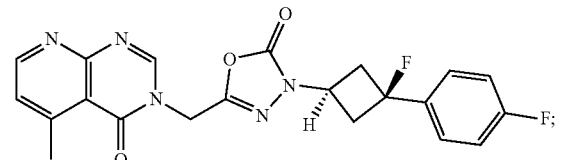
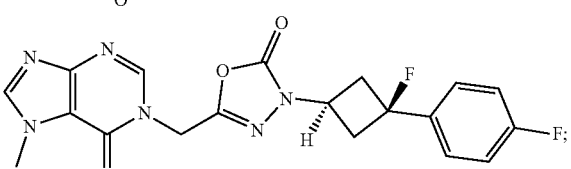
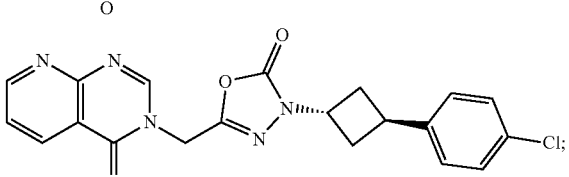
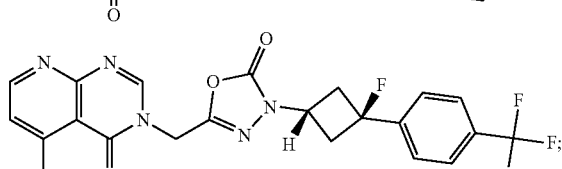
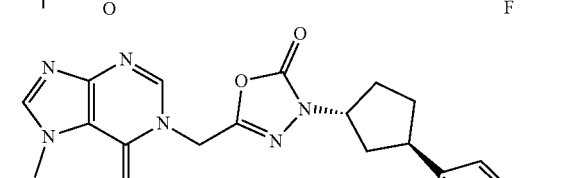
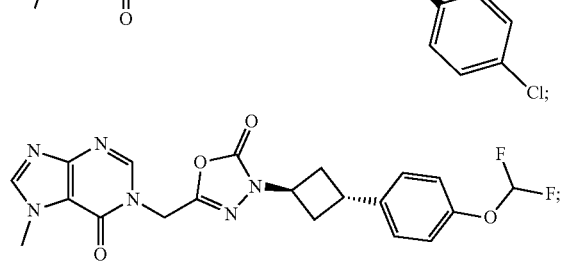

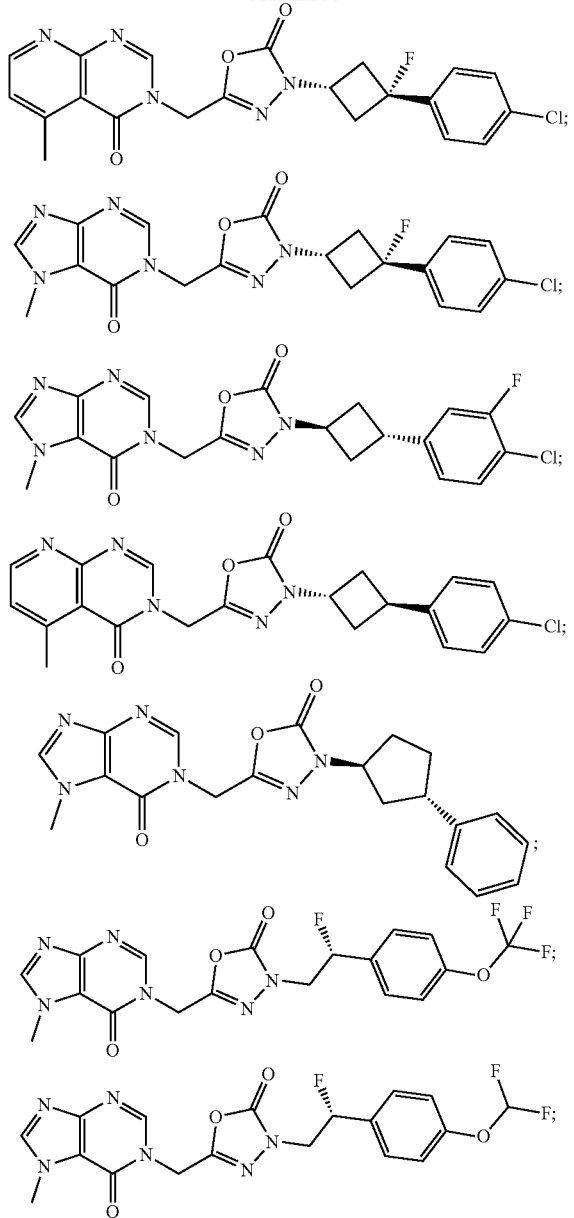
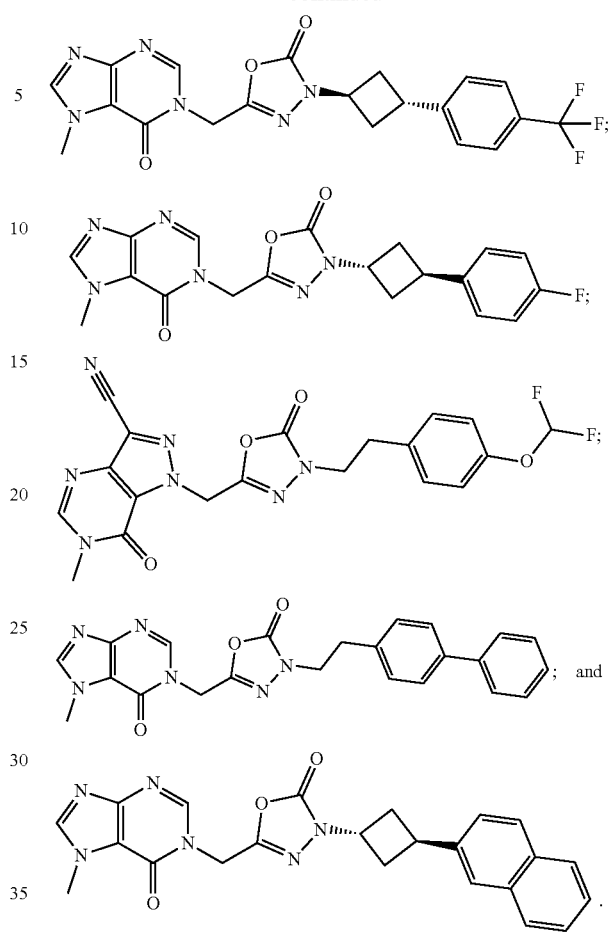
12. A pharmaceutical composition, comprising a compound of claim 1 or a pharmaceutically acceptable salt thereof, and a pharmaceutically acceptable carrier, diluent or excipient.
13. A method for treating asthma in a mammal, comprising administering an effective amount of a compound of claim 1 or a pharmaceutically acceptable salt thereof to the mammal.
* * * * *